(12) United States Patent
Boissel et al.

(10) Patent No.: US 11,547,727 B2
(45) Date of Patent: *Jan. 10, 2023

(54) CHIMERIC ANTIGEN RECEPTOR-MODIFIED NK-92 CELLS

(71) Applicant: ImmunityBio, Inc., Culver City, CA (US)

(72) Inventors: Laurent H. Boissel, San Diego, CA (US); Hans G. Klingemann, San Diejo, CA (US)

(73) Assignee: ImmunityBio, Inc., Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/969,152

(22) PCT Filed: May 21, 2019

(86) PCT No.: PCT/US2019/033411
§ 371 (c)(1),
(2) Date: Aug. 11, 2020

(87) PCT Pub. No.: WO2020/096646
PCT Pub. Date: May 14, 2020

(65) Prior Publication Data
US 2021/0260116 A1 Aug. 26, 2021

Related U.S. Application Data

(60) Provisional application No. 62/756,395, filed on Nov. 6, 2018, provisional application No. 62/756,402, filed on Nov. 6, 2018.

(51) Int. Cl.
| | |
|---|---|
| *A61K 35/17* | (2015.01) |
| *A61P 35/00* | (2006.01) |
| *A61K 35/28* | (2015.01) |
| *A61K 39/395* | (2006.01) |
| *A61K 45/06* | (2006.01) |
| *C07K 14/705* | (2006.01) |
| *C07K 14/735* | (2006.01) |
| *C07K 16/10* | (2006.01) |
| *C07K 16/28* | (2006.01) |
| *C07K 16/32* | (2006.01) |
| *C12N 5/0783* | (2010.01) |

(52) U.S. Cl.
CPC ............. *A61K 35/17* (2013.01); *A61K 35/28* (2013.01); *A61K 39/3955* (2013.01); *A61K 45/06* (2013.01); *A61P 35/00* (2018.01); *C07K 14/70517* (2013.01); *C07K 14/70521* (2013.01); *C07K 14/70535* (2013.01); *C07K 16/10* (2013.01); *C07K 16/109* (2013.01); *C07K 16/1018* (2013.01); *C07K 16/1027* (2013.01); *C07K 16/1063* (2013.01); *C07K 16/2803* (2013.01); *C07K 16/2827* (2013.01); *C07K 16/2863* (2013.01); *C07K 16/2866* (2013.01); *C07K 16/2878* (2013.01); *C07K 16/2887* (2013.01); *C07K 16/32* (2013.01); *C12N 5/0646* (2013.01); *C07K 2317/53* (2013.01); *C07K 2317/622* (2013.01); *C07K 2319/03* (2013.01); *C12N 2510/00* (2013.01)

(58) Field of Classification Search
CPC .... A61K 35/17; A61K 35/28; A61K 39/3955; A61K 45/06; A61P 35/00; C07K 14/70517; C07K 14/70521; C07K 14/70535; C07K 16/10; C07K 16/1018; C07K 16/1027; C07K 16/1063; C07K 16/109; C07K 16/2803; C07K 16/2827; C07K 16/2863; C07K 16/2866; C07K 16/2878; C07K 16/2887; C07K 16/32; C12N 5/0646
See application file for complete search history.

(56) References Cited

U.S. PATENT DOCUMENTS

| | | |
|---|---|---|
| 7,098,008 B2 | 8/2006 | Park et al. |
| 7,618,817 B2 | 11/2009 | Campbell |
| 8,034,332 B2 | 10/2011 | Klingemann |
| 8,313,943 B2 | 11/2012 | Campbell |
| 9,150,636 B2 | 10/2015 | Campbell |
| 9,181,322 B2 | 11/2015 | Campbell |
| 10,138,462 B2 | 11/2018 | Klingemann |

(Continued)

FOREIGN PATENT DOCUMENTS

| | | |
|---|---|---|
| CA | 2 977 106 A1 | 9/2016 |
| CA | 3 055 202 A1 | 9/2018 |

(Continued)

OTHER PUBLICATIONS

Eiseman et al. "Signal transduction by the cytoplasmic domains of Fc epsilon RI-gamma and TCR-zeta in rat basophilic leukemia cells", J Biol Chem. Oct. 15, 1992;267(29):21027-32. (Year: 1992).*

(Continued)

*Primary Examiner* — Amy E Juedes
*Assistant Examiner* — Peter Johansen
(74) *Attorney, Agent, or Firm* — Martin Fessenmaier; Umberg Zipser LLP

(57) ABSTRACT

Provided are NK-92 cells expressing a chimeric antigen receptor (CAR). The CAR can comprise an intracellular domain of FcεRIγ. Also described are methods for treating a patient having or suspected of having a disease that is treatable with NK-92 cells, such as cancer or a viral infection, comprising administering to the patient NK-92-CAR cells.

13 Claims, 65 Drawing Sheets

Specification includes a Sequence Listing.

(56) References Cited

U.S. PATENT DOCUMENTS

| | | | |
|---|---|---|---|
| 2002/0068044 | A1 | 6/2002 | Klingemann |
| 2013/0189268 | A1 | 7/2013 | Du et al. |
| 2013/0280285 | A1 | 10/2013 | Schonfeld et al. |
| 2014/0242701 | A1 | 8/2014 | Shiku et al. |
| 2014/0274909 | A1 | 9/2014 | Orentas et al. |
| 2016/0067356 | A1* | 3/2016 | Campbell ............. C07K 16/28 435/372 |
| 2016/0347854 | A1 | 12/2016 | Hombach et al. |
| 2017/0260268 | A1* | 9/2017 | Beatty .................... A61P 43/00 |
| 2021/0187024 | A1* | 6/2021 | Klingemann ...... A61K 38/1774 |

FOREIGN PATENT DOCUMENTS

| | | | | |
|---|---|---|---|---|
| CA | 3 092 305 | A1 | 5/2020 | |
| CN | 106701685 | A | 5/2017 | |
| CN | 112352048 | A | 2/2021 | |
| KR | 1020180008862 | A | 1/2018 | |
| KR | 10-2020-0118904 | A | 10/2020 | |
| WO | 98/49268 | A1 | 11/1998 | |
| WO | 99/24566 | A1 | 5/1999 | |
| WO | 90/20460 | A1 | 4/2000 | |
| WO | 2014/039523 | A1 | 3/2014 | |
| WO | 2014/099671 | A1 | 6/2014 | |
| WO | 2016/138491 | A1 | 9/2016 | |
| WO | 2016/201304 | A1 | 12/2016 | |
| WO | WO-2016201304 | A1 * | 12/2016 | ............. A61K 35/17 |
| WO | 2017192440 | A1 | 11/2017 | |
| WO | WO-2017192440 | A1 * | 11/2017 | ......... C07K 16/2866 |
| WO | 2018/076391 | A1 | 5/2018 | |
| WO | 2020/091869 | A1 | 5/2020 | |
| WO | 2020/096646 | A1 | 5/2020 | |

OTHER PUBLICATIONS

Office Action received for Canadian Patent Application Serial No. CA3092305 dated Aug. 27, 2021, 4 Pages.

First Substantive Examination Report received for Israeli Patent Application Serial No. 277414 dated Nov. 4, 2021, 12 pages. (Including English Translation).

Eiseman, E. et al., 'Signal transduction by the cytoplasmic domains of FCεRI-γ and TCR-ζ in rat basophilic leukemia cells'. The Journal of Biological Chemistry, Oct. 15, 1992, vol. 267, No. 29, pp. 21027-21032 See abstract.

Zhang, C. et al., 'Chimeric antigen receptor-engineered NK-92 cells: an off-the-shelf cellular therapeutic for targeted elimination of cancer cells and induction of protective antitumor immunity', Frontiers in Immunology, May 18, 2017, vol. 8, Article 533, pp. 1-17 See the whole document.

International Search Report with International Application No. PCT/US2019/033411 dated May 21, 2019, pp. 1-6.

Delsner et al., "Continuously expanding Car NK-92 cells display selective cytotoxicity against B-cell leukemia and lymphoma," Cytotherapy, 2017; 19:235-249.

Haynes et al., "Redirecting Mouse CTL Against Colon Carcinoma: Superior Signaling Efficacy of Single-Chain Variable Domain Chimeras Containing TCR-ζ vs FcεRI-γ", The Journal of Immunology, 2001, vol. 166, pp. 182-187 (Cited from Specification).

Cartellier et al., "Chimeric Antigen Receptor-Engineered T Cells for Immunotherapy of Cancer", Journal of Biomedicine and Biotechnology, vol. 2010, No. 956304, pp. 1-13 (Cited from Specification).

Hermanson et al., "Utilizing Chimeric Antigen Receptors to Direct Natural Killer Cell Activity", Frontiers in Immunology, 2015, vol. 6, No. 195, pp. 1-6 (Cited from Specification).

Bruhns et al., "Specificity and affinity of human Fcγ receptors and their polymorphic variants for human IgG subclasses", Blood, 2009, vol. 113, No. 16, pp. 3716-3725 (Cited from Specification).

Konstantinidis et al., "Targeting IL-2 to the endoplasmic reticulum confines autocrine growth stimulation to NK-92 sells", Exp Hematol., 2005, vol. 33, No. 2, pp. 159-164 (Cited from Specification).

Sarcia-Sanchez et al., "Cytosine Deaminase Adenoviral Vector and 5-fluorocytosine Selectively Reduce Breast Cancer Cells 1 Million-Fold When They Contaminate Hemalopoielic Cells: A Potential Purging Method for Autologous Transplantation", Blood, 1998, vol. 92, No. 2, pp. 672-682 (Cited from Specification).

Touati et al., "A Suicide Gene Therapy Combining the Improvement of Cyclophosphamide Tumor Cytotoxicity and the Development of an Anti-Tumor Immune Response", Current Gene Therapy, 2014, vol. 14, pp. 236-246 (Cited from Specification).

Stasi et al., "Inducible Apoptosis as a Safety Switch for Adoptive Cell Therapy", The New England journal of Medicine, 2011, vol. 365, No. 18, pp. 1673-1683 (Cited from Specification).

Morgan Richard A, "Live and Let Die: A New Suicide Gene Therapy Moves to the Clinic", Molecular Therapy, Jan. 2012, vol. 20, No. 1, pp. 11-13 (Cited from Specification).

Smith et al., "Comparison of biosequences", Advances in Applied Mathematics, Dec. 1981, vol. 2, No. 4, pp. 482-489 (Cited from Specification).

Altschul et al., "Gapped BLAST and PSI-BLAST: a new generation of protein database search programs", Nucleic Acids Research, 1997, vol. 25, No. 17, 3389-3402 (Cited from Specification).

Altschul et al., "Basic local alignment search tool", Journal of Molecular Biology, 1990, vol. 215, No. 3, pp. 403-410 (Cited from Specification).

Henikoff et al., "Amino acid substitution matrices from protein blocks", PNAS, 1992, vol. 89, No. 22, pp. 10915-10919 (Cited from Specification).

Yazawa et al., "Current progress in suicide gene therapy for cancer", World Journal of Surgery, 2002, vol. 26, pp. 783-789 (Cited from Specification).

Gong et al., "Characterization of a human cell line (NK-92) with phenotypical and functional characteristics of activated natural killer cells", Leukemia, 1994, vol. 8, No. 4, pp. 652-658 (Cited from Specification).

Bollino et al., "Chimeric antigen receptor engineered natural killer and natural killer T cells for cancer immunotherapy", 2017, vol. 187, 21 pages.

International Preliminary Report on Patentability Chapter I received for International PCT Application Serial No. PCT/US2019/033411 dated May 20, 2021, 8 pages.

Examination Report received for Australian Patent Application Serial No. 2019375375, dated Nov. 12, 2021, 4 pages.

Extended European Search Report received for European Patent Application Serial No. 19882519.2, dated Oct. 21, 2021, 8 pages.

Second Office Action received for Canadian Patent Application Serial No. 3092305 dated Jul. 29, 2022, 4 pages.

Office Action received for Israel Patent Application Serial No. 277414 dated May 17, 2022, 10 pages. (Including English Translation).

Request for the Submission of an Opinion received for Korean Patent Application Serial No. 10-2020-7028467 dated Aug. 16, 2022, 9 pages. (Including English Translation).

Examination Report No. 2 received for Australian Patent Application Serial No. 2019375375 dated Sep. 16, 2022, 4 pages.

\* cited by examiner

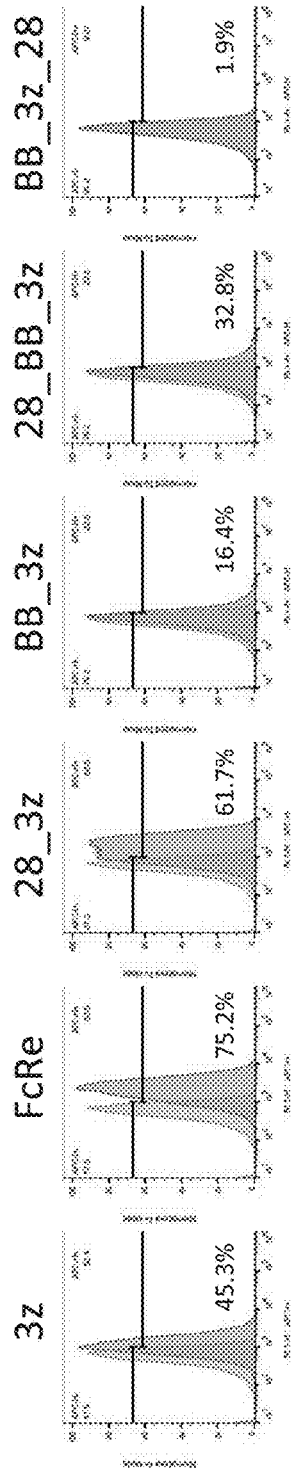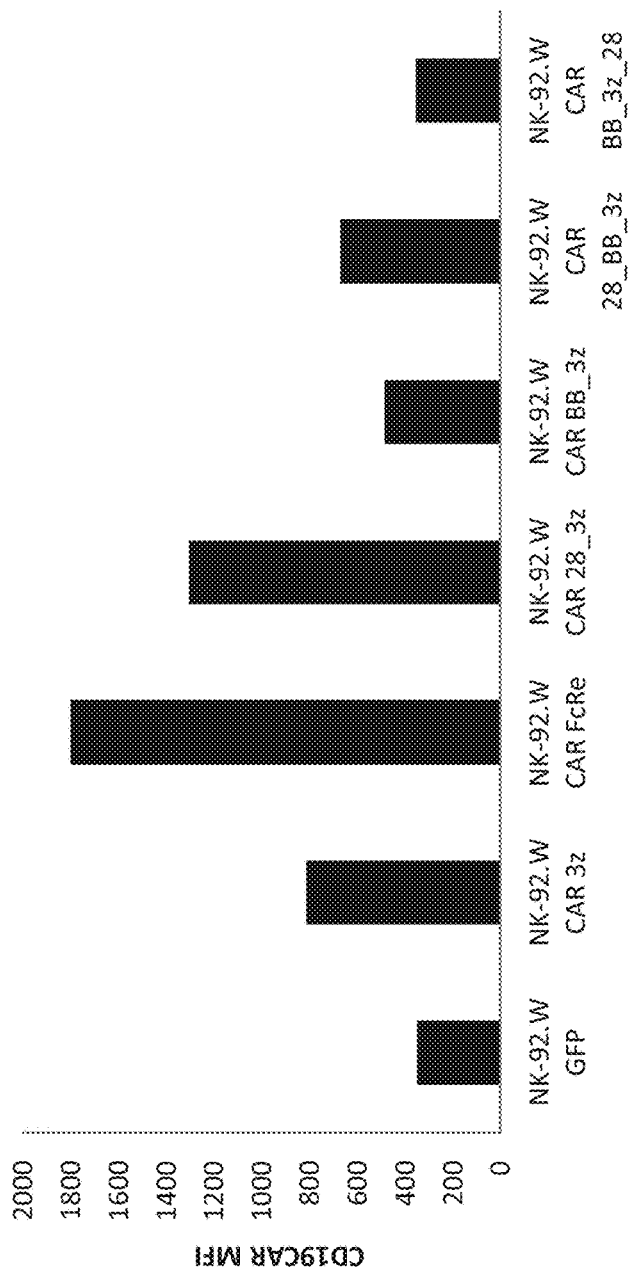
FIG. 2A % Expression of CD19 CAR in NK-92.W cells
FIG. 2B

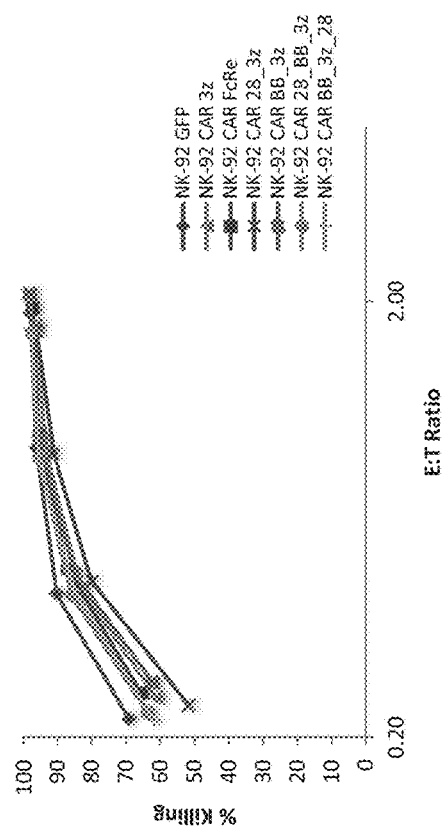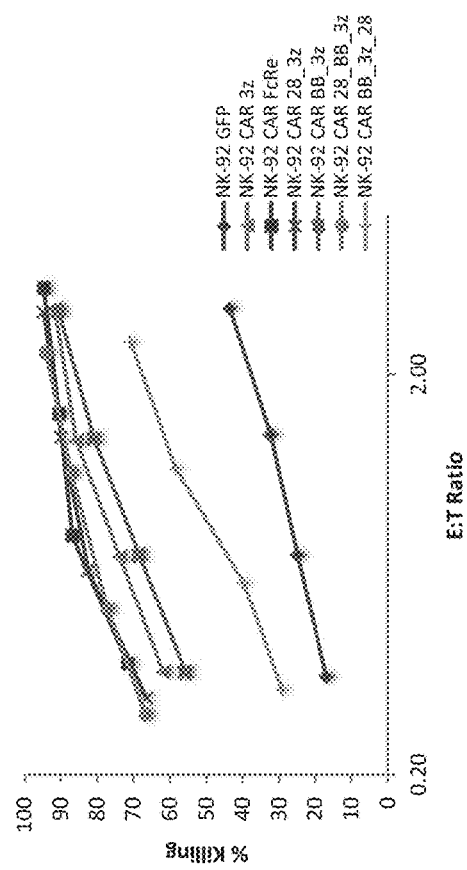

Survival curve of IV Raji tumor bearing animals

Animal body weight change in the IV Raji tumor model

Tumor growth curve for the SC Raji model

CD19 t-haNK reduced metastatic disease burden in the livers of SC Raji tumor-bearing mice Animal body weight change in the SC Raji tumor model Kaplan-Meier survival curve of mice injected with L1210-Luc tumor cells following intratumor treatment with mCD19-CAR NK-92 cells vs. vehicle control Tumor size of complete responders vs. naïve controls re-challenged with L1210-Luc tumor cells Kaplan-Meier survival curve of mice injected with A20 tumor cells following intratumor treatment with mCD19-CAR NK-92 cells vs. vehicle control Fig. 13: Tumor size of complete responders vs. naïve controls re-challenged with A20 tumor cells

SEQUENCE LISTING

```
<160> NUMBER OF SEQ ID NOS: 76

<210> SEQ ID NO 1
<211> LENGTH: 41
<212> TYPE: PRT
<213> ORGANISM: Artificial Sequence
<220> FEATURE:
<223> OTHER INFORMATION: FceRIgamma Intracellular Domain peptide

<400> SEQUENCE: 1

Leu Lys Ile Gln Val Arg Lys Ala Ala Ile Thr Ser Tyr Glu Lys Ser
1               5                   10                  15

Asp Gly Val Tyr Thr Gly Leu Ser Thr Arg Asn Gln Glu Thr Tyr Glu
            20                  25                  30

Thr Leu Lys His Glu Lys Pro Pro Gln
        35                  40

<210> SEQ ID NO 2
<211> LENGTH: 123
<212> TYPE: DNA
<213> ORGANISM: Artificial Sequence
<220> FEATURE:
<223> OTHER INFORMATION: FceRIgamma Intracellular Domain

<400> SEQUENCE: 2
ctgaagatcc aggtccgaaa ggccgccatc accagctacg agaagtctga tggcgtgtac      60
accggcctga gcaccagaaa ccaggaaacc tacgagacac tgaagcacga gaagcccccc     120
cag                                                                    123

<210> SEQ ID NO 3
<211> LENGTH: 398
<212> TYPE: PRT
<213> ORGANISM: Artificial Sequence
<220> FEATURE:
<223> OTHER INFORMATION: CD19CAR FceRIgamma
```

<400> SEQUENCE: 3

```
Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Thr Thr Ser
            20                  25                  30

Ser Leu Ser Ala Ser Leu Gly Asp Arg Val Thr Ile Ser Cys Arg Ala
        35                  40                  45

Ser Gln Asp Ile Ser Lys Tyr Leu Asn Trp Tyr Gln Gln Lys Pro Asp
    50                  55                  60

Gly Thr Val Lys Leu Leu Ile Tyr His Thr Ser Arg Leu His Ser Gly
65                  70                  75                  80

Val Pro Ser Arg Phe Ser Gly Ser Gly Ser Gly Thr Asp Tyr Ser Leu
                85                  90                  95

Thr Ile Ser Asn Leu Glu Gln Glu Asp Ile Ala Thr Tyr Phe Cys Gln
            100                 105                 110

Gln Gly Asn Thr Leu Pro Tyr Thr Phe Gly Gly Gly Thr Lys Leu Glu
        115                 120                 125

Leu Lys Arg Gly Gly Gly Gly Ser Gly Gly Gly Gly Ser Gly Gly Gly
130                 135                 140

Gly Ser Gly Gly Gly Gly Ser Glu Val Gln Leu Gln Gln Ser Gly Pro
145                 150                 155                 160

Gly Leu Val Ala Pro Ser Gln Ser Leu Ser Val Thr Cys Thr Val Ser
                165                 170                 175

Gly Val Ser Leu Pro Asp Tyr Gly Val Ser Trp Ile Arg Gln Pro Pro
            180                 185                 190

Arg Lys Gly Leu Glu Trp Leu Gly Val Ile Trp Gly Ser Glu Thr Thr
        195                 200                 205

Tyr Tyr Asn Ser Ala Leu Lys Ser Arg Leu Thr Ile Ile Lys Asp Asn
    210                 215                 220

Ser Lys Ser Gln Val Phe Leu Lys Met Asn Ser Leu Gln Thr Asp Asp
225                 230                 235                 240

Thr Ala Ile Tyr Tyr Cys Ala Lys His Tyr Tyr Tyr Gly Gly Ser Tyr
                245                 250                 255

Ala Met Asp Tyr Trp Gly Gln Gly Thr Thr Val Thr Val Ser Ser Ala
            260                 265                 270

Ala Ala Leu Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Phe Trp Val Leu Val Val Val
                325                 330                 335

Gly Gly Val Leu Ala Cys Tyr Ser Leu Leu Val Thr Val Ala Phe Ile
            340                 345                 350

Ile Phe Trp Val Arg Leu Lys Ile Gln Val Arg Lys Ala Ala Ile Thr
        355                 360                 365

Ser Tyr Glu Lys Ser Asp Gly Val Tyr Thr Gly Leu Ser Thr Arg Asn
    370                 375                 380

Gln Glu Thr Tyr Glu Thr Leu Lys His Glu Lys Pro Pro Gln
385                 390                 395
```

```
<210> SEQ ID NO 4
<211> LENGTH: 259
<212> TYPE: PRT
<213> ORGANISM: Artificial Sequence
<220> FEATURE:
<223> OTHER INFORMATION: CD19CAR scFv

<400> SEQUENCE: 4

Ala Ala Thr Gly Ala His Ser Ala Gln Pro Ala Asp Ile Gln Met Thr
1               5                   10                  15

Gln Thr Thr Ser Ser Leu Ser Ala Ser Leu Gly Asp Arg Val Thr Ile
            20                  25                  30

Ser Cys Arg Ala Ser Gln Asp Ile Ser Lys Tyr Leu Asn Trp Tyr Gln
        35                  40                  45

Gln Lys Pro Asp Gly Thr Val Lys Leu Leu Ile Tyr His Thr Ser Arg
    50                  55                  60

Leu His Ser Gly Val Pro Ser Arg Phe Ser Gly Ser Gly Ser Gly Thr
65                  70                  75                  80

Asp Tyr Ser Leu Thr Ile Ser Asn Leu Glu Gln Glu Asp Ile Ala Thr
                85                  90                  95

Tyr Phe Cys Gln Gln Gly Asn Thr Leu Pro Tyr Thr Phe Gly Gly Gly
            100                 105                 110

Thr Lys Leu Glu Leu Lys Arg Gly Gly Gly Gly Ser Gly Gly Gly Gly
        115                 120                 125

Ser Gly Gly Gly Gly Ser Gly Gly Gly Ser Glu Val Gln Leu Gln
    130                 135                 140

Gln Ser Gly Pro Gly Leu Val Ala Pro Ser Gln Ser Leu Ser Val Thr
145                 150                 155                 160

Cys Thr Val Ser Gly Val Ser Leu Pro Asp Tyr Gly Val Ser Trp Ile
                165                 170                 175

Arg Gln Pro Pro Arg Lys Gly Leu Glu Trp Leu Gly Val Ile Trp Gly
            180                 185                 190

Ser Glu Thr Thr Tyr Tyr Asn Ser Ala Leu Lys Ser Arg Leu Thr Ile
        195                 200                 205

Ile Lys Asp Asn Ser Lys Ser Gln Val Phe Leu Lys Met Asn Ser Leu
    210                 215                 220

Gln Thr Asp Asp Thr Ala Ile Tyr Tyr Cys Ala Lys His Tyr Tyr Tyr
225                 230                 235                 240

Gly Gly Ser Tyr Ala Met Asp Tyr Trp Gly Gln Gly Thr Thr Val Thr
                245                 250                 255

Val Ser Ser

<210> SEQ ID NO 5
<211> LENGTH: 1197
<212> TYPE: DNA
<213> ORGANISM: Artificial Sequence
<220> FEATURE:
<223> OTHER INFORMATION: CD19CAR FceRIgamma DNA

<400> SEQUENCE: 5
atggactgga tctggcggat cctgtttctc gtgggagctg ccacaggcgc tcattctgct      60
cagcctgccg atatccagat gacccagaca acaagcagcc tgagcgcctc tctgggcgat     120
agagtgacaa tcagctgcag agccagccag gacatcagca agtacctgaa ctggtatcag     180
cagaaacccg acggcaccgt gaagctgctg atctaccaca caagcagact gcacagcggc     240
gtgccaagca gattttctgg cagcggcagc ggcaccgatt acagcctgac catcagcaac     300
```

```
ctggaacagg aagatatcgc tacctacttc tgtcagcagg gcaacaccct gccttacacc    360
tttggcggcg gaacaaagct ggaactgaaa agaggcggcg gaggaagcgg aggcggagga    420
tctgggggcg gaggctctgg cggaggggga tctgaagtgc agctgcagca gtctggacct    480
ggactggtgg ctccttctca gtccctgtct gtgacctgta cagtgtctgg cgtgtccctg    540
cctgattacg gcgtgtcctg gatcagacag cctcccagaa aaggcctgga atggctggga    600
gtgatctggg gcagcgagac aacctactac aacagcgccc tgaagtcccg gctgaccatc    660
atcaaggaca cagcaagag ccaggtgttc ctgaagatga cagcctgca gaccgacgac    720 accgccatct actactgcgc caagcactac tactacggcg cagctacgc catggattat    780 tggggccagg gcaccaccgt gacagtgtca tctgctgctg ctctgttcgt gcctgtgttc    840
ctgcctgcca agcctacaac aacaccagcc cctagacctc aaccccctgc ccctacaatt    900
gcctctcagc ctctgtctct gaggcccgaa gcttgtagac ctgctgctgg cggagctgtg    960
cacaccagag gactggattt cgcctgcttt tgggtgctgg tggtcgtggg cggagtgctg   1020
gcttgttatt ctctgctggt caccgtggcc ttcatcatct tttgggtccg actgaagatc   1080
caggtccgaa aggccgccat caccagctac gagaagtctg atggcgtgta caccggcctg   1140
agcaccgaaa accaggaaac ctacgagaca ctgaagcacg agaagccccc ccagtaa     1197
```

```
<210> SEQ ID NO 6
<211> LENGTH: 54
<212> TYPE: PRT
<213> ORGANISM: Artificial Sequence
<220> FEATURE:
<223> OTHER INFORMATION: CD8 Hinge

<400> SEQUENCE: 6

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Phe Trp
        35                  40                  45

Val Leu Val Val Val Gly
            50

<210> SEQ ID NO 7
<211> LENGTH: 20
<212> TYPE: PRT
<213> ORGANISM: Artificial Sequence
<220> FEATURE:
<223> OTHER INFORMATION: CD28 Transmembrane domain

<400> SEQUENCE: 7

Gly Val Leu Ala Cys Tyr Ser Leu Leu Val Thr Val Ala Phe Ile Ile
1               5                   10                  15

Phe Trp Val Arg
            20

<210> SEQ ID NO 8
<211> LENGTH: 41
<212> TYPE: PRT
<213> ORGANISM: Artificial Sequence
<220> FEATURE:
<223> OTHER INFORMATION: CD28 signaling domain

<400> SEQUENCE: 8

Arg Ser Lys Arg Ser Arg Leu Leu His Ser Asp Tyr Met Asn Met Thr
```

```
1               5                   10                  15
Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 9
<211> LENGTH: 42
<212> TYPE: PRT
<213> ORGANISM: Artificial Sequence
<220> FEATURE:
<223> OTHER INFORMATION: 4-1BB signaling domain

<400> SEQUENCE: 9

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 10
<211> LENGTH: 113
<212> TYPE: PRT
<213> ORGANISM: Artificial Sequence
<220> FEATURE:
<223> OTHER INFORMATION: CD3 zeta signaling domain

<400> SEQUENCE: 10

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
        50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 11
<211> LENGTH: 339
<212> TYPE: DNA
<213> ORGANISM: Artificial Sequence
<220> FEATURE:
<223> OTHER INFORMATION: Human CD3 zeta (codon optimized):

<400> SEQUENCE: 11
gtgaagttta gcagatctgc cgacgcccct gcctaccagc agggacagaa tcagctgtac      60
aacgagctga acctgggcag acgggaagag tacgacgtgc tggataagag aagaggcaga     120
gatcccgaga tgggcggcaa gccccagaga agaagaatc cccaggaagg cctgtataac      180
gaactgcaga aagacaagat ggccgaggcc tacagcgaga tcggcatgaa gggcgagaga     240
agaagaggca gggccacga tggactgtac cagggactga gcacagccac caaggatacc     300
```

```
tacgatgccc tgcacatgca ggccctgcct ccaagataa                          339
```

<210> SEQ ID NO 12
<211> LENGTH: 339
<212> TYPE: DNA
<213> ORGANISM: Artificial Sequence
<220> FEATURE:
<223> OTHER INFORMATION: Human CD3 zeta (non-codon optimized)

<400> SEQUENCE: 12

```
gtgaagttca gcaggagcgc agacgccccc gcgtaccagc agggccagaa ccagctctat    60
aacgagctca atctaggacg aagagaggag tacgatgttt tggacaagag acgtggccgg   120
gaccctgaga tgggggaaa gccgcagaga aggaagaacc ctcaggaagg cctgtacaat    180
gaactgcaga agataagat ggcggaggcc tacagtgaga ttgggatgaa aggcgagcgc    240
cggaggggca aggggcacga tggcctttac cagggtctca gtacagccac caaggacacc   300
tacgacgccc ttcacatgca ggccctgccc cctcgctaa                          339
```

<210> SEQ ID NO 13
<211> LENGTH: 1410
<212> TYPE: DNA
<213> ORGANISM: Artificial Sequence
<220> FEATURE:
<223> OTHER INFORMATION: CD19CAR CD3z (DNA sequence)

<400> SEQUENCE: 13

```
atggactgga tctggcggat cctgtttctc gtgggagctg ccacaggcgc tcattctgct    60
cagcctgccg atatccagat gacccagaca acaagcagcc tgagcgcctc tctgggcgat   120
agagtgacaa tcagctgcag agccagccag gacatcagca gtacctgaa ctggtatcag    180 cagaaacccg acggcaccgt gaagctgctg atctaccaca agcagact gcacagcggc    240 gtgccaagca gattttctgg cagcggcagc ggcaccgatt acagcctgac catcagcaac   300
ctggaacagg aagatatcgc tacctacttc tgtcagcaag caacaccct gccttacacc   360 tttggcggcg aacaaagct ggaactgaaa agaggcggcg gaggaagcgg aggcggagga    420 tctggggcg gaggctctgg cggagggga tctgaagtgc agctgcagca gtctggacct    480
ggactggtgg ctccttctca gtccctgtct gtgacctgta cagtgtctgg cgtgtccctg   540
cctgattacg gcgtgtcctg gatcagacag cctcccagaa aggcctgga atggctggga    600 gtgatctggg gcagcgagac aacctactac aacagcgccc tgaagtcccg gctgaccatc    660
atcaaggaca caagcaagag ccaggtgttc ctgaagatga acagcctgca gaccgacgac    720
accgccatct actactgcgc caagcactac tactacggcg gcagctacgc catggattat    780
tggggccagg gcaccaccgt gacagtgtca tctgctgctg ctctgttcgt gcctgtgttc    840
ctgcctgcca agcctacaac aacaccagcc ctagacctc aacccctgc cctacaatt     900 gcctctcagc ctctgtctct gaggcccgaa gcttgtagac tgctgctgg cggagctgtg    960 cacaccagag gactggattt cgcctgcttt tgggtgctgg tggtcgtggg cggagtgctg   1020
gcttgttatt ctctgctggt caccgtggcc ttcatcatct ttgggtccg agtgaagttc   1080 agcagatccg ccgatgcccc tgcttaccag cagggccaga atcagctgta caacgagctg   1140
aacctgggca gacgggaaga gtacgacgtg ctggataaga aagaggcag agatcccgag    1200 atgggcggca gccccagag aagaaagaat ccccaggaag gcctgtataa cgaactgcag   1260
aaagacaaga tggccgaggc ctacagcgag atcggcatga agggcgagag aagaagaggc   1320
```
aagggccacg atggactgta ccagggactg agcacagcca ccaaggatac ctacgatgcc    1380
ctgcacatgc aggccctgcc tccaagataa                                    1410

<210> SEQ ID NO 14
<211> LENGTH: 1533
<212> TYPE: DNA
<213> ORGANISM: Artificial Sequence
<220> FEATURE:
<223> OTHER INFORMATION: CD19CAR CD28/CD3z (DNA sequence)

<400> SEQUENCE: 14
atggactgga tctggcggat cctgtttctc gtgggagctg ccacaggcgc tcattctgct      60
cagcctgccg atatccagat gacccagaca acaagcagcc tgagcgcctc tctgggcgat     120
agagtgacaa tcagctgcag agccagccag gacatcagca gtacctgaa ctggtatcag      180 cagaaacccg acggcaccgt gaagctgctg atctaccaca agcagact gcacagcggc       240 gtgccaagca gattttctgg cagcggcagc ggcaccgatt acagcctgac catcagcaac     300
ctggaacagg aagatatcgc tacctacttc tgtcagcagg caacaccct gccttacacc      360 tttggcggcg gaacaaagct ggaactgaaa agaggcggcg aggaagcgg aggcggagga     420 tctggggggcg gaggctctgg cggaggggga tctgaagtgc agctgcagca gtctggacct     480
ggactggtgg ctccttctca gtccctgtct gtgacctgta cagtgtctgg cgtgtccctg     540
cctgattacg gcgtgtcctg gatcagacag cctcccagaa aaggcctgga atggctggga    600
gtgatctggg gcagcgagac aacctactac aacagcgccc tgaagtcccg gctgaccatc    660
atcaaggaca cagcaagag ccaggtgttc ctgaagatga cagcctgca gaccgacgac     720 accgccatct actactgcgc caagcactac tactacggcg gcagctacgc catggattat    780
tggggccagg gcaccaccgt gacagtgtca tctgctgctg ctctgttcgt gcctgtgttc    840
ctgcctgcca gcctacaac aacaccagcc ctagacctc aaccccctgc cctacaatt     900 gcctctcagc tctgtctct gaggcccgaa gcttgtagac tgctgctgg cggagctgtg    960 cacaccagag gactggattt cgcctgctt tgggtgctgg tggtcgtggg cggagtgctg   1020
gcttgttatt ctctgctggt caccgtggcc ttcatcatct tttgggtccg aagcaagcgg   1080
agcaggctgc tgcacagcga ctacatgaac atgacccta aaggcctgg ccccaccaga     1140 aagcactatc agccttacgc ccctcccaga gacttcgccg cctacagatc cagagtgaag    1200
ttcagcagat ctgccgacgc ccctgcttac cagcagggcc agaatcagct gtacaacgag   1260
ctgaacctgg gcagacggga agagtacgac gtgctggata gagaagagg cagagatccc    1320 gagatgggcg gcaagcccca gagaagaaag aatccccagg aaggcctgta taacgaactg   1380
cagaaagaca gatggccga ggcctacagc gagatcggca tgaagggcga gagaagaaga   1440
ggcaagggcc acgatggact gtaccaggga ctgagcacag ccaccaagga tacctacgat   1500
gccctgcaca tgcaggccct gcctccaaga taa                               1533

<210> SEQ ID NO 15
<211> LENGTH: 1536
<212> TYPE: DNA
<213> ORGANISM: Artificial Sequence
<220> FEATURE:
<223> OTHER INFORMATION: CD19CAR_4-1BB/CD3z (DNA sequence)

<400> SEQUENCE: 15
atggactgga tctggcggat cctgtttctc gtgggagctg ccacaggcgc tcattctgct      60
cagcctgccg atatccagat gacccagaca acaagcagcc tgagcgcctc tctgggcgat    120

```
agagtgacaa tcagctgcag agccagccag acatcagca agtacctgaa ctggtatcag    180
cagaaacccg acggcaccgt gaagctgctg atctaccaca caagcagact gcacagcggc    240
gtgccaagca gattttctgg cagcggcagc ggcaccgatt acagcctgac catcagcaac    300
ctggaacagg aagatatcgc tacctacttc tgtcagcagg gcaacaccct gccttacacc    360
tttggcggcg gaacaaagct ggaactgaaa agaggcggcg gaggaagcgg aggcggagga    420
tctgggggcg gaggctctgg cggagggga tctgaagtgc agctgcagca gtctggacct    480
ggactggtgg ctccttctca gtccctgtct gtgacctgta cagtgtctgg cgtgtccctg    540
cctgattacg gcgtgtcctg gatcagacag cctcccagaa aggcctgga atggctggga    600 gtgatctggg gcagcgagac aacctactac aacagcgccc tgaagtcccg gctgaccatc    660
atcaaggaca cagcaagag ccaggtgttc ctgaagatga cagcctgca gaccgacgac    720 accgccatct actactgcgc caagcactac tactacggcg gcagctacgc catggattat    780
tggggccagg gcaccaccgt gacagtgtca tctgctgctg ctctgttcgt gcctgtgttc    840
ctgcctgcca agcctacaac aacaccagcc ctagacctc caaccctgc ccctacaatt    900 gcctctcagc ctctgtctct gaggcccgaa gcttgtagac ctgctgctgg cggagctgtg    960
cacaccagag gactggattt cgcctgcttt tgggtgctgg tggtcgtggg cggagtgctg    1020
gcttgttatt ctctgctggt caccgtggcc ttcatcatct tggtcaa gcggggcaga    1080 aagaagctgc tgtacatctt caagcagccc ttcatgagc ccgtgcagac cacacaggaa    1140
gaggacggct gcagctgtag attccctgag gaagaagaag gcggctgcga gctgagagtg    1200
aagtttagca gatctgccga cgccctgcc taccagcagg gacagaatca gctgtacaac    1260
gagctgaacc tgggcagacg ggaagagtac gacgtgctgg ataagagaag aggcagagat    1320
cccgagatgg gcggcaagcc ccagagaaga aagaatcccc aggaaggcct gtataacgaa    1380
ctgcagaaag acaagatggc cgaggcctac agcgagatcg gcatgaaggg cgagagaaga    1440
agaggcaagg gccacgatgg actgtaccag ggactgagca cagccaccaa ggatacctac    1500
gatgccctgc acatgcaggc cctgcctcca agataa                               1536
```

<210> SEQ ID NO 16
<211> LENGTH: 1659
<212> TYPE: DNA
<213> ORGANISM: Artificial Sequence
<220> FEATURE:
<223> OTHER INFORMATION: CD19CAR_CD28/4-1BB/CD3z (DNA sequence)

<400> SEQUENCE: 16

```
atggactgga tctggcggat cctgtttctc gtgggagctg ccacaggcgc tcattctgct     60
cagcctgccg atatccagat gacccagaca acaagcagcc tgagcgcctc tctgggcgat    120
agagtgacaa tcagctgcag agccagccag acatcagca agtacctgaa ctggtatcag    180
cagaaacccg acggcaccgt gaagctgctg atctaccaca caagcagact gcacagcggc    240
gtgccaagca gattttctgg cagcggcagc ggcaccgatt acagcctgac catcagcaac    300
ctggaacagg aagatatcgc tacctacttc tgtcagcagg gcaacaccct gccttacacc    360
tttggcggcg gaacaaagct ggaactgaaa agaggcggcg gaggaagcgg aggcggagga    420
tctgggggcg gaggctctgg cggagggga tctgaagtgc agctgcagca gtctggacct    480
ggactggtgg ctccttctca gtccctgtct gtgacctgta cagtgtctgg cgtgtccctg    540
cctgattacg gcgtgtcctg gatcagacag cctcccagaa aggcctgga atggctggga    600
```

```
gtgatctggg gcagcgagac aacctactac aacagcgccc tgaagtcccg gctgaccatc    660
atcaaggaca acagcaagag ccaggtgttc ctgaagatga acagcctgca gaccgacgac    720
accgccatct actactgcgc caagcactac tactacggcg gcagctacgc catggattat    780
tggggccagg gcaccaccgt gacagtgtca tctgctgctg ctctgttcgt gcctgtgttc    840
ctgcctgcca agcctacaac aacaccagcc cctagacctc aaccccctgc ccctacaatt    900
gcctctcagc ctctgtctct gaggcccgaa gcttgtagac ctgctgctgg cggagctgtg    960
cacaccagag gactggattt cgcctgcttt tgggtgctgg tggtcgtggg cggagtgctg   1020
gcttgttatt ctctgctggt caccgtggcc ttcatcatct tttgggtccg aagcaagcgg   1080
agcaggctgc tgcacagcga ctacatgaac atgaccccta aaggcctgg ccccaccaga   1140 aagcactatc agcccttacgc ccctcccaga gacttcgccg cctatagatc aagcggggc   1200 agaaagaagc tgctgtacat cttcaagcag cccttcatga ggcccgtgca gaccacacag   1260
gaagaggacg gctgcagctg tagattccct gaggaagaag aaggcggctg cgagctgaga   1320
gtgaagttta gcagatctgc cgacgcccct gcctaccagc agggacagaa tcagctgtac   1380
aacgagctga acctgggcag acgggaagag tacgacgtgc tggataagag aagaggcaga   1440
gatcccgaga tgggcggcaa gccccagaga gaaagaatc cccaggaagg cctgtataac   1500
gaactgcaga agacaagat ggccgaggcc tacagcgaga tcggcatgaa gggcgagaga   1560
agaagaggca agggccacga tggactgtac cagggactga gcacagccac caaggatacc   1620
tacgatgccc tgcacatgca ggccctgcct ccaagataa                         1659

<210> SEQ ID NO 17
<211> LENGTH: 1659
<212> TYPE: DNA
<213> ORGANISM: Artificial Sequence
<220> FEATURE:
<223> OTHER INFORMATION: CD19CAR_4-1BB/CD3z/CD28 (DNA sequence)

<400> SEQUENCE: 17
atggactgga tctggcggat cctgtttctc gtgggagctg ccacaggcgc tcattctgct     60
cagcctgccg atatccagat gacccagaca acaagcagcc tgagcgcctc tctgggcgat    120
agagtgacaa tcagctgcag agccagccag gacatcagca gtacctgaa ctggtatcag    180 cagaaacccg acggcaccgt gaagctgctg atctaccaca aagcagact gcacagcggc    240 gtgccaagca gatttctctgg cagcggcagc ggcaccgatt acagcctgac catcagcaac    300
ctggaacaga agatatcgc tacctacttc tgtcagcagg caacacccct gccttacacc    360
tttggcggcg gaacaaagct ggaactgaaa agaggcggcg gaggaagcgg aggcggagga    420
tctgggggcg gaggctctgg cggagggggga tctgaagtgc agctgcagca gtctggacct    480
ggactggtgg ctccttctca gtccctgtct gtgacctgta cagtgtctgg cgtgtccctg    540
cctgattacg gcgtgtcctg gatcagacag cctcccagaa aaggcctgga atggctggga    600
gtgatctggg gcagcgagac aacctactac aacagcgccc tgaagtcccg gctgaccatc    660
atcaaggaca acagcaagag ccaggtgttc ctgaagatga acagcctgca gaccgacgac    720
accgccatct actactgcgc caagcactac tactacggcg gcagctacgc catggattat    780
tggggccagg gcaccaccgt gacagtgtca tctgctgctg ctctgttcgt gcctgtgttc    840
ctgcctgcca agcctacaac aacaccagcc cctagacctc aaccccctgc ccctacaatt    900
gcctctcagc ctctgtctct gaggcccgaa gcttgtagac ctgctgctgg cggagctgtg    960
cacaccagag gactggattt cgcctgcttt tgggtgctgg tggtcgtggg cggagtgctg   1020
```

```
gcttgttatt ctctgctggt caccgtggcc ttcatcatct tttgggtcaa gcggggcaga    1080
aagaagctgc tgtacatctt caagcagccc ttcatgaggc ccgtgcagac acacaggaa    1140 gaggacggct gcagctgtag attccctgag gaagaagaag gcggctgcga gctgagagtg    1200
aagtttagca gatctgccga cgcccctgcc taccagcagg gacagaatca gctgtacaac    1260
gagctgaacc tgggcagacg ggaagagtac gacgtgctgg ataagagaag aggcagagat    1320
cccgagatgg gcggcaagcc ccagagaaga aagaatcccc aggaaggcct gtataacgaa    1380
ctgcagaaag acaagatggc cgaggcctac agcgagatcg gcatgaaggg cgagagaaga    1440
agaggcaagg ccacgatgg actgtaccag ggactgagca cagccaccaa ggataccctac   1500 gatgccctgc acatgcaggc cctgcctcca agaagaagca agagatctag actgctgcac    1560
agcgactaca tgaacatgac ccctagaagg cctggcccca ccagaaagca ctatcagcct    1620
tacgcccctc ccagagactt cgccgcctac agatcttga                          1659
```

<210> SEQ ID NO 18
<211> LENGTH: 153
<212> TYPE: PRT
<213> ORGANISM: Artificial Sequence
<220> FEATURE:
<223> OTHER INFORMATION: Wild-Type IL-2 (amino acid sequence)

<400> SEQUENCE: 18

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 19
<211> LENGTH: 160
<212> TYPE: PRT
<213> ORGANISM: Artificial Sequence
<220> FEATURE:
<223> OTHER INFORMATION: IL-2-ER (amino acid sequence)

<400> SEQUENCE: 19

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30
```

```
Gln Leu Glu His Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
 50                  55                  60

Tyr Met Pro Lys Lys Ala Thr Glu Leu Lys His Leu Gln Cys Leu Glu
 65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr Gly Ser Glu Lys Asp Glu Leu
145                 150                 155                 160

<210> SEQ ID NO 20
<211> LENGTH: 765
<212> TYPE: DNA
<213> ORGANISM: Artificial Sequence
<220> FEATURE:
<223> OTHER INFORMATION: Polynucleotide Encoding the Low Affinity
      Immunoglobulin Gamma Fc Region Receptor III-A

<400> SEQUENCE: 20
atgtggcagc tgctcctccc aactgctctg ctacttctag tttcagctgg catgcggact      60
gaagatctcc caaaggctgt ggtgttcctg gagcctcaat ggtacagggt gctcgagaag     120
gacagtgtga ctctgaagtg ccaggggagcc tactcccctg aggacaattc acacagtggg   180
tttcacaatg agagcctcat ctcaagccag gcctcgagct acttcattga cgctgccaca     240
gtcgacgaca gtggagagta caggtgccag acaaacctct ccaccctcag tgacccggtg     300
cagctagaag tccatatcgg ctggctgttg ctccaggccc ctcggtgggt gttcaaggag     360
gaagacccta ttcacctgag gtgtcacagc tggaagaaca ctgctctgca taaggtcaca     420
tatttacaga tggcaaagg caggaagtat tttcatcata attctgactt ctacattcca      480
aaagccacac tcaaagacag cggctcctac ttctgcaggg ggcttttggg agtaaaaat     540 gtgtcttcag agactgtgaa catcaccatc actcaaggtt tggcagtgtc aaccatctca     600
tcattctttc cacctgggta ccaagtctct ttctgcttgg tgatggtact ccttttttgca   660 gtggacacag gactatattt ctctgtgaag acaaacattc gaagctcaac aagagactgg     720
aaggaccata atttaaatg gagaaaggac cctcaagaca atga                      765

<210> SEQ ID NO 21
<211> LENGTH: 1455
<212> TYPE: DNA
<213> ORGANISM: Artificial Sequence
<220> FEATURE:
<223> OTHER INFORMATION: CD19-CAR DNA sequence (murine)

<400> SEQUENCE: 21
cccgggaatt cgccaccatg gactggatct ggcggatcct gttcctcgtg ggagccgcca      60
caggcgccca ttctgcccag cccgccgaca tccagatgac ccagaccacc agcagcctga    120
gcgccagcct gggcgacaga gtgaccatca gctgccgggc cagccaggac atcagcaagt    180
acctgaactg gtatcagcag aaacccgacg gcaccgtgaa gctgctgatc taccacacca    240
```

```
gccggctgca cagcggcgtg cccagcagat tttctggcag cggcagcggc accgactaca    300
gcctgaccat ctccaacctg aacaggaag atatcgctac ctacttctgt cagcaaggca     360
acaccctgcc ctacaccttc ggcggaggca ccaagctgga actgaagaga ggcggcggag    420
gctctggtgg aggcggatct ggggggcgag aagtggcgg gggaggatct gaagtgcagc    480
tgcagcagag cggccctggc ctggtggccc ctagccagag cctgtccgtg acctgtaccg    540
tgtccggcgt gtccctgccc gactacgcg tgtcctggat ccggcagccc cccagaaagg     600
gcctggaatg gctgggcgtg atctggggca gcagacaac ctactacaac agcgccctga     660
agtcccggct gaccatcatc aaggacaaca gcaagagcca ggtgttcctg aagatgaaca    720
gcctgcagac cgacgacacc gccatctact actgcgccaa gcactactac tacggcggca    780
gctacgccat ggactactgg ggccaggca ccaccgtgac cgtgtccagc gccctgtcca     840
acagcatcat gtacttcagc cacttcgtgc ccgtgtttct gcccgccaag cccaccacca    900 ccccctgcccc tagacctccc accccagccc aacaatcgc cagccagcct ctgtccctgc    960
ggcccgaagc tagcagacct gctgccggcg agccgtgca ccagagggc ctgacccca     1020 agctgtgcta cctgctggac ggcatcctgt tcatctatgg cgtgatcctg accgccctgt   1080
tcctgagagt gaagttcagc agaagcgccg acgcccctgc ctaccagcag gccagaaacc   1140
agctgtacaa cgagctgaac ctgggcagac gggaagagta cgacgtgctg acaagcgga   1200 gaggcaggga ccccgagatg ggcggcaagc ccagacggaa gaaccccag gaaggcctgt   1260 ataacgaact gcagaaagac aagatggccg aggcctacag cgagatcggc atgaagggcg   1320
agcggcggag gggcaaggc cacgatggac tgtaccaggg cctgagcacc gccaccaagg    1380
acacctacga cgccctgcac atgcaggccc tgccccccag atgacagcca gggcatttct    1440
ccctcgagcg gccgc                                                    1455
```

<210> SEQ ID NO 22
<211> LENGTH: 468
<212> TYPE: PRT
<213> ORGANISM: Artificial Sequence
<220> FEATURE:
<223> OTHER INFORMATION: CD19-CAR amino acids sequence (murine)

<400> SEQUENCE: 22

```
Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Thr Thr Ser
            20                  25                  30

Ser Leu Ser Ala Ser Leu Gly Asp Arg Val Thr Ile Ser Cys Arg Ala
        35                  40                  45

Ser Gln Asp Ile Ser Lys Tyr Leu Asn Trp Tyr Gln Gln Lys Pro Asp
    50                  55                  60

Gly Thr Val Lys Leu Leu Ile Tyr His Thr Ser Arg Leu His Ser Gly
65                  70                  75                  80

Val Pro Ser Arg Phe Ser Gly Ser Gly Ser Gly Thr Asp Tyr Ser Leu
                85                  90                  95

Thr Ile Ser Asn Leu Glu Gln Glu Asp Ile Ala Thr Tyr Phe Cys Gln
            100                 105                 110

Gln Gly Asn Thr Leu Pro Tyr Thr Phe Gly Gly Gly Thr Lys Leu Glu
        115                 120                 125

Leu Lys Arg Gly Gly Gly Gly Ser Gly Gly Gly Gly Ser Gly Gly Gly
    130                 135                 140
```

```
Gly Ser Gly Gly Gly Gly Ser Glu Val Gln Leu Gln Gln Ser Gly Pro
145                 150                 155                 160
Gly Leu Val Ala Pro Ser Gln Ser Leu Ser Val Thr Cys Thr Val Ser
                165                 170                 175
Gly Val Ser Leu Pro Asp Tyr Gly Val Ser Trp Ile Arg Gln Pro Pro
            180                 185                 190
Arg Lys Gly Leu Glu Trp Leu Gly Val Ile Trp Gly Ser Glu Thr Thr
        195                 200                 205
Tyr Tyr Asn Ser Ala Leu Lys Ser Arg Leu Thr Ile Ile Lys Asp Asn
    210                 215                 220
Ser Lys Ser Gln Val Phe Leu Lys Met Asn Ser Leu Gln Thr Asp Asp
225                 230                 235                 240
Thr Ala Ile Tyr Tyr Cys Ala Lys His Tyr Tyr Gly Gly Ser Tyr
                245                 250                 255
Ala Met Asp Tyr Trp Gly Gln Gly Thr Thr Val Thr Val Ser Ser Ala
            260                 265                 270
Leu Ser Asn Ser Ile Met Tyr Phe Ser His Phe Val Pro Val Phe Leu
        275                 280                 285
Pro Ala Lys Pro Thr Thr Thr Pro Ala Pro Arg Pro Pro Thr Pro Ala
290                 295                 300
Pro Thr Ile Ala Ser Gln Pro Leu Ser Leu Arg Pro Glu Ala Ser Arg
305                 310                 315                 320
Pro Ala Ala Gly Gly Ala Val His Thr Arg Gly Leu Asp Pro Lys Leu
                325                 330                 335
Cys Tyr Leu Leu Asp Gly Ile Leu Phe Ile Tyr Gly Val Ile Leu Thr
            340                 345                 350
Ala Leu Phe Leu Arg Val Lys Phe Ser Arg Ser Ala Asp Ala Pro Ala
        355                 360                 365
Tyr Gln Gln Gly Gln Asn Gln Leu Tyr Asn Glu Leu Asn Leu Gly Arg
    370                 375                 380
Arg Glu Glu Tyr Asp Val Leu Asp Lys Arg Arg Gly Arg Asp Pro Glu
385                 390                 395                 400
Met Gly Gly Lys Pro Arg Arg Lys Asn Pro Gln Glu Gly Leu Tyr Asn
                405                 410                 415
Glu Leu Gln Lys Asp Lys Met Ala Glu Ala Tyr Ser Glu Ile Gly Met
            420                 425                 430
Lys Gly Glu Arg Arg Arg Gly Lys Gly His Asp Gly Leu Tyr Gln Gly
        435                 440                 445
Leu Ser Thr Ala Thr Lys Asp Thr Tyr Asp Ala Leu His Met Gln Ala
    450                 455                 460
Leu Pro Pro Arg
465

<210> SEQ ID NO 23
<211> LENGTH: 813
<212> TYPE: DNA
<213> ORGANISM: Artificial Sequence
<220> FEATURE:
<223> OTHER INFORMATION: Codon-optimized CD19 scFv - DNA sequence

<400> SEQUENCE: 23
atggactgga tctggcggat tctgtttctc gtgggagctg ccacaggcgc tcattctgct      60
cagcctgccg atatccagat gacccagaca acaagcagcc tgagcgcctc tctgggcgat     120
agagtgacaa tcagctgcag agccagccag gacatcagca gtacctgaa ctggtatcag      180
```

| | | |
|---|---|---|
| cagaaacccg acggcaccgt gaagctgctg atctaccaca caagcagact gcacagcggc | 240 |
| gtgccaagca gattttctgg cagcggcagc ggcaccgatt acagcctgac catcagcaac | 300 |
| ctggaacagg aagatatcgc tacctacttc tgtcagcagg caacaccct gccttacacc | 360 |
| tttggcggcg aacaaagct ggaactgaaa agaggcggcg aggaagcgg aggcggagga | 420 |
| tctgggggcg aggctctgg cggaggggga tctgaagtgc agctgcagca gtctggacct | 480 |
| ggactggtgg ctccttctca gtccctgtct gtgacctgta cagtgtctgg cgtgtccctg | 540 |
| cctgattacg gcgtgtcctg gatcagacag cctcccagaa aaggcctgga atggctggga | 600 |
| gtgatctggg gcagcgagac aacctactac aacagcgccc tgaagtcccg gctgaccatc | 660 |
| atcaaggaca acagcaagag ccaggtgttc ctgaagatga cagcctgca gaccgacgac | 720 |
| accgccatct actactgcgc caagcactac tactacggcg gcagctacgc catggattat | 780 |
| tggggccagg gcaccaccgt gacagtgtca tct | 813 |

<210> SEQ ID NO 24
<211> LENGTH: 271
<212> TYPE: PRT
<213> ORGANISM: Artificial Sequence
<220> FEATURE:
<223> OTHER INFORMATION: CD19 scFv - Protein sequence

<400> SEQUENCE: 24

Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Thr Thr Ser
            20                  25                  30

Ser Leu Ser Ala Ser Leu Gly Asp Arg Val Thr Ile Ser Cys Arg Ala
        35                  40                  45

Ser Gln Asp Ile Ser Lys Tyr Leu Asn Trp Tyr Gln Gln Lys Pro Asp
    50                  55                  60

Gly Thr Val Lys Leu Leu Ile Tyr His Thr Ser Arg Leu His Ser Gly
65                  70                  75                  80

Val Pro Ser Arg Phe Ser Gly Ser Gly Ser Gly Thr Asp Tyr Ser Leu
                85                  90                  95

Thr Ile Ser Asn Leu Glu Gln Glu Asp Ile Ala Thr Tyr Phe Cys Gln
            100                 105                 110

Gln Gly Asn Thr Leu Pro Tyr Thr Phe Gly Gly Gly Thr Lys Leu Glu
        115                 120                 125

Leu Lys Arg Gly Gly Gly Gly Ser Gly Gly Gly Gly Ser Gly Gly Gly
    130                 135                 140

Gly Ser Gly Gly Gly Gly Ser Glu Val Gln Leu Gln Gln Ser Gly Pro
145                 150                 155                 160

Gly Leu Val Ala Pro Ser Gln Ser Leu Ser Val Thr Cys Thr Val Ser
                165                 170                 175

Gly Val Ser Leu Pro Asp Tyr Gly Val Ser Trp Ile Arg Gln Pro Pro
            180                 185                 190

Arg Lys Gly Leu Glu Trp Leu Gly Val Ile Trp Gly Ser Glu Thr Thr
        195                 200                 205

Tyr Tyr Asn Ser Ala Leu Lys Ser Arg Leu Thr Ile Ile Lys Asp Asn
    210                 215                 220

Ser Lys Ser Gln Val Phe Leu Lys Met Asn Ser Leu Gln Thr Asp Asp
225                 230                 235                 240

Thr Ala Ile Tyr Tyr Cys Ala Lys His Tyr Tyr Tyr Gly Gly Ser Tyr
                245                 250                 255

```
Ala Met Asp Tyr Trp Gly Gln Gly Thr Thr Val Thr Val Ser Ser
            260                 265                 270
```

```
<210> SEQ ID NO 25
<211> LENGTH: 807
<212> TYPE: DNA
<213> ORGANISM: Artificial Sequence
<220> FEATURE:
<223> OTHER INFORMATION: Codon-optimized CD20 scFv - DNA sequence

<400> SEQUENCE: 25
atggactgga tctggcgcat cctcttcctc gtcggcgctg ctaccggcgc tcattcggcc      60
cagccggcca tggcgcaagt aaaactccaa gaatctgggg cggagctggt gaaaccgggg     120
gcgtctgtga agatgagctg taaagcatca ggctacacct tcacctccta taatatgcac     180
tgggtgaaac aaacacccgg acagggcctc gaatggattg gtgccatcta tcctggaaat     240
ggtgatacct catataatca gaagtttaag ggcaaggcta cgcttactgc ggataaaagc     300
tcttccactg cttacatgca actgagcagt ctcacttcag aggactcagc cgattattat     360
tgtgcccgca gcaactacta tggtagttca tactggtttt tcgacgtttg ggggcaaggt     420
accaccgtca cggtttcttc tggtgggggc ggaagcgggg gtggaggatc tgggggcggt     480
ggttcagaca ttgaactcac ccagagccct actattctga gcgcgtctcc aggtgaaaaa     540
gttacgatga cgtgcagagc atcaagtagt gtgaattata tggattggta tcaaaagaag     600
ccaggctcat ccccaaaacc gtggatctat gcaactagca acctcgcgtc aggggtgcca     660
gcaaggtttt ccggaagtgg ttctggcaca tcttatagtc tcaccatttc ccgagtggag     720
gctgaggatg cggccactta ttactgccag caatggtcat tcaatccccc aacatttggt     780
ggcggaacaa aactcgaaat taaacgg                                         807
```

```
<210> SEQ ID NO 26
<211> LENGTH: 269
<212> TYPE: PRT
<213> ORGANISM: Artificial Sequence
<220> FEATURE:
<223> OTHER INFORMATION: CD20 scFv - Protein sequence

<400> SEQUENCE: 26

Met Asp Trp Ile Trp Arg Ile Leu Phe Leu Val Gly Ala Ala Thr Gly
1               5                   10                  15

Ala His Ser Ala Gln Pro Ala Met Ala Gln Val Lys Leu Gln Glu Ser
            20                  25                  30

Gly Ala Glu Leu Val Lys Pro Gly Ala Ser Val Lys Met Ser Cys Lys
        35                  40                  45

Ala Ser Gly Tyr Thr Phe Thr Ser Tyr Asn Met His Trp Val Lys Gln
    50                  55                  60

Thr Pro Gly Gln Gly Leu Glu Trp Ile Gly Ala Ile Tyr Pro Gly Asn
65                  70                  75                  80

Gly Asp Thr Ser Tyr Asn Gln Lys Phe Lys Gly Lys Ala Thr Leu Thr
                85                  90                  95

Ala Asp Lys Ser Ser Ser Thr Ala Tyr Met Gln Leu Ser Ser Leu Thr
            100                 105                 110

Ser Glu Asp Ser Ala Asp Tyr Tyr Cys Ala Arg Ser Asn Tyr Tyr Gly
        115                 120                 125

Ser Ser Tyr Trp Phe Phe Asp Val Trp Gly Gln Gly Thr Thr Val Thr
    130                 135                 140
```

```
Val Ser Ser Gly Gly Gly Gly Ser Gly Gly Gly Ser Gly Gly Gly
145                 150                 155                 160

Gly Ser Asp Ile Glu Leu Thr Gln Ser Pro Thr Ile Leu Ser Ala Ser
                165                 170                 175

Pro Gly Glu Lys Val Thr Met Thr Cys Arg Ala Ser Ser Ser Val Asn
            180                 185                 190

Tyr Met Asp Trp Tyr Gln Lys Pro Gly Ser Ser Pro Lys Pro Trp
        195                 200                 205

Ile Tyr Ala Thr Ser Asn Leu Ala Ser Gly Val Pro Ala Arg Phe Ser
        210                 215                 220

Gly Ser Gly Ser Gly Thr Ser Tyr Ser Leu Thr Ile Ser Arg Val Glu
225                 230                 235                 240

Ala Glu Asp Ala Ala Thr Tyr Tyr Cys Gln Gln Trp Ser Phe Asn Pro
                245                 250                 255

Pro Thr Phe Gly Gly Gly Thr Lys Leu Glu Ile Lys Arg
            260                 265
```

<210> SEQ ID NO 27
<211> LENGTH: 795
<212> TYPE: DNA
<213> ORGANISM: Artificial Sequence
<220> FEATURE:
<223> OTHER INFORMATION: Codon-optimized CD33 scfV - DNA sequence:

<400> SEQUENCE: 27

```
atggactgga tctggcgcat cctcttcctc gtcggcgctg ctaccggcgc tcattcggcc    60
cagccggccg acattcaaat gactcagtcc ccttccagct tgtcagcctc agtaggggac   120
cgggtcacga tcacctgtcg agcgtctgag tcagtggata actacgggat ttctttcatg   180
aactggttcc agcagaagcc cggcaaagct cctaagctcc ttatatatgc agcctcaaat   240
caggggagcg gtgttcctag tcgcttcagt ggaagcggta gcggtacgga cttttacgttg  300
acgataagta gccttcagcc agatgacttt gccacttatt attgtcagca gtctaaggaa   360
gttccttgga cgtttggcca aggaacgaag gtcgaaatca aggggggagg gggctcagga   420
gggggcggca gtggtggtgg aggctctcaa gtccaactcg tacagtctgg cgcggaggtt   480
aaaaagccgg gaagctccgt gaaagtatcc tgtaaggcaa gcggatacac ctttaccgat   540
tataacatgc actgggttag gcaggcgccc ggccaaggtc tggaatggat cggttatatt   600
tatcccataca acggtggtac cggctataat cagaagttta agagtaaggc tactattaca   660
gcggatgagt caaccaatac tgcatacatg gagctctcct cactcaggag cgaagatacc   720
gcagtgtatt actgtgcccg agggagacca gccatggact actggggtca gggtacccct   780
gtgacagtat ctagc                                                    795
```

<210> SEQ ID NO 28
<211> LENGTH: 265
<212> TYPE: PRT
<213> ORGANISM: Artificial Sequence
<220> FEATURE:
<223> OTHER INFORMATION: CD33 scfV - Protein sequence

<400> SEQUENCE: 28

```
Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Ser Pro Ser
            20                  25                  30

Ser Leu Ser Ala Ser Val Gly Asp Arg Val Thr Ile Thr Cys Arg Ala
```

```
                35                  40                  45
Ser Glu Ser Val Asp Asn Tyr Gly Ile Ser Phe Met Asn Trp Phe Gln
 50                  55                  60

Gln Lys Pro Gly Lys Ala Pro Lys Leu Leu Ile Tyr Ala Ala Ser Asn
 65                  70                  75                  80

Gln Gly Ser Gly Val Pro Ser Arg Phe Ser Gly Ser Gly Ser Gly Thr
                 85                  90                  95

Asp Phe Thr Leu Thr Ile Ser Ser Leu Gln Pro Asp Asp Phe Ala Thr
                100                 105                 110

Tyr Tyr Cys Gln Gln Ser Lys Glu Val Pro Trp Thr Phe Gly Gln Gly
            115                 120                 125

Thr Lys Val Glu Ile Lys Gly Gly Gly Gly Ser Gly Gly Gly Gly Ser
130                 135                 140

Gly Gly Gly Gly Ser Gln Val Gln Leu Val Gln Ser Gly Ala Glu Val
145                 150                 155                 160

Lys Lys Pro Gly Ser Ser Val Lys Val Ser Cys Lys Ala Ser Gly Tyr
                165                 170                 175

Thr Phe Thr Asp Tyr Asn Met His Trp Val Arg Gln Ala Pro Gly Gln
                180                 185                 190

Gly Leu Glu Trp Ile Gly Tyr Ile Tyr Pro Tyr Asn Gly Gly Thr Gly
            195                 200                 205

Tyr Asn Gln Lys Phe Lys Ser Lys Ala Thr Ile Thr Ala Asp Glu Ser
210                 215                 220

Thr Asn Thr Ala Tyr Met Glu Leu Ser Ser Leu Arg Ser Glu Asp Thr
225                 230                 235                 240

Ala Val Tyr Tyr Cys Ala Arg Gly Arg Pro Ala Met Asp Tyr Trp Gly
                245                 250                 255

Gln Gly Thr Leu Val Thr Val Ser Ser
            260                 265
```

<210> SEQ ID NO 29
<211> LENGTH: 840
<212> TYPE: DNA
<213> ORGANISM: Artificial Sequence
<220> FEATURE:
<223> OTHER INFORMATION: Codon-optimized CSPG4 scfV - DNA sequence

<400> SEQUENCE: 29

```
atggactgga tctggcgcat cctcttcctc gtcggcgctg ctaccggcgc tcattcggcc    60
cagccggccg atatcgagct cacccaatct ccaaaattca gtccacatc agtaggagac    120
agggtcagcg tcacctgcaa ggccagtcag aatgtggata ctaatgtagc gtggtatcaa   180
caaaaaccag gcaatctcc tgaaccactg cttttctcgg catcctaccg ttacactgga    240
gtccctgatc gcttcacagg cagtggatct gggacagatt tcactctcac catcagcaat    300
gtgcagtctg aagacttggc agagtatttc tgtcagcaat ataacagcta tcctctgacg   360
ttcggtggcg gcaccaagct ggaaatcaaa cgggctgccg cagaaggtgg aggcggttca   420
ggtggcggag gttccggcgg aggtggctct ggcggtggcg gatcggccat ggcccaggtg   480
aagctgcagc agtcaggagg gggcttggtg caacctggag ctccatgaa actctcctgt    540
gttgtctctg gattcacttt cagtaattac tggatgaact gggtccgcca gtctccagag   600
aagggcttg agtggattgc agaaattaga ttgaaatcca ataatttgg aagatattat     660
gcggagtctg tgaaagggag gttcaccatc tcaagagatg attccaaaag tagtgcctac   720
ctgcaaatga tcaacctaag agctgaagat actggcattt attactgtac cagttatggt   780
```

```
aactacgttg ggcactattt tgaccactgg ggccaaggga ccacggtcac cgtatcgagt    840
```

<210> SEQ ID NO 30
<211> LENGTH: 280
<212> TYPE: PRT
<213> ORGANISM: Artificial Sequence
<220> FEATURE:
<223> OTHER INFORMATION: CSPG4 scfV - Protein sequence

<400> SEQUENCE: 30

```
Met Asp Trp Ile Trp Arg Ile Leu Phe Leu Val Gly Ala Ala Thr Gly
1               5                   10                  15

Ala His Ser Ala Gln Pro Ala Asp Ile Glu Leu Thr Gln Ser Pro Lys
            20                  25                  30

Phe Met Ser Thr Ser Val Gly Asp Arg Val Ser Val Thr Cys Lys Ala
        35                  40                  45

Ser Gln Asn Val Asp Thr Asn Val Ala Trp Tyr Gln Gln Lys Pro Gly
    50                  55                  60

Gln Ser Pro Glu Pro Leu Leu Phe Ser Ala Ser Tyr Arg Tyr Thr Gly
65                  70                  75                  80

Val Pro Asp Arg Phe Thr Gly Ser Gly Ser Gly Thr Asp Phe Thr Leu
                85                  90                  95

Thr Ile Ser Asn Val Gln Ser Glu Asp Leu Ala Glu Tyr Phe Cys Gln
            100                 105                 110

Gln Tyr Asn Ser Tyr Pro Leu Thr Phe Gly Gly Gly Thr Lys Leu Glu
        115                 120                 125

Ile Lys Arg Ala Ala Ala Glu Gly Gly Gly Gly Ser Gly Gly Gly Gly
    130                 135                 140

Ser Gly Gly Gly Gly Ser Gly Gly Gly Gly Ser Ala Met Ala Gln Val
145                 150                 155                 160

Lys Leu Gln Gln Ser Gly Gly Gly Leu Val Gln Pro Gly Gly Ser Met
                165                 170                 175

Lys Leu Ser Cys Val Val Ser Gly Phe Thr Phe Ser Asn Tyr Trp Met
            180                 185                 190

Asn Trp Val Arg Gln Ser Pro Glu Lys Gly Leu Glu Trp Ile Ala Glu
        195                 200                 205

Ile Arg Leu Lys Ser Asn Asn Phe Gly Arg Tyr Tyr Ala Glu Ser Val
    210                 215                 220

Lys Gly Arg Phe Thr Ile Ser Arg Asp Asp Ser Lys Ser Ser Ala Tyr
225                 230                 235                 240

Leu Gln Met Ile Asn Leu Arg Ala Glu Asp Thr Gly Ile Tyr Tyr Cys
                245                 250                 255

Thr Ser Tyr Gly Asn Tyr Val Gly His Tyr Phe Asp His Trp Gly Gln
            260                 265                 270

Gly Thr Thr Val Thr Val Ser Ser
        275                 280
```

<210> SEQ ID NO 31
<211> LENGTH: 807
<212> TYPE: DNA
<213> ORGANISM: Artificial Sequence
<220> FEATURE:
<223> OTHER INFORMATION: Codon-optimized EGFR scFv - DNA sequence

<400> SEQUENCE: 31

```
atggactgga tctggcggat tctgtttctc gtgggagctg ccacaggcgc tcattctgct    60
```

```
cagcctgccg atattcttct tactcaatct cccgttattt tgtcagtatc cccaggtgag    120
cgagtcagct tctcttgtcg agcgtcacaa tccattggca ccaacataca ttggtaccaa    180
cagcgcacca acgggtctcc ccggctcttg attaagtacg catcagaaag tatttctggg    240
atacccagta ggttctcagg gagcgggagt ggcactgact ttaccctgtc cataaacagc    300
gttgagtctg aggacatcgc ggactactat tgtcagcaga caacaattg gccgaccacg    360 tttggtgcgg gaacaaaact tgaactcaaa ggcggcggag aagcggagg cggaggatct    420 ggggcggag gctctggcgg aggggatct caggtgcagc tcaaacagtc aggacctggc    480
ctcgttcagc caagccaatc actgagtata acgtgcacgg tgagcggctt tagcctgaca    540
aactatggtg tccactgggt ccgccaatct cctggaaaag gcttggagtg gctcggtgtt    600
atctggtccg gtggtaacac agactacaac acgccattca ccgtcgcct tagtattaac     660 aaggacaact ccaagtctca ggttttcttt aaaatgaact ctctgcagtc taatgatacc    720
gcaatttact actgtgcgag ggcactcacg tactatgact atgagttcgc gtattgggc     780 caagggactc tcgttactgt ctcagcg                                          807
```

<210> SEQ ID NO 32
<211> LENGTH: 269
<212> TYPE: PRT
<213> ORGANISM: Artificial Sequence
<220> FEATURE:
<223> OTHER INFORMATION: EGFR scFv - Protein sequence

<400> SEQUENCE: 32

```
Met Asp Trp Ile Trp Arg Ile Leu Phe Leu Val Gly Ala Ala Thr Gly
1               5                   10                  15

Ala His Ser Ala Gln Pro Ala Asp Ile Leu Leu Thr Gln Ser Pro Val
            20                  25                  30

Ile Leu Ser Val Ser Pro Gly Glu Arg Val Ser Phe Ser Cys Arg Ala
        35                  40                  45

Ser Gln Ser Ile Gly Thr Asn Ile His Trp Tyr Gln Gln Arg Thr Asn
    50                  55                  60

Gly Ser Pro Arg Leu Leu Ile Lys Tyr Ala Ser Glu Ser Ile Ser Gly
65                  70                  75                  80

Ile Pro Ser Arg Phe Ser Gly Ser Gly Ser Gly Thr Asp Phe Thr Leu
                85                  90                  95

Ser Ile Asn Ser Val Glu Ser Glu Asp Ile Ala Asp Tyr Tyr Cys Gln
            100                 105                 110

Gln Asn Asn Asn Trp Pro Thr Thr Phe Gly Ala Gly Thr Lys Leu Glu
        115                 120                 125

Leu Lys Gly Gly Gly Gly Ser Gly Gly Gly Gly Ser Gly Gly Gly Gly
    130                 135                 140

Ser Gly Gly Gly Gly Ser Gln Val Gln Leu Lys Gln Ser Gly Pro Gly
145                 150                 155                 160

Leu Val Gln Pro Ser Gln Ser Leu Ser Ile Thr Cys Thr Val Ser Gly
                165                 170                 175

Phe Ser Leu Thr Asn Tyr Gly Val His Trp Val Arg Gln Ser Pro Gly
            180                 185                 190

Lys Gly Leu Glu Trp Leu Gly Val Ile Trp Ser Gly Gly Asn Thr Asp
        195                 200                 205

Tyr Asn Thr Pro Phe Thr Ser Arg Leu Ser Ile Asn Lys Asp Asn Ser
    210                 215                 220

Lys Ser Gln Val Phe Phe Lys Met Asn Ser Leu Gln Ser Asn Asp Thr
```

```
                225                 230                 235                 240
Ala Ile Tyr Tyr Cys Ala Arg Ala Leu Thr Tyr Tyr Asp Tyr Glu Phe
                    245                 250                 255

Ala Tyr Trp Gly Gln Gly Thr Leu Val Thr Val Ser Ala
            260                 265
```

<210> SEQ ID NO 33
<211> LENGTH: 822
<212> TYPE: DNA
<213> ORGANISM: Artificial Sequence
<220> FEATURE:
<223> OTHER INFORMATION: Codon-optimized IGF1R scFv - DNA sequence

<400> SEQUENCE: 33

```
atggactgga tctggcggat tctgtttctc gtgggagctg ccacaggcgc tcattctgct    60
cagcctgccg atgttgtaat gacgcagtca cccctgtcac tcccggtcac acccggagaa   120
ccagcgtcaa ttagctgccg atctagccaa agtttgcttc attccaatgg ttacaattat   180
ctcgactggt acttgcagaa acccggccaa tcccctcagc tgctcatcta ccttgggtct   240
aatgggcat ctggggttcc cgataggttc tctggctccg ggagcggcac cgactttacg   300
ttgaaaatct cagggttga ggcggaagac gtaggcgttt actattgcat gcaggggacc   360
cactggccgc tgaccttcgg ccagggcacc aaggttgaaa taaaaggcgg cggaggaagc   420
ggaggcggag gatctggggg cggaggctct ggcgagggg gatctcaggt acagctccag   480
gaatcaggac ccggtttggt taagccctcc gggacccttt ccctcacgtg tgcagtctca   540
ggtgggtcaa ttagttcttc caattggtgg tcttgggtgc ggcaaccacc tggtaaaggt   600
ctcgagtgga tagggaaat ttatcatagt ggctccacca attataaccc ctcactcaag   660
tccaggggta cgatatctgt ggacaaaagt aaaaaccaat ctcccctcaa acttagtagt   720
gtaacagcgg cagacaccgc ggtgtactac tgcgcacggt ggacaggccg aactgatgcc   780
tttgacattt ggggacaggg aactatggtg actgtgtcat cc                      822
```

<210> SEQ ID NO 34
<211> LENGTH: 274
<212> TYPE: PRT
<213> ORGANISM: Artificial Sequence
<220> FEATURE:
<223> OTHER INFORMATION: IGF1R scFv -Protein sequence

<400> SEQUENCE: 34

```
Met Asp Trp Ile Trp Arg Ile Leu Phe Leu Val Gly Ala Ala Thr Gly
1               5                   10                  15

Ala His Ser Ala Gln Pro Ala Asp Val Val Met Thr Gln Ser Pro Leu
            20                  25                  30

Ser Leu Pro Val Thr Pro Gly Glu Pro Ala Ser Ile Ser Cys Arg Ser
        35                  40                  45

Ser Gln Ser Leu Leu His Ser Asn Gly Tyr Asn Tyr Leu Asp Trp Tyr
    50                  55                  60

Leu Gln Lys Pro Gly Gln Ser Pro Gln Leu Leu Ile Tyr Leu Gly Ser
65                  70                  75                  80

Asn Arg Ala Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Val Gly
            100                 105                 110

Val Tyr Tyr Cys Met Gln Gly Thr His Trp Pro Leu Thr Phe Gly Gln
        115                 120                 125
```

Gly Thr Lys Val Glu Ile Lys Gly Gly Gly Ser Gly Gly Gly Gly
            130                 135                 140
Ser Gly Gly Gly Ser Gly Gly Gly Ser Gln Val Gln Leu Gln
145                 150                 155                 160
Glu Ser Gly Pro Gly Leu Val Lys Pro Ser Gly Thr Leu Ser Leu Thr
                165                 170                 175
Cys Ala Val Ser Gly Gly Ser Ile Ser Ser Ser Asn Trp Trp Ser Trp
            180                 185                 190
Val Arg Gln Pro Pro Gly Lys Gly Leu Glu Trp Ile Gly Glu Ile Tyr
            195                 200                 205
His Ser Gly Ser Thr Asn Tyr Asn Pro Ser Leu Lys Ser Arg Val Thr
            210                 215                 220
Ile Ser Val Asp Lys Ser Lys Asn Gln Phe Ser Leu Lys Leu Ser Ser
225                 230                 235                 240
Val Thr Ala Ala Asp Thr Ala Val Tyr Tyr Cys Ala Arg Trp Thr Gly
                245                 250                 255
Arg Thr Asp Ala Phe Asp Ile Trp Gly Gln Gly Thr Met Val Thr Val
            260                 265                 270
Ser Ser

<210> SEQ ID NO 35
<211> LENGTH: 822
<212> TYPE: DNA
<213> ORGANISM: Artificial Sequence
<220> FEATURE:
<223> OTHER INFORMATION: Codon-optimized CD30 scFv - DNA sequence

<400> SEQUENCE: 35

```
atggactgga tctggcggat tctgtttctc gtgggagctg ccacaggcgc tcattctgct    60
cagcctgccg atatccaaat gactcaatct cctagttcac tgtcagcctc tgttggtgat   120
cgcgtgacca ttacctgcca agctagccag gatattagca actacttgaa ctggtatcag   180
cagaagcctg gcaaagcccc aaagctgttg atctacgatg taagtaactt ggaaactggc   240
gtcccaagcc gcttctctgg atctggttca ggcaccgact tcactttcac tatcagcagc   300
ctgcagcctg aagatatcgc aacctactat tgccagcagg ttgctaatgt tcctctgact   360
ttcggccaag gcaccaaggt ggagatcaag ggcggcggag aagcggaggc ggaggatct    420
ggggcggag ctctggcgg aggggatct gaagttcagc ttgtagaatc tggaggtgga    480
ttggttcaac tggtggctc tcttcgcctg agttgtgcag cctctggttt tacttctct    540
agttactgga tgcattgggt tcgtcaggct cctgggaaag gcctggaatg ggtttcagct   600
attagtggga gtgagatag tacttactac gcagacagtg tgaaaggtcg cttcaccatc   660
agccgtgata ttctaagaa cactttgtac ctgcaaatga actccttgcg cgcagaagac   720
acggctgtgt actattgtgc ccgtgatcgc tctgcgactt ggtattatct ggggcttggt   780
ttcgatgtat ggggacaagg taccctggta acggtttcta gc                      822
```

<210> SEQ ID NO 36
<211> LENGTH: 274
<212> TYPE: PRT
<213> ORGANISM: Artificial Sequence
<220> FEATURE:
<223> OTHER INFORMATION: CD30 scFv - Protein sequence

<400> SEQUENCE: 36

Met Asp Trp Ile Trp Arg Ile Leu Phe Leu Val Gly Ala Ala Thr Gly

```
  1               5                  10                 15
Ala His Ser Ala Gln Pro Ala Asp Ile Gln Met Thr Gln Ser Pro Ser
               20                  25                 30

Ser Leu Ser Ala Ser Val Gly Asp Arg Val Thr Ile Thr Cys Gln Ala
               35                  40                 45

Ser Gln Asp Ile Ser Asn Tyr Leu Asn Trp Tyr Gln Gln Lys Pro Gly
           50                  55                 60

Lys Ala Pro Lys Leu Leu Ile Tyr Asp Val Ser Asn Leu Glu Thr Gly
65                  70                  75                 80

Val Pro Ser Arg Phe Ser Gly Ser Gly Ser Gly Thr Asp Phe Thr Phe
                   85                  90                 95

Thr Ile Ser Ser Leu Gln Pro Glu Asp Ile Ala Thr Tyr Tyr Cys Gln
               100                 105                110

Gln Val Ala Asn Val Pro Leu Thr Phe Gly Gln Gly Thr Lys Val Glu
               115                 120                125

Ile Lys Gly Gly Gly Gly Ser Gly Gly Gly Ser Gly Gly Gly Gly
           130                 135                 140

Ser Gly Gly Gly Gly Ser Glu Val Gln Leu Val Glu Ser Gly Gly Gly
145                 150                 155                160

Leu Val Gln Pro Gly Gly Ser Leu Arg Leu Ser Cys Ala Ala Ser Gly
                   165                 170                175

Phe Thr Phe Ser Ser Tyr Trp Met His Trp Val Arg Gln Ala Pro Gly
               180                 185                190

Lys Gly Leu Glu Trp Val Ser Ala Ile Ser Trp Ser Gly Asp Ser Thr
               195                 200                 205

Tyr Tyr Ala Asp Ser Val Lys Gly Arg Phe Thr Ile Ser Arg Asp Asn
           210                  215                 220

Ser Lys Asn Thr Leu Tyr Leu Gln Met Asn Ser Leu Arg Ala Glu Asp
225                 230                  235                240

Thr Ala Val Tyr Tyr Cys Ala Arg Asp Arg Ser Ala Thr Trp Tyr Tyr
                   245                 250                255

Leu Gly Leu Gly Phe Asp Val Trp Gly Gln Gly Thr Leu Val Thr Val
               260                 265                 270

Ser Ser
```

<210> SEQ ID NO 37
<211> LENGTH: 825
<212> TYPE: DNA
<213> ORGANISM: Artificial Sequence
<220> FEATURE:
<223> OTHER INFORMATION: Codon-optimized HER2/neu scFv - DNA sequence

<400> SEQUENCE: 37

```
atggactgga tctggcggat tctgtttctc gtgggagctg ccacaggcgc tcattctgct      60
cagcctgccg acatccagat gacccagagc cccagcagcc tgagcgccag cgtgggcgac     120
agagtgacca tcacctgcag agccagccag gacgtgaaca ccgccgtggc ctggtaccag     180
cagaagcccg gcaaggcccc caagctgctg atctacagcg ccagcttcct gtacagcggc     240
gtgcccagca gattcagcgg cagcagaagc ggcaccgact caccctgac catcagcagc      300 ctgcagcccg aggacttcgc cacctactac tgccagcagc actacaccac ccccccccacc    360 ttcggccagg gcaccaaggt ggagatcaag tcctcagggg cggggggaag tggtggggc      420 ggcagcggcg aggggggctc aggaggaggc ggatcaggcg atcagaggt gcagctggtg      480 gagagcggcg gcggcctggt gcagcccggc ggcagcctga ctgagctg cgccgccagc       540
```

```
ggcttcaaca tcaaggacac ctacatccac tgggtgagac aggccccccgg caagggcctg    600 gagtgggtgg ccagaatcta ccccaccaac ggctacacca gatacgccga cagcgtgaag    660
ggcagattca ccatcagcgc cgacaccagc aagaacaccg cctacctgca gatgaacagc    720
ctgagagccg aggacaccgc cgtgtactac tgcagcagat ggggcggcga cggcttctac    780
gccatggact actggggcca gggcaccctg gtgaccgtga gcagc                     825
```

<210> SEQ ID NO 38
<211> LENGTH: 275
<212> TYPE: PRT
<213> ORGANISM: Artificial Sequence
<220> FEATURE:
<223> OTHER INFORMATION: HER2/neu scFv - Protein sequence
<400> SEQUENCE: 38

```
Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Ser Pro Ser
            20                  25                  30

Ser Leu Ser Ala Ser Val Gly Asp Arg Val Thr Ile Thr Cys Arg Ala
        35                  40                  45

Ser Gln Asp Val Asn Thr Ala Val Ala Trp Tyr Gln Gln Lys Pro Gly
    50                  55                  60

Lys Ala Pro Lys Leu Leu Ile Tyr Ser Ala Ser Phe Leu Tyr Ser Gly
65                  70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln His Tyr Thr Thr Pro Pro Thr Phe Gly Gln Gly Thr Lys Val Glu
        115                 120                 125

Ile Lys Ser Ser Gly Gly Gly Ser Gly Gly Gly Ser Gly Gly
    130                 135                 140

Gly Gly Ser Gly Gly Gly Gly Ser Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Phe Asn Ile Lys Asp Thr Tyr Ile His Trp Val
            180                 185                 190

Arg Gln Ala Pro Gly Lys Gly Leu Glu Trp Val Ala Arg Ile Tyr Pro
        195                 200                 205

Thr Asn Gly Tyr Thr Arg Tyr Ala Asp Ser Val Lys Gly Arg Phe Thr
    210                 215                 220

Ile Ser Ala Asp Thr Ser Lys Asn Thr Ala Tyr Leu Gln Met Asn Ser
225                 230                 235                 240

Leu Arg Ala Glu Asp Thr Ala Val Tyr Tyr Cys Ser Arg Trp Gly Gly
                245                 250                 255

Asp Gly Phe Tyr Ala Met Asp Tyr Trp Gly Gln Gly Thr Leu Val Thr
            260                 265                 270

Val Ser Ser
        275
```

<210> SEQ ID NO 39
<211> LENGTH: 798
<212> TYPE: DNA

<213> ORGANISM: Artificial Sequence
<220> FEATURE:
<223> OTHER INFORMATION: Codon-optimized GD2 scFv - DNA sequence VL/VH

<400> SEQUENCE: 39

```
atggactgga tctggcggat tctgtttctc gtgggagctg ccacaggcgc tcattctgct    60
cagcctgcca gcatcgtgat gacccagact cctaagttcc tgctggtgtc tgccggcgac   120
agagtgacca tcacctgtaa agccagccag agcgtgtcca cgacgtggc ctggtatcag    180
cagaagcctg gacagagccc caagctgctg atctacagcg ccagcaacag atacaccggc   240
gtgcccgata gattcaccgg ctctggctac ggcaccgact tcacctttac catcagcacc   300
gtgcaggccg aggatctggc cgtgtacttc tgccagcaag actacagctc tctcggcgga   360
ggcaccaagc tggaaatcaa aggcggcgga ggaagcggag gcggaggatc tgggggcgga   420
ggctctggcg aggggggatc tcaggtgcaa gtgaaagagt ctggccctgg actggtggcc   480
ccaagccagt ctctgagcat cacatgtacc gtgtccggct tcagcctgac caactatggc   540
gtgcactggg tccgacagcc tccaggcaaa ggactggaat ggctgggagt gatttgggct   600
ggcggcagca ccaactacaa cagcgccctg atgagccggc tgagcatctc caaggacaac   660
agcaagagcc aggtgttcct gaagatgaac agcctgcaga ccgacgacac cgccatgtac   720
tactgtgcta gcagaggcgg caactacggc tacgccctgg attattgggg ccagggcaca   780
agcgtgaccg tgtcatct                                                 798
```

<210> SEQ ID NO 40
<211> LENGTH: 798
<212> TYPE: DNA
<213> ORGANISM: Artificial Sequence
<220> FEATURE:
<223> OTHER INFORMATION: Codon-optimized GD2 scFv - DNA sequence VH/VL

<400> SEQUENCE: 40

```
atggactgga tctggcggat tctgtttctc gtgggagctg ccacaggcgc tcattctgct    60
cagcctgccc aggtgcaagt gaaagagtct ggccctggac tggtggcccc aagccagtct   120
ctgagcatca catgtaccgt gtccggcttc agcctgacca actatggcgt gcactgggtc   180
cgacagcctc caggcaaagg actggaatgg ctgggagtga tttggctgg cggcagcacc    240
aactacaaca gcgccctgat gagccggctg agcatctcca aggacaacag caagagccag   300
gtgttcctga agatgaacag cctgcagacc gacgacaccg ccatgtacta ctgtgctagc   360
agaggcggca actacggcta cgccctggat tattggggcc agggcacaag cgtgaccgtg   420
tcatctggcg gcggaggaag cggaggcgga ggatctgggg gcggaggctc tggcggaggg   480
ggatctagca tcgtgatgac ccagactcct aagttcctgc tggtgtctgc cggcgacaga   540
gtgaccatca cctgtaaagc cagccagagc gtgtccaacg acgtggcctg gtatcagcag   600
aagcctggac agagccccaa gctgctgatc tacagcgcca gcaacagata caccggcgtg   660
cccgatagat tcaccggctc tggctacggc accgacttca cctttaccat cagcaccgtg   720
caggccgagg atctggccgt gtacttctgc cagcaagact acagctctct cggcggaggc   780
accaagctgg aaatcaaa                                                 798
```

<210> SEQ ID NO 41
<211> LENGTH: 266
<212> TYPE: PRT
<213> ORGANISM: Artificial Sequence
<220> FEATURE:
<223> OTHER INFORMATION: GD2 scFv - Protein sequence VL/VH -continued

```
<400> SEQUENCE: 41

Met Asp Trp Ile Trp Arg Ile Leu Phe Leu Val Gly Ala Ala Thr Gly
1               5                   10                  15

Ala His Ser Ala Gln Pro Ala Ser Ile Val Met Thr Gln Thr Pro Lys
            20                  25                  30

Phe Leu Leu Val Ser Ala Gly Asp Arg Val Thr Ile Thr Cys Lys Ala
        35                  40                  45

Ser Gln Ser Val Ser Asn Asp Val Ala Trp Tyr Gln Lys Pro Gly
    50                  55                  60

Gln Ser Pro Lys Leu Leu Ile Tyr Ser Ala Ser Asn Arg Tyr Thr Gly
65                  70                  75                  80

Val Pro Asp Arg Phe Thr Gly Ser Gly Tyr Gly Thr Asp Phe Thr Phe
                85                  90                  95

Thr Ile Ser Thr Val Gln Ala Glu Asp Leu Ala Val Tyr Phe Cys Gln
                100                 105                 110

Gln Asp Tyr Ser Ser Leu Gly Gly Gly Thr Lys Leu Glu Ile Lys Gly
            115                 120                 125

Gly Gly Gly Ser Gly Gly Gly Gly Ser Gly Gly Gly Gly Ser Gly Gly
130                 135                 140

Gly Gly Ser Gln Val Gln Val Lys Glu Ser Gly Pro Gly Leu Val Ala
145                 150                 155                 160

Pro Ser Gln Ser Leu Ser Ile Thr Cys Thr Val Ser Gly Phe Ser Leu
            165                 170                 175

Thr Asn Tyr Gly Val His Trp Val Arg Gln Pro Pro Lys Gly Leu
        180                 185                 190

Glu Trp Leu Gly Val Ile Trp Ala Gly Gly Ser Thr Asn Tyr Asn Ser
        195                 200                 205

Ala Leu Met Ser Arg Leu Ser Ile Ser Lys Asp Asn Ser Lys Ser Gln
    210                 215                 220

Val Phe Leu Lys Met Asn Ser Leu Gln Thr Asp Asp Thr Ala Met Tyr
225                 230                 235                 240

Tyr Cys Ala Ser Arg Gly Gly Asn Tyr Gly Tyr Ala Leu Asp Tyr Trp
                245                 250                 255

Gly Gln Gly Thr Ser Val Thr Val Ser Ser
            260                 265

<210> SEQ ID NO 42
<211> LENGTH: 266
<212> TYPE: PRT
<213> ORGANISM: Artificial Sequence
<220> FEATURE:
<223> OTHER INFORMATION: GD2 scFv - Protein sequence VH/VL

<400> SEQUENCE: 42

Met Asp Trp Ile Trp Arg Ile Leu Phe Leu Val Gly Ala Ala Thr Gly
1               5                   10                  15

Ala His Ser Ala Gln Pro Ala Gln Val Gln Leu Lys Glu Ser Gly Pro
            20                  25                  30

Gly Leu Val Ala Pro Ser Gln Ser Leu Ser Ile Thr Cys Thr Val Ser
        35                  40                  45

Gly Phe Ser Leu Thr Asn Tyr Gly Val His Trp Val Arg Gln Pro Pro
    50                  55                  60

Gly Lys Gly Leu Glu Trp Leu Gly Val Ile Trp Ala Gly Gly Ser Thr
65                  70                  75                  80
```

```
Asn Tyr Asn Ser Ala Leu Met Ser Arg Leu Ser Ile Ser Lys Asp Asn
                85                  90                  95

Ser Lys Ser Gln Val Phe Leu Lys Met Asn Ser Leu Gln Thr Asp Asp
            100                 105                 110

Thr Ala Met Tyr Tyr Cys Ala Ser Arg Gly Gly Asn Tyr Gly Tyr Ala
        115                 120                 125

Leu Asp Tyr Trp Gly Gln Gly Thr Ser Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Ser Ile Val Met Thr Gln Thr Pro Lys Phe Leu Leu Val Ser
                165                 170                 175

Ala Gly Asp Arg Val Thr Ile Thr Cys Lys Ala Ser Gln Ser Val Ser
            180                 185                 190

Asn Asp Val Ala Trp Tyr Gln Gln Lys Pro Gly Gln Ser Pro Lys Leu
        195                 200                 205

Leu Ile Tyr Ser Ala Ser Asn Arg Tyr Thr Gly Val Pro Asp Arg Phe
    210                 215                 220

Thr Gly Ser Gly Tyr Gly Thr Asp Phe Thr Phe Thr Ile Ser Thr Val
225                 230                 235                 240

Gln Ala Glu Asp Leu Ala Val Tyr Phe Cys Gln Gln Asp Tyr Ser Ser
                245                 250                 255

Leu Gly Gly Gly Thr Lys Leu Glu Ile Lys
            260                 265

<210> SEQ ID NO 43
<211> LENGTH: 254
<212> TYPE: PRT
<213> ORGANISM: Artificial Sequence
<220> FEATURE:
<223> OTHER INFORMATION: High Affinity Variant Ig gamma FcRIII-A amino
      acid sequence

<400> SEQUENCE: 43

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175
```

```
Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

```
<210> SEQ ID NO 44
<211> LENGTH: 765
<212> TYPE: DNA
<213> ORGANISM: Artificial Sequence
<220> FEATURE:
<223> OTHER INFORMATION: High Affinity Variant IgGamma FcRIII-A nucleic
      acid sequence

<400> SEQUENCE: 44
atgtggcagc tgctgctgcc tacagctctc ctgctgctgg tgtccgccgg catgagaacc      60
gaggatctgc ctaaggccgt ggtgttcctg aaccccagt ggtacagagt gctggaaaag     120
gacagcgtga ccctgaagtg ccagggcgcc tacagcccg aggacaatag cacccagtgg     180
ttccacaacg agagcctgat cagcagccag gccagcagct acttcatcga cgccgccacc    240
gtggacgaca cggcgagta tagatgccag accaacctga gcaccctgag cgaccccgtg     300
cagctggaag tgcacatcgg atggctgctg ctgcaggccc ccagatgggt gttcaaagaa    360 gaggaccccca tccacctgag atgccactct tggaagaaca ccgccctgca caaagtgacc   420
tacctgcaga acggcaaggg cagaaagtac ttccaccaca cagcgactt ctacatcccc     480 aaggccaccc tgaaggactc cggctcctac ttctgcagag gcctcgtggg cagcaagaac    540
gtgtccagcg agacagtgaa catcaccatc acccagggcc tggccgtgtc taccatcagc    600
agctttttcc cacccggcta ccaggtgtcc ttctgcctcg tgatggtgct gctgttcgcc    660
gtggacaccg gcctgtactt cagcgtgaaa acaaacatca gaagcagcac ccgggactgg   720
aaggaccaca gttcaagtg gcggaaggac ccccaggaca gtga                      765
```

```
<210> SEQ ID NO 45
<211> LENGTH: 61
<212> TYPE: PRT
<213> ORGANISM: Artificial Sequence
<220> FEATURE:
<223> OTHER INFORMATION: CD8 Hinge peptide (Human)

<400> SEQUENCE: 45

Leu Ser Asn Ser Ile Met Tyr Phe Ser His Phe Val Pro Val Phe Leu
1               5                   10                  15

Pro Ala Lys Pro Thr Thr Thr Pro Ala Pro Arg Pro Thr Pro Ala
            20                  25                  30

Pro Thr Ile Ala Ser Gln Pro Leu Ser Leu Arg Pro Glu Ala Cys Arg
            35                  40                  45

Pro Ala Ala Gly Gly Ala Val His Thr Arg Gly Leu Asp
            50                  55                  60
```

```
<210> SEQ ID NO 46
<211> LENGTH: 183
<212> TYPE: DNA
```

<213> ORGANISM: Artificial Sequence
<220> FEATURE:
<223> OTHER INFORMATION: CD8 Hinge DNA (Human)

<400> SEQUENCE: 46

```
ctgagcaaca gcatcatgta cttcagccac ttcgtgcctg tgttcctgcc tgccaagcct        60
acaacaacac cagcccctag acctccaacc cctgcccta caattgcctc tcagcctctg       120
tctctgaggc ccgaagcttg tagacctgct gctggcggag ctgtgcacac cagaggactg       180
gat                                                                    183
```

<210> SEQ ID NO 47
<211> LENGTH: 135
<212> TYPE: PRT
<213> ORGANISM: Artificial Sequence
<220> FEATURE:
<223> OTHER INFORMATION: Human T-cell surface glycoprotein CD3 zeta

<400> SEQUENCE: 47

Pro Lys Leu Cys Tyr Leu Leu Asp Gly Ile Leu Phe Ile Tyr Gly Val
1               5                   10                  15

Ile Leu Thr Ala Leu Phe Leu Arg Val Lys Phe Ser Arg Ser Ala Asp
            20                  25                  30

Ala Pro Ala Tyr Gln Gln Gly Gln Asn Gln Leu Tyr Asn Glu Leu Asn
        35                  40                  45

Leu Gly Arg Arg Glu Glu Tyr Asp Val Leu Asp Lys Arg Arg Gly Arg
    50                  55                  60

Asp Pro Glu Met Gly Gly Lys Pro Arg Arg Lys Asn Pro Gln Glu Gly
65                  70                  75                  80

Leu Tyr Asn Glu Leu Gln Lys Asp Lys Met Ala Glu Ala Tyr Ser Glu
                85                  90                  95

Ile Gly Met Lys Gly Glu Arg Arg Arg Gly Lys Gly His Asp Gly Leu
            100                 105                 110

Tyr Gln Gly Leu Ser Thr Ala Thr Lys Asp Thr Tyr Asp Ala Leu His
        115                 120                 125

Met Gln Ala Leu Pro Pro Arg
    130                 135

<210> SEQ ID NO 48
<211> LENGTH: 822
<212> TYPE: DNA
<213> ORGANISM: Artificial Sequence
<220> FEATURE:
<223> OTHER INFORMATION: Codon-optimized CD123 scFv DNA

<400> SEQUENCE: 48

```
atggactgga tctggcggat tctgtttctc gtgggagctg ccacaggcgc tcattctgct        60
cagcctgccc tgcccgtcct gacacagtcc gcaagtgtga gtggatcacc tggacaatca       120
attactatca gttgcacagg cacttcctca gacgtaggga gtatgattac gtgtcatgg        180
tatcaacagc atccaggcaa agctcctcag ctcatgattt atgatgtgtc aacagaccg        240
tccggagtat ctaatcgctt cagtggatct aaatccggta atactgcctc cctcaccata       300
tcagggctcc aggccgaaga tgaagcagac tactattgca gtagttacac tggttcaagt       360
acgctttacg tttttggcac ggggaccaag gtaacggtcc tgggccaacc caaaggcgga       420
ggagggtccg gtggcggtgg cagtggtgga ggggatcag aggtgcaatt ggttgagagc       480
ggtggtgggc tggttaaacc tggcgggtcc ctccgcttgt cttgtgccgc aagcgggttt       540
```

```
acctttagta atgcgtggat gagctgggtg cgacaagcac ccggaaaggg cctggagtgg      600
gtcggtagga ttaaaagcaa aacagatggt ggaacaaccg attatgcggc cccagtcaag      660
ggaaggttca ctatttcaag agacgattcc aagaacactc tttacctcca aatgaatagt      720
ttgaaaacag aggatacagc agtgtactat tgcacaacgg actacgactt ttggagcgga      780
tattactact gggggcaagg taccctggtc acagtttcat ca                         822
```

<210> SEQ ID NO 49
<211> LENGTH: 274
<212> TYPE: PRT
<213> ORGANISM: Artificial Sequence
<220> FEATURE:
<223> OTHER INFORMATION: CD123 scFv Protein sequence

<400> SEQUENCE: 49

```
Met Asp Trp Ile Trp Arg Ile Leu Phe Leu Val Gly Ala Ala Thr Gly
1               5                   10                  15

Ala His Ser Ala Gln Pro Ala Leu Pro Val Leu Thr Gln Ser Ala Ser
            20                  25                  30

Val Ser Gly Ser Pro Gly Gln Ser Ile Thr Ile Ser Cys Thr Gly Thr
        35                  40                  45

Ser Ser Asp Val Gly Arg Tyr Asp Tyr Val Ser Trp Tyr Gln Gln His
    50                  55                  60

Pro Gly Lys Ala Pro Gln Leu Met Ile Tyr Asp Val Ser Asn Arg Pro
65                  70                  75                  80

Ser Gly Val Ser Asn Arg Phe Ser Gly Ser Lys Ser Gly Asn Thr Ala
                85                  90                  95

Ser Leu Thr Ile Ser Gly Leu Gln Ala Glu Asp Glu Ala Asp Tyr Tyr
            100                 105                 110

Cys Ser Ser Tyr Thr Gly Ser Ser Thr Leu Tyr Val Phe Gly Thr Gly
        115                 120                 125

Thr Lys Val Thr Val Leu Gly Gln Pro Lys Gly Gly Gly Gly Ser Gly
    130                 135                 140

Gly Gly Gly Ser Gly Gly Gly Ser Glu Val Gln Leu Val Glu Ser
145                 150                 155                 160

Gly Gly Gly Leu Val Lys Pro Gly Gly Ser Leu Arg Leu Ser Cys Ala
                165                 170                 175

Ala Ser Gly Phe Thr Phe Ser Asn Ala Trp Met Ser Trp Val Arg Gln
            180                 185                 190

Ala Pro Gly Lys Gly Leu Glu Trp Val Gly Arg Ile Lys Ser Lys Thr
        195                 200                 205

Asp Gly Gly Thr Thr Asp Tyr Ala Ala Pro Val Lys Gly Arg Phe Thr
    210                 215                 220

Ile Ser Arg Asp Asp Ser Lys Asn Thr Leu Tyr Leu Gln Met Asn Ser
225                 230                 235                 240

Leu Lys Thr Glu Asp Thr Ala Val Tyr Tyr Cys Thr Thr Asp Tyr Asp
                245                 250                 255

Phe Trp Ser Gly Tyr Tyr Tyr Trp Gly Gln Gly Thr Leu Val Thr Val
            260                 265                 270

Ser Ser
```

<210> SEQ ID NO 50
<211> LENGTH: 807
<212> TYPE: DNA
<213> ORGANISM: Artificial Sequence
<220> FEATURE:

<223> OTHER INFORMATION: Codon-optimized PD-L1 scFv DNA

<400> SEQUENCE: 50

```
atggactgga tctggcggat tctgtttctc gtgggagctg ccacaggcgc tcattctgct      60
cagcctgcca acatccagat gacccagtct ccatcttctg tgtctgcatc tgtaggagac     120
agagtcacca tcacttgtcg ggcgagtcag gatattagcc gctggttagc ctggtatcag     180
cagaaaccag ggaaagcccc taaactcctg atctatgctg catccagttt gcaaagtggg     240
gtcccatcga ggttcagcgg cagtggatct gggacagatt tcgctctcac tatcagcagc     300
ctgcagcctg aagattttgc aacttactat tgtcaacagg ctgacagtcg tttctcgatc     360
accttcggcc aagggacacg actggagatt aaaggcggcg gaggaagcgg aggcggagga     420
tctgggggcg gaggctctgg cggaggggga tctgaggtgc agctggtgca gtctggggga     480
ggcttggtac agcctggggg gtccctgaga ctctcctgtg cagcctctgg attcaccttc     540
agtagctata gcatgaactg ggtccgccag gctccaggga aggggctgga gtgggtttca     600
tacattagta gtagtagtag taccatacag tacgcagact ctgtgaaggg ccgattcacc     660
atctccagag acaatgccaa gaactcactg tatctgcaaa tgaacagcct gagagacgag     720
gacacggctg tgtattactg tgcgagaggg gactactact acggtatgga cgtctggggc     780
caagggacca cggtcaccgt gagctca                                         807
```

<210> SEQ ID NO 51
<211> LENGTH: 269
<212> TYPE: PRT
<213> ORGANISM: Artificial Sequence
<220> FEATURE:
<223> OTHER INFORMATION: PD-L1 scFv Protein

<400> SEQUENCE: 51

```
Met Asp Trp Ile Trp Arg Ile Leu Phe Leu Val Gly Ala Ala Thr Gly
1               5                   10                  15
Ala His Ser Ala Gln Pro Ala Asn Ile Gln Met Thr Gln Ser Pro Ser
            20                  25                  30
Ser Val Ser Ala Ser Val Gly Asp Arg Val Thr Ile Thr Cys Arg Ala
        35                  40                  45
Ser Gln Asp Ile Ser Arg Trp Leu Ala Trp Tyr Gln Gln Lys Pro Gly
    50                  55                  60
Lys Ala Pro Lys Leu Leu Ile Tyr Ala Ala Ser Ser Leu Gln Ser Gly
65                  70                  75                  80
Val Pro Ser Arg Phe Ser Gly Ser Gly Ser Gly Thr Asp Phe Ala Leu
                85                  90                  95
Thr Ile Ser Ser Leu Gln Pro Glu Asp Phe Ala Thr Tyr Tyr Cys Gln
            100                 105                 110
Gln Ala Asp Ser Arg Phe Ser Ile Thr Phe Gly Gln Gly Thr Arg Leu
        115                 120                 125
Glu Ile Lys Gly Gly Gly Gly Ser Gly Gly Gly Gly Ser Gly Gly Gly
    130                 135                 140
Gly Ser Gly Gly Gly Gly Ser Glu Val Gln Leu Val Gln Ser Gly Gly
145                 150                 155                 160
Gly Leu Val Gln Pro Gly Gly Ser Leu Arg Leu Ser Cys Ala Ala Ser
                165                 170                 175
Gly Phe Thr Phe Ser Ser Tyr Ser Met Asn Trp Val Arg Gln Ala Pro
            180                 185                 190
Gly Lys Gly Leu Glu Trp Val Ser Tyr Ile Ser Ser Ser Ser Ser Thr
```

```
            195                 200                 205
Ile Gln Tyr Ala Asp Ser Val Lys Gly Arg Phe Thr Ile Ser Arg Asp
        210                 215                 220

Asn Ala Lys Asn Ser Leu Tyr Leu Gln Met Asn Ser Leu Arg Asp Glu
225                 230                 235                 240

Asp Thr Ala Val Tyr Tyr Cys Ala Arg Gly Asp Tyr Tyr Tyr Gly Met
                245                 250                 255

Asp Val Trp Gly Gln Gly Thr Thr Val Thr Val Ser Ser
            260                 265

<210> SEQ ID NO 52
<211> LENGTH: 807
<212> TYPE: DNA
<213> ORGANISM: Artificial Sequence
<220> FEATURE:
<223> OTHER INFORMATION: Codon-optimized B7-H4 scFv  DNA

<400> SEQUENCE: 52
atggactgga tctggcggat tctgtttctc gtgggagctg ccacaggcgc tcattctgct      60
cagcctgccg aagttcagct tgtagaatct ggaggtggat tggttcaacc tggtggctct     120
cttcgcctga gttgtgcagc ctctggtttt actttcaata gttacgctat gcattgggtt     180
cgtcaggctc tgggaaagg cctggaatgg gtttcagcta ttagtggtaa tggaggtagt      240
actcgttacg cagacagtgt gaaaggtcgc ttcaccatca gccgtgataa ttctaagaac     300
actttgtacc tgcaaatgaa ctccttgcgc gcagaagaca cggctgtgta ctattgtgcc     360
cgtgatcgct tcggaaggt tcatggtttc gatgtatggg gacaaggtac cctggtaacg     420
gtttctagcg gaggtggtgg gagtggtgga ggcggctcgg gtggaggtgg ttcaggagga     480
ggcggagata tccaaatgac tcaatctcct agttcactgt cagcctctgt tggtgatcgc     540
gtgaccatta cctgccaagc tagccaggat attagcaact acttgaactg gtatcagcag     600
aagcctggca agcccccaaa gctgttgatc tacgatgcaa gtaacttgga aactggcgtc     660
ccaagccgct ctctggatc tggttcaggc accgacttca ctttcactat cagcagcctg     720
cagcctgaag atatcgcaac ctactattgc cagcaggatg ctactttcc tttgactttc     780 ggccaaggca ccaaggtgga gatcaag                                         807

<210> SEQ ID NO 53
<211> LENGTH: 269
<212> TYPE: PRT
<213> ORGANISM: Artificial Sequence
<220> FEATURE:
<223> OTHER INFORMATION: B7-H4 scFv  Protein

<400> SEQUENCE: 53

Met Asp Trp Ile Trp Arg Ile Leu Phe Leu Val Gly Ala Ala Thr Gly
1               5                   10                  15

Ala His Ser Ala Gln Pro Ala Glu Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Thr Phe Asn Ser Tyr Ala Met His Trp Val Arg Gln Ala Pro
    50                  55                  60

Gly Lys Gly Leu Glu Trp Val Ser Ala Ile Ser Gly Asn Gly Gly Ser
65                  70                  75                  80

Thr Arg Tyr Ala Asp Ser Val Lys Gly Arg Phe Thr Ile Ser Arg Asp
                85                  90                  95
```

Asn Ser Lys Asn Thr Leu Tyr Leu Gln Met Asn Ser Leu Arg Ala Glu
            100                 105                 110

Asp Thr Ala Val Tyr Tyr Cys Ala Arg Asp Arg Phe Arg Lys Val His
        115                 120                 125

Gly Phe Asp Val Trp Gly Gln Gly Thr Leu Val Thr Val Ser Ser Gly
    130                 135                 140

Gly Gly Gly Ser Gly Gly Gly Gly Ser Gly Gly Gly Ser Gly Gly
145                 150                 155                 160

Gly Gly Asp Ile Gln Met Thr Gln Ser Pro Ser Ser Leu Ser Ala Ser
            165                 170                 175

Val Gly Asp Arg Val Thr Ile Thr Cys Gln Ala Ser Gln Asp Ile Ser
        180                 185                 190

Asn Tyr Leu Asn Trp Tyr Gln Gln Lys Pro Gly Lys Ala Pro Lys Leu
    195                 200                 205

Leu Ile Tyr Asp Ala Ser Asn Leu Glu Thr Gly Val Pro Ser Arg Phe
210                 215                 220

Ser Gly Ser Gly Ser Gly Thr Asp Phe Thr Phe Thr Ile Ser Ser Leu
225                 230                 235                 240

Gln Pro Glu Asp Ile Ala Thr Tyr Tyr Cys Gln Gln Asp Ala Thr Phe
            245                 250                 255

Pro Leu Thr Phe Gly Gln Gly Thr Lys Val Glu Ile Lys
        260                 265

<210> SEQ ID NO 54
<211> LENGTH: 1188
<212> TYPE: DNA
<213> ORGANISM: Artificial Sequence
<220> FEATURE:
<223> OTHER INFORMATION: Codon-optimized HIV-gp120 binding domain (CD4)
      DNA

<400> SEQUENCE: 54
atgaaccggg gagtcccttt taggcacttg cttctggtgc tgcaactggc gctcctccca      60
gcagccactc agggaaagaa agtggtgctg ggcaaaaaag gggatacagt ggaactgacc     120
tgtacagctt cccagaagaa gagcatacaa ttccactgga aaaactccaa ccagataaag     180
attctgggaa atcagggctc cttcttaact aaaggtccat ccaagctgaa tgatcgcgct     240
gactcaagaa gaagcctttg gaccaaggaa actttcccc tgatcatcaa gaatcttaag     300
atagaagact cagatactta catctgtgaa gtggaggacc agaaggagga ggtgcaattg     360
ctagtgttcg gattgactgc caactctgac acccacctgc ttcaggggca gagcctgacc     420
ctgaccttgg agaccccccc tggtagtagc ccctcagtgc aatgtaggag tccaagggt     480 aaaacatac agggggggaa gaccctctcc gtgtctcagc tggagctcca ggatagtggc     540
acctggacat gcactgtctt gcagaaccag aagaaggtgg agttcaaaat agacatcgtg     600
gtgctagctt ccagaaggc ctccagcata gtctataaga agaggggga acaggtggag     660 ttctccttcc cactcgcctt tacagttgaa aagctgacgg cagtggcga gctgtggtgg     720 caggcggaga gggcttcctc ctccaagtct tggatcacct ttgacctgaa gaacaaggaa     780
gtgtctgtaa acgggttac ccaggaccct aagctccaga tggcaagaa gctcccgctc     840 cacctcaccc tgccccaggc cttgcctcag tatgctggct ctggaaacct caccctggcc     900
cttgaagcga aaacaggaaa gttgcatcag gaagtgaacc tggtggtgat gagagccact     960
cagctccaga aaaatttgac ctgtgaggtg tggggaccca cctcccctaa gctgatgctg    1020

-continued

```
agtttgaaac tggagaacaa ggaggcaaag gtctcgaagc gggagaaggc ggtgtgggtg   1080
ctgaaccctg aggcggggat gtggcagtgt ctgctgagtg actcgggaca ggtcctgctg   1140
gaatccaaca tcaaggttct gcccacatgg tccaccccgg tgcagcca                1188
```

<210> SEQ ID NO 55
<211> LENGTH: 396
<212> TYPE: PRT
<213> ORGANISM: Artificial Sequence
<220> FEATURE:
<223> OTHER INFORMATION: HIV-gp120 binding domain (CD4) Protein

<400> SEQUENCE: 55

```
Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335
```

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro
385                 390                 395

<210> SEQ ID NO 56
<211> LENGTH: 840
<212> TYPE: DNA
<213> ORGANISM: Artificial Sequence
<220> FEATURE:
<223> OTHER INFORMATION: Codon-optimized FAP scFv VL/VH DNA

<400> SEQUENCE: 56
atggactgga tctggcggat tctgtttctc gtgggagctg ccacaggcgc tcattctgct      60
cagcctgccg acatcgtgat gacacagagc ccttctagcc tggccgtgtc cgtgggagag     120
aaagtgacca tgagctgcaa gagcagccag agcctgctgt actcccggaa ccagaagaac     180
tacctggcct ggttccagca gaagcccggc cagtctccta agctgctgat cttctgggcc     240
agcaccagag aaagcggcgt gcccgataga ttcaccggca gcggctttgg caccgacttc     300
aacctgacaa tcagcagcgt gcaggccgag gacctggctg tgtacgattg ccagcagtac     360
ttcagctacc ctctgacctt tggagccggc accaagctgg aactgagagg cggcggagga     420
agcggaggcg gaggatctgg gggcggaggc tctggcggag ggggatctca ggttcagctg     480
cagcagtctg gacctgagct ggttaagcct ggcgcctccg tgaagatgag ctgcaagacc     540
agccggtaca ccttcaccga gtacaccatc cactgggtcc gacagagcca cggcaagagc     600
ctggaatgga tcggcggcat caaccccaac aacggcatcc caactacaa ccagaagttc     660 aagggcagag ccacactgac cgtgggcaag tctagcagca ccgcctacat ggaactgcgg     720
agcctgacaa gcgaggacag cgccgtgtac ttctgcgcca agaagaat cgcctacggc     780 tacgatgagg ccacgccat ggattattgg ggccagggaa caagcgtgac cgtgtctagt     840

<210> SEQ ID NO 57
<211> LENGTH: 840
<212> TYPE: DNA
<213> ORGANISM: Artificial Sequence
<220> FEATURE:
<223> OTHER INFORMATION: Codon-optimized FAP scFv VH/VL DNA

<400> SEQUENCE: 57
atggactgga tctggcggat tctgtttctc gtgggagctg ccacaggcgc tcattctgct      60
cagcctgccc aggttcagct gcagcagtct ggacctgagc tggttaagcc tggcgcctcc     120
gtgaagatga gctgcaagac cagccggtac accttcaccg agtacaccat ccactgggtc     180
cgacagagcc acggcaagag cctggaatgg atcggcggca tcaaccccaa caacggcatc     240 ccaactaca accagaagtt caagggcaga gccacactga ccgtgggcaa gtctagcagc     300
accgcctaca tggaactgcg gagcctgaca agcgaggaca gcgccgtgta cttctgcgcc     360
agaagaagaa tcgcctacgg ctacgatgag gccacgccca tggattattg gggccaggga     420
acaagcgtga ccgtgtctag tggcggcgga ggaagcggag cggaggatc tgggggcgga     480 ggctctggcg aggggggatc tgacatcgtg atgacacaga gcccttctag cctggccgtg     540
tccgtgggag agaaagtgac catgagctgc aagagcagcc agagcctgct gtactcccgg     600

```
aaccagaaga actacctggc ctggttccag cagaagcccg gccagtctcc taagctgctg      660
atcttctggg ccagcaccag agaaagcggc gtgcccgata gattcaccgg cagcggcttt      720
ggcaccgact tcaacctgac aatcagcagc gtgcaggccg aggacctggc tgtgtacgat      780
tgccagcagt acttcagcta ccctctgacc tttggagccg gcaccaagct ggaactgaga      840
```

```
<210> SEQ ID NO 58
<211> LENGTH: 280
<212> TYPE: PRT
<213> ORGANISM: Artificial Sequence
<220> FEATURE:
<223> OTHER INFORMATION: FAP scFv  VL/VH protein

<400> SEQUENCE: 58
```

```
Met Asp Trp Ile Trp Arg Ile Leu Phe Leu Val Gly Ala Ala Thr Gly
1               5                   10                  15

Ala His Ser Ala Gln Pro Ala Asp Ile Val Met Thr Gln Ser Pro Ser
            20                  25                  30

Ser Leu Ala Val Ser Val Gly Glu Lys Val Thr Met Ser Cys Lys Ser
        35                  40                  45

Ser Gln Ser Leu Leu Tyr Ser Arg Asn Gln Lys Asn Tyr Leu Ala Trp
    50                  55                  60

Phe Gln Gln Lys Pro Gly Gln Ser Pro Lys Leu Leu Ile Phe Trp Ala
65                  70                  75                  80

Ser Thr Arg Glu Ser Gly Val Pro Asp Arg Phe Thr Gly Ser Gly Phe
                85                  90                  95

Gly Thr Asp Phe Asn Leu Thr Ile Ser Ser Val Gln Ala Glu Asp Leu
            100                 105                 110

Ala Val Tyr Asp Cys Gln Gln Tyr Phe Ser Tyr Pro Leu Thr Phe Gly
        115                 120                 125

Ala Gly Thr Lys Leu Glu Leu Arg Gly Gly Gly Gly Ser Gly Gly Gly
    130                 135                 140

Gly Ser Gly Gly Gly Gly Ser Gly Gly Gly Gly Ser Gln Val Gln Leu
145                 150                 155                 160

Gln Gln Ser Gly Pro Glu Leu Val Lys Pro Gly Ala Ser Val Lys Met
                165                 170                 175

Ser Cys Lys Thr Ser Arg Tyr Thr Phe Thr Glu Tyr Thr Ile His Trp
            180                 185                 190

Val Arg Gln Ser His Gly Lys Ser Leu Glu Trp Ile Gly Gly Ile Asn
        195                 200                 205

Pro Asn Asn Gly Ile Pro Asn Tyr Asn Gln Lys Phe Lys Gly Arg Ala
    210                 215                 220

Thr Leu Thr Val Gly Lys Ser Ser Ser Thr Ala Tyr Met Glu Leu Arg
225                 230                 235                 240

Ser Leu Thr Ser Glu Asp Ser Ala Val Tyr Phe Cys Ala Arg Arg Arg
                245                 250                 255

Ile Ala Tyr Gly Tyr Asp Glu Gly His Ala Met Asp Tyr Trp Gly Gln
            260                 265                 270

Gly Thr Ser Val Thr Val Ser Ser
        275                 280
```

```
<210> SEQ ID NO 59
<211> LENGTH: 280
<212> TYPE: PRT
<213> ORGANISM: Artificial Sequence
<220> FEATURE:
```

<223> OTHER INFORMATION: FAP scFv VH/VL protein

<400> SEQUENCE: 59

Met Asp Trp Ile Trp Arg Ile Leu Phe Leu Val Gly Ala Ala Thr Gly
1               5                   10                  15

Ala His Ser Ala Gln Pro Ala Gln Val Gln Leu Gln Gln Ser Gly Pro
            20                  25                  30

Glu Leu Val Lys Pro Gly Ala Ser Val Lys Met Ser Cys Lys Thr Ser
        35                  40                  45

Arg Tyr Thr Phe Thr Glu Tyr Thr Ile His Trp Val Arg Gln Ser His
    50                  55                  60

Gly Lys Ser Leu Glu Trp Ile Gly Gly Ile Asn Pro Asn Asn Gly Ile
65                  70                  75                  80

Pro Asn Tyr Asn Gln Lys Phe Lys Gly Arg Ala Thr Leu Thr Val Gly
                85                  90                  95

Lys Ser Ser Ser Thr Ala Tyr Met Glu Leu Arg Ser Leu Thr Ser Glu
            100                 105                 110

Asp Ser Ala Val Tyr Phe Cys Ala Arg Arg Ile Ala Tyr Gly Tyr
        115                 120                 125

Asp Glu Gly His Ala Met Asp Tyr Trp Gly Gln Gly Thr Ser Val Thr
    130                 135                 140

Val Ser Ser Gly Gly Gly Gly Ser Gly Gly Gly Ser Gly Gly Gly
145                 150                 155                 160

Gly Ser Gly Gly Gly Ser Asp Ile Val Met Thr Gln Ser Pro Ser
                165                 170                 175

Ser Leu Ala Val Ser Val Gly Glu Lys Val Thr Met Ser Cys Lys Ser
            180                 185                 190

Ser Gln Ser Leu Leu Tyr Ser Arg Asn Gln Lys Asn Tyr Leu Ala Trp
        195                 200                 205

Phe Gln Gln Lys Pro Gly Gln Ser Pro Lys Leu Leu Ile Phe Trp Ala
    210                 215                 220

Ser Thr Arg Glu Ser Gly Val Pro Asp Arg Phe Thr Gly Ser Gly Phe
225                 230                 235                 240

Gly Thr Asp Phe Asn Leu Thr Ile Ser Ser Val Gln Ala Glu Asp Leu
                245                 250                 255

Ala Val Tyr Asp Cys Gln Gln Tyr Phe Ser Tyr Pro Leu Thr Phe Gly
            260                 265                 270

Ala Gly Thr Lys Leu Glu Leu Arg
        275                 280

<210> SEQ ID NO 60
<211> LENGTH: 1233
<212> TYPE: DNA
<213> ORGANISM: Artificial Sequence
<220> FEATURE:
<223> OTHER INFORMATION: artificial sequence

<400> SEQUENCE: 60
atggactgga tctggcggat tctgtttctc gtgggagctg ccacaggcgc tcattctgct    60
cagcctgccg acatccagat gacccagagc cccagcagcc tgagcgccag cgtgggcgac   120
agagtgacca tcacctgcag agccagccag gacgtgaaca ccgccgtggc ctggtaccag   180
cagaagcccg gcaaggcccc caagctgctg atctacagcg ccagcttcct gtacagcggc   240
gtgcccagca gattcagcgg cagcagaagc ggcaccgact tcaccctgac catcagcagc   300
ctgcagcccg aggacttcgc cacctactac tgccagcagc actacaccac ccccccccacc   360

-continued

```
ttcggccagg gcaccaaggt ggagatcaag tcctcagggg gcgggggaag tggtgggggc    420
ggcagcggcg gagggggctc aggaggaggc ggatcaggcg gatcagaggt gcagctggtg    480
gagagcggcg gcggcctggt gcagcccggc ggcagcctga gactgagctg cgccgccagc    540
ggcttcaaca tcaaggacac ctacatccac tgggtgagac aggcccccgg caagggcctg    600
gagtgggtgg ccagaatcta ccccaccaac ggctacacca gatacgccga cagcgtgaag    660
ggcagattca ccatcagcgc cgacaccagc aagaacaccg cctacctgca gatgaacagc    720
ctgagagccg aggacaccgc cgtgtactac tgcagcagat ggggcggcga cggcttctac    780
gccatggact actggggcca gggcaccctg gtgaccgtga gcagcgcggc cgcgctgagc    840
aacagcatca tgtacttcag ccacttcgtg cctgtgttcc tgcctgccaa gcctacaaca    900
acaccagccc ctagacctcc aacccctgcc cctacaattg cctctcagcc tctgtctctg    960
aggcccgaag cttgtagacc tgctgctggc ggagctgtgc acaccagagg actggatttc   1020
gcctgctttt gggtgctggt ggtcgtgggc ggagtgctgg cttgttattc tctgctggtc   1080
accgtggcct tcatcatctt tgggtccga ctgaagatcc aggtccgaaa ggccgccatc   1140
accagctacg agaagtctga tggcgtgtac accggcctga gcaccagaaa ccaggaaacc   1200
tacgagacac tgaagcacga gaagcccccc cag                                1233
```

<210> SEQ ID NO 61
<211> LENGTH: 1230
<212> TYPE: DNA
<213> ORGANISM: Artificial Sequence
<220> FEATURE:
<223> OTHER INFORMATION: artificial sequence

<400> SEQUENCE: 61

```
atggactgga tctggcggat tctgtttctc gtgggagctg ccacaggcgc tcattctgct     60
cagcctgccg atatccaaat gactcaatct cctagttcac tgtcagcctc tgttggtgat    120
cgcgtgacca ttacctgcca agctagccag gatattgca actacttgaa ctggtatcag    180
cagaagcctg gcaaagcccc aaagctgttg atctacgatg taagtaactt ggaaactggc    240
gtcccaagcc gcttctctgg atctggttca ggcaccgact tcactttcac tatcagcagc    300
ctgcagcctg aagatatcgc aacctactat tgccagcagg ttgctaatgt tcctctgact    360
ttcggccaag gcaccaaggt ggagatcaag ggcggcggag aagcggaggc ggaggatct    420 ggggcggag gctctggcgg agggggatct gaagttcagc ttgtagaatc tggaggtgga    480
ttggttcaac ctggtggctc tcttcgcctg agttgtgcag cctctggttt tactttctct    540
agttactgga tgcattgggt tcgtcaggct cctgggaaag gcctggaatg ggtttcagct    600
attagttgga atagtggaag tacttactac gcagacagtg tgaaaggtcg cttcaccatc    660
agccgtgata attctaagaa cactttgtac ctgcaaatga actccttgcg cgcagaagac    720
acggctgtgt actattgtgc ccgtgatcgc tctgcgactt ggtattatct gggcttggt    780 ttcgatgtat ggggacaagg taccctggta acggtttcta gcgcggccgc gctgagcaac    840
agcatcatgt acttcagcca cttcgtgcct gtgttcctgc ctgccaagcc tacaacaaca    900 ccagcccta gacctccaac ccctgcccct acaattgcct ctcagcctct gtctctgagg    960
cccgaagctt gtagacctgc tgctggcgga gctgtgcaca ccagaggact ggatttcgcc   1020
tgcttttggg tgctggtggt cgtgggcgga gtgctggctt gttattctct gctggtcacc   1080
gtggccttca tcatcttttg gtccgactg aagatccagg tccgaaaggc cgccatcacc   1140
```

| | |
|---|---|
| agctacgaga agtctgatgg cgtgtacacc ggcctgagca ccagaaacca ggaaacctac | 1200 |
| gagacactga agcacgagaa gccccccag | 1230 |

<210> SEQ ID NO 62
<211> LENGTH: 1215
<212> TYPE: DNA
<213> ORGANISM: Artificial Sequence
<220> FEATURE:
<223> OTHER INFORMATION: artificial sequence

<400> SEQUENCE: 62

| | |
|---|---|
| atggactgga tctggcggat tctgtttctc gtgggagctg ccacaggcgc tcattctgct | 60 |
| cagcctgccg atattcttct tactcaatct cccgttattt tgtcagtatc cccaggtgag | 120 |
| cgagtcagct tctcttgtcg agcgtcacaa tccattggca ccaacataca ttggtaccaa | 180 |
| cagcgcacca acgggtctcc ccggctcttg attaagtacg catcagaaag tatttctggg | 240 |
| atacccagta ggttctcagg gagcgggagt ggcactgact ttaccctgtc cataaacagc | 300 |
| gttgagtctg aggacatcgc ggactactat tgtcagcaga caacaattg gccgaccacg | 360 |
| tttggtgcgg gaacaaaact tgaactcaaa ggcggcggag aagcggagg cggaggatct | 420 |
| gggggcggag gctctggcgg aggggggatct caggtgcagc tcaaacagtc aggacctggc | 480 |
| ctcgttcagc aagccaatc actgagtata acgtgcacgg tgagcggctt tagcctgaca | 540 |
| aactatggtg tccactgggt ccgccaatct cctggaaaag gcttggagtg gctcggtgtt | 600 |
| atctggtccg gtggtaacac agactacaac acgccattca ccagtcgcct tagtattaac | 660 |
| aaggacaact ccaagtctca ggttttcttt aaaatgaact ctctgcagtc taatgatacc | 720 |
| gcaatttact actgtgcgag ggcactcacg tactatgact atgagttcgc gtattggggc | 780 |
| caagggactc tcgttactgt ctcagcggcg gccgcgctga gcaacagcat catgtacttc | 840 |
| agccacttcg tgcctgtgtt cctgcctgcc aagcctacaa caacaccagc ccctagacct | 900 |
| ccaacccctg cccctacaat tgcctctcag cctctgtctc tgaggcccga agcttgtaga | 960 |
| cctgctgctg gcggagctgt gcacaccaga ggactggatt cgcctgctt ttgggtgctg | 1020 |
| gtggtcgtgg gcggagtgct ggcttgttat tctctgctgg tcaccgtggc cttcatcatc | 1080 |
| ttttgggtcc gactgaagat ccaggtccga aaggccgcca tcaccagcta cgagaagtct | 1140 |
| gatggcgtgt acaccggcct gagcaccaga accaggaaaa cctacgagac actgaagcac | 1200 |
| gagaagcccc cccag | 1215 |

<210> SEQ ID NO 63
<211> LENGTH: 1230
<212> TYPE: DNA
<213> ORGANISM: Artificial Sequence
<220> FEATURE:
<223> OTHER INFORMATION: artificial sequence

<400> SEQUENCE: 63

| | |
|---|---|
| atggactgga tctggcggat tctgtttctc gtgggagctg ccacaggcgc tcattctgct | 60 |
| cagcctgccg atgttgtaat gacgcagtca cccctgtcac tcccggtcac acccggagaa | 120 |
| ccagcgtcaa ttagctgccg atctagccaa agtttgcttc attccaatgg ttacaattat | 180 |
| ctcgactggt acttgcagaa accggccaa tcccctcagc tgctcatcta ccttgggtct | 240 |
| aatagggcat ctggggttcc cgataggttc tctggctccg ggagcggcac cgactttacg | 300 |
| ttgaaaatct ctagggttga ggcggaagac gtaggcgttt actattgcat gcaggggacc | 360 |
| cactggccgc tgaccttcgg ccagggcacc aaggttgaaa taaaaggcgg cggaggaagc | 420 |

```
ggaggcggag gatctggggg cggaggctct ggcggagggg gatctcaggt acagctccag    480
gaatcaggac ccggtttggt taagccctcc gggacccttt ccctcacgtg tgcagtctca    540
ggtgggtcaa ttagttcttc caattggtgg tcttgggtgc ggcaaccacc tggtaaaggt    600
ctcgagtgga tagggaaat ttatcatagt ggctccacca attataaccc ctcactcaag    660
tccagggtta cgatatctgt ggacaaaagt aaaaaccaat tctccctcaa acttagtagt    720
gtaacagcgg cagacaccgc ggtgtactac tgcgcacggt ggacaggccg aactgatgcc    780
tttgacattt ggggacaggg aactatggtg actgtgtcat ccgcggccgc gctgagcaac    840
agcatcatgt acttcagcca cttcgtgcct gtgttcctgc ctgccaagcc tacaacaaca    900
ccagccccta gacctccaac ccctgcccct acaattgcct ctcagcctct gtctctgagg    960
cccgaagctt gtagacctgc tgctggcgga gctgtgcaca ccagaggact ggatttcgcc   1020
tgcttttggg tgctggtggt cgtgggcgga gtgctggctt gttattctct gctggtcacc   1080
gtggccttca tcatcttttg gtccgactg aagatccagg tccgaaaggc cgccatcacc   1140
agctacgaga agtctgatgg cgtgtacacc ggcctgagca ccagaaacca ggaaacctac   1200
gagacactga agcacgagaa gcccccccag                                    1230

<210> SEQ ID NO 64
<211> LENGTH: 1203
<212> TYPE: DNA
<213> ORGANISM: Artificial Sequence
<220> FEATURE:
<223> OTHER INFORMATION: artificial sequence

<400> SEQUENCE: 64
atggactgga tctggcgcat cctcttcctc gtcggcgctg ctaccggcgc tcattcggcc     60
cagccggccg acattcaaat gactcagtcc ccttccagct tgtcagcctc agtaggggac    120
cgggtcacga tcacctgtcg agcgtctgag tcagtggata actacgggat ttctttcatg    180
aactggttcc agcagaagcc cggcaaagct cctaagctcc ttatatatgc agcctcaaat    240
caggggagcg tgttcctag tcgcttcagt ggaagcggta gcgtacgga ctttacgttg    300 acgataagta gccttcagcc agatgacttt gccacttatt attgtcagca gtctaaggaa    360
gttccttgga cgtttggcca aggaacgaag gtcgaaatca aaggggagg gggctcagga    420 gggggcggca gtgtggtgg aggctctcaa gtccaactcg tacagtctgg cgcggaggtt    480
aaaaagccgg gaagctccgt gaaagtatcc tgtaaggcaa gcggatacac ctttaccgat    540
tataacatgc actgggttag gcaggcgccc ggccaaggtc tggaatggat cggttatatt    600
tatccataca cggtggtac cggctataat cagaagttta agagtaaggc tactattaca    660
gcggatgagt caaccaatac tgcatacatg gagctctcct cactcaggag cgaagatacc    720
gcagtgtatt actgtgcccg agggagacca gccatggact actggggtca gggtacccct    780
gtgacagtat ctagcgcggc cgcgctgagc aacagcatca tgtacttcag ccacttcgtg    840
cctgtgttcc tgcctgccaa gcctacaaca caccagccc ctagacctcc aaccctgcc    900 cctacaattg cctctcagcc tctgtctctg aggcccgaag cttgtagacc tgctgctggc    960
ggagctgtgc acaccagagg actggatttc gcctgctttt gggtgctggt ggtcgtgggc   1020
ggagtgctgg cttgttattc tctgctggtc accgtggcct tcatcatctt ttgggtccga   1080
ctgaagatcc aggtccgaaa ggccgccatc accagctacg agaagtctga tggcgtgtac   1140
accggcctga gcaccagaaa ccaggaaacc tacgagacac tgaagcacga gaagcccccc   1200
``` cag                                                                    1203

<210> SEQ ID NO 65
<211> LENGTH: 1215
<212> TYPE: DNA
<213> ORGANISM: Artificial Sequence
<220> FEATURE:
<223> OTHER INFORMATION: artificial sequence

<400> SEQUENCE: 65
atggactgga tctggcggat tctgtttctc gtgggagctg ccacaggcgc tcattctgct      60
cagcctgcca acatccagat gacccagtct ccatcttctg tgtctgcatc tgtaggagac     120
agagtcacca tcacttgtcg ggcgagtcag gatattagcc gctggttagc ctggtatcag     180
cagaaaccag ggaaagcccc taaactcctg atctatgctg catccagttt gcaaagtggg     240
gtcccatcga ggttcagcgg cagtggatct gggacagatt tcgctctcac tatcagcagc     300
ctgcagcctg aagattttgc aacttactat tgtcaacagg ctgacagtcg tttctcgatc     360
accttcggcc aagggacacg actggagatt aaaggcggcg aggaagcgg aggcggagga     420 tctgggggcg aggctctgg cgaggggga tctgaggtgc agctggtgca gtctggggga     480
ggcttggtac agcctggggg gtccctgaga ctctcctgtg cagcctctgg attcaccttc     540
agtagctata gcatgaactg ggtccgccag gctccaggga aggggctgga gtgggtttca     600
tacattagta gtagtagtag taccatacag tacgcagact ctgtgaaggg ccgattcacc     660
atctccagag acaatgccaa gaactcactg tatctgcaaa tgaacagcct gagagacgag     720
gacacggctg tgtattactg tgcgagaggg gactactact acggtatgga cgtctggggc     780
caagggacca cggtcaccgt gagctcagcg gccgcgctga gcaacagcat catgtacttc     840
agccacttcg tgcctgtgtt cctgcctgcc aagcctacaa caacaccagc ccctagacct     900 ccaaccctg cccctacaat tgcctctcag cctctgtctc tgaggcccga agcttgtaga     960
cctgctgctg gcggagctgt gcacaccaga ggactggatt tcgcctgctt ttgggtgctg    1020
gtggtcgtgg gcggagtgct ggcttgttat tctctgctgg tcaccgtggc cttcatcatc    1080
ttttgggtcc gactgaagat ccaggtccga aaggccgcca tcaccagcta cgagaagtct    1140
gatggcgtgt acaccggcct gagcaccaga aaccaggaaa cctacgagac actgaagcac    1200
gagaagcccc cccag                                                     1215

<210> SEQ ID NO 66
<211> LENGTH: 1203
<212> TYPE: DNA
<213> ORGANISM: Artificial Sequence
<220> FEATURE:
<223> OTHER INFORMATION: artificial sequence

<400> SEQUENCE: 66
atggactgga tctggcgcat cctcttcctc gtcggcgctg ctaccggcgc tcattcggcc      60
cagccggccg acattcaaat gactcagtcc ccttccagct gtcagcctc agtagggac     120 cgggtcacga tcacctgtcg agcgtctgag tcagtggata ctacgggat ttctttcatg     180 aactggttcc agcagaagcc cggcaaagct cctaagctcc ttatatatgc agcctcaaat     240
caggggagcg tgttcctag tcgcttcagt ggaagcggta gcggtacgga ctttacgttg     300
acgataagta gccttcagcc agatgacttt gccacttatt attgtcagca gtctaaggaa     360
gttccttgga cgtttggcca aggaacgaag gtcgaaatca aaggggagg gggctcagga     420 gggggcggca gtggtggtgg aggctctcaa gtccaactcg tacagtctgg cgcggaggtt     480

```
aaaaagccgg gaagctccgt gaaagtatcc tgtaaggcaa gcggatacac ctttaccgat    540
tataacatgc actgggttag gcaggcgccc ggccaaggtc tggaatggat cggttatatt    600
tatccataca acgtggtac cggctataat cagaagttta agagtaaggc tactattaca    660
gcggatgagt caaccaatac tgcatacatg gagctctcct cactcaggag cgaagatacc    720
gcagtgtatt actgtgcccg agggagacca gccatggact actggggtca gggtacccct    780
gtgacagtat ctagcgcggc cgcgctgagc aacagcatca tgtacttcag ccacttcgtg    840
cctgtgttcc tgcctgccaa gcctacaaca caccagccc ctagacctcc aaccccctgcc    900 cctacaattg cctctcagcc tctgtctctg aggcccgaag cttgtagacc tgctgctggc    960
ggagctgtgc acaccagagg actggatttc gcctgctttt gggtgctggt ggtcgtgggc   1020
ggagtgctgg cttgttattc tctgctggtc accgtggcct tcatcatctt ttgggtccga   1080
ctgaagatcc aggtccgaaa ggccgccatc accagctacg agaagtctga tggcgtgtac   1140
accggcctga gcaccagaaa ccaggaaacc tacgagacac tgaagcacga aagccccc    1200 cag                                                                  1203

<210> SEQ ID NO 67
<211> LENGTH: 1596
<212> TYPE: DNA
<213> ORGANISM: Artificial Sequence
<220> FEATURE:
<223> OTHER INFORMATION: artificial sequence

<400> SEQUENCE: 67
atgaaccggg gagtcccttt taggcacttg cttctggtgc tgcaactggc gctcctccca     60
gcagccactc agggaaagaa agtggtgctg gcaaaaaag gggatacagt ggaactgacc    120
tgtacagctt cccagaagaa gagcatacaa ttccactgga aaaactccaa ccagataaag    180
attctgggaa atcagggctc cttcttaact aaaggtccat ccaagctgaa tgatcgcgct    240
gactcaagaa gaagcctttg ggaccaagga aactttcccc tgatcatcaa gaatcttaag    300
atagaagact cagatactta catctgtgaa gtggaggacc agaaggagga ggtgcaattg    360
ctagtgttcg gattgactgc caactctgac acccacctgc ttcaggggca gagcctgacc    420
ctgaccttgg agaccccccc tggtagtagc ccctcagtgc aatgtaggag tccaagggt    480 aaaaacatac agggggggaa gaccctctcc gtgtctcagc tggagctcca ggatagtggc    540
acctggacat gcactgtctt gcagaaccag aagaaggtgg agttcaaaat agacatcgtg    600
gtgctagctt ccagaaggc ctccagcata gtctataaga agaggggga acaggtggag    660 ttctccttcc cactcgcctt tacagttgaa aagctgacgg gcagtggcga gctgtggtgg    720
caggcggaga gggcttcctc ctccaagtct tggatcacct tgacctgaa gaacaaggaa    780 gtgtctgtaa acgggttac ccaggaccct aagctccaga tgggcaagaa gctcccgctc    840
cacctcaccc tgccccaggc cttgcctcag tatgctggct ctggaaacct cacccctggcc    900 cttgaagcga aaacaggaaa gttgcatcag gaagtgaacc tggtggtgat gagagccact    960
cagctccaga aaaatttgac ctgtgaggtg tggggaccca cctcccctaa gctgatgctg   1020
agtttgaaac tggagaacaa ggaggcaaag gtctcgaagc gggagaaggc ggtgtgggtg   1080
ctgaaccctg aggcgggat gtggcagtgt ctgctgagtg actcgggaca ggtcctgctg   1140
gaatccaaca tcaaggttct gcccacatgg tccacccgg tgcagccagc ggccgcgctg   1200
agcaacagca tcatgtactt cagccacttc gtgcctgtgt tcctgcctgc caagcctaca   1260
```

| | |
|---|---|
| acaacaccag cccctagacc tccaacccct gccoctacaa ttgcctctca gcctctgtct | 1320 |
| ctgaggcccg aagcttgtag acctgctgct ggcggagctg tgcacaccag aggactggat | 1380 |
| ttcgcctgct tttgggtgct ggtggtcgtg ggcggagtgc tggcttgtta ttctctgctg | 1440 |
| gtcaccgtgg ccttcatcat cttttgggtc cgactgaaga tccaggtccg aaaggccgcc | 1500 |
| atcaccagct acgagaagtc tgatggcgtg tacaccggcc tgagcaccag aaaccaggaa | 1560 |
| acctacgaga cactgaagca cgagaagccc cccag | 1596 |

<210> SEQ ID NO 68
<211> LENGTH: 1215
<212> TYPE: DNA
<213> ORGANISM: Artificial Sequence
<220> FEATURE:
<223> OTHER INFORMATION: artificial sequence

<400> SEQUENCE: 68

| | |
|---|---|
| atggactgga tctggcggat tctgtttctc gtgggagctg ccacaggcgc tcattctgct | 60 |
| cagcctgccg aagttcagct tgtagaatct ggaggtggat tggttcaacc tggtggctct | 120 |
| cttcgcctga gttgtgcagc ctctggtttt actttcaata gttacgctat gcattgggtt | 180 |
| cgtcaggctc ctgggaaagg cctggaatgg gtttcagcta ttagtggtaa tggaggtagt | 240 |
| actcgttacg cagacagtgt gaaaggtcgc ttcaccatca gccgtgataa ttctaagaac | 300 |
| actttgtacc tgcaaatgaa ctccttgcgc gcagaagaca cggctgtgta ctattgtgcc | 360 |
| cgtgatcgct tcggaaggt tcatggtttc gatgtatggg gacaaggtac cctggtaacg | 420 |
| gtttctagcg gaggtggtgg gagtggtgga ggcggctcgg tgaggtgg ttcaggagga | 480 |
| ggcggagata tccaaatgac tcaatctcct agttcactgt cagcctctgt tggtgatcgc | 540 |
| gtgaccatta cctgccaagc tagccaggat attagcaact acttgaactg gtatcagcag | 600 |
| aagcctggca agcccccaaa gctgttgatc tacgatgcaa gtaacttgga aactggcgtc | 660 |
| ccaagccgct ctctggatc tggttcaggc accgacttca ctttcactat cagcagcctg | 720 |
| cagcctgaag atatcgcaac ctactattgc cagcaggatg ctacttttcc tttgactttc | 780 |
| ggccaaggca ccaaggtgga gatcaaggcg ccgcgctga gcaacagcat catgtacttc | 840 |
| agccacttcg tgcctgtgtt cctgcctgcc aagcctacaa caacaccagc ccctagacct | 900 |
| ccaacccctg cccctacaat tgcctctcag cctctgtctc tgaggcccga agcttgtaga | 960 |
| cctgctgctg gcggagctgt gcacaccaga ggactggatt tcgcctgctt tgggtgctg | 1020 |
| gtggtcgtgg gcggagtgct ggcttgttat tctctgctgg tcaccgtggc cttcatcatc | 1080 |
| ttttgggtcc gactgaagat ccaggtccga aaggccgcca tcaccagcta cgagaagtct | 1140 |
| gatggcgtgt acaccggcct gagcaccaga aaccaggaaa cctacgagac actgaagcac | 1200 |
| gagaagcccc cccag | 1215 |

<210> SEQ ID NO 69
<211> LENGTH: 1194
<212> TYPE: DNA
<213> ORGANISM: Artificial Sequence
<220> FEATURE:
<223> OTHER INFORMATION: artificial sequence

<400> SEQUENCE: 69

| | |
|---|---|
| atggactgga tctggcggat tctgtttctc gtgggagctg ccacaggcgc tcattctgct | 60 |
| cagcctgccg tccagctgca gcagtctgga cctgagctgg taaagcctgg gcttcagtg | 120 |
| aagatgtcct gcaaggcttc tggatacaca ttcactagct atgttatgca ctgggtgaag | 180 |

```
cagaagcctg ggcagggcct tgagtggatt ggatatatta ttccttacaa tgatgctact    240
aagtacaatg agaagttcaa aggcaaggcc acactgactt cagacaaatc ctccagcaca    300
gcctacatgg agctcagcag cctgacctct gaggactctg cggtctatta ctgtgcacgc    360
tataattacg acgggtactt cgatgtctgg ggcgcaggga ccacggtcac cgtctcctca    420
ggcggcggag gaagcggagg cggaggatct ggggcggag gctctgacat tgtgatgact    480
cagtctccag ccaccctgtc tgtgactcca ggagatagag tctctctttc ctgcagggcc    540
agccagagta ttagcgacta cttacactgg tatcaacaaa aatcacatga gtctccaagg    600
cttctcatca aatatgcttc ccaatccatc tctggaatcc cctccaggtt cagtggcagt    660
ggatcagggt cagatttcac tctcagtatc aacagtgtgg aacctgaaga tgttggagtg    720
tattactgtc aaaatggtca cagctttcct ccgacgttcg gtggaggcac caagctggaa    780
atcaaagcgg ccgcgctgag caacagcatc atgtacttca gccacttcgt gcctgtgttc    840
ctgcctgcca agcctacaac aacaccagcc cctagacctc caaccctgc ccctacaatt    900 gcctctcagc ctctgtctct gaggcccgaa gcttgtagac ctgctgctgg cggagctgtg    960
cacaccagag gactggattt cgcctgcttt tgggtgctgg tggtcgtggg cggagtgctg   1020
gcttgttatt ctctgctggt caccgtggcc ttcatcatct tttgggtccg actgaagatc   1080
caggtccgaa aggccgccat caccagctac gagaagtctg atggcgtgta caccggcctg   1140
agcaccagaa accaggaaac ctacgagaca ctgaagcacg agaagccccc ccag         1194
```

<210> SEQ ID NO 70
<211> LENGTH: 1206
<212> TYPE: DNA
<213> ORGANISM: Artificial Sequence
<220> FEATURE:
<223> OTHER INFORMATION: artificial sequence

<400> SEQUENCE: 70

```
atggactgga tctggcggat tctgtttctc gtgggagctg ccacaggcgc tcattctgct     60
cagcctgccc aggtgcaagt gaaagagtct ggccctggac tggtggcccc aagccagtct    120
ctgagcatca catgtaccgt gtccggcttc agcctgacca ctatggcgt gcactgggtc    180 cgacagcctc caggcaaagg actggaatgg ctgggagtga tttgggctgg cggcagcacc    240
aactacaaca gcgccctgat gagccggctg agcatctcca aggacaacag caagagccag    300
gtgttcctga agatgaacag cctgcagacc gacgacaccg ccatgtacta ctgtgctagc    360
agaggcggca actacggcta cgccctggat tattgggcc agggcacaag cgtgaccgtg    420
tcatctggcg gcggaggaag cggaggcgga ggatctgggg cggaggctc tggcggaggg    480 ggatctagca tcgtgatgac ccagactcct aagttcctgc tggtgtctgc cggcgacaga    540
gtgaccatca cctgtaaagc cagccagagc gtgtccaacg acgtggcctg gtatcagcag    600
aagcctggac agagccccaa gctgctgatc tacagcgcca gcaacagata caccggcgtg    660
cccgatagat tcaccggctc tggctacggc accgacttca cctttaccat cagcaccgtg    720
caggccgagg atctggccgt gtacttctgc cagcaagact acagctctct cggcggaggc    780
accaagctgg aaatcaaagc ggccgcgctg agcaacagca tcatgtactt cagccacttc    840
gtgcctgtgt tcctgcctgc caagcctaca acaaccag ccctagacc tccaaccct     900 gccctacaa ttgcctctca gcctctgtct ctgaggcccg aagcttgtag acctgctgct    960
ggcggagctg tgcacaccag aggactggat ttcgcctgct tttgggtgct ggtggtcgtg   1020
```

```
ggcggagtgc tggcttgtta ttctctgctg gtcaccgtgg ccttcatcat cttttgggtc    1080
cgactgaaga tccaggtccg aaaggccgcc atcaccagct acgagaagtc tgatggcgtg    1140
tacaccggcc tgagcaccag aaaccaggaa acctacgaga cactgaagca cgagaagccc    1200
ccccag                                                               1206

<210> SEQ ID NO 71
<211> LENGTH: 1248
<212> TYPE: DNA
<213> ORGANISM: Artificial Sequence
<220> FEATURE:
<223> OTHER INFORMATION: artificial sequence

<400> SEQUENCE: 71
atggactgga tctggcggat tctgtttctc gtgggagctg ccacaggcgc tcattctgct      60
cagcctgccc aggttcagct gcagcagtct ggacctgagc tggttaagcc tggcgcctcc     120
gtgaagatga gctgcaagac cagccggtac accttcaccg agtacaccat ccactgggtc     180
cgacagagcc acggcaagag cctggaatgg atcggcggca tcaaccccaa caacggcatc     240
cccaactaca accagaagtt caagggcaga gccacactga ccgtgggcaa gtctagcagc     300
accgcctaca tggaactgcg gagcctgaca agcgaggaca cgccgtgta cttctgcgcc     360 agaagaagaa tcgcctacgg ctacgatgag ggccacgcca tggattattg gggccaggga     420
acaagcgtga ccgtgtctag tggcggcgga ggaagcggag cggaggatc tggggcgga     480 ggctctggcg agggggatc tgacatcgtg atgacacaga gcccttctag cctggccgtg     540
tccgtgggag agaaagtgac catgagctgc aagagcagcc agagcctgct gtactcccgg     600
aaccagaaga actacctggc ctggttccag cagaagcccg gccagtctcc taagctgctg     660
atcttctggg ccagcaccag agaaagcggc gtgcccgata gattcaccgg cagcggcttt     720
ggcaccgact tcaacctgac aatcagcagc gtgcaggccg aggacctggc tgtgtacgat     780
tgccagcagt acttcagcta ccctctgacc tttggagccg gcaccaagct ggaactgaga     840
gcggccgcgc tgagcaacag catcatgtac ttcagccact cgtgcctgt gttcctgcct     900 gccaagccta caacaacacc agcccctaga cctccaaccc ctgccctac aattgcctct     960 cagcctctgt ctctgaggcc gaagcttgt agacctgctg ctggcggagc tgtgcacacc    1020
agaggactgg atttcgcctg cttttgggtg ctggtggtcg tgggcggagt gctggcttgt    1080
tattctctgc tggtcaccgt ggccttcatc atcttttggg tccgactgaa gatccaggtc    1140
cgaaaggccg ccatcaccag ctacgagaag tctgatggcg tgtacaccgg cctgagcacc    1200
agaaaccagg aaacctacga gacactgaag cacgagaagc ccccccag                1248

<210> SEQ ID NO 72
<211> LENGTH: 510
<212> TYPE: DNA
<213> ORGANISM: Artificial Sequence
<220> FEATURE:
<223> OTHER INFORMATION: artificial sequence

<400> SEQUENCE: 72
atgcgcatca gcaagcccca cctgcgcagc atcagcatcc agtgctacct gtgcctgctg      60
ctgaacagcc acttcctgac cgaggccggc atccacgtgt catcctgggg ctgcttcagc     120
gccggcctgc ccaagaccga ggccaactgg gtgaacgtga tcagcgacct gaagaagatc     180
gaggacctga tccagagcat gcacatcgac gccaccctgt acaccgagag cgacgtgcac     240
cccagctgca aggtgaccgc catgaagtgc ttcctgctgg agctgcaggt gatcagcctg     300
```

```
gagagcggcg acgccagcat ccacgacacc gtggagaacc tgatcatcct ggccaacaac      360
agcctgagca gcaacggcaa cgtgaccgag agcggctgca aggagtgcga ggagctggag      420
gagaagaaca tcaaggagtt cctgcagagc ttcgtgcaca tcgtgcagat gttcatcaac      480
accagcggct ccgagaagga cgagctgtaa                                      510
```

<210> SEQ ID NO 73
<211> LENGTH: 169
<212> TYPE: PRT
<213> ORGANISM: Artificial Sequence
<220> FEATURE:
<223> OTHER INFORMATION: artificial sequence

<400> SEQUENCE: 73

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser Gly Ser Glu Lys Asp Glu Leu
                165
```

<210> SEQ ID NO 74
<211> LENGTH: 1215
<212> TYPE: DNA
<213> ORGANISM: Artificial Sequence
<220> FEATURE:
<223> OTHER INFORMATION: artificial sequence

<400> SEQUENCE: 74

```
atggactgga tctggcgcat cctcttcctc gtcggcgctg ctaccggcgc tcattcggcc       60
cagccggcca tggcgcaagt aaaactccaa gaatctgggg cggagctggt gaaaccgggg      120
gcgtctgtga agatgagctg taaagcatca ggctacacct tcacctccta taatatgcac      180
tgggtgaaac aaacacccgg acagggcctc gaatggattg gtgccatcta tcctggaaat      240
ggtgataccc catataatca gaagtttaag ggcaaggcta cgcttactgc ggataaaagc      300
tcttccactg cttacatgca actgagcagt ctcacttcag aggactcagc cgattattat      360
tgtgcccgca gcaactacta tggtagttca tactggtttt tcgacgtttg ggggcaaggt      420
accaccgtca cggtttcttc tggtggggc ggaagcgggg gtgaggatc tggggggcggt      480 ggttcagaca ttgaactcac ccagagccct actattctga gcgcgtctcc aggtgaaaaa      540
```

```
gttacgatga cgtgcagagc atcaagtagt gtgaattata tggattggta tcaaaagaag      600
ccaggctcat ccccaaaacc gtggatctat gcaactagca acctcgcgtc agggqtgcca      660 gcaaggtttt ccggaagtgg ttctggcaca tcttatagtc tcaccatttc ccgagtggag      720
gctgaggatg cggccactta ttactgccag caatggtcat tcaatcccccc aacatttggt      780 ggcggaacaa aactcgaaat taaacgggcg ccgcgctga gcaacagcat catgtacttc      840
agccacttcg tgcctgtgtt cctgcctgcc aagcctacaa caacaccagc ccctagacct      900 ccaaccccctg ccctacaat tgcctctcag cctctgtctc tgaggcccga agcttgtaga      960
cctgctgctg gcggagctgt gcacaccaga ggactggatt tcgcctgctt ttgggtgctg      1020
gtggtcgtgg gcggagtgct ggcttgttat tctctgctgg tcaccgtggc cttcatcatc      1080 tttgggtcc gactgaagat ccaggtccga aaggccgcca tcaccagcta cgagaagtct      1140
gatggcgtgt acaccggcct gagcaccaga aaccaggaaa cctacgagac actgaagcac      1200
gagaagcccc cccag                                                        1215

<210> SEQ ID NO 75
<211> LENGTH: 1248
<212> TYPE: DNA
<213> ORGANISM: Artificial Sequence
<220> FEATURE:
<223> OTHER INFORMATION: artificial sequence

<400> SEQUENCE: 75
atggactgga tctggcgcat cctcttcctc gtcggcgctg ctaccggcgc tcattcggcc       60
cagccggccg atatcgagct cacccaatct ccaaaattca tgtccacatc agtaggagac      120
agggtcagcg tcacctgcaa ggccagtcag aatgtggata ctaatgtagc gtggtatcaa      180
caaaaaccag ggcaatctcc tgaaccactg cttttctcgg catcctaccg ttacactgga      240
gtccctgatc gcttcacagg cagtggatct gggacagatt tcactctcac catcagcaat      300
gtgcagtctg aagacttggc agagtatttc tgtcagcaat ataacagcta tcctctgacg      360
ttcggtggcg gcaccaagct ggaaatcaaa cgggctgccg cagaaggtgg aggcggttca      420
ggtggcggag gttccggcgg aggtggctct ggcggtggcg gatcggccat ggcccaggtg      480
aagctgcagc agtcaggagg gggcttggtg caacctggag gctccatgaa actctcctgt      540
gttgtctctg gattcacttt cagtaattac tggatgaact gggtccgcca gtctccagag      600
aaggggcttg agtggattgc agaaattaga ttgaaatcca ataattttgg aagatattat      660
gcggagtctg tgaaagggag gttcaccatc tcaagagatg attccaaaag tagtgcctac      720
ctgcaaatga tcaacctaag agctgaagat actggcatt tattactgtac cagttatggt      780 aactacgttg gcactatttt tgaccactgg ggccaaggga ccacggtcac cgtatccgagt      840 gcggccgcgc tgagcaacag catcatgtac ttcagccact tcgtgcctgt gttcctgcct      900
gccaagccta caacaacacc agcccctaga cctccaaccc ctgcccctac aattgcctct      960
cagcctctgt ctctgaggcc cgaagcttgt agacctgctg ctggcggagc tgtgcacacc      1020
agaggactgg atttcgcctg cttttgggtg ctggtggtcg tgggcggagt gctggcttgt      1080
tattctctgc tggtcaccgt ggccttcatc atcttttggg tccgactgaa gatccaggtc      1140
cgaaaggccg ccatcaccag ctacgagaag tctgatggcg tgtacaccgg cctgagcacc      1200
agaaaccagg aaacctacga gacactgaag cacgagaagc cccccccag                  1248

<210> SEQ ID NO 76
```

<211> LENGTH: 6787
<212> TYPE: DNA
<213> ORGANISM: Artificial Sequence
<220> FEATURE:
<223> OTHER INFORMATION: artificial sequence

<400> SEQUENCE: 76

```
tgtatttaga aaaataaaca aatagggggtt ccgcgcacat ttccccgaaa agtgccacct        60
gacgtcgacg gatcgggaga tctcccgatc ccctatggtg cactctcagt acaatctgct       120
ctgatgccgc atagttaagc cagtatctgc tccctgcttg tgtgttggag gtcgctgagt       180
agtgcgcgag caaaatttaa gctacaacaa ggcaaggctt gaccgacaat tgcatgaaga       240
atctgcttag ggttaggcgt tttgcgctgc ttcgggatcc gctgaccaaa agagcaccaa       300
aggcgccctg accttcagcc cctacctgcg ctccggtgcc cgtcagtggg cagagcgcac       360
atcgcccaca gtccccgaga agttgggggg agggtcggc aattgaaccg gtgcctagag       420
aaggtggcgc ggggtaaact gggaaagtga tgtcgtgtac tggctccgcc ttttcccga       480
gggtggggga gaaccgtata taagtgcagt agtcgccgtg aacgttcttt ttcgcaacgg       540
gtttgccgcc agaacacagg taagtgccgt gtgtggttcc cgcgggcctg gcctctttac       600
gggttatggc ccttgcgtgc cttgaattac ttccacctgg ctgcagtacg tgattcttga       660
tcccgagctt cgggttggaa gtgggtggga gagttcgagg ccttgcgctt aaggagcccc       720
ttcgcctcgt gcttgagttg aggcctgcc tgggcgctgg ggccgccgcg tgcgaatctg       780
gtggcacctt cgcgcctgtc tcgctgcttt cgataagtct ctagccattt aaaattttg       840
atgacctgct gcgacgcttt ttttctggca agatagtctt gtaaatgcgg gccaagatct       900
gcacactggt atttcggttt ttggggccgc gggcggcgac ggggcccgtg cgtcccagcg       960
cacatgttcg gcgaggcggg gcctgcgagc gcggccaccg agaatcggac gggggtagtc      1020
tcaagctggc cggcctgctc tggtgcctgg cctcgcgccg ccgtgtatcg ccccgccctg      1080
ggcggcaagg ctggcccggt cggcaccagt tgcgtgagcg gaaagatggc cgcttccccgg     1140
ccctgctgca gggagctcaa aatggaggac gcggcgctcg ggagagcggg cgggtgagtc      1200
acccacacaa aggaaaaggg cctttccgtc ctcagccgtc gcttcatgtg actccacgga      1260
gtaccgggcg ccgtccaggc acctcgatta gttctcgagc ttttggagta cgtcgtcttt      1320
aggttgggg gagggttttt atgcgatgga gtttccccac actgagtggg tggagactga      1380
agttaggcca gcttggcact tgatgtaatt ctccttggaa tttgcccttt ttgagtttgg      1440
atcttggttc attctcaagc ctcagacagt ggttcaaagt ttttttcttc catttcaggt      1500
gtcgtgataa tacgactcac tatagggaga cccaagctgg aattcgccac catggactgg      1560
atctggcgga ttctgttct cgtgggagct gccacaggcg ctcattctgc tcagcctgcc      1620
gatgttgtaa tgacgcagtc acccctgtca ctcccggtca cacccggaga accagcgtca      1680
attagctgcc gatctagcca aagtttgctt cattccaatg gttacaatta tctgactgg      1740
tacttgcaga aacccggcca atcccctcag ctgctcatct accttgggtc taataggggca     1800
tctggggttc ccgataggtt ctctggctcc gggagcggca ccgactttac gttgaaaatc      1860
tctaggggttg aggcggaaga cgtaggcgtt tactattgca tgcaggggac ccactggccg     1920
ctgaccttcg gccagggcac caaggttgaa ataaaaggcg gcggaggaag cggaggcgga      1980
ggatctgggg gcggaggctc tggcggaggg ggatctcagg tacagctcca ggaatcagga      2040
cccggtttgg ttaagccctc cgggacccctt tccctcacgt gtgcagtctc aggtgggtca      2100
attagttctt ccaattggtg gtcttgggtg cggcaaccac ctggtaaagg tctcgagtgg      2160
```

```
ataggggaaa tttatcatag tggctccacc aattataacc cctcactcaa gtccagggtt    2220
acgatatctg tggacaaaag taaaaaccaa ttctccctca aacttagtag tgtaacagcg    2280
gcagacaccg cggtgtacta ctgcgcacgg tggacaggcc gaactgatgc ctttgacatt    2340
tggggacagg aactatggt gactgtgtca tccgcggccg cgctgagcaa cagcatcatg     2400
tacttcagcc acttcgtgcc tgtgttcctg cctgccaagc ctacaacaac accagcccct    2460
agacctccaa cccctgcccc tacaattgcc tctcagcctc tgtctctgag gcccgaagct    2520
tgtagacctg ctgctggcgg agctgtgcac accagaggac tggatttcgc ctgcttttgg    2580
gtgctggtgg tcgtgggcgg agtgctggct tgttattctc tgctggtcac cgtggccttc    2640
atcatctttt gggtccgact gaagatccag gtccgaaagg ccgccatcac cagctacgag    2700
aagtctgatg gcgtgtacac cggcctgagc accagaaacc aggaaaccta cgagacactg    2760
aagcacgaga agccccccca gggatctgga gctactaact tcagcctgct gaagcaggct    2820
ggagacgtgg aggagaaccc tggacctatg tggcagctgc tgctgcctac agctctcctg    2880
ctgctggtgt ccgccggcat gagaaccgag gatctgccta aggccgtggt gttcctggaa    2940
ccccagtggt acagagtgct ggaaaaggac agcgtgaccc tgaagtgcca gggcgcctac    3000
agccccgagg acaatagcac ccagtggttc cacaacgaga gcctgatcag cagccaggcc    3060
agcagctact catcgacgc cgccaccgtg acgacagcg gcgagtatag atgccagacc    3120
aacctgagca ccctgagcga ccccgtgcag ctggaagtgc acatcggatg gctgctgctg    3180
caggccccca gatgggtgtt caaagaagag gaccccatcc acctgagatg ccactcttgg    3240
aagaacaccg ccctgcacaa agtgacctac ctgcagaacg gcaagggcag aaagtacttc    3300
caccacaaca gcgacttcta catccccaag gccaccctga aggactccgg ctcctacttc    3360
tgcagaggcc tcgtgggcag caagaacgtg tccagcgaga cagtgaacat caccatcacc    3420
cagggcctgg ccgtgtctac catcagcagc ttttttcccac ccggctacca ggtgtccttc    3480
tgcctcgtga tggtgctgct gttcgccgtg gacaccggcc tgtacttcag cgtgaaaaca    3540
aacatcagaa gcagcacccg ggactggaag gaccacaagt tcaagtggcg gaaggacccc    3600
caggacaagt gaaattccgc ccctctcccc cccccccctc tccctccccc ccccctaacg    3660
ttactggccg aagccgcttg gaataaggcc ggtgtgcgtt tgtctatatg ttatttttcca   3720 ccatattgcc gtcttttggc aatgtgaggg cccggaaacc tggccctgtc ttcttgacga    3780
gcattcctag gggtctttcc cctctcgcca aaggaatgca aggtctgttg aatgtcgtga    3840
aggaagcagt tcctctggaa gcttcttgaa gacaaacaac gtctgtagcg accctttgca    3900
ggcagcggaa cccccaccct ggcgacaggt gcctctgcgg ccaaaagcca cgtgtataag    3960
atacacctgc aaaggcggca caaccccagt gccacgttgt gagttggata gttgtggaaa    4020
gagtcaaatg gctctcctca agcgtattca acaagggct gaaggatgcc cagaaggtac     4080
cccattgtat gggatctgat ctggggcctc ggtgcacatg ctttacatgt gtttagtcga    4140
ggttaaaaaa acgtctaggc ccccgaacc acggggacgt ggttttcctt tgaaaaacac     4200
gataaccgcc accatgtacc ggatgcagct gctgagctgt atcgccctgt ctctggccct    4260
cgtgaccaac agcgccccta ccagcagcag caccaagaaa acccagctgc agctggaaca    4320
tctgctgctg gacctgcaga tgatcctgaa cggcatcaac aactacaaga accccaagct    4380
gacccggatg ctgaccttca agttctacat gcccaagaag gccaccgaac tgaaacatct    4440
gcagtgcctg gaagaggaac tgaagcccct ggaagaagtg ctgaacctgg cccagagcaa    4500
```

-continued

```
gaacttccac ctgaggccca gggacctgat cagcaacatc aacgtgatcg tgctggaact    4560
gaaaggcagc gagacaacct tcatgtgcga gtacgccgac gagacagcta ccatcgtgga    4620
atttctgaac cggtggatca ccttctgcca gagcatcatc agcaccctga ccggctccga    4680
gaaggacgag ctgtgagcgg ccgcccgctg atcagcctcg aacgagattt cgattccacc    4740
gccgccttct atgaaaggtt gggcttcgga atcgttttcc gggacgccgg ctggatgatc    4800
ctccagcgcg gggatctcat gctggagttc ttcgcccacc ccaacttgtt tattgcagct    4860
tataatggtt acaaataaag caatagcatc acaaatttca caaataaagc attttttca    4920 ctgcattcta gttgtggttt gtccaaactc atcaatgtat cttatcatgt ctgtgcggtg    4980
ggctctatgg cttctgaggc ggaaagaacc agctggggct cctaggggta tccccggatc    5040
ctgagcaaaa ggccagcaaa aggccaggaa ccgtaaaaag gccgcgttgc tggcgttttt    5100
ccataggctc cgcccccctg acgagcatca caaaaatcga cgctcaagtc agaggtggcg    5160
aaacccgaca ggactataaa gataccaggc gtttccccct ggaagctccc tcgtgcgctc    5220
tcctgttccg accctgccgc ttaccggata cctgtccgcc tttctccctt cgggaagcgt    5280
ggcgctttct catagctcac gctgtaggta tctcagttcg gtgtaggtcg ttcgctccaa    5340
gctgggctgt gtgcacgaac cccccgttca gcccgaccgc tgcgccttat ccggtaacta    5400
tcgtcttgag tccaacccgg taagacacga cttatcgcca ctggcagcag ccactggtaa    5460
caggattagc agagcgaggt atgtaggcgg tgctacagag ttcttgaagt ggtggcctaa    5520
ctacggctac actagaagaa cagtatttgg tatctgcgct ctgctgaagc cagttacctt    5580
cggaaaaaga gttggtagct cttgatccgg caaacaaacc accgctggta gcggtggttt    5640
ttttgtttgc aagcagcaga ttacgcgcag aaaaaaagga tctcaagaag atcctttgat    5700
cttttctacg gggtctgacg ctcagtggaa cgaaaactca cgttaaggga ttttggtcat    5760
gagattatca aaaaggatct tcacctagat ccttttaaat taaaaatgaa gttttaaatc    5820
aatctaaagt atatatgagt aaacttggtc tgacagttac caatgcttaa tcagtgaggc    5880
acctatctca gcgatctgtc tatttcgttc atccatagtt gcctgactcc ccgtcgtgta    5940
gataactacg atacgggagg gcttaccatc tggccccagt gctgcaatga taccgcgaga    6000
accacgctca ccggctccag atttatcagc aataaaccag ccagccggaa gggccgagcg    6060
cagaagtggt cctgcaactt tatccgcctc catccagtct attaattgtt gccgggaagc    6120
tagagtaagt agttcgccag ttaatagttt gcgcaacgtt gttgccattg ctacaggcat    6180
cgtggtgtca cgctcgtcgt ttggtatggc ttcattcagc tccggttccc aacgatcaag    6240
gcgagttaca tgatccccca tgttgtgcaa aaaagcggtt agctccttcg gtcctccgat    6300
cgttgtcaga agtaagttgg ccgcagtgtt atcactcatg gttatggcag cactgcataa    6360
ttctcttact gtcatgccat ccgtaagatg cttttctgtg actggtgagt actcaaccaa    6420
gtcattctga gaatagtgta tgcggcgacc gagttgctct tgcccggcgt caatacggga    6480
taataccgcg ccacatagca gaactttaaa agtgctcatc attggaaaac gttcttcggg    6540
gcgaaaactc tcaaggatct taccgctgtt gagatccagt tcgatgtaac ccactcgtgc    6600
acccaactga tcttcagcat cttttacttt caccagcgtt tctgggtgag caaaaacagg    6660
aaggcaaaat gccgcaaaaa agggaataag ggcgacacgg aaatgttgaa tactcatact    6720 cttcctttt caatattatt gaagcattta tcagggttat tgtctcatga gcggatacat    6780
atttgaa                                                              6787
```

CHIMERIC ANTIGEN RECEPTOR-MODIFIED NK-92 CELLS

This application claims priority to our U.S. provisional applications with the Ser. Nos. 62/756,395 and 62/756,402, both filed Nov. 6, 2018.

SEQUENCE LISTING

The content of the ASCII text file of the sequence listing named 104077.0003PCT5 Sequence Listing_ST25, which is 134 kb in size was created on May 20, 2019 and electronically submitted via EFS-Web along with the application is incorporated by reference in its entirety.

FIELD OF THE INVENTION

The field of the invention is genetically modified immune competent cells that express a chimeric antigen receptor (CAR), and particularly modified NK-92 cells expressing a CAR with an Fc epsilon receptor gamma (FcεRIγ) signaling domain.

BACKGROUND OF THE INVENTION

Natural killer (NK) cells are cytotoxic lymphocytes that constitute a significant component of the innate immune system. In most cases, NK cells represent about 10-15% of circulating lymphocytes, and bind and kill targeted cells, including virus-infected cells and many malignant cells. NK cell killing is non-specific with regard to particular antigens and can occur without prior immune sensitization. Killing of targeted cells is typically mediated by cytolytic proteins, including perforin, granzyme, and granulysin.

Autologous NK cells have been used as therapeutic entities. To that end, NK cells are isolated from the peripheral blood lymphocyte fraction of whole blood, expanded in cell culture to obtain sufficient numbers of cells, and then re-infused into a subject. Autologous NK cells have shown in at least some cases moderate effectiveness in both ex vivo therapy and in vivo treatment. However, isolation and growth of autologous NK cell is time and cost intensive. Moreover, autologous NK cell therapy is further limited by the fact that not all NK cells are cytolytic.

At least some of these difficulties can be overcome by use of NK-92 cells, which are a cytolytic cancer cell line which was discovered in the blood of a subject suffering from a non-Hodgkins lymphoma and then immortalized in vitro (Gong et al., *Leukemia* 8:652-658 (1994)). While NK-92 cells are NK cell derivatives, NK-92 cells lack the major of inhibitory receptors that are otherwise displayed by normal NK cells, and retain the majority of the activating receptors. NK-92 cells do not, however, attack normal cells nor do they elicit an unacceptable immune rejection response in humans. Due to these desirable characteristics, NK-92 cells were characterized in detail and explored as therapeutic agent in the treatment of certain cancers as is described, for example, in WO 1998/049268 or US 2002/068044.

Phenotypic changes distinguishing a tumor cell from normal cells derived from the same tissue are often associated with one or more changes in the expression of specific gene products, including the loss of normal cell surface components or the gain of others (i.e., antigens not detectable in corresponding normal, non-cancerous tissue). The antigens which are expressed in neoplastic or tumor cells, but not in normal cells, or which are expressed in neoplastic cells at levels substantially above those found in normal cells, have been termed "tumor-specific antigens" or "tumor-associated antigens." Such tumor-specific antigens may serve as markers for tumor phenotype. Tumor-specific antigens include cancer/testis-specific antigen (e.g. MAGE, BAGE, GAGE, PRAME and NY-ESP-1), melanocyte differentiation antigens (e.g. tyrosinase, Melan-A/MART, gp100, TRP-1 and TRP-2), mutated or aberrantly expressed antigens (e.g. MUM-1, CDK4, beta-catenin, gp100-in4, p15 and N-acetylglucos-aminyltransferase V), and antigens that are expressed at higher levels in tumors (e.g., CD19 and CD20).

Tumor-specific antigens have been used as targets for cancer immunotherapies. One such therapy utilizes chimeric antigen receptors (CARs) expressed on the surface of immune cells, including T cells and NK cells, to improve cytotoxicity against cancer cells. CARs comprise a single-chain variable fragment (scFv) linked to at least one intracellular signaling domain. The scFv recognizes and binds an antigen on the target cell (e.g., a cancer cell) and triggers effector cell activation. The signaling domains contain immunoreceptor tyrosine-based activation domains (ITAMs) that are important for intracellular signaling by the receptor.

The first generation of CARs used in T-cells contained one cytoplasmic signaling domain. For example, one version of a first-generation CAR in T-cells included a signaling domain from the Fc epsilon receptor gamma (FcεRIγ) which contained one ITAM, while another version contained the signaling domain from CD3ζ which contained three ITAMs. In vivo and in vitro studies showed that the CD3ζ CAR T-cells were more efficient at tumor eradication than FcεRIγ CAR T-cells (e.g., Haynes, et al. 2001, *J. Immunology* 166:182-187; Cartellieri, et al. 2010, *J. Biomed and Biotech, Vol.* 2010, Article ID 956304). Additional studies then revealed that certain costimulatory signals were required for full activation and proliferation of such recombinant T-cells, and second and third generation CARs combined multiple signaling domains in to a single CAR to enhance efficacy of the recombinant CAR T-cells. Due to their less desirable philological effects in the tested T-cells, first generation CARs and the FcεRIγ signaling domains were largely discarded in favor of the new, more efficient CARs using CD3ζ in combination with one or more additional signaling domains (e.g., Hermanson and Kaufman 2015, *Frontiers in Immunol., Vol.* 6, Article 195).

More recently, selected CARs have also been expressed in NK cells. For example, CAR-modified NK-92 cells have used first generation CARs with only a CD3ζ intracellular signaling domain. Several antigens have been targeted by these first generation CAR-NK cells, including CD19 and CD20 for B cell lymphoma, ErbB2 for breast, ovarian, and squamous cell carcinoma, GD2 for neuroblastoma, and CD138 for multiple myeloma. Second generation CAR-NK cells from the NK-92 line have also been created for several antigens, including EpCAM for multiple carcinomas HLA-A2 EBNA3 complex for Epstein-Barr virus, CS1 for multiple myeloma, and ErbB2 for HER2 positive epithelial cancers. The most common intracellular costimulatory domain used alongside CD3ζ in second generation NK-92 CARs is CD28. However, the potential effect of the CD28 domain is unclear since NK cells do not naturally express CD28. Additional second generation CARs have incorporated the 4-1BB intracellular signaling domain along with CD3ζ to improve NK cell persistence. Others compared functionality of different intracellular domains using an ErbB2 scFv fused with CD3ζ alone, CD28 and CD3ζ, or 4-1BB and CD3ζ tested against breast cancer cells. They found that both of the second generation constructs improved killing compared to the first generation CARs and the CD28 and CD3ζ had 65% target lysis, the 4-1BB and CD3ζ lysed 62%, and CD3ζ alone killed 51% of targets. 4-1BB and CD28 intracellular domains were also compared in a recent study using anti-CD19 CARs expressed on NK-92 cells for B cell malignancies. Still others found that CD3ζ/4-1BB constructs were less effective than CD3ζ/CD28 in cell killing and cytokine production, highlighting differential effects of CD28 and 4-1BB costimulatory domains.

Third generation NK-92 CARs were constructed of an anti-CD5 scFv with CD3ζ, CD28, and 4-1BB intracellular signaling domains and demonstrated specific and potent anti-tumor activity against a variety of T-cell leukemia and lymphoma cell lines and primary tumor cells. Such cells were also able to inhibit disease progression in xenograft mouse models of T cell Acute lymphoblastic leukemia (ALL) cell lines as well as primary tumor cells (*Transl Res.* 2017 September; 187: 32-43). In further examples, WO 2016/201304 and WO 2018/076391 teach use of third generation CD3ζ CARs expressed in NK cells and NK-92 cells.

However, NK cells (and particularly NK-92 cells) are often difficult to genetically modify as evidenced by numerous failures to engineer NK-92 cells to express an Fc receptor. Such difficulties are further compounded where NK-92 cells are transfected with multiple recombinant genes or relatively large recombinant nucleic acid payload for heterologous expression. Additionally, NK-92 cells also exhibit a significant lack of predictability with respect to recombinant expression of exogenous proteins (e.g., CD16). On a functional level, while exhibiting in most cases targeted cytotoxicity, most if not all CAR NK-92 cells require a high effector to target cell ratio.

Therefore, even though numerous recombinant NK-92 cells are known in the art, all or almost all of them suffer from various difficulties. Consequently, there remains a need for CAR-expressing NK-92 cells that express a high-activity CAR in significant quantities, and that can be readily cultivated in a simple and effective manner.

SUMMARY OF THE INVENTION

The inventors have discovered that NK-92 cells expressing an FcεRIγ-containing CAR unexpectedly exhibit superior cytolytic activity, typically at a relatively low effector to target cell ratio as compared to other constructs, and high levels of expression of the FcεRIγ-containing CAR. Moreover, such recombinant cells also expressed CD16 at desirable levels, and where further modified to express a stimulatory cytokine, recombinant NK-92 cells were also readily cultivated without the need for exogenous IL-2.

Therefore, in one aspect of the inventive subject matter, the inventors contemplate a genetically modified NK cell carrying a membrane bound recombinant chimeric antigen receptor (CAR) that comprises in a single polypeptide chain (i) an extracellular binding domain, (ii) a hinge domain, (iii) a transmembrane domain, and (iv) a FcεRIγ signaling domain. Most typically, but not necessarily, the NK cell is an NK-92 cell.

In some embodiments, the extracellular binding domain comprises a scFv, which may specifically bind to a tumor-specific antigen (e.g., CD19, CD20, GD2, HER-2, CD30, EGFR, FAP, CD33, CD123, PD-L1, IGF1R, CSPG4, or B7-H4), a tumor associated antigen (e.g., MUC-2, brachyury, CEA), or a patient- and tumor-specific antigen (e.g., neoepitope with high affinity to the patient's MHC I and/or MHC II). Alternatively, the extracellular binding domain may also specifically bind to a virus-specific antigen, and typical viruses contemplated herein include an HIV virus, an HPV virus, an RSV virus, an influenza virus, an ebolavirus, or an HCV virus. For example, suitable viral antigens include gp120 of an HIV virus.

In further embodiments, the hinge domain and/or the transmembrane domain comprise a CD8 hinge domain and/or a CD28 transmembrane domain, and/or the FcεRIγ signaling domain has an amino acid sequence of SEQ ID NO: 1.

Additionally, it is contemplated that the genetically modified NK cell may further carry a membrane bound recombinant CD16 (and especially a high-affinity variant of CD16), and/or the genetically modified NK cell may express a recombinant cytokine with an endoplasmic retention sequence.

Therefore, and viewed from a different perspective, the inventors also contemplate a genetically modified NK cell that comprises a recombinant nucleic acid encoding a chimeric antigen receptor (CAR), wherein the CAR includes in a single polypeptide chain (i) an extracellular binding domain, (ii) a hinge domain, (iii) a transmembrane domain, and (iv) a FcεRIγ signaling domain. As noted before, it is generally preferred that the NK cell is an NK-92 cell. In some embodiments, the recombinant nucleic acid is an RNA, which may be a polycistronic RNA that further encodes a CD16 and/or a cytokine with an endoplasmic retention sequence. With respect to the various domains, the same considerations as noted above apply.

In a still further aspect of the inventive subject matter, the inventors also contemplate a method of treating cancer in a patient in need thereof that comprises a step of administering to the patient a therapeutically effective amount of the genetically modified NK cells presented herein, thereby treating the cancer. As will be readily appreciated, contemplated methods will further include a step of administering at least one additional therapeutic entity, including a viral cancer vaccine, a bacterial cancer vaccine, a yeast cancer vaccine, N-803, an antibody, a stem cell transplant, and/or a tumor targeted cytokine.

For example, cancers treated by contemplated methods include leukemia, acute lymphocytic leukemia, acute myelocytic leukemia, chronic leukemias, chronic myelocytic (granulocytic) leukemia, chronic lymphocytic leukemia, polycythemia vera, lymphomas, Hodgkin's disease, non-Hodgkin's disease, multiple myeloma, Waldenstrom's macroglobulinemia, heavy chain disease, solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

Likewise, the inventors contemplate a method of treating a viral infection in a patient in need thereof that includes a step of administering to the patient a therapeutically effective amount of the genetically modified NK cells presented herein (having an extracellular binding domain may also specifically bind to a virus-specific antigen), thereby treating the viral infection. Of course, contemplated methods may further include a step of administering an antiviral drug.

Regardless of the type of treatment, it is contemplated that about $1 \times 10^8$ to about $1 \times 10^{11}$ cells per m$^2$ of body surface area of the patient are administered to the patient.

Therefore, the inventors also contemplate use of genetically modified NK cells as presented herein in the treatment of cancer or a viral infection.

Various objects, features, aspects and advantages of the inventive subject matter will become more apparent from the following detailed description of preferred embodiments along with the accompanying drawing figures in which like numerals represent like components.

BRIEF DESCRIPTION OF THE DRAWINGS

FIG. 2A are exemplary results for the percentage of NK-92 cells expressing the CD19-CAR of FIG. 1 after transfection with CD19-CAR mRNA as determined by flow cytometry with an anti-scFv antibody labeled with eF660.

FIG. 2B are exemplary results for the median fluorescent intensity (MFI) minus background for CD19-CAR-expressing NK-92 cells labeled with an anti-scFv antibody labeled with eF660.

FIG. 3A shows exemplary results for the percentage of NK-92 cell-sensitive target cancer cells (K562) that were killed by NK-92 cells (effector) expressing the CD19CARs at effector:target ratios of from 5:1 to 0.3:1.

FIG. 3B shows exemplary results for the percentage of NK-92 cell-resistant, CD19-positive target cancer cells (SUP-B15) that were killed by NK-92 cells (effector) expressing the CD19CARs at effector:target ratios of from 5:1 to 0.3:1.

DETAILED DESCRIPTION OF THE INVENTION

Figure 1:
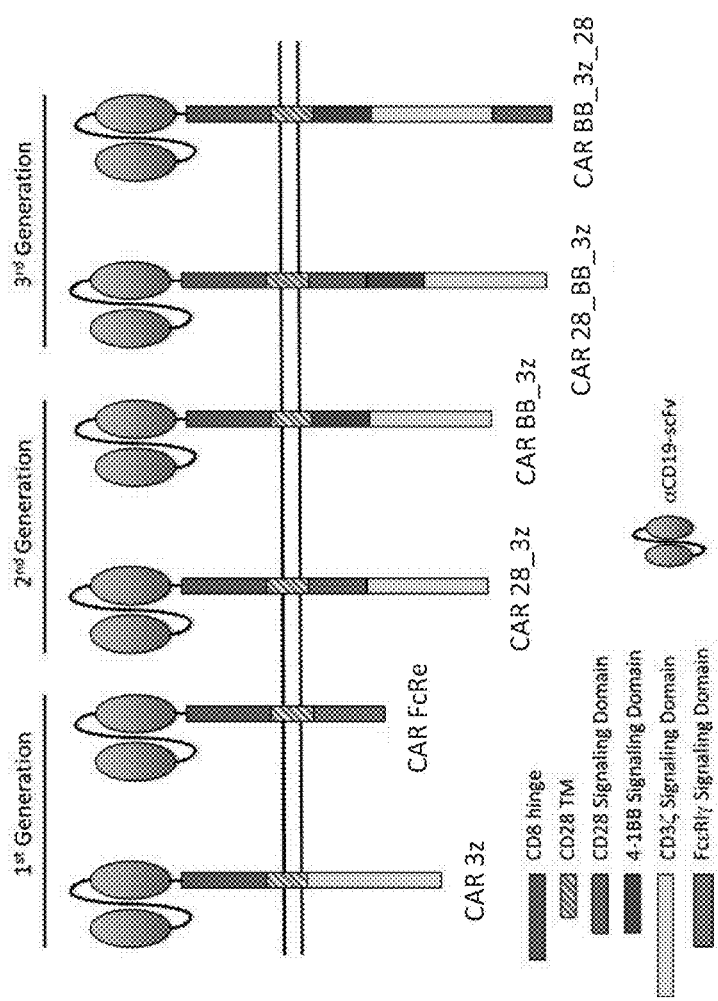
FIG. 1 is a schematic representation of exemplary CD19-CARs tested. All of the CD19-CAR variants contained an extracellular domain comprising an anti-CD19 scFv region (αCD19-scFv), a hinge region from CD8 (CD8 hinge), and a transmembrane domain from CD28 (CD28 TM). The intracellular domains of the CD19CARs were varied as indicated.

To date, FcεRIγ-containing CARs have not been utilized in NK-92 cells, other NK cell lines, or endogenous NK cells because as signaling domains (e.g., CD3ζ) were deemed more efficient, especially when combined with additional signaling domains (in second and third generation CARs). The inventors have now made the unexpected and surprising finding that NK-92 cells expressing a first-generation CAR comprising an intracellular domain from FcεRIγ, which has only one ITAM domain, have equal or higher cytotoxic activity against cancer cells expressing the antigen recognized by the CAR than NK-92 cells expressing CARs with a CD3ζ signaling domain, which has three ITAM domains, even where these ITAM domains were combined with other signaling domains (i.e., second or third generation CARs). Notably, the IgE receptor (FcεRI) in its native context includes two gamma chains coupled to each other via a disulfide bond and is normally expressed only in eosinophils, basophils, and epidermal Langerhans cells. The inventors also made the unexpected finding that a CAR comprising an intracellular domain from FcεRIγ was expressed at higher levels on the surface of NK-92 cells than other CARs, especially those comprising the CD3ζ signaling domain.

Therefore, the inventive subject matter is directed to a genetically modified NK-92 cell or NK cell line engineered to express a chimeric antigen receptor (CAR) on a cell surface. Most typically, the CAR comprises an intracellular domain from the Fc epsilon receptor gamma (FcεRIγ), however, in other embodiments the CAR may also comprise a T cell receptor (TCR) CD3 zeta (CD3ζ) intracellular domain. As will be readily appreciated, the CAR may be transiently or stably expressed by the NK-92 cell from a recombinant DNA or RNA molecule.

Consequently, in one aspect of the inventive subject matter, an NK cell, an NK-92 cell or NK/NK-92 cell line expresses a chimeric antigen receptor (CAR) on the surface of the NK-92 cell that comprises a cytoplasmic domain of FcεRIγ (e.g., having amino acid sequence of SEQ ID NO:1). Alternatively, or additionally, the CAR may also comprise a cytoplasmic domain of CD3 zeta (e.g., having amino acid sequence of SEQ ID NO: 10, which may be encoded by a nucleic acid of SEQ ID NO:11 (codon optimized) or SEQ ID NO:12 (non-codon-optimized); full-length sequence is shown in SEQ ID NO:47). In another aspect, an NK or NK-92 cell line is contemplated that is transformed with a nucleic acid encoding a chimeric antigen receptor (CAR). For example, preferred nucleic acids encode a cytoplasmic domain of FcεRIγ (e.g., comprising or consisting of SEQ ID NO:2). Alternatively, or additionally, the nucleic acid encodes a cytoplasmic domain of CD3 zeta (e.g., comprising or consisting of SEQ ID NO:11 (human, codon optimized) or SEQ ID NO:12 (human)). As will be readily appreciated, the CAR may target a cancer-associated or a virus-associated antigen via its extracellular binding domain as is described in more detail below.

In further contemplated embodiments, the NK or NK-92 cell can be modified to express at least one cytokine or variant thereof. For example, the cytokine may be transiently or stably expressed by the recombinant cell, and the cytokine may include an endoplasmic retention signal. Where desired, the NK or NK-92 cell may also be modified to express a suicide gene (e.g., suicide gene is thymidine kinase). Without being bound by any theory, it is believed that expression of a suicide gene can prevent uncontrolled proliferation of the NK-92 cells by providing a mechanism for selectively killing the cells upon introduction of a suitable stimulus.

In another aspect of the inventive subject matter, the inventors also contemplate a method of treating cancer in a patient in need thereof that includes a step of administering to the patient a therapeutically effective amount of modified NK/NK-92 cells or an NK/NK-92 cell line engineered to express a chimeric antigen receptor (CAR) as described herein. Viewed form a different perspective, the inventors also contemplate a modified NK/NK-92 cell or a NK/NK-92 cell line that expresses a chimeric antigen receptor (CAR), preferably comprising a cytoplasmic domain of FcεRIγ, for use in treating a tumor in a subject. In some embodiments, the use comprises administering to the subject an effective amount of modified cells or the cell line described herein to treat the tumor. In yet other embodiments, an in vitro method for killing tumor cells is contemplated and may include a step of contacting a tumor cell with a modified NK-92 cell or NK-92 cell line described herein. In some embodiments, the modified NK-92 cell or NK-92 cell line expresses a CAR that binds to an antigen on the tumor cell. In some embodiments, the CAR preferably comprises an intracellular domain from the Fc epsilon receptor gamma (FcεRIγ). Alternatively, or additionally, the CAR comprises a T cell receptor (TCR) CD3 zeta (CD3ζ) intracellular domain.

In still other embodiments, a method of treating a viral infection in a patient in need thereof is described, the method comprising administering to the patient a therapeutically effective amount of CAR-expressing NK-92 cells as described herein.

After reading this description, it will become apparent to one skilled in the art how to implement the invention in various alternative embodiments and alternative applications. However, not all embodiments of the present invention are described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

Titles or subtitles may be used in the specification for the convenience of a reader, which are not intended to influence the scope of the present invention. Additionally, some terms used in this specification are more specifically defined below.

With respect to suitable NK cells, it should be noted that all NK cells are deemed suitable for use herein and therefore include primary NK cells (preserved, expanded, and/or fresh cells), secondary NK cells that have been immortalized, autologous or heterologous NK cells (banked, preserved, fresh, etc.), and modified NK cells as described in more detail below. In some embodiments, it is preferred that the NK cells are NK-92 cells. The NK-92 cell line is a unique cell line that was discovered to proliferate in the presence of interleukin 2 (IL-2) (see e.g., Gong et al., *Leukemia* 8:652-658 (1994)). NK-92 cells are cancerous NK cells with broad anti-tumor cytotoxicity and predictable yield after expansion in suitable culture media. Advantageously, NK-92 cells have high cytolytic activity against a variety of cancers.

The original NK-92 cell line expressed the CD56$^{bright}$, CD2, CD7, CD11a, CD28, CD45, and CD54 surface markers and did not display the CD1, CD3, CD4, CD5, CD8, CD10, CD14, CD16, CD19, CD20, CD23, and CD34 markers. Growth of such NK-92 cells in culture is dependent upon the presence of interleukin 2 (e.g., rIL-2), with a dose as low as 1 IU/mL being sufficient to maintain proliferation. IL-7 and IL-12 do not support long-term growth, nor have various other cytokines tested, including IL-1α, IL-6, tumor necrosis factor α, interferon α, and interferon γ. Compared to primary NK cells, NK-92 typically have a high cytotoxicity even at relatively low effector:target (E:T) ratios, e.g. 1:1. Representative NK-92 cells are deposited with the American Type Culture Collection (ATCC), designation CRL-2407.

Therefore, suitable NK cells may have one or more modified KIR that are mutated such as to reduce or abolish interaction with MHC class I molecules. Of course, it should be noted that one or more KIRs may also be deleted or expression may be suppressed (e.g., via miRNA, siRNA, etc.). Most typically, more than one KIR will be mutated, deleted, or silenced, and especially contemplated KIR include those with two or three domains, with short or long cytoplasmic tail. Viewed from a different perspective, modified, silenced, or deleted KIRs will include KIR2DL1, KIR2DL2, KIR2DL3, KIR2DL4, KIR2DL5A, KIR2DL5B, KIR2DS1, KIR2DS2, KIR2DS3, KIR2DS4, KIR2DS5, KIR3DL1, KIR3DL2, KIR3DL3, and KIR3DS1. Such modified cells may be prepared using protocols well known in the art. Alternatively, such cells may also be commercially obtained from NantKwest (see URL www.nantkwest.com) as aNK cells (activated natural killer cells). Such cells may then be additionally genetically modified to a CAR as further described in more detail below.

In another aspect of the inventive subject matter, the genetically engineered NK cell may also be an NK-92 derivative that is modified to express the high-affinity Fcγ receptor (CD16). Sequences for high-affinity variants of the Fcγ receptor are well known in the art (see e.g., *Blood* 2009 113:3716-3725; SEQ ID NO:43 and 44), and all manners of generating and expression are deemed suitable for use herein. Expression of such receptor is believed to allow specific targeting of tumor cells using antibodies that are specific to a patient's tumor cells (e.g., neoepitopes), a particular tumor type (e.g., her2neu, PSA, PSMA, etc.), or that are associated with cancer (e.g., CEA-CAM). Advantageously, such antibodies are commercially available and can be used in conjunction with the cells (e.g., bound to the Fcγ receptor). Alternatively, such cells may also be commercially obtained from NantKwest as haNK cells. Such cells may then be additionally genetically modified to a CAR as further described in more detail below.

Therefore, NK cells suitable for use herein include NK-92 cells (which may be transfected with a tricistronic construct encoding a CAR, a CD16 or variant thereof, and a cytokine or variant thereof), a genetically modified NK cell or NK-92 cell that expresses a CD16 or variant thereof or a cytokine or variant thereof (which may be transfected with a nucleic acid encoding a CAR and a CD16 or variant thereof or a cytokine or variant thereof), and a genetically modified NK cell or NK-92 cell that expresses a CD16 or variant thereof and a cytokine or variant thereof (which may be transfected with a nucleic acid encoding a CAR)

Genetic modification of the NK cells contemplated herein can be performed in numerous manners, and all known manners are deemed suitable for use hereon. Moreover, it should be recognized that NK cells can be transfected with DNA or RNA, and the particular choice of transfection will at least in part depend on the type of desired recombinant cell and transfection efficiency. For example, where it is desired that NK cells are stably transfected, linearized DNA may be introduced into the cells for integration into the genome. On the other hand, where transient transfection is desired, circular DNA or linear RNA (e.g., mRNA with polyA⁺ tail) may be used.

Similarly, it should be appreciated that the manner of transfection will at least in part depend on the type of nucleic acid employed. Therefore, viral transfection, chemical transfection, mechanical transfection methods are all deemed suitable for use herein. For example, in one embodiment, the vectors described herein are transient expression vectors. Exogenous transgenes introduced using such vectors are not integrated in the nuclear genome of the cell; therefore, in the absence of vector replication, the foreign transgenes will be degraded or diluted over time.

In another embodiment, the vectors described herein allow for stable transfection of cells. In one embodiment, the vector allows incorporation of the transgene(s) into the genome of the cell. Preferably, such vectors have a positive selection marker and suitable positive selection markers include any genes that allow the cell to grow under conditions that would kill a cell not expressing the gene. Non-limiting examples include antibiotic resistance, e.g. geneticin (Neo gene from Tn5).

Alternatively, or additionally, the vector is a plasmid vector. In one embodiment, the vector is a viral vector. As would be understood by one of skill in the art, any suitable vector can be used, and suitable vectors are well-known in the art.

In still other embodiments, the cells are transfected with mRNA encoding the protein of interest (e.g., the CAR). Transfection of mRNA results in transient expression of the protein. In one embodiment, transfection of mRNA into NK-92 cells is performed immediately prior to administration of the cells. In one embodiment, "immediately prior" to administration of the cells refers to between about 15 minutes and about 48 hours prior to administration. Preferably, mRNA transfection is performed about 5 hours to about 24 hours prior to administration. In at least some embodiments as described in more detail below, NK cell transfection with mRNA resulted in unexpectedly consistent and strong expression of the CAR at a high faction of transfected cells. Moreover, such transfected cells also exhibited a high specific cytotoxicity at comparably low effector to target cell ratios.

With respect to contemplated CARs it is noted that the NK/NK-92 cells will be genetically modified to express the CAR as a membrane bound protein exposing a portion of the CAR on the cell surface while maintaining the signaling domain in the intracellular space. Most typically, the CAR will include at least the following elements (in order): an extracellular binding domain, a hinge domain, a transmembrane domain, and a FcεRIγ signaling domain.

In preferred embodiments, the cytoplasmic domain of the CAR comprises or consists of a signaling domain of FcεRIγ. For example, the FcεRIγ signaling domain comprises or consists of or consists essentially of the amino acid sequence of SEQ ID NO:1. In some embodiments, the FcεRIγ cytoplasmic domain is the sole signaling domain. However, it should be appreciated that additional elements may also be included, such as other signaling domains (e.g., CD28 signaling domain, CD3ζ signaling domain, 4-1BB signaling domain, etc.). These additional signaling domains may be positioned downstream of the FcεRIγ cytoplasmic domain and/or upstream of the FcεRIγ cytoplasmic domain.

In some embodiments, the FcεRIγ signaling domain comprises or consists of or consists essentially of an amino acid sequence having at least about 85%, 90%, 95%, 96%, 97%, 98%, or 99% sequence homology to the amino acid sequence of SEQ ID NO:1.

As noted above, in some embodiments, the cytoplasmic domain of the CAR comprises a signaling domain of CD3 zeta (CD3ζ). In one embodiment, the cytoplasmic domain of the CAR consists of a signaling domain of CD3 zeta. In one embodiment, the CD3 zeta signaling domain comprises or consists of or consists essentially of the amino acid sequence of SEQ ID NO:10. In some embodiments, the CD3 zeta signaling domain comprises or consists of or consists essentially of an amino acid sequence having at least about 85%, 90%, 95%, 96%, 97%, 98%, or 99% sequence homology to the amino acid sequence of SEQ ID NO:10.

The CAR may comprise any suitable transmembrane domain. In one aspect, the CAR comprises a transmembrane domain of CD28. In one embodiment, the CD28 transmembrane domain comprises or consists of or consists essentially of the amino acid sequence of SEQ ID NO:7. In one embodiment, the CD28 transmembrane domain comprises or consists of or consists essentially of an amino acid sequence having at least about 85%, 90%, 95%, 96%, 97%, 98%, or 99% sequence homology to the amino acid sequence of SEQ ID NO:7. In one embodiment, the transmembrane domain is selected from a CD28 transmembrane domain, 4-1BB transmembrane domain, or FcεRIγ transmembrane domain.

The CAR may comprise any suitable hinge region. In one aspect, the CAR comprises a hinge region of CD8. In one embodiment, the CD8 hinge region comprises or consists of or consists essentially of the amino acid sequence of SEQ ID NO:6. In one embodiment, the CD8 hinge region comprises or consists of or consists essentially of an amino acid sequence having at least about 85%, 90%, 95%, 96%, 97%, 98%, or 99% sequence homology to the amino acid sequence of SEQ ID NO:6.

Most typically, but not necessarily, the extracellular binding domain of the CAR will be a scFv or other natural or synthetic binding portion that specifically binds an antigen of interest. Especially suitable binding portions include small antibody fragments with single, dual, or multiple target specificities, beta barrel domain binders, page display fusion proteins, etc. Among other suitable extracellular binding domains, preferred domains will specifically bind to a tumor-specific antigen, a tumor associated antigen, or a patient- and tumor-specific antigen. For example, contemplated antigens include CD19, CD20, GD2, HER-2, CD30, EGFR, FAP, CD33, CD123, PD-L1, IGF1R, CSPG4, or B7-H4. Further tumor-specific antigens are described, by way of non-limiting example, in US2013/0189268; WO 1999024566 A1; U.S. Pat. No. 7,098,008; and WO 2000020460, each of which is incorporated herein by reference in its entirety. Likewise, other preferred domains will specifically bind to a (pathogenic) virus-specific antigen, such as an antigen of an HIV virus (e.g., gp120), an HPV virus, an RSV virus, an influenza virus, an ebolavirus, or an HCV virus.

With respect to the construction of contemplated CARs it should be recognized that CARs can be engineered in numerous manners as described, for example, in WO 2014/039523; US 2014/0242701; US 2014/0274909; US 2013/0280285 and WO 2014/099671, each of which is incorporated herein by reference in its entirety.

Therefore, and viewed from a different perspective, contemplated CARs target an antigen associated with a specific cancer type. In one embodiment, the cancer is leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, or retinoblastoma.

Therefore, contemplated CARs will generally have a structure of an extracellular binding domain that is (directly) coupled to a hinge domain, which is (directly) coupled to a transmembrane domain, which is (directly) coupled to an FcεRIγ signaling domain. In still further contemplated aspects, contemplated CARs may also include one or more signaling domains in addition to or replacing the FcεRIγ signaling domain, and especially contemplated signaling domains include CD3ζ signaling domains, 4-1BB signaling domains, and CD28 signaling domains. For example, contemplated CARs may therefore include any one of the binding domains having SEQ ID NO:4, 23-42, and 48-59 that is coupled to a hinge domain (e.g., CD8 hinge as in SEQ ID NO:6), which is in turn coupled to a transmembrane domain (e.g., CD28 TM as in SEQ ID NO:7), which is coupled to a signaling domain (e.g., FcεRIγ signaling domain as in SEQ ID NO:1, CD28 signaling domain as in SEQ ID NO:8, 4-1BB signaling domain as in SEQ ID NO:9, CD3ζ signaling domain as in SEQ ID NO:10)

In still further contemplated aspects, NK cells may be further genetically modified to express one or more cytokines to so provide a selection marker where the cytokine and the CAR are encoded on the same recombinant nucleic acid and/or to render the recombinant cells independent of exogenous IL-2. Therefore, in some embodiments, NK-92 cells are modified to express at least one cytokine. In particular, the at least one cytokine is IL-2, IL-12, IL-15, IL-18, IL-21, or a variant thereof. In preferred embodiments, the cytokine is IL-2 or a variant thereof and especially preferred variants include endoplasmic retention signals (e.g., human IL-2 as in SEQ ID NO:18, or with ER retention signal as in SEQ ID NO:19). For example, the IL-2 gene is cloned and expressed with a signal sequence that directs the IL-2 to the endoplasmic reticulum. This permits expression of IL-2 at levels sufficient for autocrine activation, but without releasing IL-2 extracellularly (e.g., *Exp Hematol.* 2005 February; 33(2): 159-64.) Alternatively, expression of a cytokine (and especially IL-15) may also be such that the cytokine will be expressed in sufficient quantities to provide an autocrine growth signal to the recombinant cells, but also to allow at least some of the expressed IL-15 to be released from the cell, which will so provide an immune stimulatory signal. For example, such expression may be achieved using a human IL-15 sequence that includes both the signal peptide and an endoplasmic retention sequence. An exemplary DNA and protein sequence for an endoplasmic retained IL-15 is shown in SEQ ID NO:72 and SEQ ID NO:73, respectively.

Where desired, contemplated cells may also express a suicide gene. The term "suicide gene" refers to a transgene that allows for the negative selection of cells expressing the suicide gene. A suicide gene is used as a safety system, allowing cells expressing the gene to be killed by introduction of a selective agent. This is desirable in case the recombinant gene causes a mutation leading to uncontrolled cell growth, or the cells themselves are capable of such growth. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene. Typically, the suicide gene encodes for a protein that has no ill effect on the cell but, in the presence of a specific compound, will kill the cell. Thus, the suicide gene is typically part of a system.

In one embodiment, the suicide gene is active in NK-92 cells. In one embodiment, the suicide gene is the thymidine kinase (TK) gene. The TK gene may be a wild-type or mutant TK gene (e.g., tk30, tk75, sr39tk). Cells expressing the TK protein can be killed using ganciclovir. In another embodiment, the suicide gene is cytosine deaminase, which is toxic to cells in the presence of 5-fluorocytosine. Garcia-Sanchez et al. "Cytosine deaminase adenoviral vector and 5-fluorocytosine selectively reduce breast cancer cells 1 million-fold when they contaminate hematopoietic cells: a potential purging method for autologous transplantation." *Blood.* 1998 Jul. 15; 92(2):672-82. In a further embodiment, the suicide gene is cytochrome P450, which is toxic in the presence of ifosfamide or cyclophosphamide. See, e.g. Touati et al. "A suicide gene therapy combining the improvement of cyclophosphamide tumor cytotoxicity and the development of an anti-tumor immune response." *Curr Gene Ther.* 2014; 14(3):236-46. In yet another embodiment, the suicide gene is iCasp9. Di Stasi, (2011) "Inducible apoptosis as a safety switch for adoptive cell therapy." *N Engl J Med* 365: 1673-1683. See also Morgan, "Live and Let Die: A New Suicide Gene Therapy Moves to the Clinic" *Molecular Therapy* (2012); 20: 11-13. iCasp9 induces apoptosis in the presence of a small molecule, AP1903. AP1903 is biologically inert small molecule, that has been shown in clinical studies to be well tolerated, and has been used in the context of adoptive cell therapy.

Of course, it should be noted that all of the recombinant proteins can be expressed from individual recombinant sequences. However, it is generally preferred that where multiple recombinant sequences are expressed (e.g., CAR, CD16, cytokine), coding regions may be arranged in a polycistronic unit with at least two or at least three coding regions encoding the recombinant proteins. Therefore, transgenes can be engineered into an expression vector by any mechanism known to those of skill in the art. Where multiple transgenes are to be inserted into a cell, transgenes may be engineered into the same expression vector or a different expression vector. In some embodiments, the cells are transfected with mRNA encoding the transgenic protein to be expressed. In some embodiments, the cells are transfected with DNA encoding the transgenic protein to be expressed. Transgenes, mRNA and DNA can be introduced into the NK-92 cells using any transfection method known in the art, including, by way of non-limiting example, infection, viral vectors, electroporation, lipofection, nucleofection, or "gene-gun."

In preferred embodiments, it should therefore be noted that the genetically modified NK cell (especially where the cell expresses a CAR and CD16 or variant thereof) will exhibit three distinct modes of cell killing: General cytotoxicity which is mediated by activating receptors (e.g., an NKG2D receptor), ADCC which is mediated by antibodies bound to a target cell, and CAR mediated cytotoxicity. As will be readily apparent, contemplated genetically modified cells can be used for treatment of various diseases, and especially of various cancers and viral infections where a diseased cell presents a disease-specific or disease-associated antigen. Consequently, the inventors contemplate methods of treating patients with modified NK or NK-92 cells as described herein. In one embodiment, the patient is suffering from cancer (e.g., a tumor) and the modified NK-92 cell or cell line expresses a CAR specific for an antigen expressed on the surface of a cell from the cancer or tumor. In one embodiment, the patient is suffering from a viral infection and the modified NK-92 cell or cell line expresses a CAR specific for an antigen expressed on the surface of a cell that has been infected by the virus. In one embodiment, the patient is suffering from a bacterial infection and the modified NK-92 cell or cell line expresses a CAR specific for an antigen expressed on the surface of a bacterial cell causing the infection.

In some embodiments, the cancer is selected from the group consisting of leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

Contemplated modified NK or NK-92 cells can be administered to an individual by absolute numbers of cells. For example, the individual can be administered from about 1000 cells/injection to up to about 10 billion cells/injection, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) modified NK-92 cells per injection, or any ranges between any two of the numbers, end points inclusive. In other embodiments, modified NK-92 cells can be administered to an individual by relative numbers of cells, e.g., said individual can be administered about 1000 cells to up to about 10 billion cells per kilogram of the individual, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) modified NK-92 cells per kilogram of the individual, or any ranges between any two of the numbers, end points inclusive. In other embodiments, the total dose may calculated by $m^2$ of body surface area, including about $1\times10^{11}$, $1\times10^{10}$, $1\times10^9$, $1\times10^8$, $1\times10^7$, per $m^2$, or any ranges between any two of the numbers, end points inclusive. The average person is about 1.6 to about 1.8 $m^2$. In a preferred embodiment, between about 1 billion and about 3 billion NK-92 cells are administered to a patient.

The modified NK-92 cells, and optionally other anti-cancer or anti-viral agents can be administered once to a patient with cancer or infected with a virus or can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy, or any ranges between any two of the numbers, end points inclusive.

In one embodiment, where the modified NK-92 cells express a suicide gene, the patient is administered an agent to trigger modified NK-92 cell death. In one embodiment, the agent is administered at a time point after administration of the modified NK-92 cells that is sufficient for the NK-92 cells to kill target cells.

In one embodiment, the modified NK-92 cells are irradiated prior to administration to the patient. Irradiation of NK-92 cells is described, for example, in U.S. Pat. No. 8,034,332, which is incorporated herein by reference in its entirety. In one embodiment, modified NK-92 cells that have not been engineered to express a suicide gene are irradiated.

Furthermore, it should be appreciated that contemplated treatments will also include administration of other immune therapeutic entities, and especially preferred immune therapeutic entities include a viral cancer vaccine (e.g., adenoviral vector encoding cancer specific antigens), a bacterial cancer vaccine (e.g., non-pyrogenic E. coli expressing one or more cancer specific antigens), a yeast cancer vaccine, N-803 (also known as ALT-803, ALTOR Biosciences), an antibody (e.g., binding to a tumor associated antigen or patient specific tumor neoantigen), a stem cell transplant (e.g., allogeneic or autologous), and a tumor targeted cytokine (e.g., NHS-IL12, IL-12 coupled to a tumor targeting antibody or fragment thereof).

EXAMPLES

The following examples are for illustrative purposes only and should not be interpreted as limitations of the claimed invention. There are a variety of alternative techniques and procedures available to those of skill in the art which would similarly permit one to successfully perform the intended invention.

Example 1: CAR mRNA Preparation

DNA sequences encoding each variant of CD19CAR schematically depicted in FIG. 1 were designed in silico, synthesized de novo, and subcloned into the mRNA expression vector, pXT7 (GeneArt, Life Technologies). Ten micrograms (μg) of plasmid were linearized by digestion with the SalI restriction enzyme (New England Biolabs) and purified using a QIAgen gel purification kit (QIAgen) according to manufacturer's instructions.

The linearized DNA was used as template for in vitro synthesis of mRNA using a T7 mMessage mMachine Ultra transcription kit (ThermoFisher Scientific, Waltham, Mass.) according to the manufacturer's instructions. This kit includes a polyadenylation extension step that increases the length of the polyA tail of the mRNA and thus enhances stability in vivo.

mRNA for six CD19-CAR variants was prepared, with a green fluorescent protein (GFP) mRNA prepared as a negative control. All of the CD19-CAR polypeptide variants contained an extracellular domain comprising an anti-CD19 scFv region (αCD19-scFv) (SEQ ID NO:4), a hinge region from CD8 (SEQ ID NO:6), and a transmembrane domain from CD28 (SEQ ID NO:7). The intracellular domains of the CD19CARs were as follows and schematically shown in FIG. 1: CAR 3z contained a CD3ζ signaling domain; CAR FcεRIγ contained a FcεRIγ signaling domain (SEQ ID NO: 1); CAR 28_3z contained a CD28 signaling domain fused to a CD3ζ signaling domain; CAR BB_3z contained a 4-1BB signaling domain fused to a CD3ζ signaling domain; CAR 28_BB_3z contained a CD28 signaling domain fused to a 4-1BB signaling domain fused to a CD3ζ signaling domain; CAR BB_3z_28 contained a 4-1BB signaling domain fused to a CD3ζ signaling domain fused to a CD28 signaling domain.

More particularly, the 1$^{st}$ generation CAR with CD3ζ signaling domain of FIG. 1 had a nucleic acid sequence of SEQ ID NO:13 (human) and SEQ ID NO:21 (murine), which translated to an amino acid sequence of SEQ ID NO:22. The 1$^{st}$ generation CAR with a FcεRIγ signaling domain nucleic had a nucleic acid sequence of SEQ ID NO:5 and an amino acid sequence of SEQ ID NO:3. The 2$^{nd}$ generation CAR with CD28/CD3ζ signaling domain had a nucleic acid sequence of SEQ ID NO:14 and the 2$^{nd}$ generation CAR with 4-1BB/CD3ζ signaling domain had a nucleic acid sequence of SEQ ID NO:15. The 3$^{rd}$ generation CAR with CD28/4-1BB/CD3ζ signaling domain had a nucleic acid sequence of SEQ ID NO:16 and the 3$^{rd}$ generation CAR with 4-1BB/CD3ζ/CD28 signaling domain had a nucleic acid sequence of SEQ ID NO:17.

Further 1$^{st}$ generation CARs with a FcεRIγ signaling domain were prepared as described below in more detail in which the hinge region was a CD8 hinge (SEQ ID NO:6 or SEQ ID NO:45 (human), encoded by SEQ ID NO:46), in which the transmembrane domain was a CD28 transmembrane domain (SEQ ID NO:7), and in which the signaling domain was a FcεRIγ signaling domain (SEQ ID NO:1, encoded by nucleic acid SEQ ID NO:2).

Target specificity was then imparted against a variety of tumor-associated targets using selected scFv portions as follows (all in a sequential arrangement as shown in FIG. 1, CAR FcRe): CD19 (using anti-CD19 scFv of SEQ ID NO:4 or SEQ ID NO:24, encoded by codon-optimized SEQ ID NO:23), CD20 (using anti-CD20 scFv of SEQ ID NO:26, encoded by codon-optimized SEQ ID NO:25), CD33 (using anti-CD33 scFv of SEQ ID NO:28, encoded by codon-optimized SEQ ID NO:27), CSPG4 (using anti-CSPG4 scFv of SEQ ID NO:30, encoded by codon-optimized SEQ ID NO:29), EGFR (using anti-EGFR scFv of SEQ ID NO:32, encoded by codon-optimized SEQ ID NO:31), IGF1R (using anti-IGF1R scFv of SEQ ID NO:34, encoded by codon-optimized SEQ ID NO:33), CD30 (using anti-CD30scFv of SEQ ID NO:36, encoded by codon-optimized SEQ ID NO:35), HER2/neu (using anti-HER2/neu scFv of SEQ ID NO:38, encoded by codon-optimized SEQ ID NO:37), GD2 (using anti-GD2 scFv or SEQ ID NO:40 or SEQ ID NO:42, encoded by codon-optimized SEQ ID NO:39 or SEQ ID NO:41), CD123 (using anti-CD123 scFv of SEQ ID NO:49, encoded by codon-optimized SEQ ID NO:48), PD-L1 (using anti-PD-L1 scFv of SEQ ID NO:51, encoded by codon-optimized SEQ ID NO:50), B7-H4 (using anti-B7-H4 scFv of SEQ ID NO:53, encoded by codon-optimized SEQ ID NO:52), and FAP (using anti-FAP scFv of SEQ ID NO:58 or SEQ ID NO:59, encoded by codon-optimized SEQ ID NO:56 or SEQ ID NO:57).

Likewise, target specificity was imparted against a variety of virus-associated targets using selected scFv portions as follows (all in a sequential arrangement as shown in FIG. 1, CAR FcRe): HIV gp120 (using anti-gp120 scFv of SEQ ID NO:55, encoded by codon-optimized SEQ ID NO:54).

All constructs as prepared above expressed well in NK-92 cells and exemplary results are shown for the physiological activity of the so modified NK-92 cells.

Example 2: Electroporation of NK-92 Cells with CD19CAR mRNA

NK-92 cells were grown in X-Vivo10 medium (Lonza, Basel, Switzerland) supplemented with 5% Human AB Serum (Valley Biomedical, Winchester, Va.) and 500 IU/mL IL-2 (Prospec, Rehovot, Israel). Cells were electroporated with mRNA using the Neon™ electroporation device (Life Technologies, Carlsbad, Calif.), following the manufacturer's parameters for NK-92 cells (1250 V, 10 ms, 3 pulses) and using 5 µg of mRNA per $10^6$ cells in a volume of 100 µl. Electroporated cells were maintained in medium (same as above) for 20 hours (h).

The CD19CAR expression on the NK-92 cell surface was determined by flow cytometry using anti-scFv antibody labeled with eF660 (eBioscience, San Diego, Calif.). FIG. 2A shows the % expression of the indicated CD19CAR in the NK-92 cell population. FIG. 2B shows the median fluorescence intensity (MFI, minus background) of cells electroporated with the indicated CD19CAR. As can be taken from FIGS. 2A and 2B, CAR FcRe unexpectedly had the highest percentage of cells (75.2%) expressing CD19CAR at the cell surface, as well as the highest MFI (quantity of expressed CAR on a recombinant cell), followed by 28_3z (61.7%).

Example 3: Cytotoxicity of NK-92 Cells Expressing CD19CAR Against Cancer Cell Lines The efficacy of CAR-expressing NK-92 cells to target cancer cells in vitro was tested 20 hours post-electroporation using a flow-based in vitro cytotoxicity assay. Effector cells (NK-92 expressing CD19CAR or GFP) were mixed with PKHGL67-labeled (Sigma-Aldrich, St. Louis, Mo.) target cells (K562; or SUPB15, B-ALL, CD19$^+$) at different effector to target ratios (5:1 to 0.3:1) in a 96-well plate and incubated 4 h at 37° C. Propidium Iodide (PI) (Sigma Aldrich, St. Louis, Mo.) was added to the cells and samples were analyzed within 2 h using an Attune flow cytometer (Life Technologies, Carlsbad, Calif.). The cytotoxicity was determined by the % of PI-positive cells within the PKH-positive target population.

Exemplary results are provided in FIGS. 3A and 3B. NK-92 cells are effective at killing K562 cells regardless of CD19CAR expression as can be seen from FIG. 3A. Thus, it should be noted that recombinant cells will not lose cytotoxicity. In contrast, GFP-expressing NK-92 cells were inefficient at killing the cancer cell line SUP-B15. SUP-B15 is an acute lymphoblastic leukemia cell line that is CD19-positive and resistant to NK-92-mediated cytotoxicity. Expression of any CD19CAR tested provided increased cytotoxic activity against the SUP-B15 cell line compared to control (GFP-expressing NK-92 cells) as can be readily taken from FIG. 3B. Surprisingly, CAR FcRe exhibited cytotoxicity similar or superior to the $2^{nd}$ and $3^{rd}$ generation CARs. Such finding is particularly unexpected as the FcεRIγ signaling domain was present only as a single unit and not combined with other signaling domains. Such arrangement, when used in CAR T-cells failed to provide desirable targeted cytotoxicity. Advantageously, tricistronic mRNA constructs were able to produce substantial quantities of desired CARs with excellent functional activity. Such constructs are especially beneficial where the CAR expression should be transient.

Figure 4:
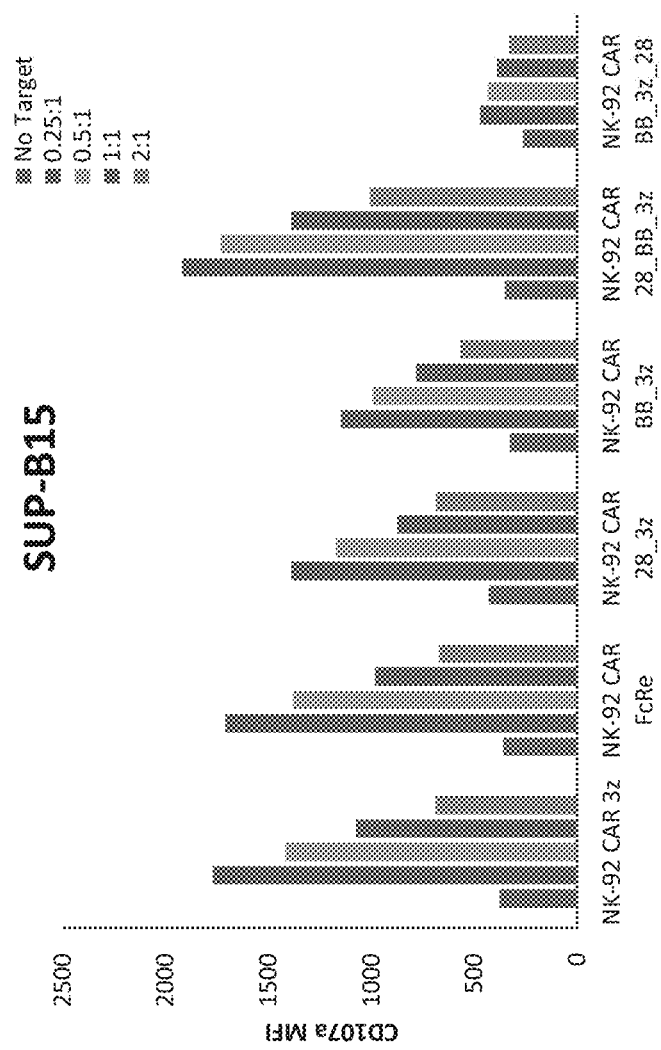
FIG. 4 shows exemplary results for the MFI of CD19-CAR-expressing NK-92 cells (effector) labeled with anti-CD107a antibody in a degranulation assay with SUP-B15 target cells at effector:target ratios of from 2:1 to 0.25:1.

Degranulation is a critical step required for the release of the lytic proteins (e.g., perforin and granzyme) from secretory granules in the NK-92 cells. Degranulation is initiated by recognition of a target cell by NK-92. To test degranulation in the constructs, effector cells (NK-92) were mixed with unlabeled target cells (SUP-B15) at different effector to target ratios (5:1 to 0.3:1) in a 96-well plate, and anti-CD107a (FITC-conjugated, BD Pharmingen, San Jose, Calif.) was added to each well. Plates were incubated at 37° C. in a $CO_2$ incubator and after 1 h monensin (Golgi-stop) was added to the wells. The plates were incubated for another 3 h at 37° C. and the samples were analyzed by flow cytometry (Attune, Life technologies, Carlsbad, Calif.). Percentage degranulation was determined by subtracting the % CD107a positive in NK-92 cells alone to the % CD107a positive in the effector+target samples, and exemplary results are provided in FIG. 4.

Example 4: CD19 t-haNK Cells Significantly Improved Animal Survival in a Raji Tumor Xenograft Model CD19 t-haNK cells (clone 19.6) comprising the Fc Epsilon intracellular signaling domain. CD19 t-haNK cells were cultured in X-VIVO™ 10 medium supplemented with 5% heat inactivated human AB serum.

Test Animals: Animal Strain/Species: NOD.Cg-PrkdcscidIl2rgtm1Wjl/SzJ (NSG) mice; Age: 9-10 weeks at study initiation (after quarantine); Sex: Female; Body Weight: 20-27 grams at study initiation. Number of Animals: 20 for the IV tumor model; 12 for the SC tumor model. Supplier: The Jackson Laboratory (610 Main Street Bar Harbor, Me. 04609 US).

Raji Tumor Model: Raji Cancer Cell Line: Raji cells were originally purchased from ATCC (Catalog #CCL-86TM; Lot #61723871) and then expanded and prepared for administration.

Cell Culture Medium: ATCC-formulated RPMI-1640 medium supplemented with 10% fetal bovine serum with penicillin (100 U/mL), streptomycin (100 μg/mL).

Cell Harvest: Raji cells (passage 12) in exponential phase were collected by centrifugation. Cells were washed and re-suspended in serum free medium at the concentration of $5\times10^5$ viable cells/mL for IV inoculations, and in medium/Matrigel (1:1 v/v) at the concentration of $2.5\times10^6$ viable cells/mL for SC implantations. Cells were stored on ice prior to animal injection. Cells used in the in vivo study had a viability of 96%.

Raji Cell Inoculation: Raji IV Model. 20 animals were injected IV via the lateral tail vein with 0.2 mL of Raji cell suspension with 27 gauge needles ($1\times10^5$ cells inocula). Raji SC Model. 12 animals were implanted SC on both flanks with 0.1 mL of Raji cell suspension with 25-gauge needles ($2.5\times10^5$ cells inocula).

Other Reagents: RPMI-1640 media, X-VIVO™ 10 media; Heated-inactivated human male AB serum (Access Cell Culture (Access Biologicals LLC); Fetal Bovine Serum (FBS); Pen Strep Glutamine (100×) (Life Technologies, Catalog #10378, Lot #1881463, Expiration date: May 2018); Matrigel Basement Membrane Matrix; Pluronic(R) F-68, 10% Solution.

Experimental Procedures

IV Raji Model—Randomization: Within 24 hours after cancer cell inoculation, which was defined as Day 1, 20 animals were pseudo-randomized into 2 groups of 10 according to body weight to achieve similar average body weight between the groups.

Test Article Administration: On Days 2, 5, 8, 10, 12, and 17, CD19 t-haNK cells grown in the exponential phase were harvested by centrifugation and formulated in X-VIVO™ 10 at the concentration of $5\times10^7$ cells/mL for IV administration at the dose of $1\times10^7$ cells per mouse with an injection volume of 200 μL. Animals in Group A received the vehicle control, while animals in Group C received CD19 t-haNK cells.

Body Weight: Animals were weighed prior to tumor cell injection and twice weekly.

Clinical Observations: Animals were observed daily for mortality/morbidity (G0 to G4) and clinical signs of toxicity. Paralyzed or moribund animals were euthanized.

Euthanasia: Animals were euthanized with $CO_2$ inhalation followed by cervical dislocation. Mortality events (euthanasia or spontaneous) were recorded in Death Log (Appendix 6) and tallied to calculate the survival curve.

SC Raji Model—Tumor Volume Measurement: After SC tumor implantation, animals were examined at least twice a week for tumor establishment. When tumors became palpable, tumor volumes (TV) were measured with a digital hand held caliper once to twice weekly, and calculated using this formula: TV=Length×Width 2/2 [Length being the greatest diameter and Width being the shortest diameter of the tumor].

Randomization: When the average tumor volume reached an injectable size (195 mm3 in this case; 24 days post-implantation), the 12 tumor-bearing animals were pseudo-randomized into 2 groups of 6 to achieve similar tumor volumes between the groups. This was defined as Day 0.

Test Article Administration: On Days 1, 4, 7, 9, 11, and 13, CD19 t-haNK cells grown in the exponential phase were harvested by centrifugation, subjected to 1000 cGy gamma irradiation, and formulated in X-VIVO™ medium at the concentration of $5\times10^7$ cells/mL for IV administration at the dose of $1\times10^7$ cells per mouse with an injection volume of 200 μL. As shown in Table 1, animals in Group D received the vehicle solution, while animals in Group F received CD19 t-haNK cells.

Body Weight. Animals were weighed prior to tumor cell injection and then twice weekly.

Clinical Observations. Animals were observed daily for mortality/morbidity (G0 to G4) and clinical signs of toxicity (T1 to T12). Paralyzed or moribund animals were euthanized.

Endpoint and Euthanasia. While moribund animals were euthanized as soon as they showed morbidity, surviving animals were subjected to scheduled euthanasia for tissue collection. Specifically, half of the surviving animals (up to 3 mice/group) were euthanized on Day 13 at 6 hours post the last dose of test article administration. The rest of the animals were euthanized on Day 15 at 48 hours post the last dosing.

Necropsy and Tumor and Tissue Collection. Upon termination, a necropsy was performed and organs with visible gross lesions were collected, fixed in 10% formalin, and submitted to a contract pathology laboratory (Seventh Wave Laboratories) for histological evaluation of tumor/metastatic disease burden.

Further, as Raji is an aggressive lymphoma model, even when inoculated SC, the cancer cells were able to disseminate and develop multiple sites of metastases that eventually led to animal morbidity and/or death. There were a total of 3 animals (50%) that were moribund between Days 11 and 13 and therefore were euthanized in the vehicle group. In contrast, there was no unscheduled death event in the CD19 t-haNK cells group (Table 3).

| Group | N | Tumor Model | Treatment | Tx Route | NK Cell Dose | Treatment Days | Endpoint |
|---|---|---|---|---|---|---|---|
| A | 10 | IV | Vehicle | IV | / | 2, 5, 8, 10, 12, and 17 | Moribund |
| C | 10 | IV | CD19 t-haNK, non-IR | IV | $1 \times 10^7$ | 2, 5, 8, 10, 12, and 17 | Moribund |
| D | 6 | SC, bilateral | Vehicle | IV | / | 1, 4, 7, 9, 11, and 13 | Days 13 and 15 or Moribund |
| F | 6 | SC, bilateral | CD19 t-haNK, IR | IV | $1 \times 10^7$ | 1, 4, 7, 9, 11, and 13 | Days 13 and 15 or Moribund |

IR, irradiated (1000 cGy); non-IR, non-irradiated; IV, intravenous; SC, subcutaneous; Tx, treatment.

Data Analysis

Tumor Volume Calculation: Tumor volume=Length× Width 2/2 (Length and Width being the longest and shortest diameters of the tumor, respectively); Tumor Growth Inhibition (TGI) Calculation: TGI=(TC−Tt)/ΔTC×100%, where TC and Tt is the average tumor volume for control and treatment groups at the end of the study, respectively, and ΔTC is the change in average tumor volume in the control group.

Statistical Analysis—Tumor Growth Curves: Tumor growth curves were analyzed by 2-way ANOVA followed by multiple comparison by Tukey test. Survival Curves: Survival curves were analyzed by Log-rank (Mantel-Cox) test.

Liver Metastasis Estimation: Differences in liver metastatic disease burden on individual days were analyzed by unpaired 2-tailed t test. Statistical Significance: P<0.05 is considered statistically significant. All statistical analyses were performed using GraphPad Prism version 7.

Results

Figure 5:
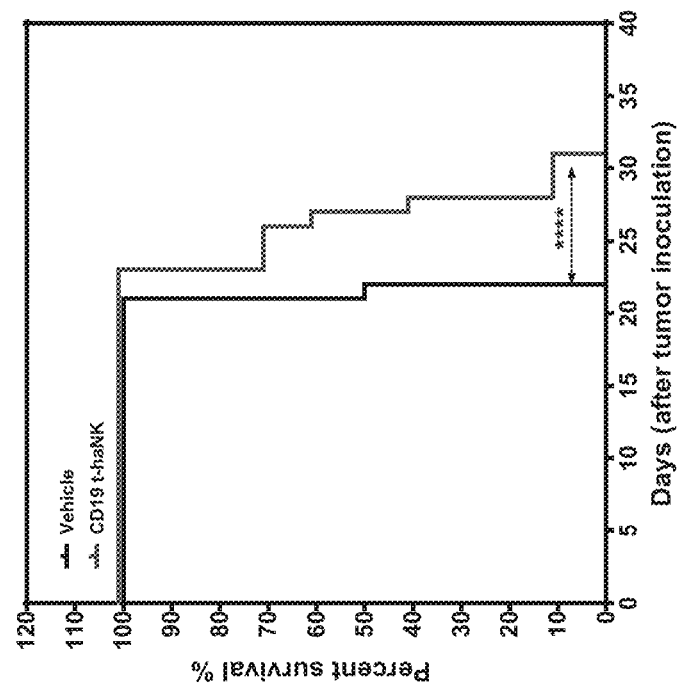
FIG. 5 shows an exemplary survival curve of IV Raji tumor bearing animals, as described in the Examples. Statistical analysis was Log-rank (Mantel-Cox) test. ****, P<0.0001.

IV Raji Model: The main readout in the IV tumor model was animal survival. A death event was counted when an animal was found dead or was euthanized due to disease-related morbidity and/or paralysis. As shown in FIG. 5, compared to vehicle control, CD19 t-haNK cell treatment was able to significantly improve the animals' rate of survival, resulting in a median survival of 27 days versus 21.5 days in the vehicle control group (P<0.0001).

Figure 6:
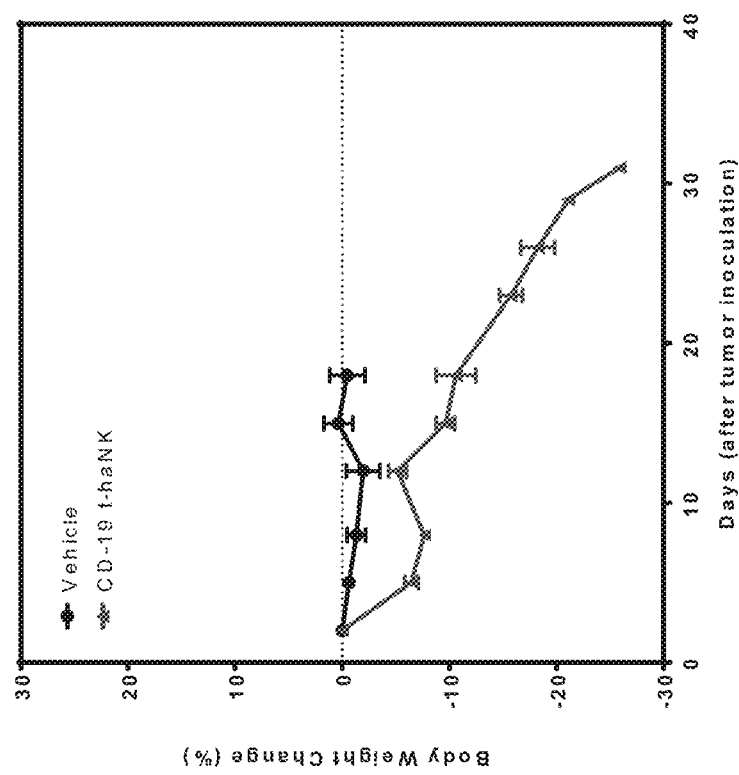
FIG. 6 shows exemplary results for animal body weight change in the IV Raji tumor model. Data are mean±SEM. SEM was calculated as Standard Deviation divided by the square root of N.

Animal body weight change was also monitored throughout the study. As shown in FIG. 6, CD19 t-haNK treated animals demonstrated a moderate (less than 10%) and short-term body weight loss when treatment was first initiated, which is not an uncommon phenomenon in animals receiving IV NK infusions, and not specific to the CD19 t-haNK cells (Reference study: LABC-TX01701). Their body weight was able to recover after the first week of treatment before decreasing again due to disease progression.

Figure 7:
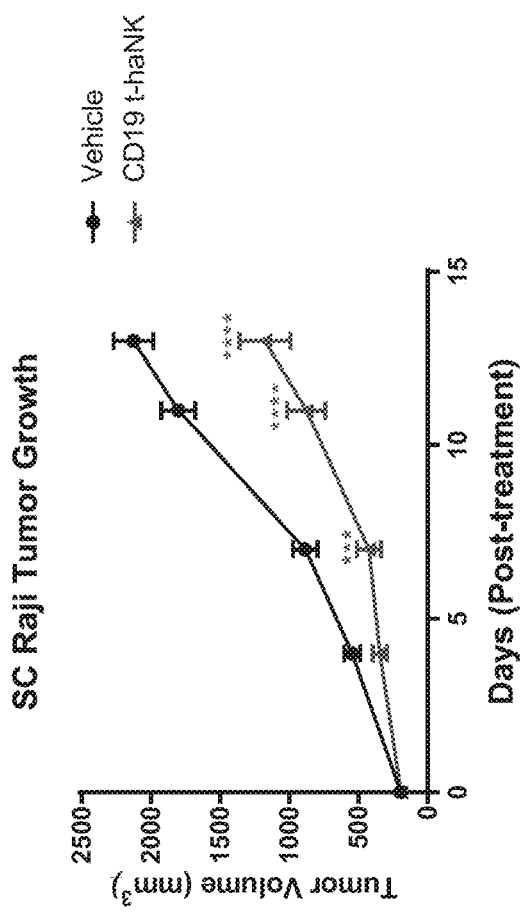
FIG. 7 shows an exemplary tumor growth curve for the SC Raji model. Data are Mean±SEM. Statistical analyses were done using 2-way ANOVA followed by multiple comparison by Tukey test; *, P<0.001; **, P<0.0001.

SC Raji Model: The primary readout in the SC tumor model was tumor growth. As shown in FIG. 7, CD19 t haNK cells demonstrated evident and statistically significant tumor growth inhibition on and after Day 7 compared to the vehicle control group, with a 49% TGI at the end of the study (Day 13).

Figure 8:
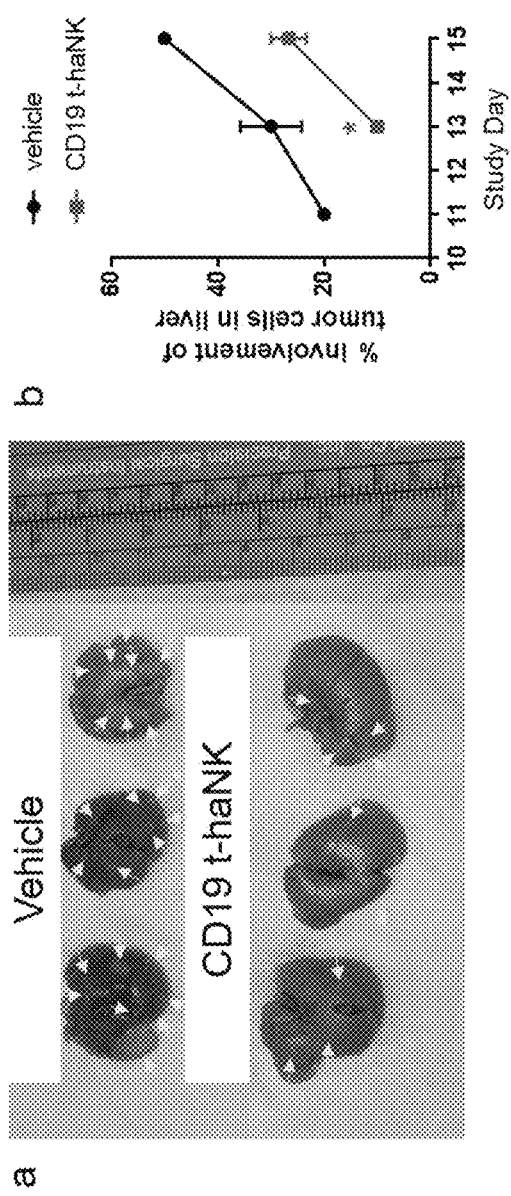
FIG. 8 shows exemplary data indicating CD19 t-haNK reduced metastatic disease burden in the livers of SC Raji tumor-bearing mice. Panel a: Whole liver images of animals from indicated treatment groups on Day 13. Arrows indicate metastatic lesions. Livers were fixed in 10% formalin for at least 24 hours prior to photography. Panel b: Quantification of percentage involvement of tumor cells in the liver (evaluated by H&E staining) on indicated days. On Day 13:*, P=0.0257 by unpaired 2-tailed t test. Statistical analyses for Days 11 and 15 could not be performed due to limited sample size. See Table 4 for raw data.

In addition, a qualitative reduction of liver metastases was observed in CD19 t-haNK treated animals during necropsy (FIG. 8A). A semi-quantitative estimation of the disease burden was performed by a contract pathology lab (Seventh Wave Laboratories) on H&E stained liver sections that were representatively sampled. As summarized in FIG. 8B and Table 4, there was a clear trend of increasing disease burden as the study advanced. Livers of CD19 t-haNK treated animals exhibited a remarkably lower percentage of cancer infiltrated areas compared to the vehicle control. Due to the small sample number and unscheduled early mortality in the control group, statistical analysis could only be performed on the Day 13 data. This analysis showed a significant difference in disease burden, with an average of 10% infiltration in CD19 t-haNK treated animals versus 30% in the control group.

Figure 9:
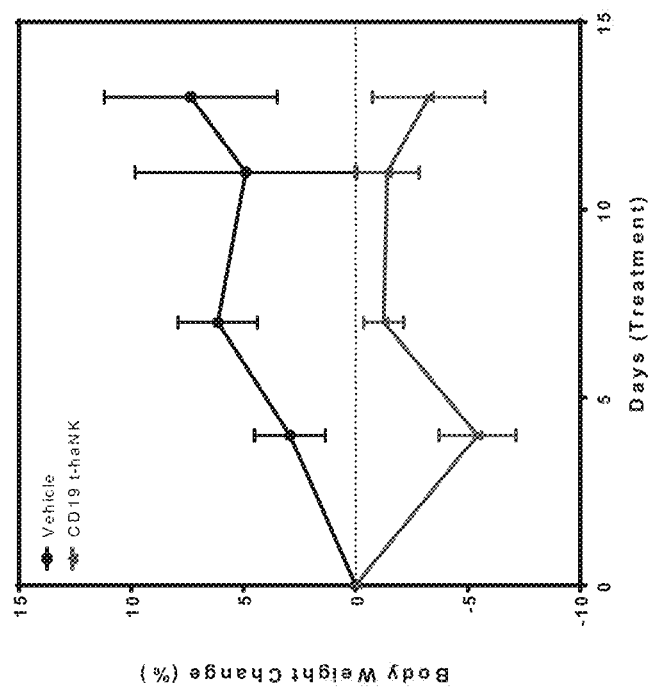
FIG. 9 shows exemplary results for animal body weight change in the SC Raji tumor model. Data are mean±SEM.

Body weight change was monitored throughout the study, and similar to the IV Raji model, CD19 t-haNK treated animals demonstrated a moderate (less than 10%) and transient body weight loss in the beginning of the treatment regimen as can be taken from FIG. 9.

| Group | Initial N | Day 11 | Day 13 | Day 15 |
|---|---|---|---|---|
| D (Vehicle) | 6 | 2 × Moribund | 1 × Moribund | |
| | | | 2 × Scheduled | 1 × Scheduled |
| F (CD19 t-haNK) | 6 | | | |
| | | | 3 × Scheduled | 3 × Scheduled |

Scheduled: scheduled euthanasia for tissue collection.

| Group (Treatment) | Animal Number | Collection Day | Estimated % Tumor | Mean |
|---|---|---|---|---|
| D (Vehicle) | 503 | 11 | 20 | 20 |
| | 520 | 11 | 20 | |
| | 487 | 13 | 40 | 30 |
| | 488 | 13 | 20 | |
| | 497 | 13 | 30 | |
| | 502 | 15 | 50 | 50 |

-continued

| Group (Treatment) | Animal Number | Collection Day | Estimated % Tumor | Mean |
|---|---|---|---|---|
| F (CD19 t-haNK) | 495 | 13 | 10 | 10 |
| | 505 | 13 | 10 | |
| | 507 | 13 | 10 | |
| | 512 | 15 | 30 | 27 |
| | 522 | 15 | 30 | |
| | 525 | 15 | 20 | |

To assess the anti-tumor efficacy of CD19 t-haNK cells in repeated IV dosing regimens, 2 variations of the Raji xenograft model with IV and SC tumor inoculations, respectively, were utilized in this study.

In the IV tumor model, CD19 t-haNK cells were able to significantly improve animal survival, prolonging median survival by 5.5 days (a 26% increase) compared to the vehicle control group. In the SC tumor model, CD19 t-haNK cells were able to significantly suppress tumor growth, resulting in a 49% TGI at the end of the study. Furthermore, CD19 t-haNK treatment was able to reduce the number of animal morbidity/death events (0/6 in CD19 t-haNK treated animals versus 3/6 in the control group), and markedly decrease metastatic disease burden in the liver of SC Raji-tumor bearing animals.

As can be seen from the above data, CD19 t-haNK cells displayed significant therapeutic efficacy compared to vehicle control in both variations of the Raji xenograft model.

Example 5. Treatment of Mice Having L1210 Tumors with CD19-CAR-NK-92 Cells Increased Survival, and Mice that Completely Responded to Treatment Rejected L1210 Tumor Allografts when Re-Challenged Experimental Design: Thirty (30) male DBA/2J mice aged 6-8 weeks (Jackson Laboratories) were enrolled following randomization on Day 0. All animals were housed under standard environmental conditions and maintained on LabDiet 5053 irradiated rodent chow and sterile water provided ad libitum. On arrival, animals were identified by ear punch and housed in cages of ten (10) and acclimated in place for a minimum of three days prior to commencement of the study. Following acclimation, the injection area of each mouse was shaved and cleaned with sterile EtOH swab. On Day PR0 (pre-randomization Day 0), animals were anesthetized with isoflurane for tumor cell injection. All animals were injected with $2\times10^5$ L1210-Luc tumor cells subcutaneously (s.c.) into the right flank in a volume of 0.1 mL serum-free DMEM on Day PR0. Beginning on Day PR 7, all animals had tumors measured daily by digital caliper. On ~Day PR7 when tumor volumes were measured at ~50-150 mm³, and mean tumor volume was measured at ~100 mm³, the twenty (20) animals bearing tumors nearest to ~100 mm³ were selected for enrollment in the study; these animals were randomized into two (2) groups consisting of ten (10) animals each. Randomization day was considered Day 0 of the study, and administration of treatments commenced on this day. Animals not enrolled on study were immediately euthanized by CO2 overdose. Animals in Group 1 were administered vehicle (serum free DMEM) as an intratumoral (i.t.) injection of 50 µl. Animals in Group 2 were administered $2\times10^6$ mCD19-CAR-aNK cells i.t. in a volume of 50 µl. Identical treatments were administered on Days 0, 2 and 4 of the study.

Animals were weighed and monitored for general health daily. Following randomization, tumors were measured by digital caliper three times each week (3×/week). Any animal bearing a tumor >2500 mm³ or a tumor that has ulcerated; that lost >30% of its initial body weight (on Day 0); or was found moribund, distressed or paralyzed was euthanized by $CO_2$ overdose with cause of death/sacrifice noted. On Day 30, completely responding animals and five (5) naïve additional male DBA/2J mice aged ~10 weeks (Jackson Laboratories; Barrier) comprising Group 4 were administered a rechallenge tumor cell inoculation of $2\times10^5$ L1210-Luc tumor cells subcutaneously (s.c.) into the left flank in a volume of 0.1 mL serum-free DMEM. All animals continued to be weighed and monitored daily and tumor measurements continued 3×/week through Day 60.

Results

Animal Survival to Welfare Thresholds—Initial Tumor Challenge: Animals were monitored for survival daily. Animals requiring euthanasia according to animal health and welfare thresholds, including loss of greater than 30% of their initial body weight, tumors exceeding 2500 mm³, inability to obtain food/water, or found moribund, were included for survival analysis. Animals requiring euthanasia due to ulcerated tumors were not included in survival analysis.

Figure 10:
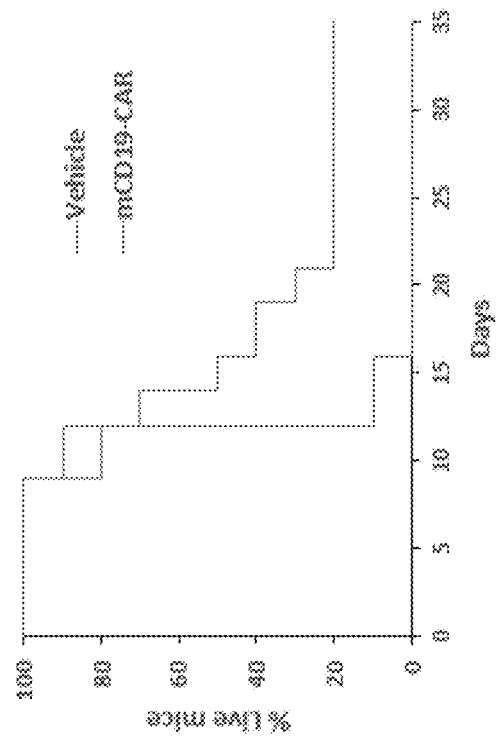
FIG. 10 shows an exemplary Kaplan-Meier survival curve of mice injected with L1210-Luc tumor cells following intratumoral treatment with mCD19-CAR NK-92 cells vs. vehicle control, as described in the Examples.

Cumulative survival to animal welfare thresholds over time is shown in FIG. 10. L1210 is an extremely fast-growing, aggressive tumor cell line and 0% of vehicle treated control animals survived further than twenty-three (23) days post tumor challenge. In contrast, treatment with CD19-CAR-aNK cells enhanced survival compared to treatment with vehicle. Indeed, 25% (⅖) of animals treated with CD19-CAR-aNK cells survived through study completion at Day 61 through tumor graft challenge.

The statistical significance of the observed survival enhancements provided by the test treatments was assessed by Log-rank (Mantel-Cox) and Gehan-Breslow Wilcoxon tests. Treatment with mCD19-CAR-aNK cells produced a statistically significant enhancement of survival, (p=0.05 (Mantel-Cox); p=0.04 (Gehan-Breslow-Wilcoxon). These results indicate that treatment with CD19-CAR-aNK produced statistically significant improvement of survival to welfare threshold compared to vehicle in this preclinical subcutaneous model of murine lymphocytic leukemia.

Tumor Re-challenge of Complete Responders: On Day 33, the two (2) complete responding animals from Group 2, along with five (5) age-matched naïve animals were challenged/rechallenged with a second inoculum of $2\times10^5$ L1210-Luc cells, injected into the opposite (left) flank (primary tumor was seeded into the right flank). Animals were monitored for survival daily. Animals requiring euthanasia according to animal health and welfare thresholds, including loss of greater than 30% of their initial body weight, tumors exceeding 2500 mm³, inability to obtain food/water, or found moribund, were included for survival analysis. Animals requiring euthanasia due to ulcerated tumors were not included in survival analysis.

All (5 of 5) survival analysis eligible naïve animals required euthanization due to tumor volume by Day 52; in contrast, all completely responding animals previously treated with 2M CD19-CAR-aNK (N=2) cells survived through study completion (Day 62). The statistical significance of the observed survival enhancement provided by the test treatments was assessed by Log-rank (Mantel-Cox) and Gehan-Breslow Wilcoxon tests, however the enhancement in survival was not statistically distinguishable, most likely to due to small sample sizes.

Figure 11:
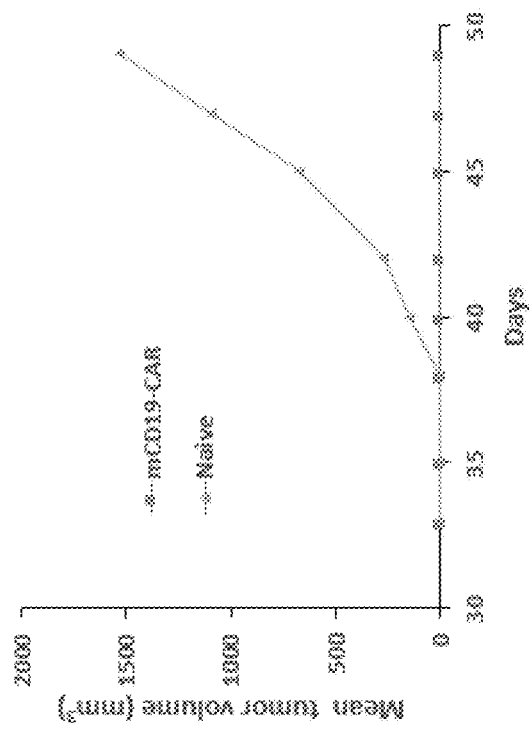
FIG. 11 shows exemplary results for tumor size of complete responders vs. naïve controls re-challenged with L1210-Luc tumor cells, as described in the Examples.

Tumors continued to be measured three times each week (3×/week) during the rechallenge phase. The mean tumor volume+SEM for each group from administration of challenge/rechallenge L1210-Luc cells to 0% control group survival (Day 52) are displayed in FIG. 11.

Tumors of naïve animals were first detectable about seven days after administration (on study Day 40) and increased steadily and rapidly. In contrast, no tumors were detected following rechallenge into completely responding animals previously treated with 2M CD19-CAR-aNK cells at any point over the full course of the rechallenge phase (Day 33-61).

The data provided in this example suggest that completely responding animals previously treated with 2M CD19-CAR-aNK cells may have developed an effective immune response to L1210 tumor cells.

Example 6: Treatment of Mice Having A20 Tumors with mCD19-CAR-NK-92 Cells Increased Survival, and Mice that Completely Responded to Treatment Rejected A20 Tumor Allografts when Re-Challenged Experimental Design Part A: Forty (40) 5-7 week old BALB/c mice (20 males and 20 females) were sourced Taconic Biosciences to serve Part A. On pre-randomization (PR) Day 0, animals were injected subcutaneously (s.c.) into the left flank with $2.5 \times 10^6$ A20 murine lymphoma cells in 100 µL volume of serum free media. Beginning on Day PR7, tumors were measured daily. Ten (10) days after tumor cell implantation (Day PR10; Day 0), mice were randomized into treatment groups, such that each group contained animals bearing tumors of similar volume and range. The day of randomization was considered Day 0 of the study. Tumors were measured three times each week (3×/week) by digital caliper to monitor tumor growth until completion of Part A on Day 26.

On Day 0, Day 3, and Day 5, mice were injected intratumorally (i.t.) with test cells or vehicle in 50 µl volume of serum free media into the tumor mass of each animal according to pre-established i.t. procedure (see Experimental Procedures). Briefly, animals were administered vehicle only or were administered $5 \times 10^6$ mCD19-CAR-NK-92. On Day 26, animals that did not develop a tumor of volume>40 mm³ were unenrolled from the study and euthanized by $CO_2$ asphyxiation; enrolled animals that displayed a complete response to treatment (CR; tumors>40 mm³ regressing so as to be undetectable (0 mm³) over multiple days without relapse prior to Day 26) were enrolled in Part B.

Part B: Part B began on Day 26. Animals from Part A without tumors were enrolled in Part B, along with twelve (12) naïve animals (6 males and 6 females). All Part B animals were administered $2.5 \times 10^6$ A20 cells into the right flank. Tumors were measured 2 times/week. Animals were euthanized on Day 57.

Figure 12:
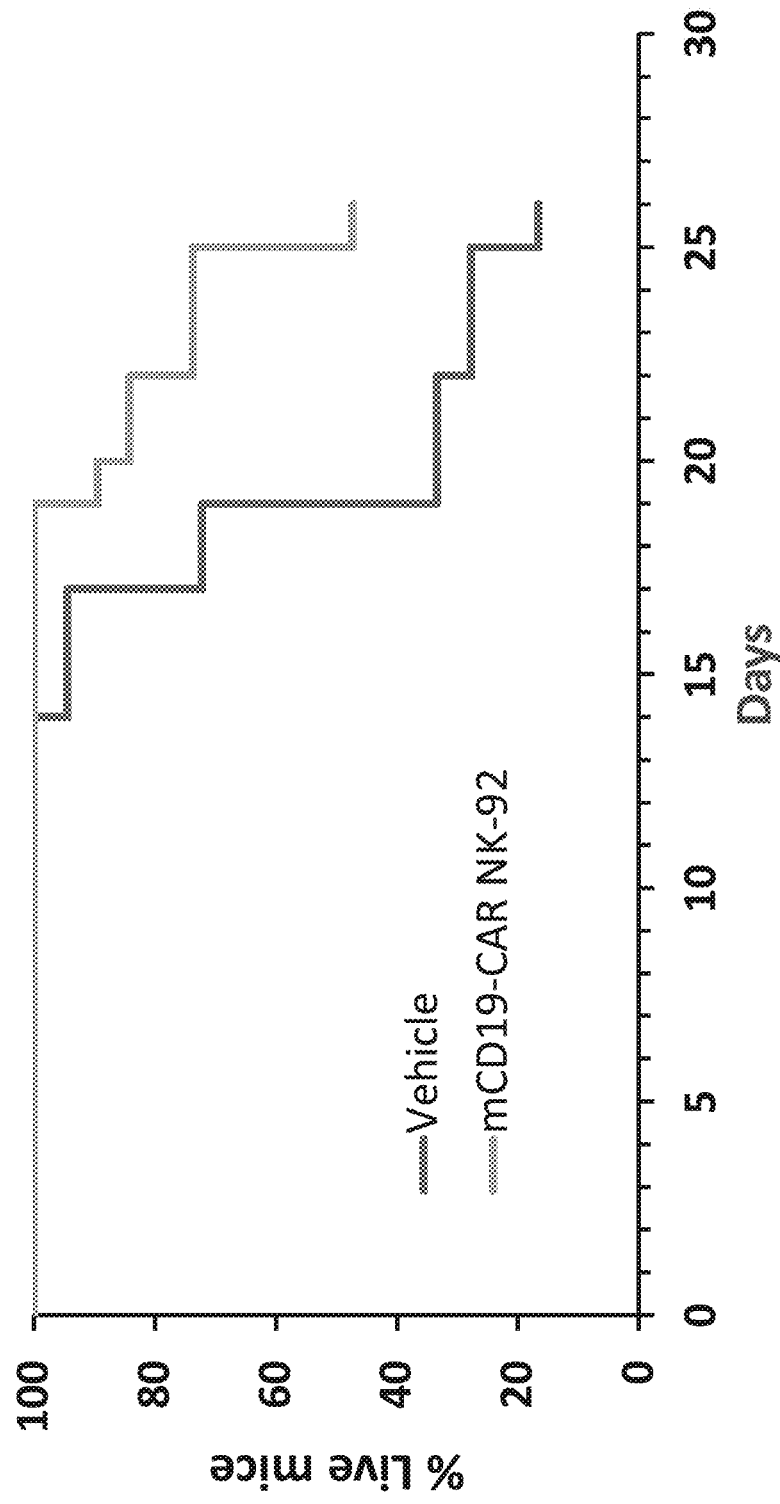
FIG. 12 shows an exemplary Kaplan-Meier survival curve of mice injected with A20 tumor cells following intratumoral treatment with mCD19-CAR NK-92 cells vs. vehicle control, as described in the Examples.

Results: Part A—Animal Survival: Animals were monitored for general health and survival daily. Animals requiring euthanasia according to animal health and welfare thresholds, including loss of greater than 30% of their initial body weight, tumors exceeding 1500 mm³, inability to obtain food/water or found moribund were included for survival analysis. Animals requiring euthanasia due to ulcerated tumors were not included in survival analysis. In this study, all animals considered in survival analysis were euthanized due to tumor burden exceeding 1500 mm³. As a subcutaneous tumor burden threshold represents an arbitrary cut-off point, the analysis of "survival" in this case must be considered only as an indicator of relative tumor growth. Cumulative survival over time for all animals considered is displayed in FIG. 12.

Of control animals administered vehicle intratumorally (i.t.) on Days 1, 3, and 5: 0 of 15 animals (0%) survived to Part A completion on Day 26. Survival through Day 26 was increased for animals for all animals receiving treatment: 9 out 18 (50%) animals administered 5M mCD19-CAR-NK92 cells. All groups were intercompared by log-rank (Mantel-Cox) test. Compared to animals administered vehicle, a statistically significant enhancement of survival was observed for animals administered 5M mCD19-CAR-NK92 cells (p=<0.0001). These results suggest that all treatments improved survival through Day 26 compared to treatment with vehicle.

Figure 13:
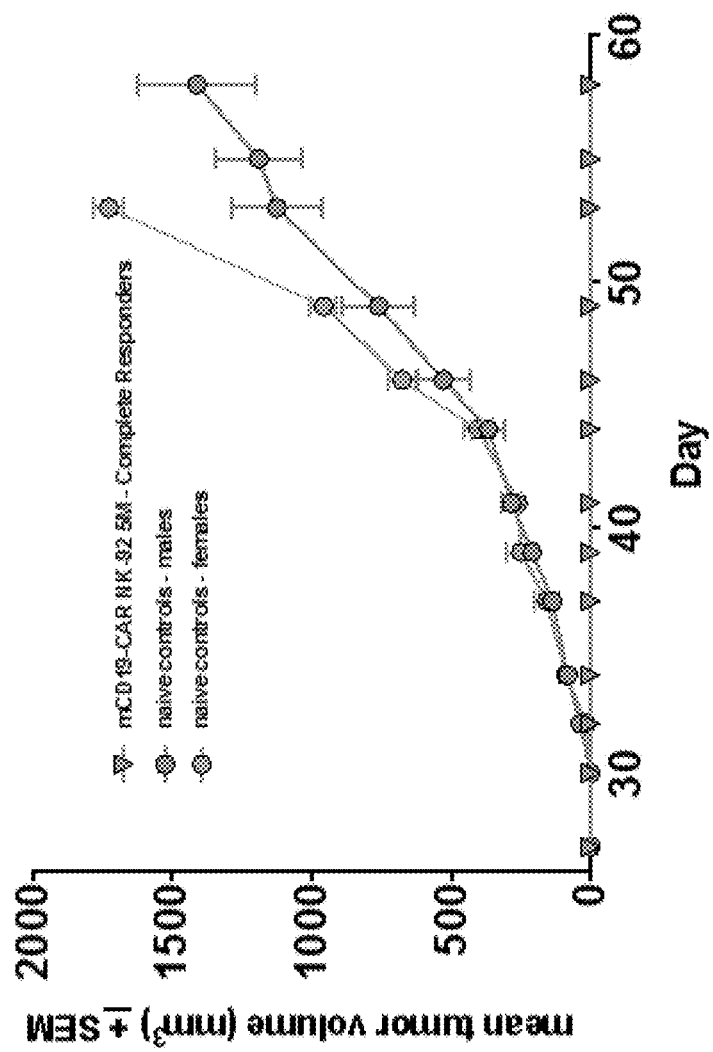
FIG. 13 shows exemplary results for tumor size of complete responders vs. naïve controls re-challenged with A20 tumor cells, as described in the Examples.

Part B—Tumor Re-challenge of Complete Responders: Animals that completely responded to treatment (bearing a tumor >40 mm³ that responded to treatment over the course of Day 0-26 (Part A) such that the tumor volume measured 0.00 mm³ through Day 26 without regrowth or relapse) were re-challenged with a second subcutaneous inoculation into the flank (opposite side from the first graft), with $2.5 \times 10^6$ A20 tumor cells in 0.1 mL serum free RPMI-1640 media on Day 27; the rechallenge portion of the study was designated as Part B. An additional twelve animals were enrolled into Part B the study to serve as naïve controls; six (6) male and six (6) female age-matched BALB/c mice sourced at the same time and vendor as Part A mice were administered $2.5 \times 10^6$ A20 tumor cells on Day 27. Tumors were measured 3 times/week for all animals through Day 57. Mean tumor volumes+SEM of each Part A treatment group and naïve controls are shown in FIG. 13. Tumors derived from cell inoculations into naïve animals grew steadily as expected; whereas re-challenge tumor cell inoculations into complete responder animals did not produce viable tumors (>40 mm³).

In summary, the data presented in this example indicates that, in contrast to naïve mice, previously treated mice that completely responded to treatment were able to reject A20 tumor allografts applied as re-challenge regardless of the treatment, and suggests that that these animals developed a memory response to tumor antigens.

The following examples for targeted CAR constructs and associated functional data were from linearized DNA vector constructs, which allowed transfected cells to integrate the linearized DNA into the genome and to so provide an avenue for non-transient expression of the specific CARs.

Example 7: HER2-CAR with FcεcRIγ Signaling Domain

In this example, the inventors constructed a $1^{st}$ generation CARs with a FcεRIγ signaling domain that included an anti-HER2 scFv coupled to a CD8 hinge, that in turn was coupled to a CD28 transmembrane domain, which was coupled to a FcεRIγ signaling domain. The so constructed HER2-CAR had a nucleic acid sequence of SEQ ID NO:60.

Figure 14:
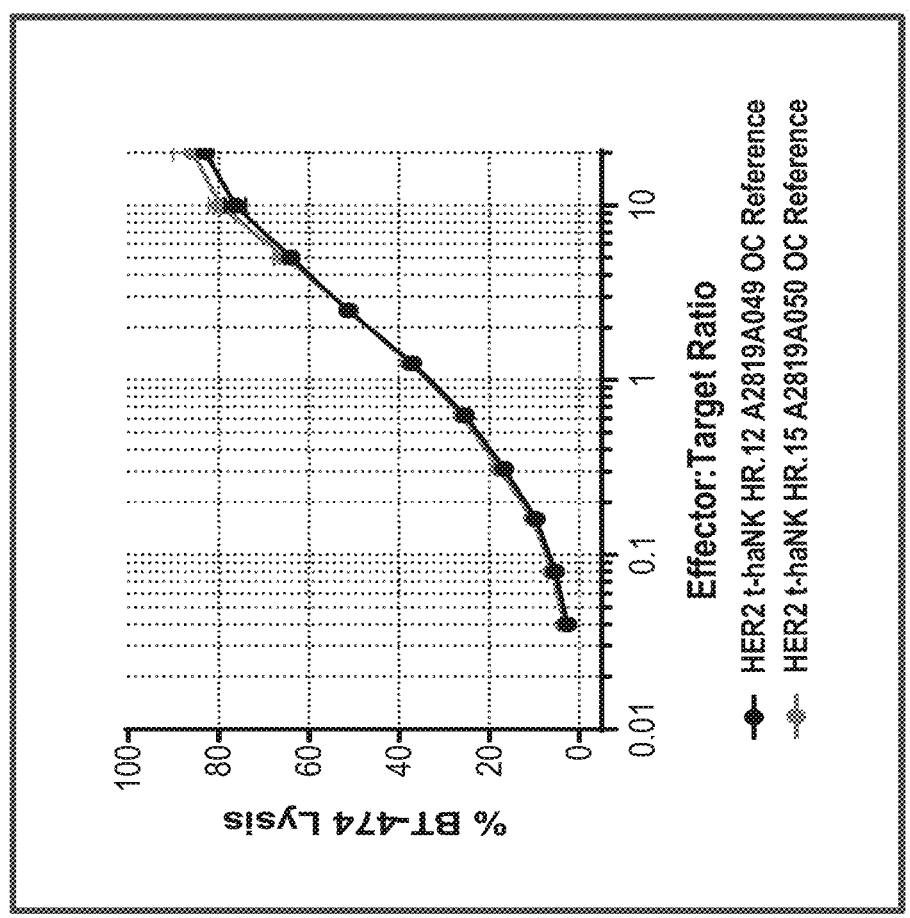
FIG. 14 shows exemplary results for cytotoxicity of HER2.CAR-t-haNK cells against BT-474 cells.

Functionality of the so constructed HER2.CAR-t-haNK cells was tested against BT-474 cells using a standard cytotoxicity assay and exemplary results are shown in FIG. 14. As can be readily seen from the data, the HER2.CAR-t-haNK cells expressing the CAR with the FcεRIγ signaling domain exhibited significant cytotoxicity against the BT-474 target cells.

Figure 40:
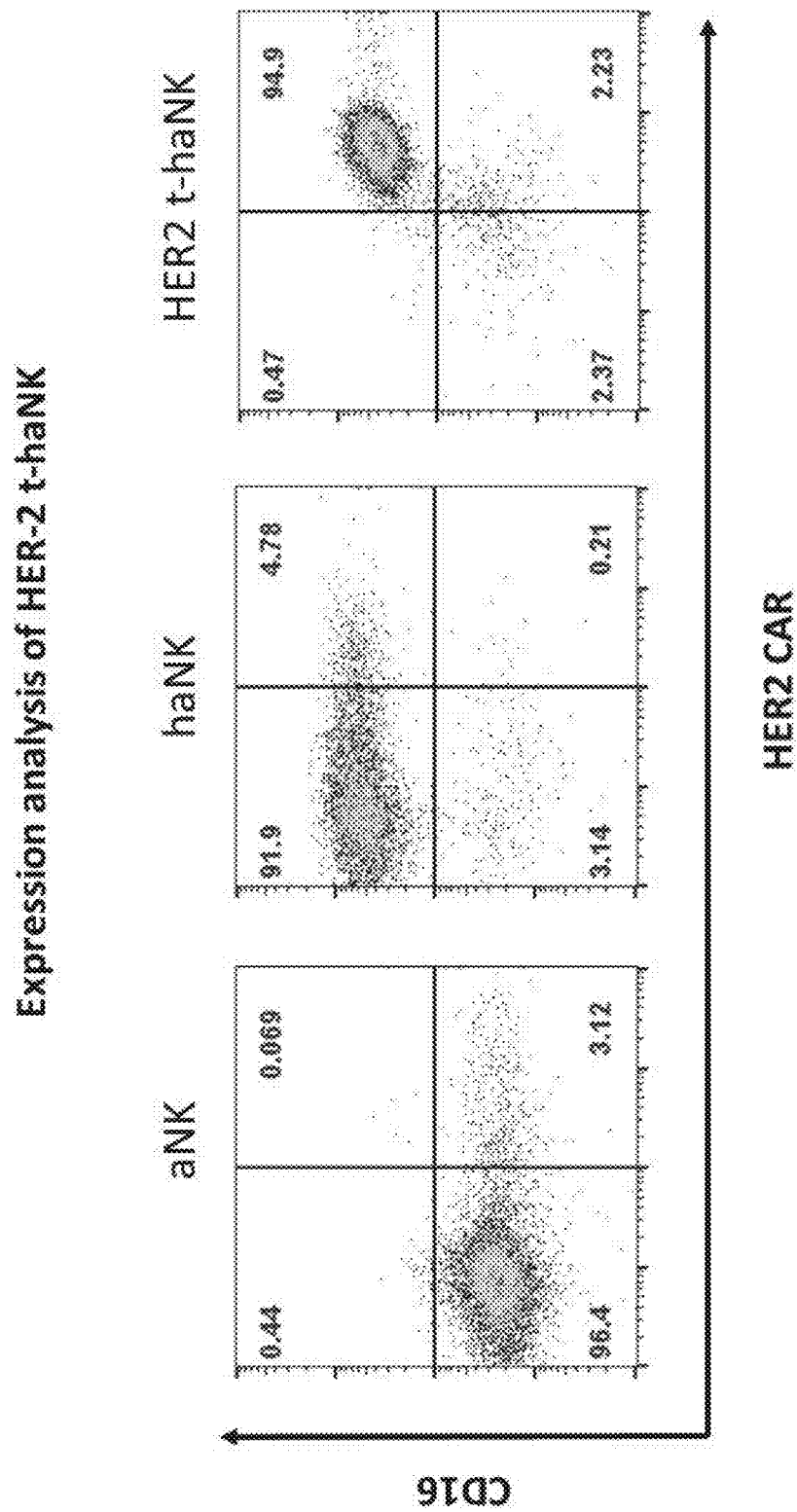
FIG. 40 shows exemplary results for expression of CD16 and HER2.CAR.
Figure 41:
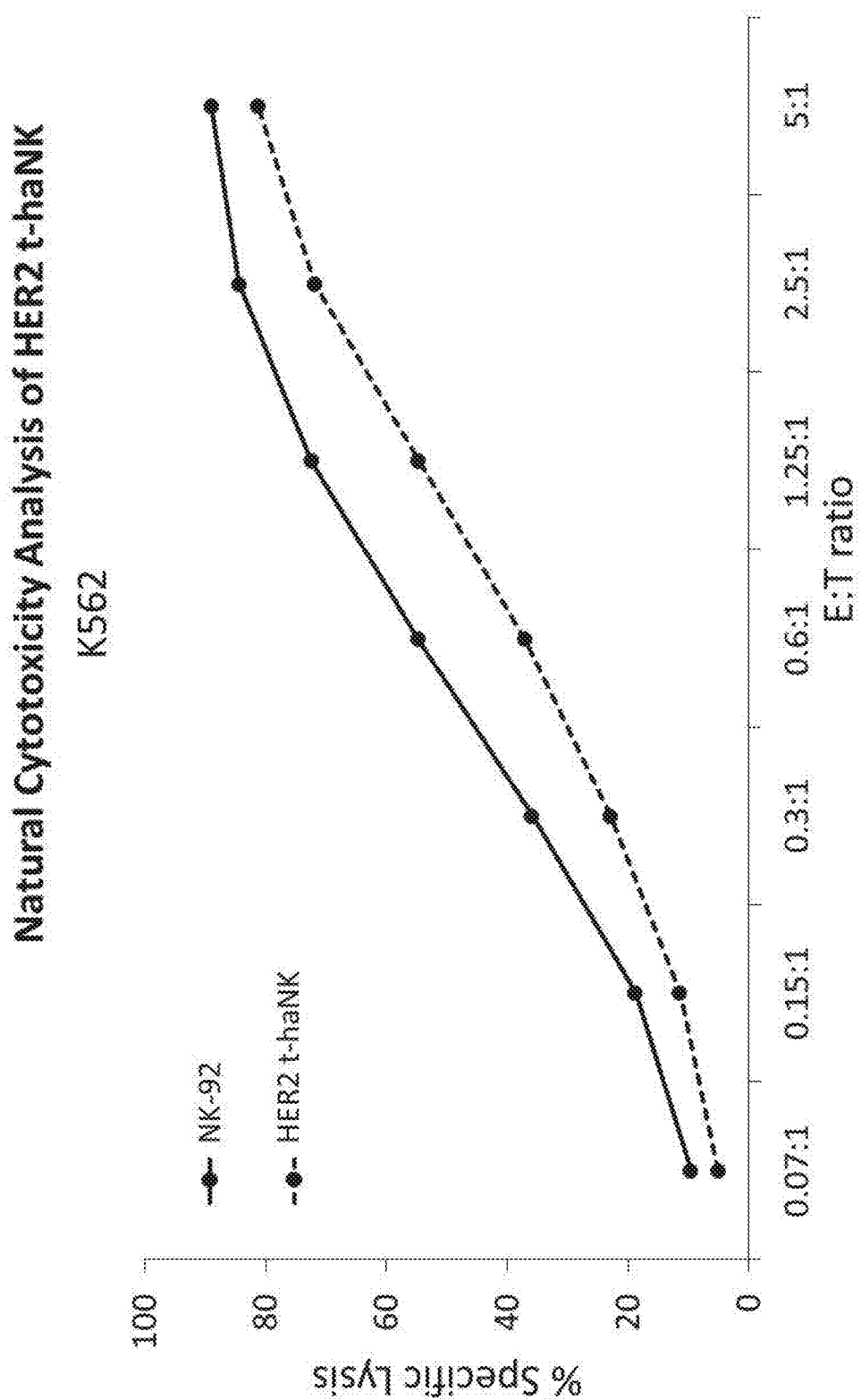
FIG. 41 shows exemplary results for natural cytotoxicity of HER2.CAR-t-haNK cells.
Figure 42:
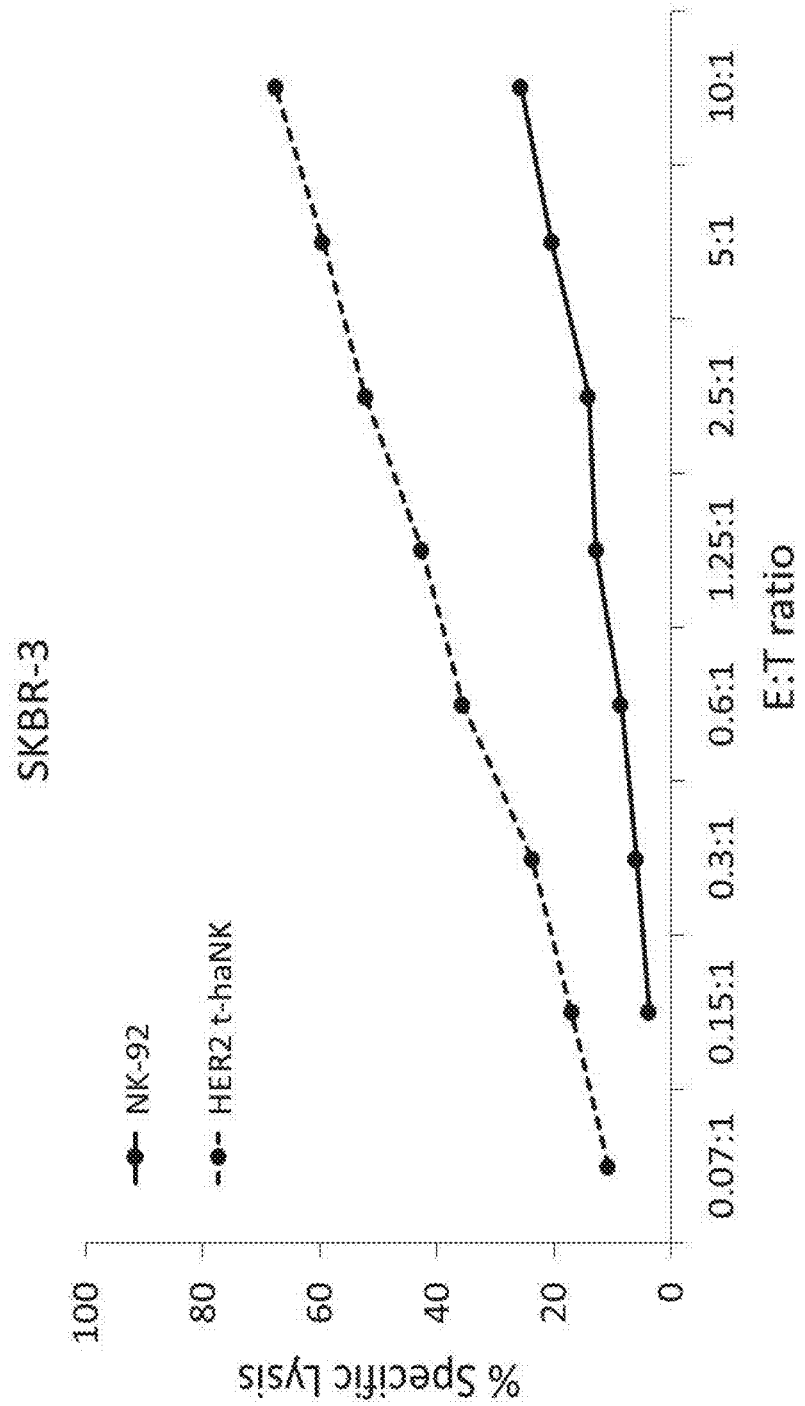
FIG. 42 shows exemplary results for CAR mediated cytotoxicity of HER2.CAR-t-haNK cells.
Figure 43:
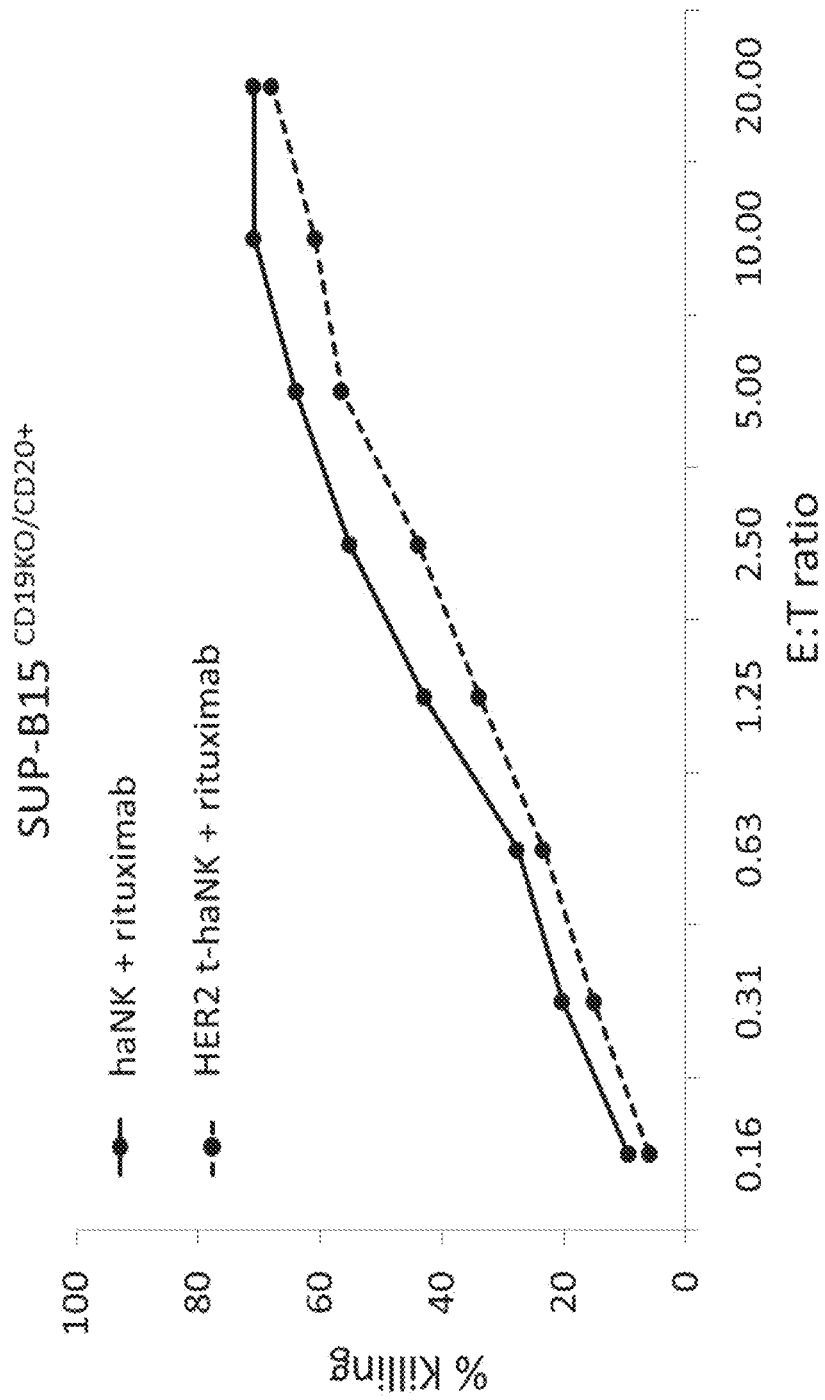
FIG. 43 shows exemplary results for ADCC of HER2.CAR-t-haNK cells.

In further experiments, the inventor demonstrated expression of the HER2.CAR in HER2.CAR-t-haNK cells as is illustrated in FIG. 40. Natural cytotoxicity of the HER2.CAR-t-haNK cells is shown in the results of FIG. 41, while results for CAR mediated cytotoxicity are shown in FIG. 42. Exemplary data for ADCC of HER2.CAR-t-haNK cells are shown in the graph of FIG. 43.

Example 8: CD30-CAR with FcεRIγ Signaling Domain

In this example, the inventors constructed a $1^{st}$ generation CARs with a FcεRIγ signaling domain that included an anti-CD30 scFv coupled to a CD8 hinge, that in turn was coupled to a CD28 transmembrane domain, which was coupled to a FcεRIγ signaling domain. The so constructed CD30-CAR had a nucleic acid sequence of SEQ ID NO: 61.

Figure 50:
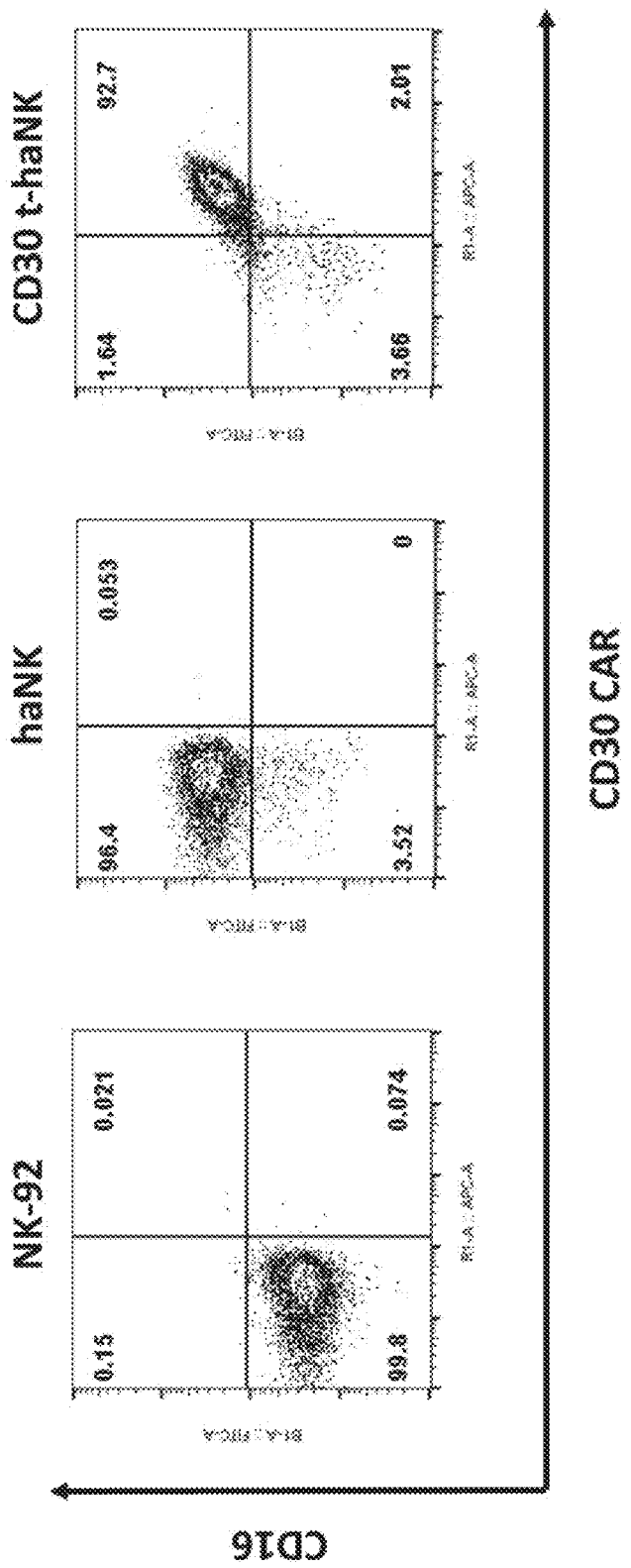
FIG. 50 shows exemplary results for expression of CD16 and CD30.CAR.
Figure 51:
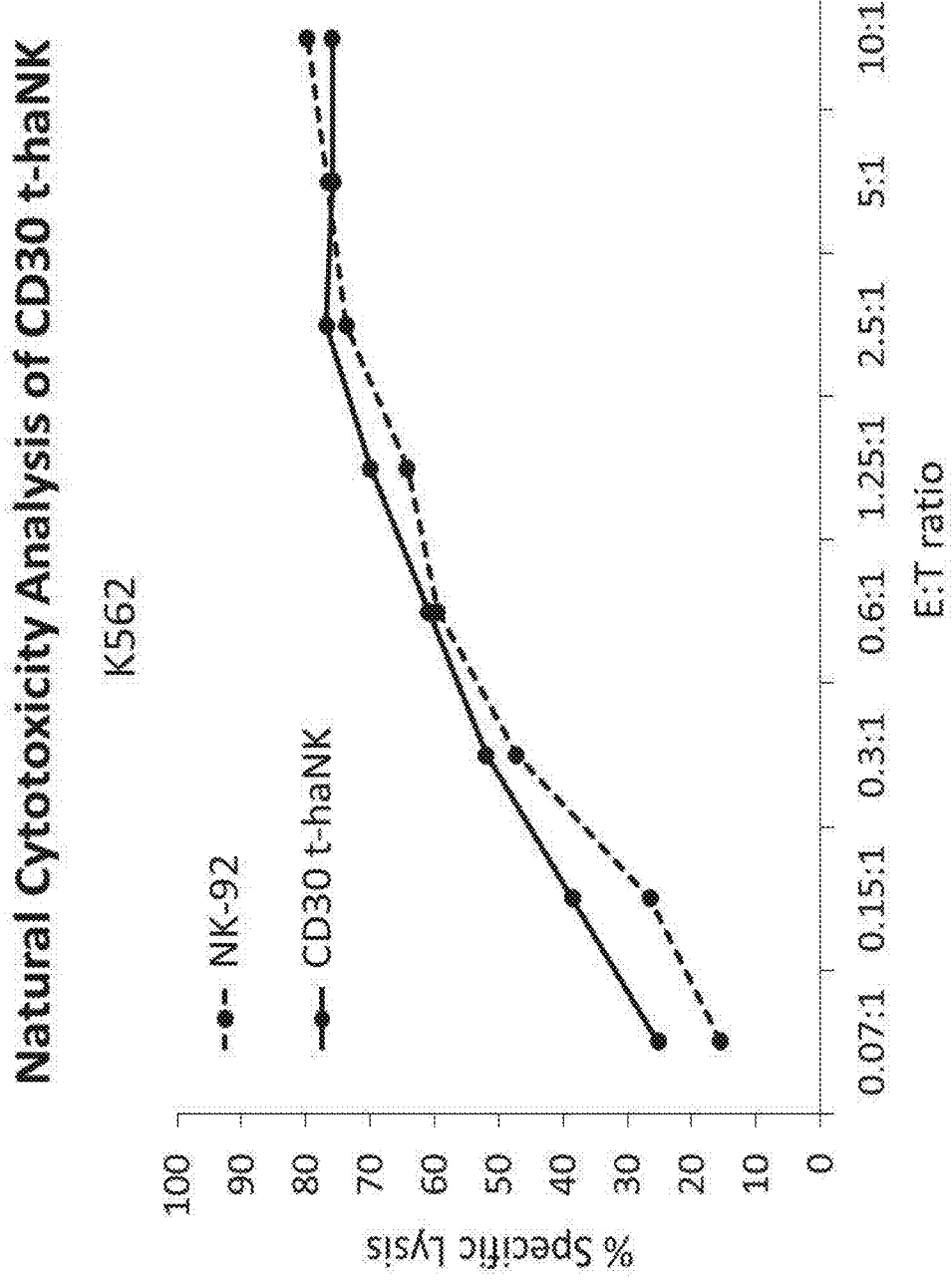
FIG. 51 shows exemplary results for natural cytotoxicity of CD30.CAR-t-haNK cells.
Figure 52:
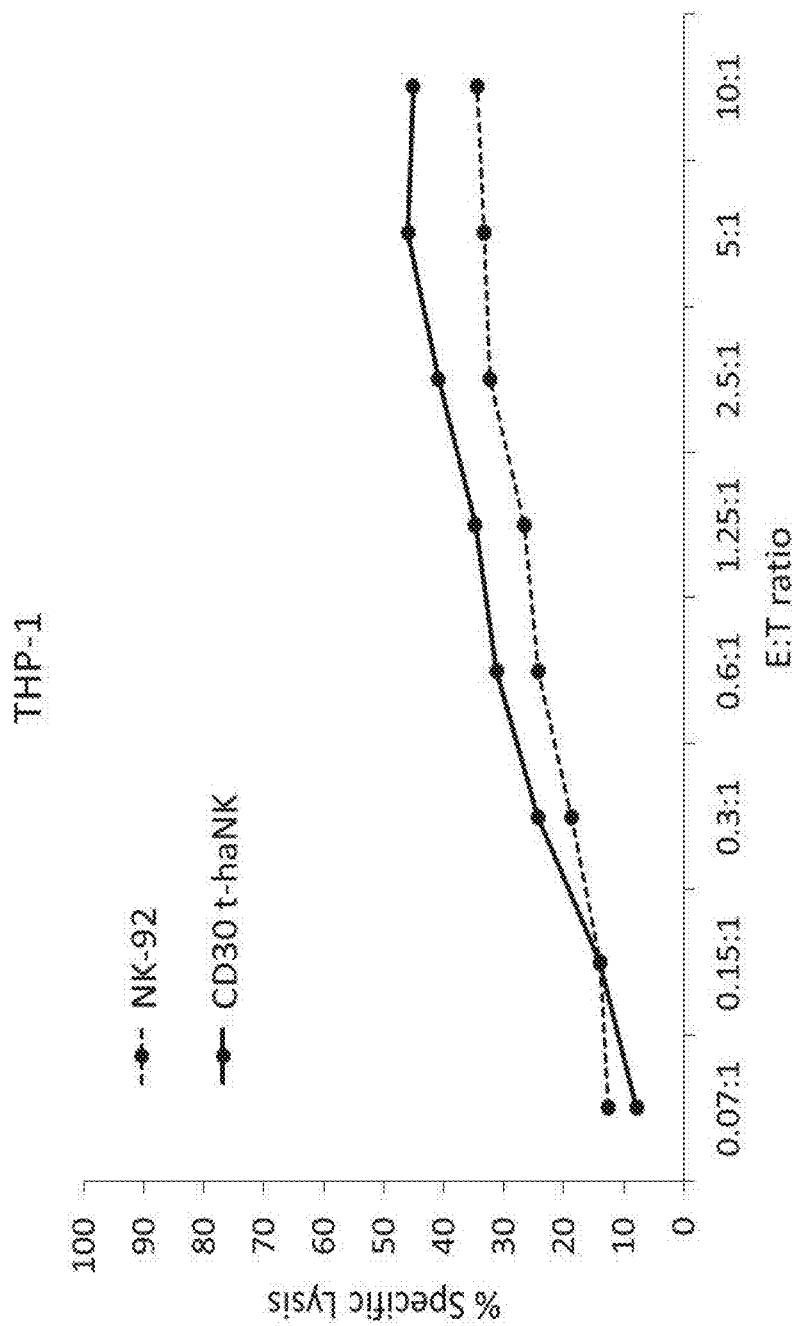
FIG. 52 shows exemplary results for CAR mediated cytotoxicity of CD30.CAR-t-haNK cells.
Figure 53:
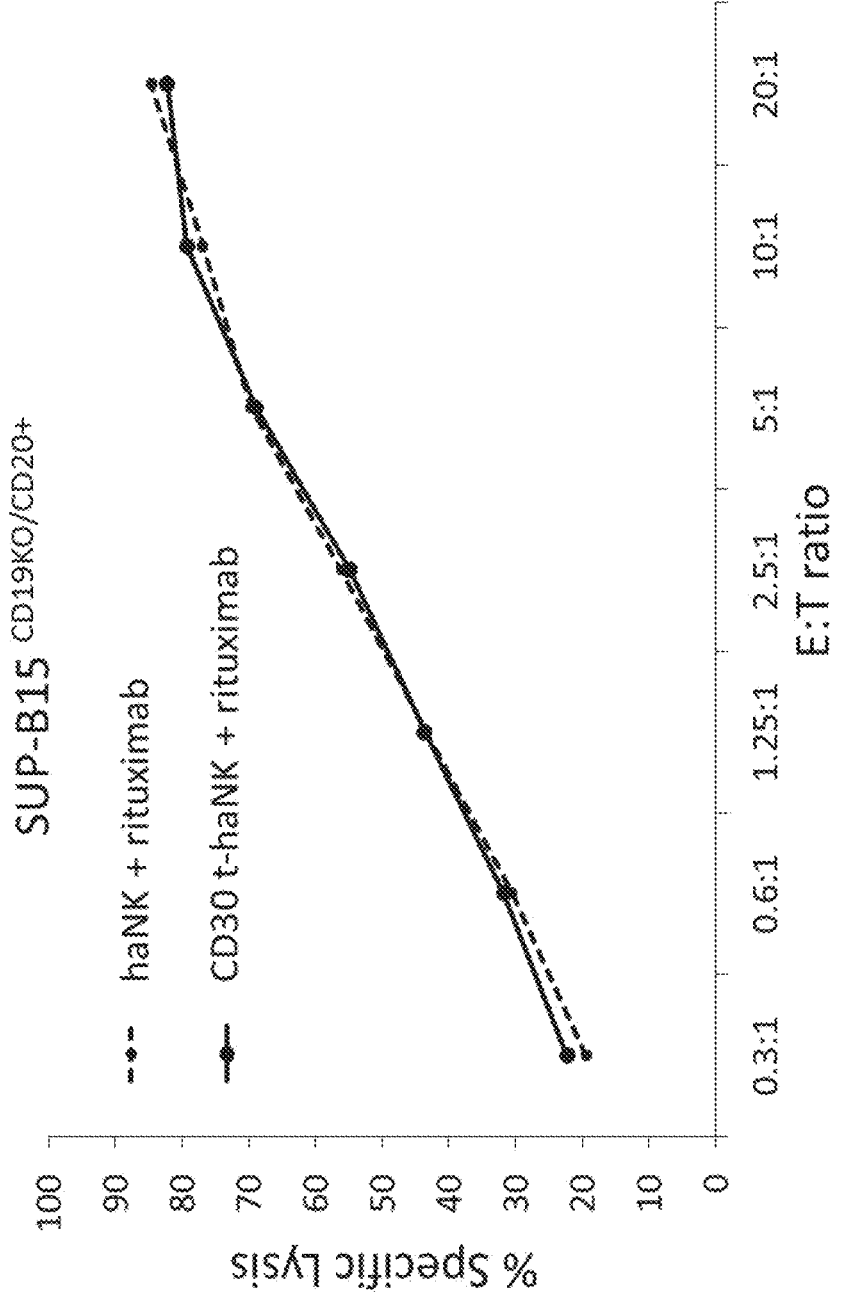
FIG. 53 shows exemplary results for ADCC of CD30.CAR-t-haNK cells.

Expression of the CD30-CAR is demonstrated in the results of FIG. 50, while the results for natural cytotoxicity of the recombinant cells are shown in FIG. 51. CAR mediated cytotoxicity was demonstrated in the results of FIG. 52, while exemplary results for ADCC are shown in the data of FIG. 53.

Example 9: EGFR-CAR with FcεRIγ Signaling Domain

In this example, the inventors constructed a $1^{st}$ generation CARs with a FcεRIγ signaling domain that included an anti-EGFR scFv coupled to a CD8 hinge, that in turn was coupled to a CD28 transmembrane domain, which was coupled to a FcεRIγ signaling domain. The so constructed EGFR-CAR had a nucleic acid sequence of SEQ ID NO:62.

Figure 17:
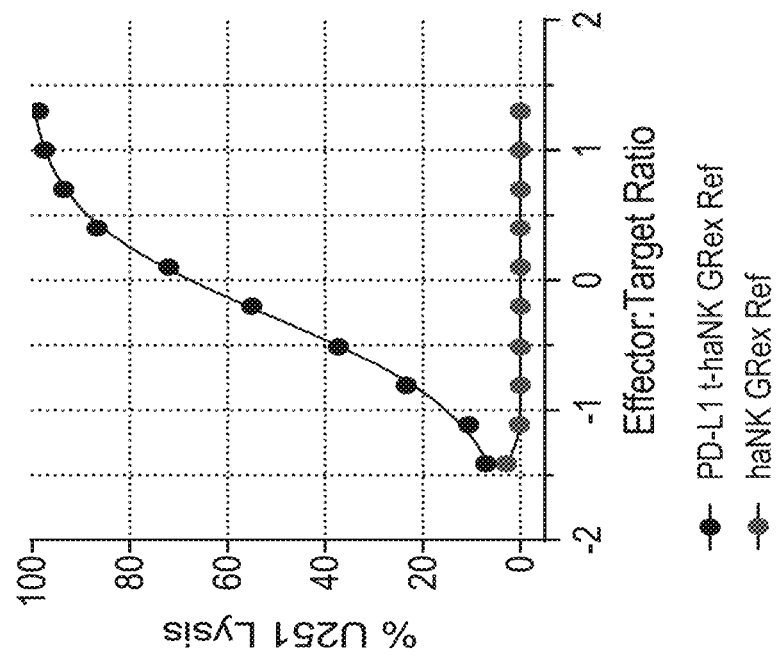
FIG. 17 shows exemplary results for cytotoxicity of PD-L1.CAR-t-haNK cells against U251 cells.
Figure 18:
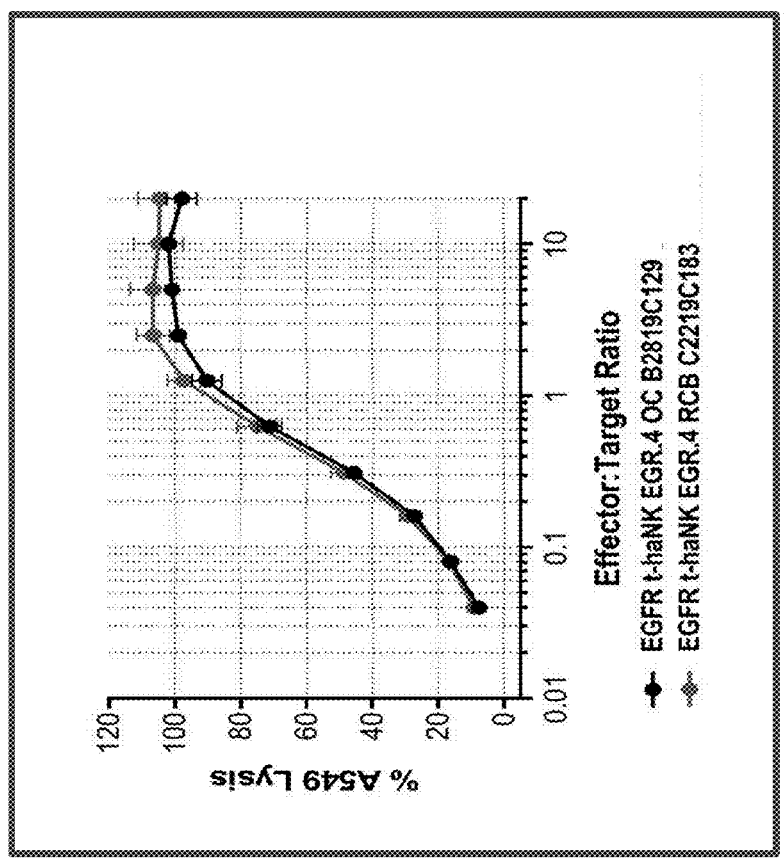
FIG. 18 shows exemplary results for cytotoxicity of EGFR.CAR-t-haNK cells against A-549 cells.
Figure 35:
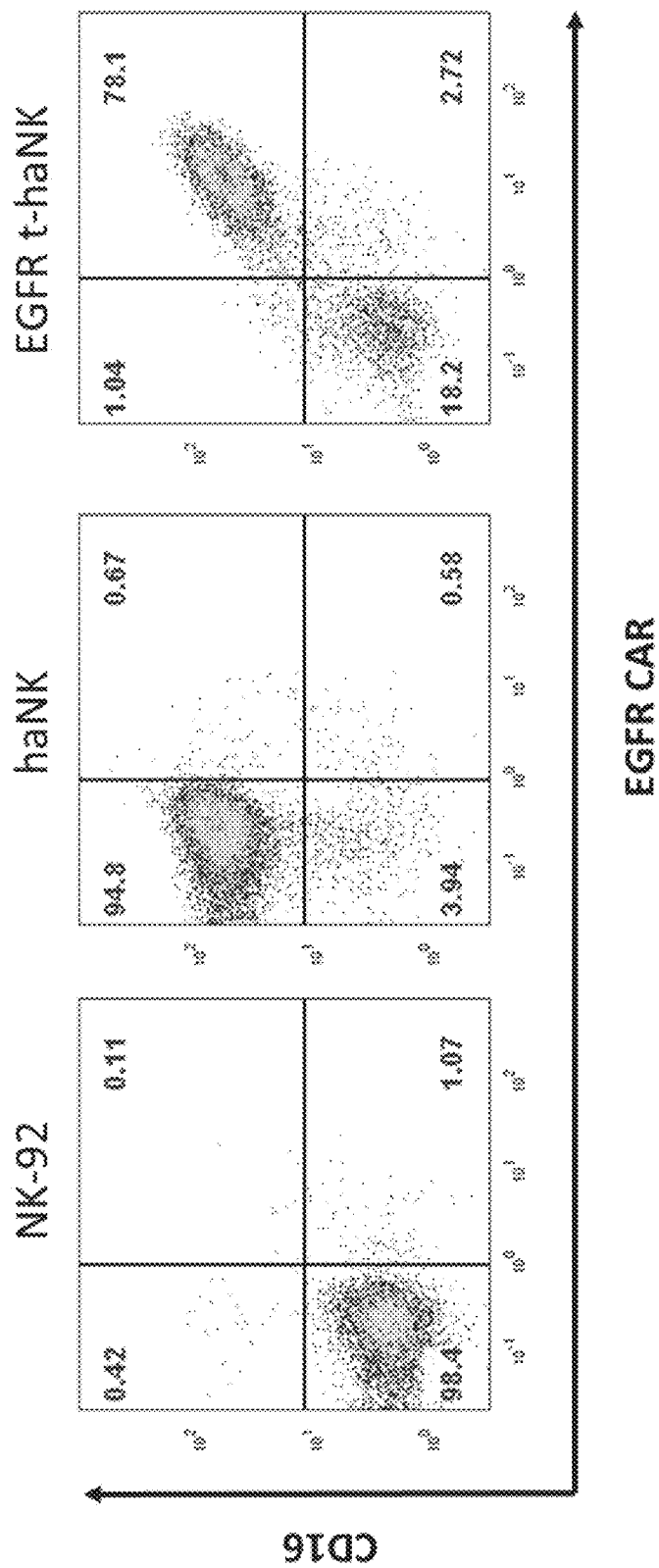
FIG. 35 shows exemplary results for expression of CD16 and EGFR.CAR.
Figure 36:
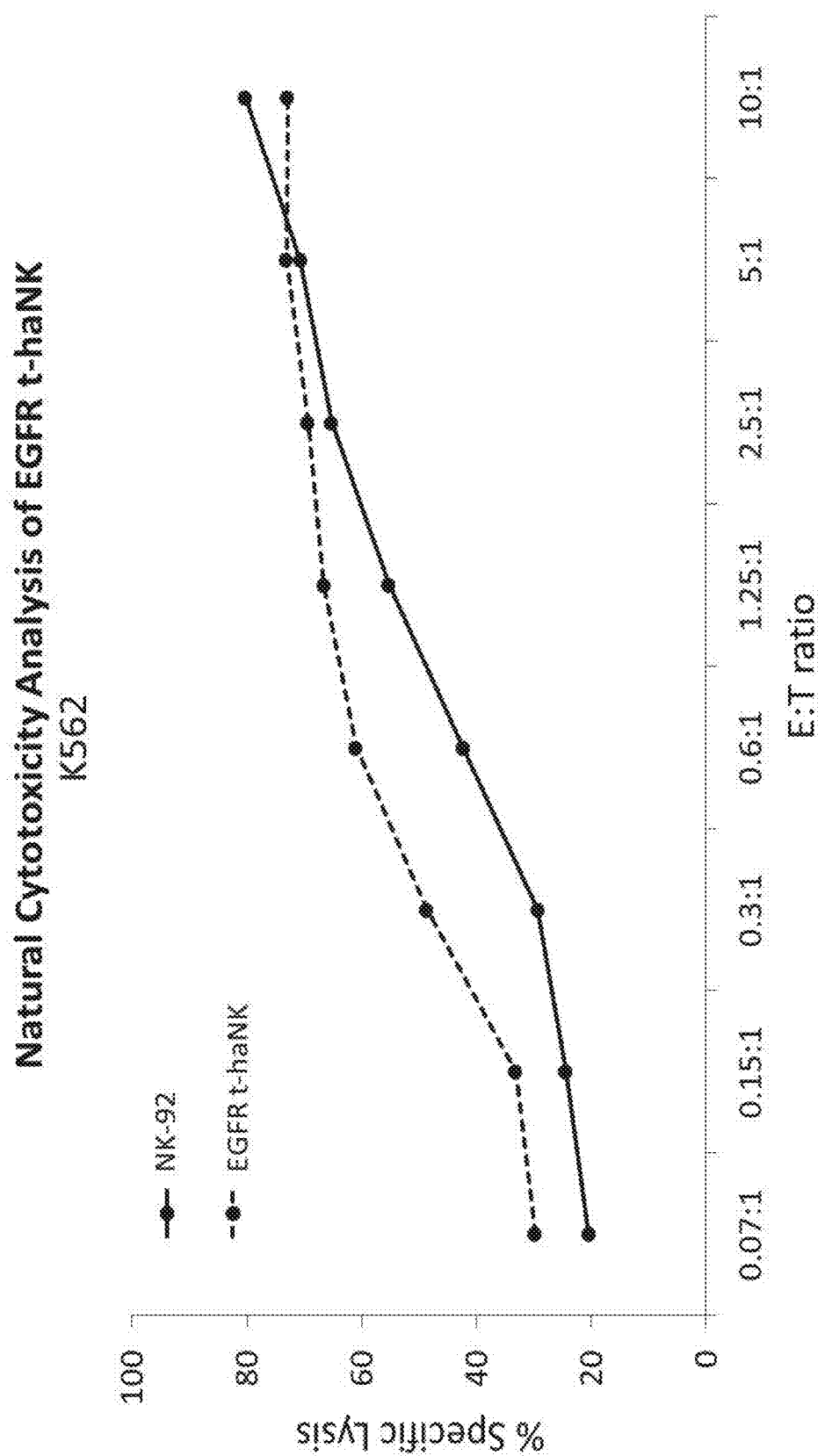
FIG. 36 shows exemplary results for natural cytotoxicity of EGFR.CAR-t-haNK cells.
Figure 37:
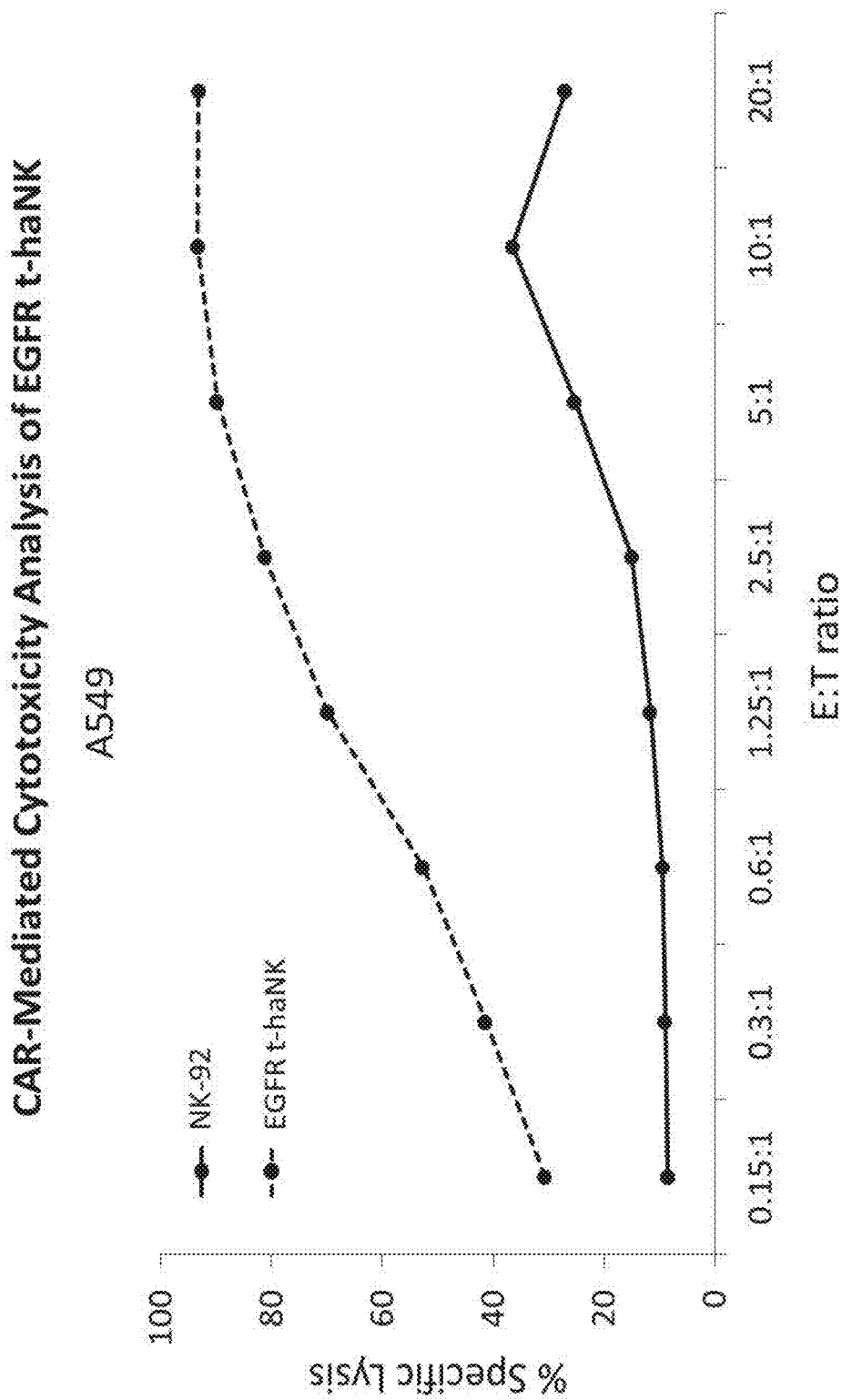
FIG. 37 shows exemplary results for CAR mediated cytotoxicity of EGFR.CAR-t-haNK cells.
Figure 38:
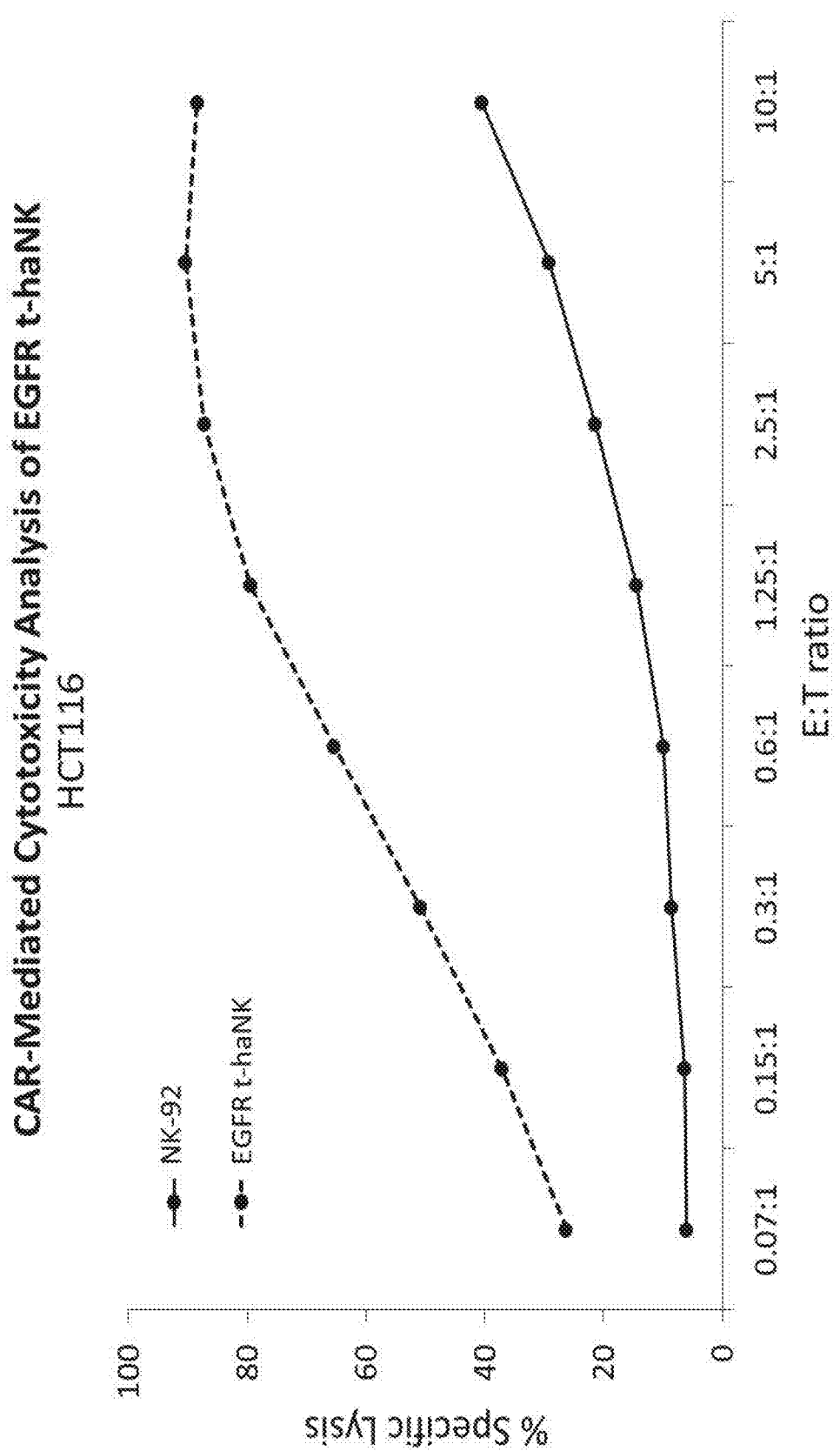
FIG. 38 shows exemplary results for CAR mediated cytotoxicity of EGFR.CAR-t-haNK cells.
Figure 39:
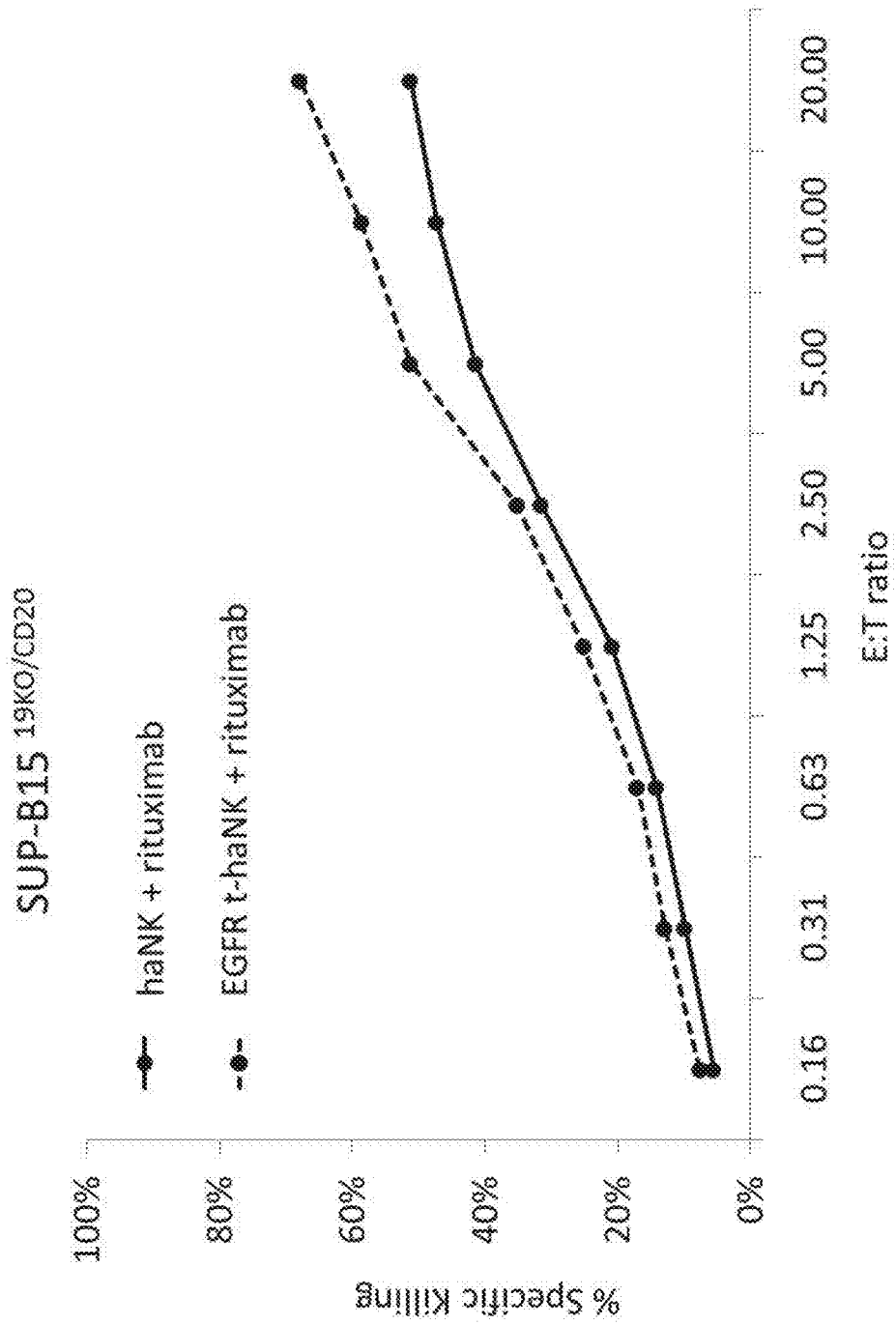
FIG. 39 shows exemplary results for ADCC of EGFR-.CAR-t-haNK cells.

Functionality of the so constructed EGFR.CAR-t-haNK cells was tested against A-549 cells using a standard cytotoxicity assay and exemplary results are shown in FIG. 17. As can be readily seen from the data, the EGFR.CAR-t-haNK cells expressing the CAR with the FcεRIγ signaling domain exhibited significant cytotoxicity against the A-549 target cells. Expression of the EGFR-CAR in the EGFR-.CAR-t-haNK cells is shown in FIG. 35, while natural cytotoxicity results are shown in FIG. 36. Exemplary results for CAR mediated cytotoxicity of EGFR.CAR-t-haNK cells are shown in FIG. 37 and FIG. 38, while results for ADCC of EGFR.CAR-t-haNK cells are shown in FIG. 39.

Example 10: IGF1R-CAR with FcεRIγ Signaling Domain

Figure 65:
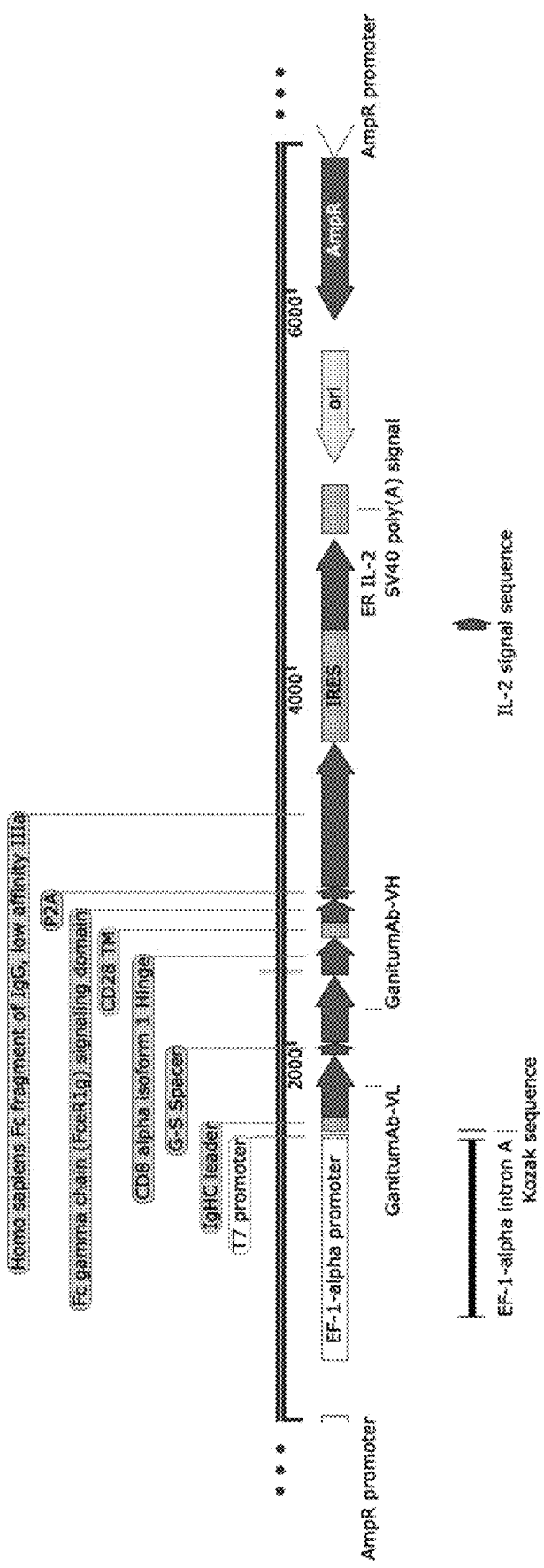
FIG. 65 depicts an exemplary tricistronic construct encoding IGF1R-CAR, CD16, and IL-2$^{ER}$.

In this example, the inventors constructed a $1^{st}$ generation CARs with a FcεRIγ signaling domain that included an anti-IGF1R scFv coupled to a CD8 hinge, that in turn was coupled to a CD28 transmembrane domain, which was coupled to a FcεRIγ signaling domain. The so constructed IGF1R-CAR had a nucleic acid sequence of SEQ ID NO:63, and a tricistronic construct encoding IGF1R-CAR, CD16, and IL-2$^{ER}$ had a nucleic acid sequence of SEQ ID NO:76, which is also schematically illustrated in FIG. 65.

Figure 22:
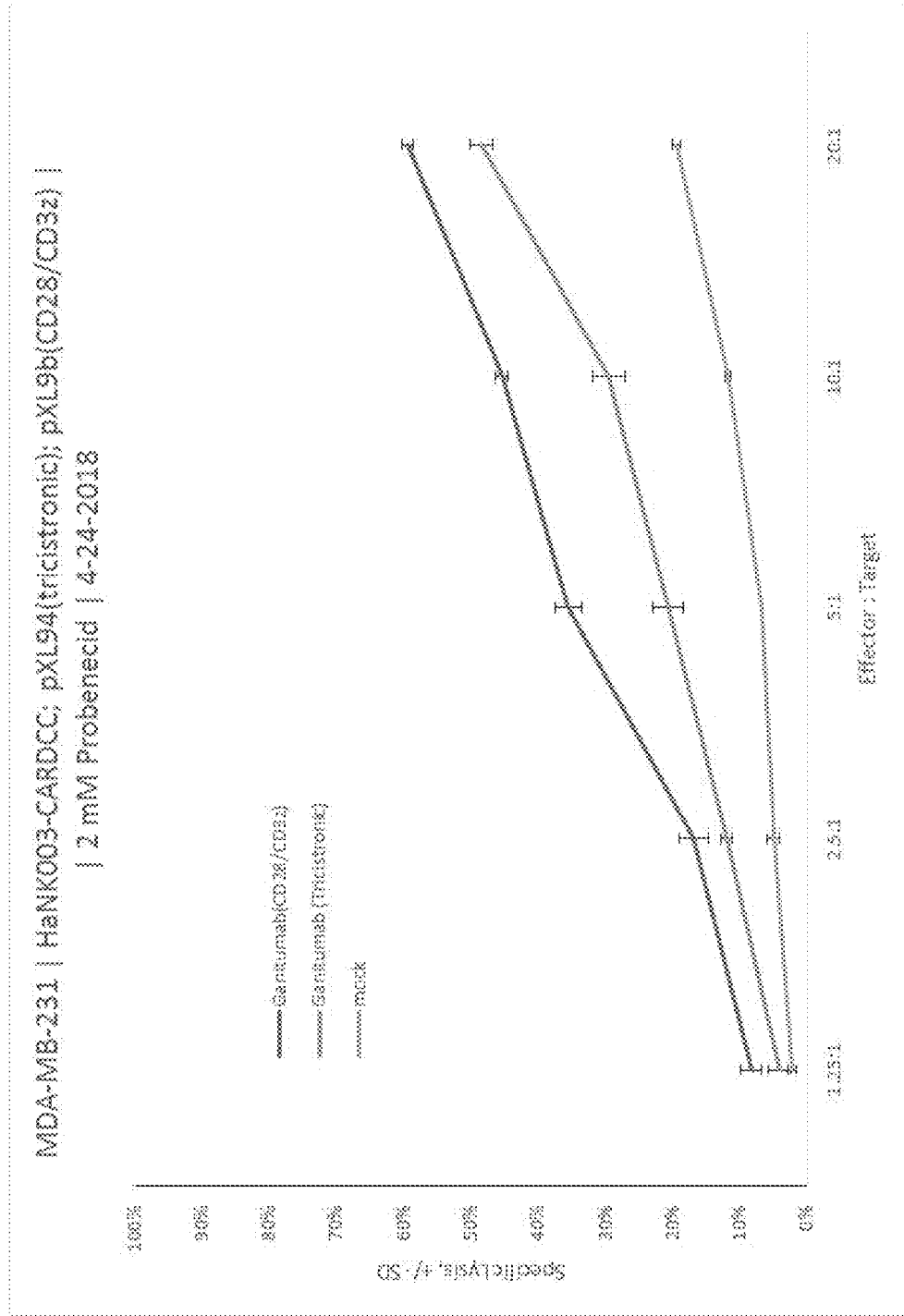
FIG. 22 shows exemplary results for cytotoxicity of IGF1R.CAR-t-haNK cells against MDA-MB-231 cells.
Figure 23:
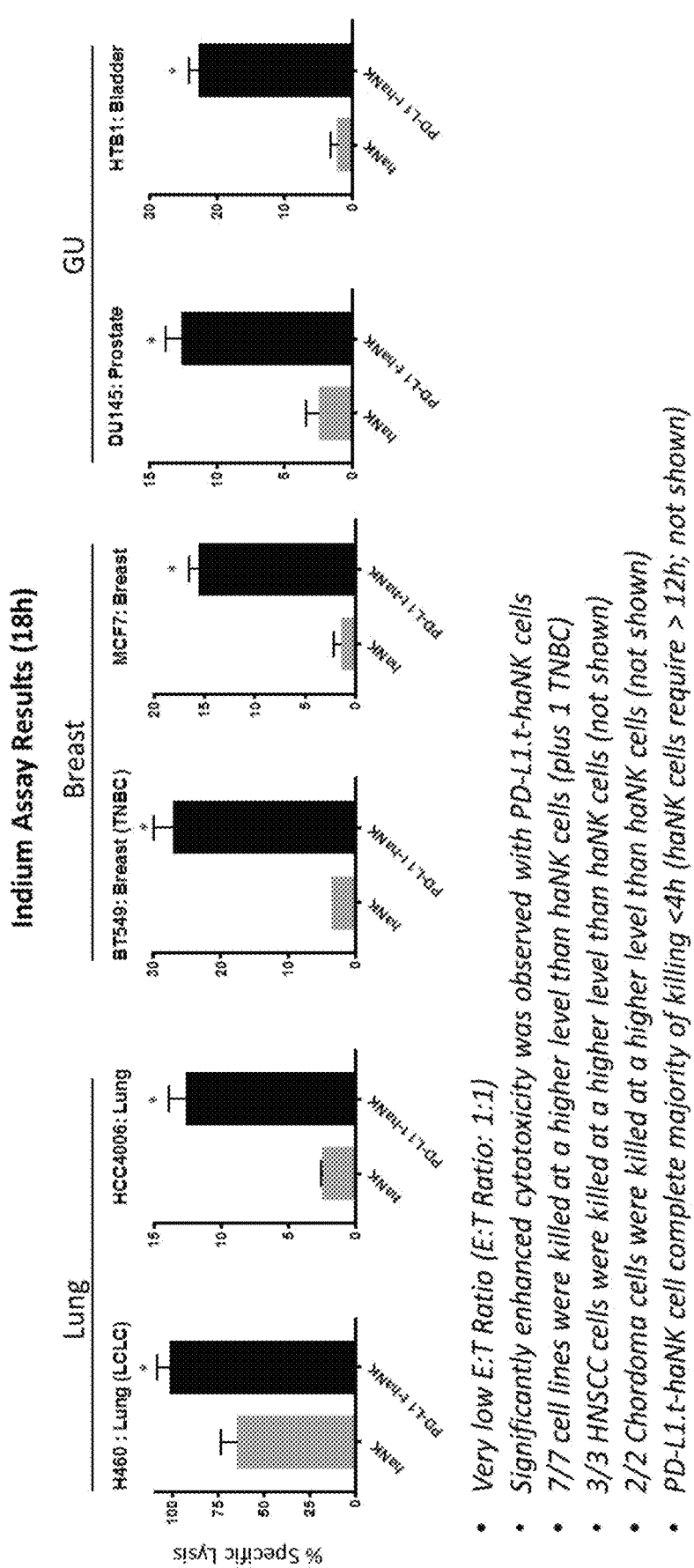
FIG. 23 shows exemplary results for cytotoxicity of PD-L1.CAR-t-haNK cells against a variety of cancer cells.

Functionality of the so constructed IGF1R.CAR-t-haNK cells was tested against MDA-MB-231 cells using a standard cytotoxicity assay in comparison with a $2^{nd}$ generation CAR (CD28/CD3z) and exemplary results are shown in FIG. 22. As can be readily seen from the data, the IGF1R.CAR-t-haNK cells expressing the CAR with the FcεRIγ signaling domain exhibited significant and target specific cytotoxicity against the MDA-MB-231 target cells, which was comparable with the cytotoxicity of the $2^{nd}$ generation CAR.

Example 11: CD123-CAR with FcεRIγ Signaling Domain

Figure 48:
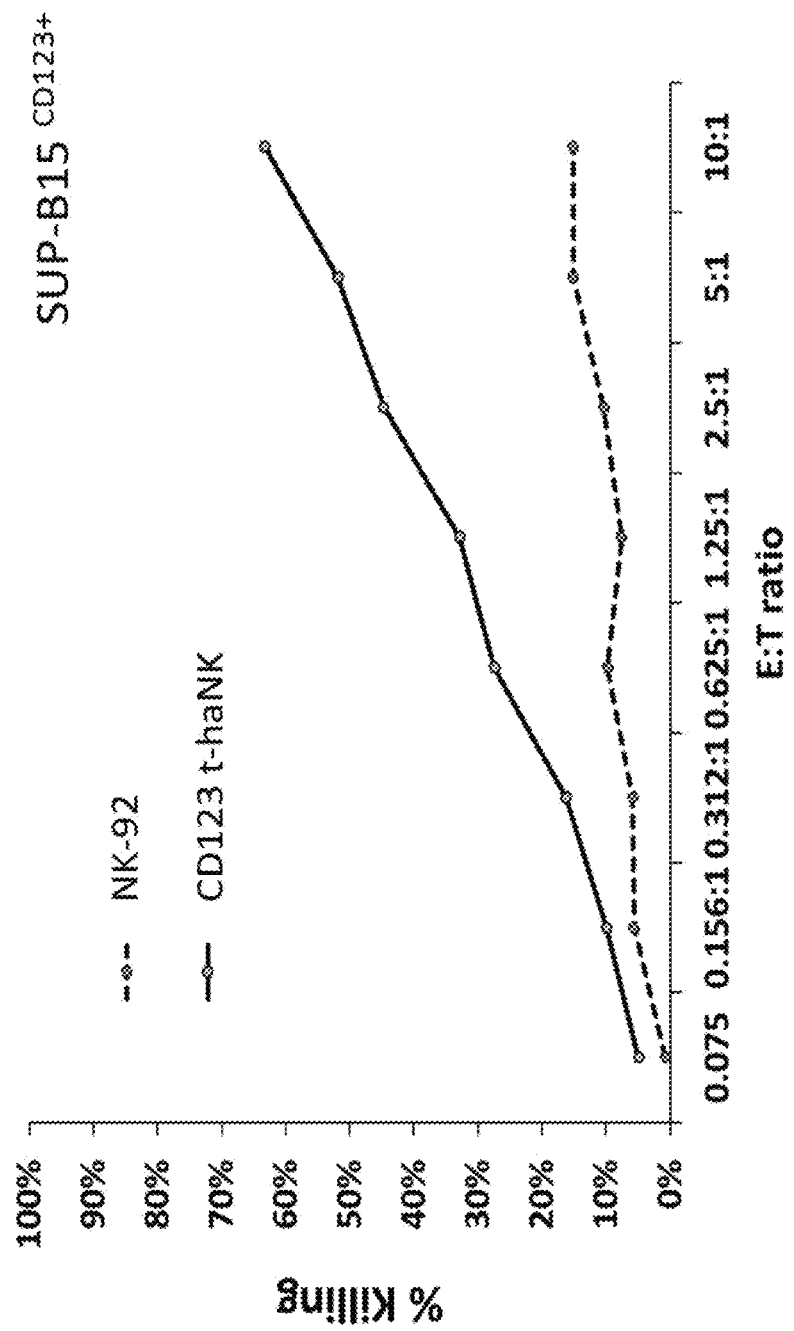
FIG. 48 shows exemplary results for CAR mediated cytotoxicity of CD123.CAR-t-haNK cells.
Figure 49:
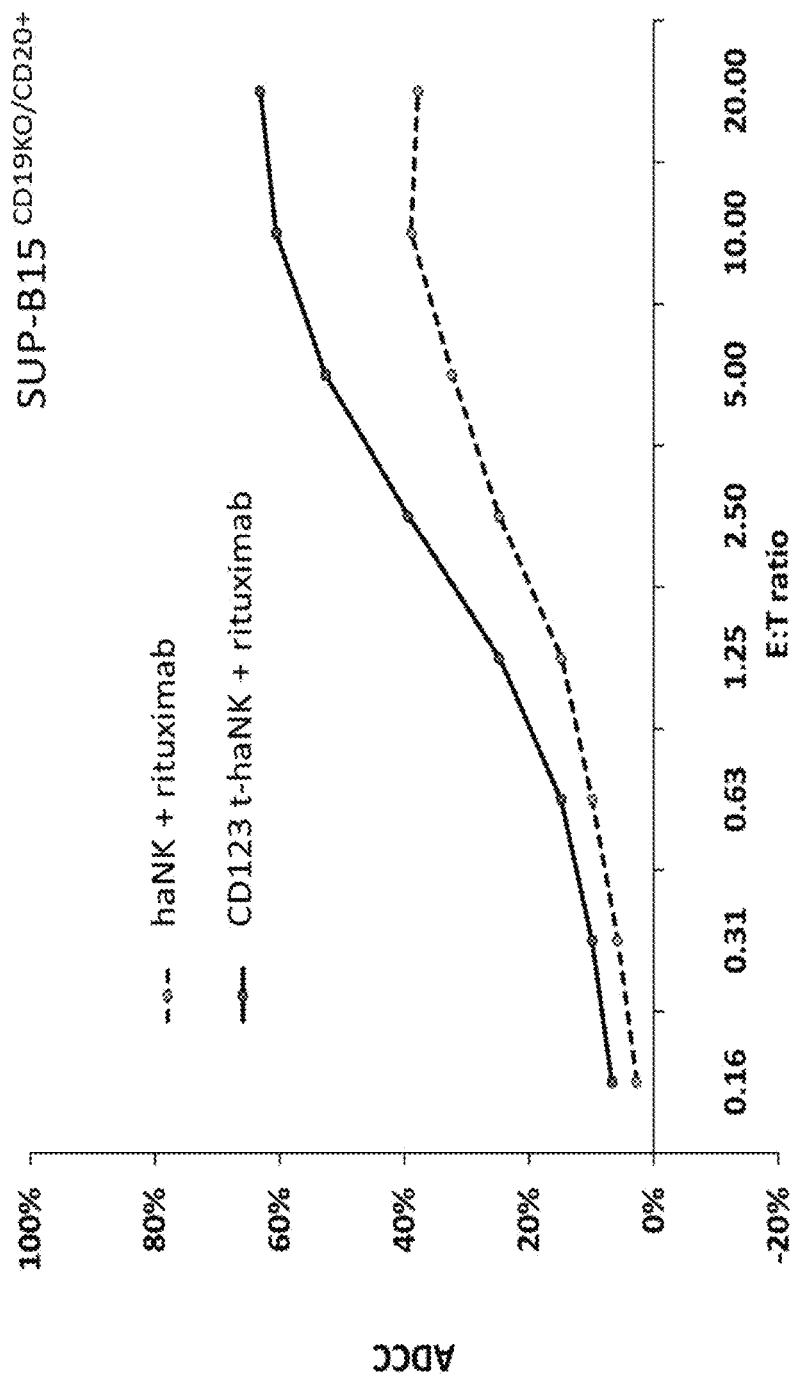
FIG. 49 shows exemplary results for ADCC of CD123.CAR-t-haNK cells.

In this example, the inventors constructed a $1^{st}$ generation CARs with a FcεRIγ signaling domain that included an anti-CD123 scFv coupled to a CD8 hinge, that in turn was coupled to a CD28 transmembrane domain, which was coupled to a FcεRIγ signaling domain. The so constructed CD123-CAR had a nucleic acid sequence of SEQ ID NO:64. Data for the CAR mediated cytotoxicity of the CD123-CAR expressing recombinant NK cells is shown in FIG. 48, and FIG. 49 shows exemplary data for ADCC of CD123-CAR expressing recombinant NK cells.

Example 12: PD-L1-CAR with FcεRIγ Signaling Domain

In this example, the inventors constructed a $1^{st}$ generation CARs with a FcεRIγ signaling domain that included an anti-PD-L1 scFv coupled to a CD8 hinge, that in turn was coupled to a CD28 transmembrane domain, which was coupled to a FcεRIγ signaling domain. The so constructed PD-L1-CAR had a nucleic acid sequence of SEQ ID NO:65.

Figure 16:
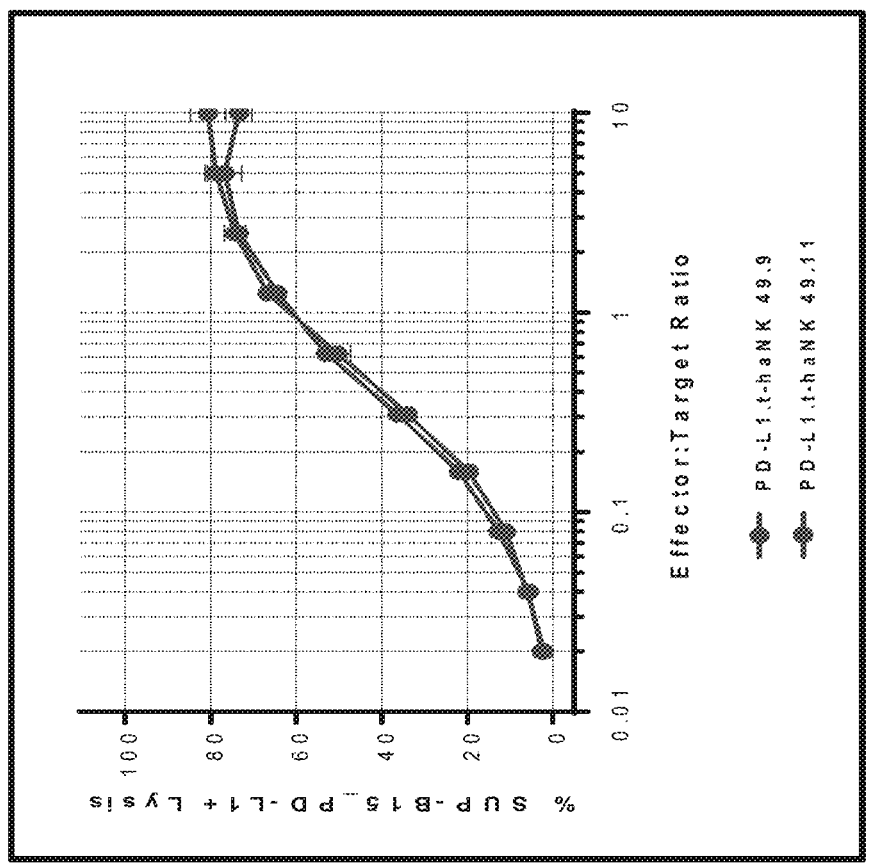
FIG. 16 shows exemplary results for cytotoxicity of PD-L1.CAR-t-haNK cells against SUP-B15.PD-L1+ cells.

Functionality of the so constructed PD-L1.CAR-t-haNK cells was tested against SUP-B15.PD-L1$^{+}$ cells using a standard cytotoxicity assay and exemplary results are shown in FIG. 16. As can be readily seen from the data, the PD-L1.CAR-t-haNK cells expressing the CAR with the FcεRIγ signaling domain exhibited significant cytotoxicity against the SUP-B15.PD-L1$^{+}$ target cells.

Functionality of the so constructed PD-L1.CAR-t-haNK cells was also tested against U251 cells using a standard cytotoxicity assay and exemplary results are shown in FIG. 17 along with non-transfected haNK cells. As can be readily seen from the data, the PD-L1.CAR-t-haNK cells expressing the CAR with the FcεRIγ signaling domain exhibited target specific and significant cytotoxicity against the U251 target cells, whereas the haNK control cells had substantially no cytotoxicity against the same U251 cells.

In still further experiments on target cell specificity with respect to PD-L1, the inventors tested several PD-L1 positive tumor cell lines using the PD-L1.CAR-t-haNK cells along with haNK cells as control for general cytotoxicity. As can be readily seen from FIG. 24, the PD-L1.CAR-t-haNK cells had superior cytotoxicity across a wide variety of tumor cells (lung, breast, genitury tumor cells, and additionally, head and neck small cell cancer, chordoma). Notably, the PD-L1.CAR-t-haNK cells required less than 4 hours for the majority (>85%) of cell killing whereas the control haNK cells required more than 12 hours.

Figure 24:
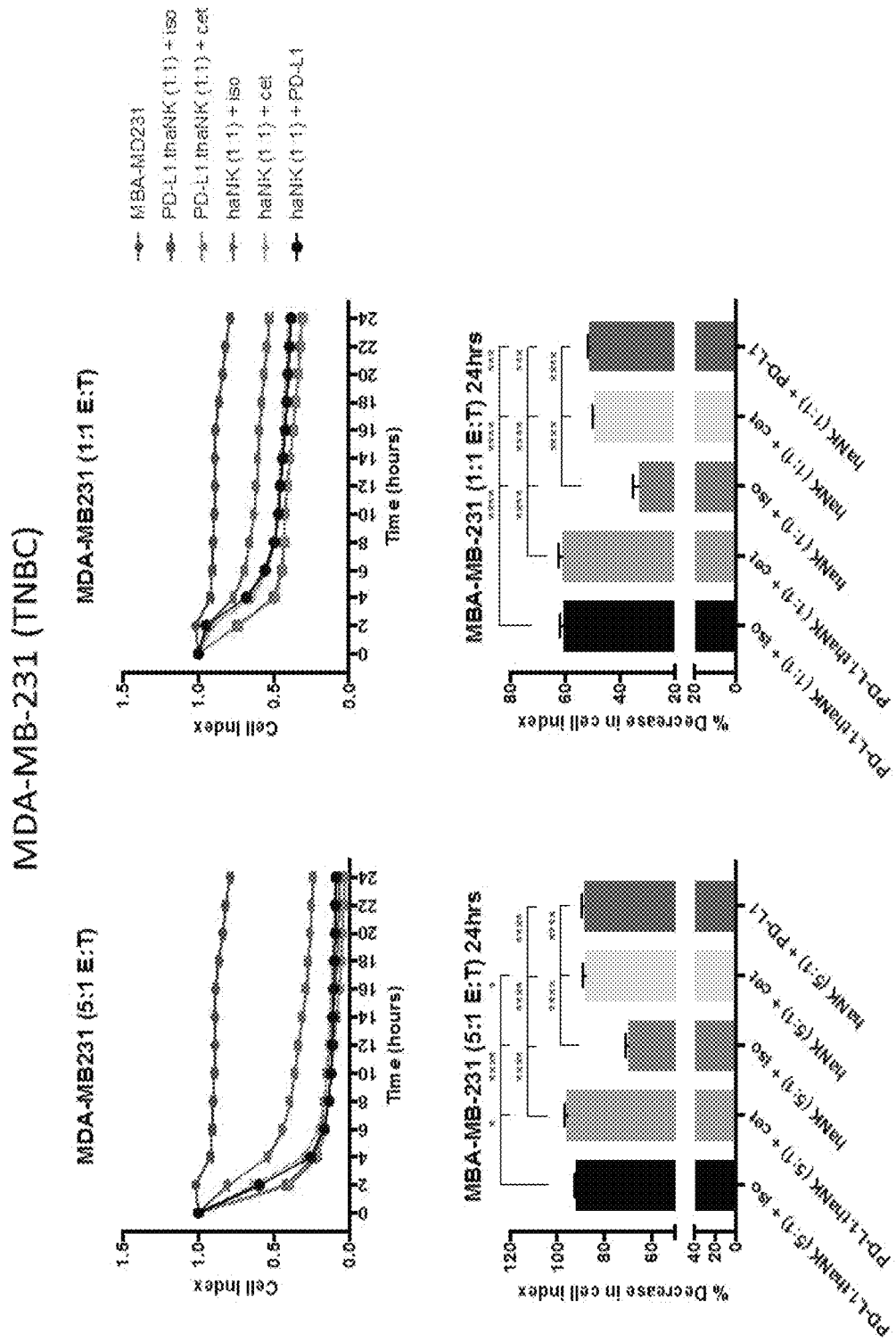
FIG. 24 shows exemplary comparative results for cytotoxicity of PD-L1.CAR-t-haNK cells against MDA-MB-231 cells.

FIG. 24 further illustrates cytotoxicity of the PD-L1.CAR-t-haNK cells against MDA-MB-231 cells as compared to various other control cells (haNK cells as indicated). As can be taken from the data, at a 5:1 E:T ratio, MDA-MB-231 lysis by PD-L1.thaNK was improved by cetuximab, and haNK activity was improved by the addition of cetuximab and a-PD-L1. Plain PD-L1.thank had improved cytotoxic activity compared to haNK and haNK+ cetuximab, and plain PD-L1.thank killing was comparable to that of haNK+PD-L1 antibody but PD-L1.thank+cetuximab outperformed haNK+cetuximab and haNK+PD-L1. At a 1:1 E:T ratio, PD-L1.thaNK activity was the same with or without cetuximab, and PD-L1.thaNK significantly outperformed intrinsic and ADCC-mediated killing by hank. haNK activity was improved by the addition of cetuximab and a-PD-L1.

Figure 44:
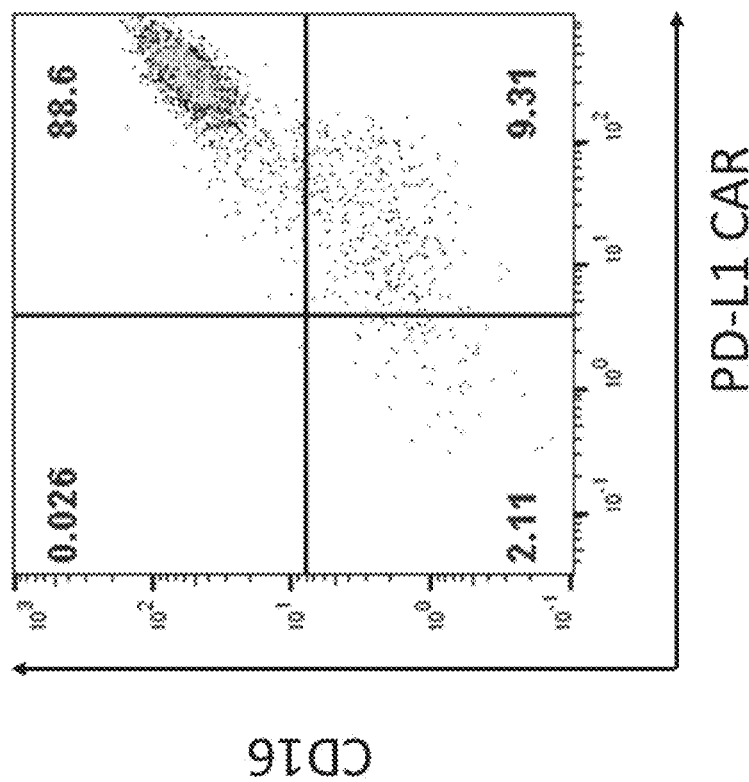
FIG. 44 shows exemplary results expression of CD16 and PD-L1.CAR.
Figure 45:
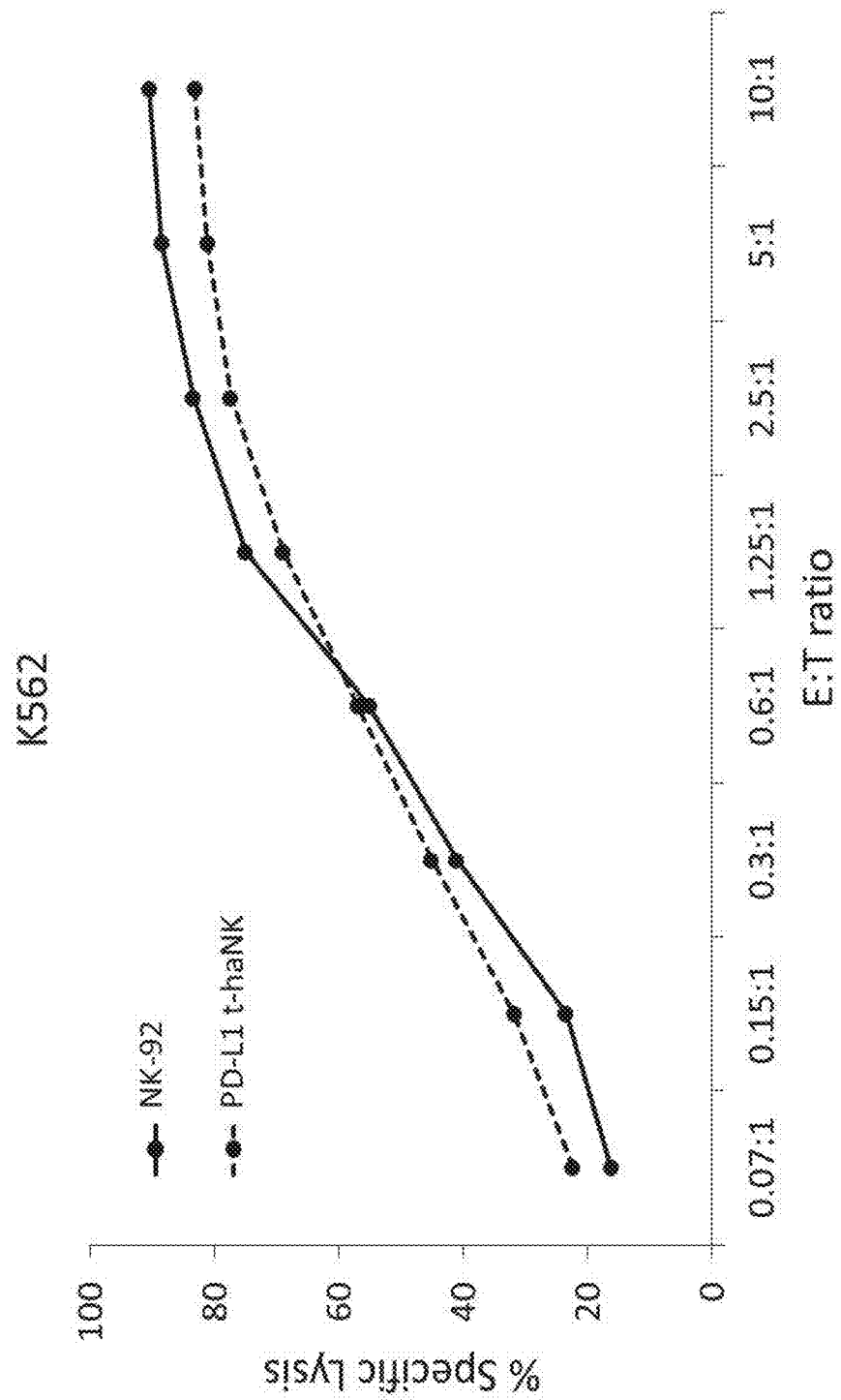
FIG. 45 shows exemplary results for natural cytotoxicity of PD-L1.CAR-t-haNK cells.
Figure 46:
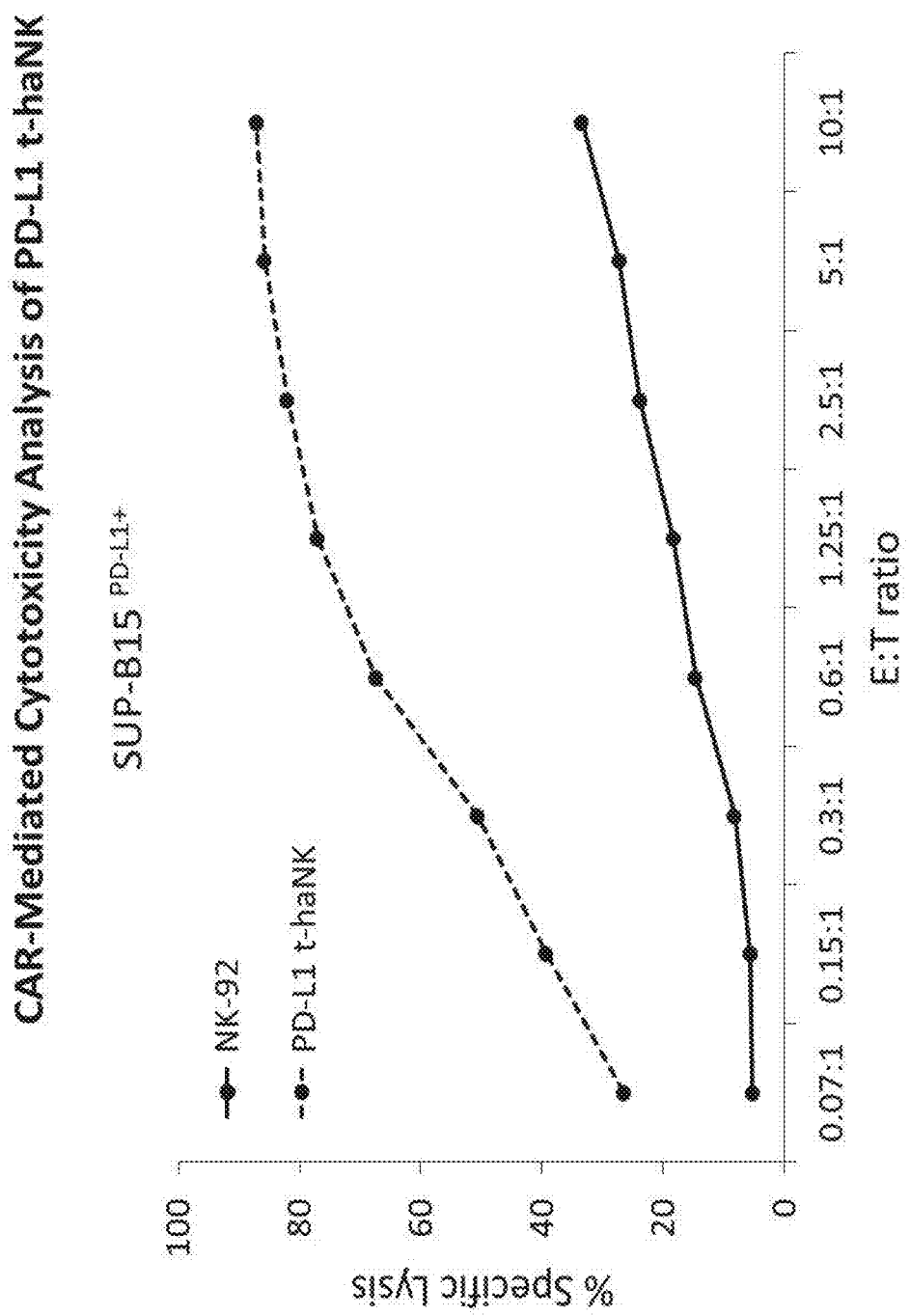
FIG. 46 shows exemplary results for CAR mediated cytotoxicity of PD-L1.CAR-t-haNK cells.
Figure 47:
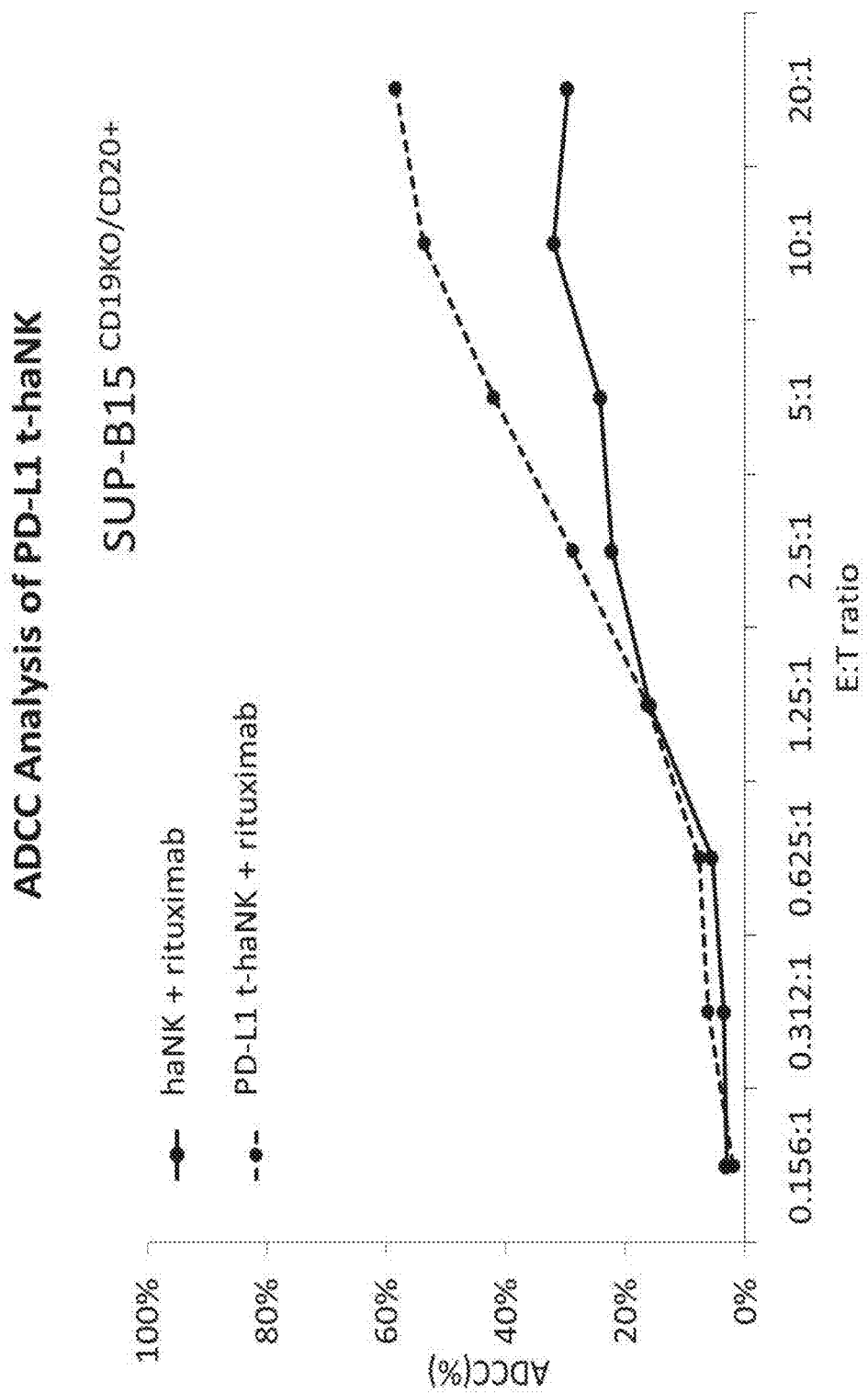
FIG. 47 shows exemplary results for ADCC of PD-L1.CAR-t-haNK cells.

In further experiments, the inventors demonstrated expression of the PD-L1.CAR in PD-L1.CAR-t-haNK cells as is illustrated in FIG. 44. Natural cytotoxicity of the PD-L1.CAR-t-haNK cells is shown in the results of FIG. 45, while results for CAR mediated cytotoxicity are shown in FIG. 46. Exemplary data for ADCC of PD-L1.CAR-t-haNK cells are shown in the graph of FIG. 47.

Example 13: CD33-CAR with FcεRIγ Signaling Domain

In this example, the inventors constructed a $1^{st}$ generation CARs with a FcεRIγ signaling domain that included an anti-HER2 scFv coupled to a CD8 hinge, that in turn was coupled to a CD28 transmembrane domain, which was coupled to a FcεRIγ signaling domain. The so constructed CD33.CAR had a nucleic acid sequence of SEQ ID NO:66.

Figure 15:
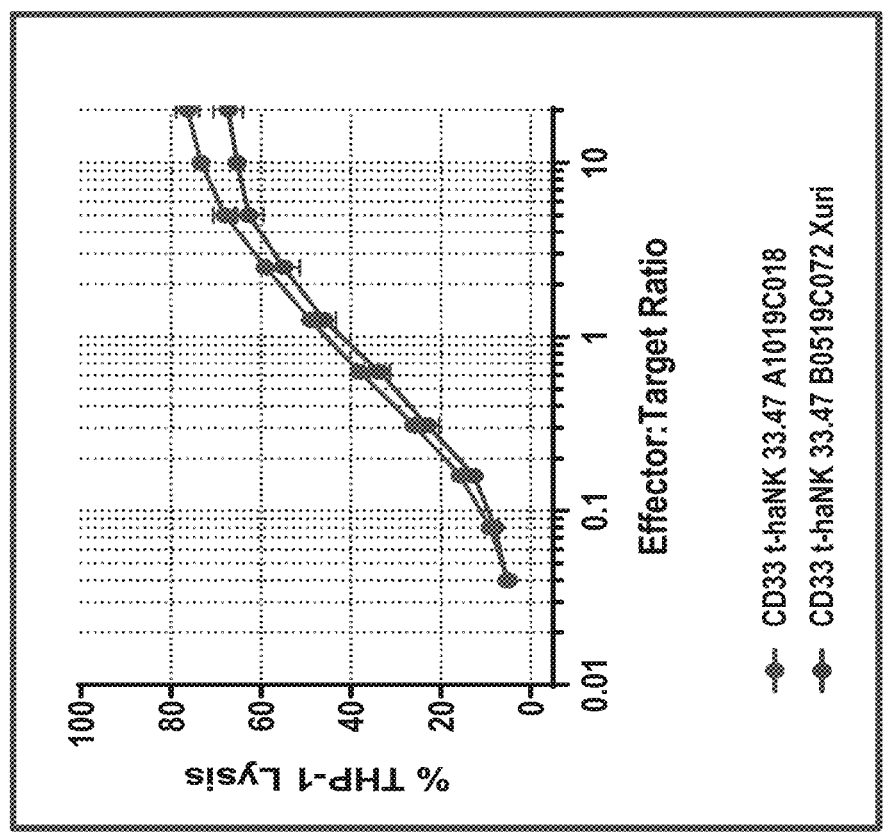
FIG. 15 shows exemplary results for cytotoxicity of CD33.CAR-t-haNK cells against THP-1 cells.
Figure 31:
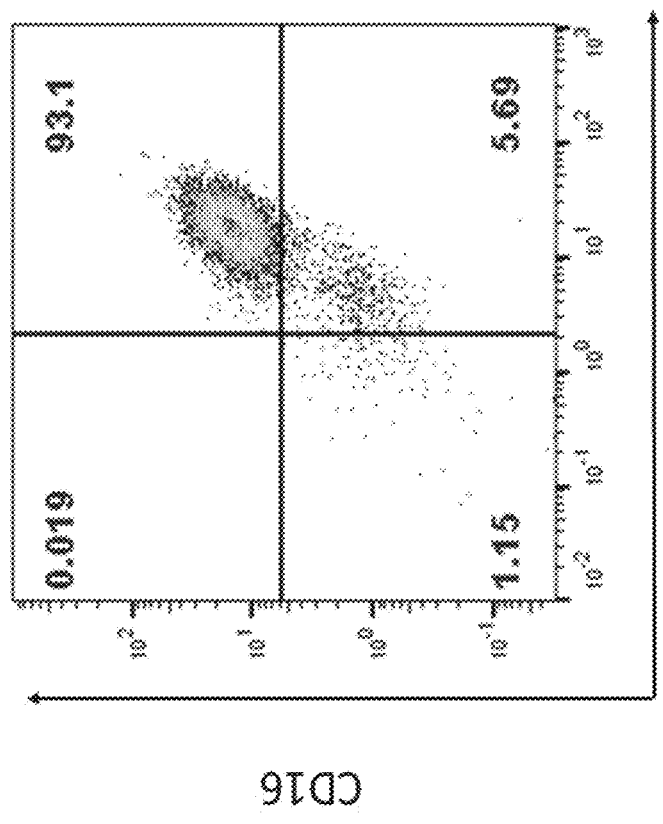
FIG. 31 shows exemplary results for expression of CD16 and CD33.CAR.
Figure 32:
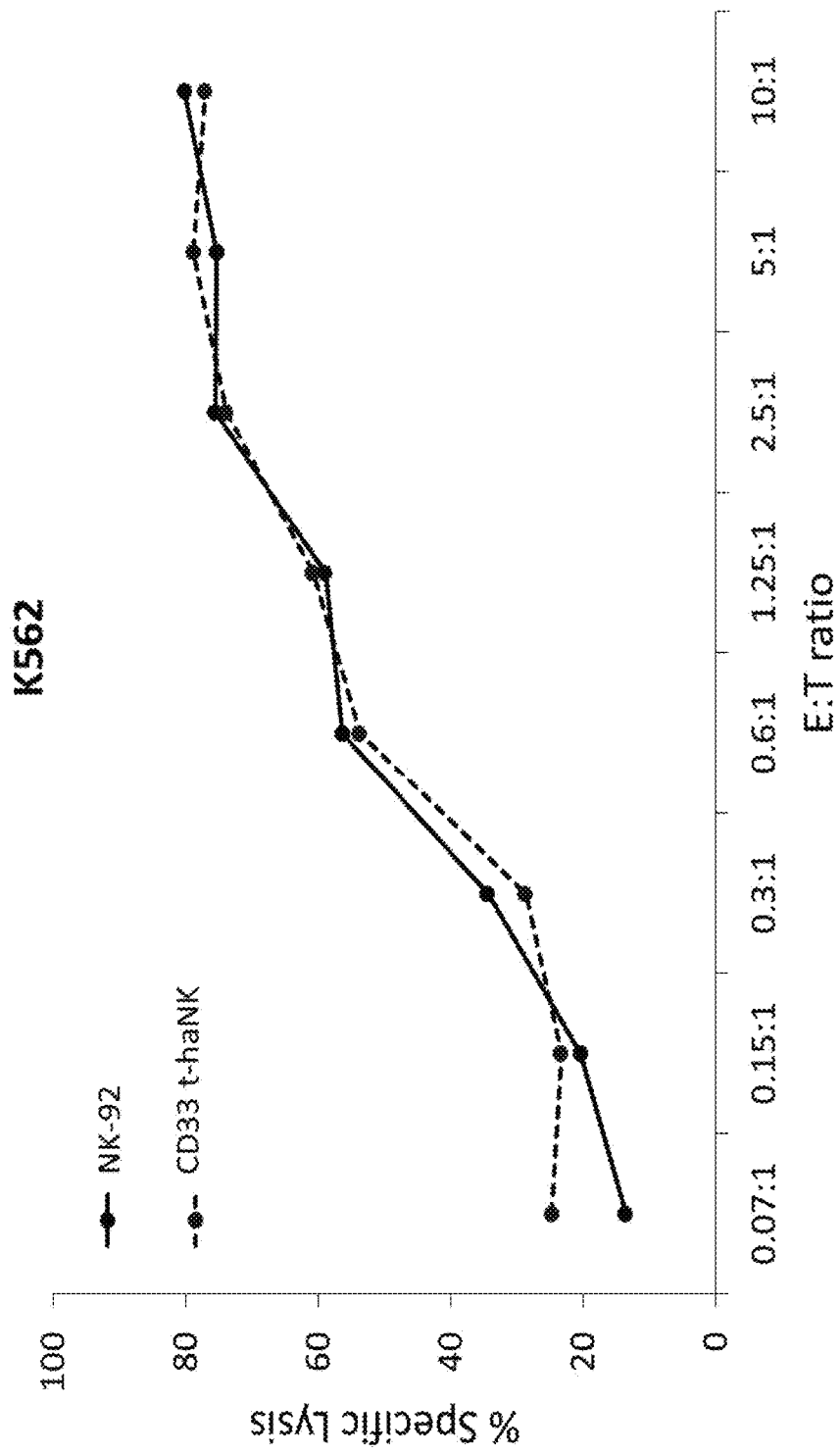
FIG. 32 shows exemplary results for natural cytotoxicity of CD33.CAR-t-haNK cells.
Figure 33:
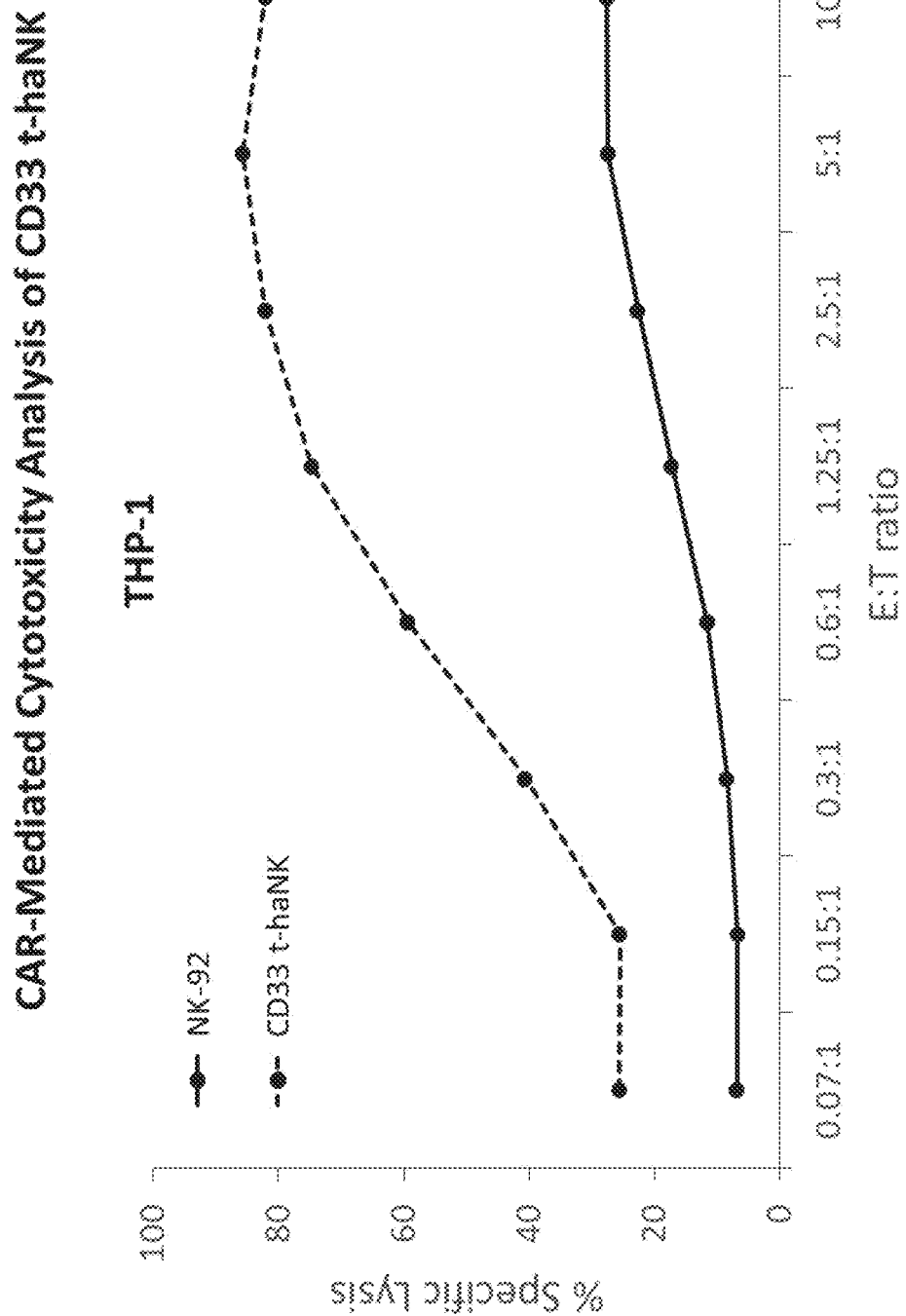
FIG. 33 shows exemplary results for CAR mediated cytotoxicity of CD33.CAR-t-haNK cells.
Figure 34:
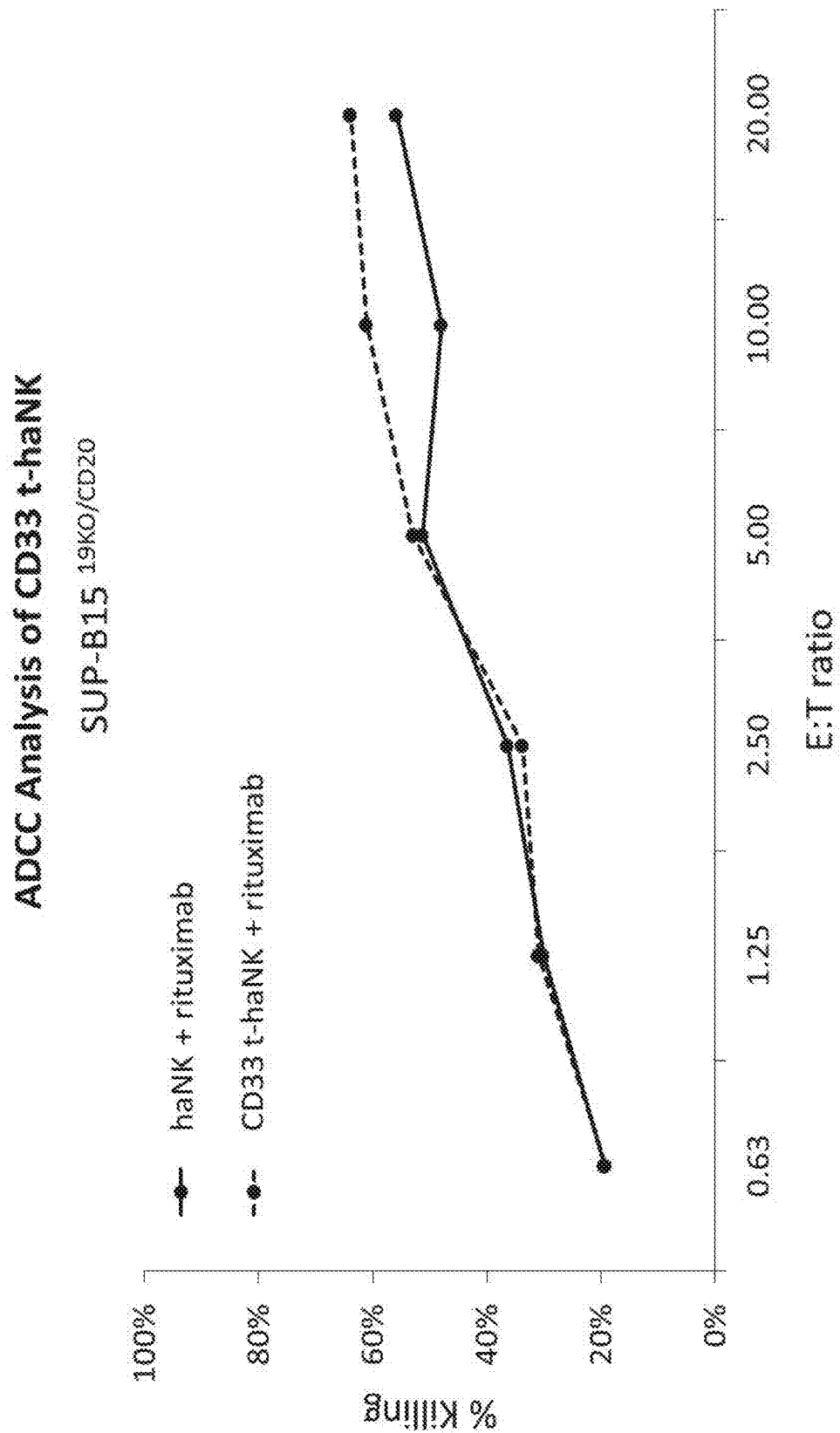
FIG. 34 shows exemplary results for ADCC of CD33.CAR-t-haNK cells.

Functionality of the so constructed CD33.CAR-t-haNK cells was tested against THP-1 cells using a standard cytotoxicity assay and exemplary results are shown in FIG. 15. As can be readily seen from the data, the CD33.CAR-t-haNK cells expressing the CAR with the FcεRIγ signaling domain exhibited significant cytotoxicity against the THP-1 target cells. Further data depicting strong expression of the CD33CAR in NK-92 cells are presented in FIG. 31. Natural cytotoxicity of the CD33.CAR-t-haNK cells against K562 cells is shown in FIG. 32, and FIG. 33 depicts results for CAR mediated cytotoxicity against THP-1 cells. FIG. 34 shows further results for ADCC of CD33.CAR-t-haNK cells against SUP-B15 CD19$^{KO}$/CD20$^+$ with rituximab.

Example 14: gp120-CAR with FcεRIγ Signaling Domain

In this example, the inventors constructed a $1^{st}$ generation CARs with a FcεRIγ signaling domain that included an anti-gp120 scFv coupled to a CD8 hinge, that in turn was coupled to a CD28 transmembrane domain, which was coupled to a FcεRIγ signaling domain. The so constructed gp120-CAR had a nucleic acid sequence of SEQ ID NO:67.

Figure 57:
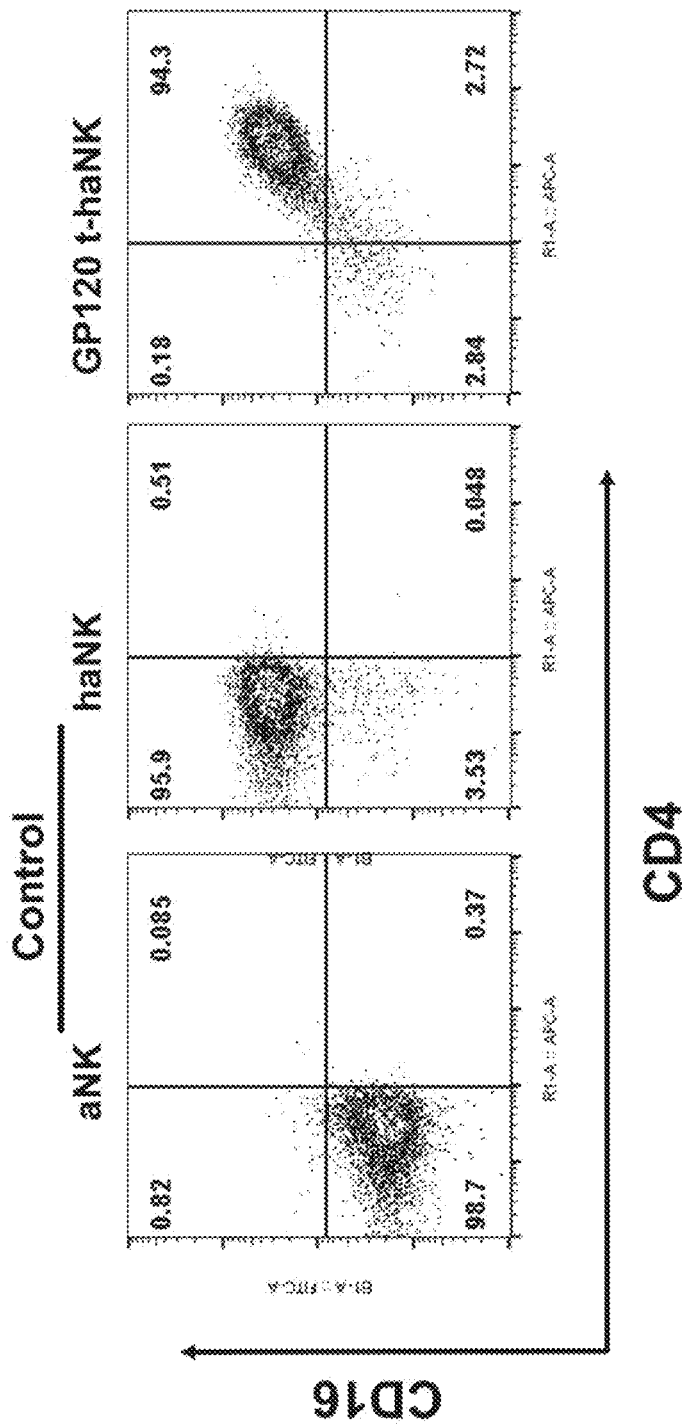
FIG. 57 shows exemplary results for expression of CD16 and gp120.CAR.
Figure 58:
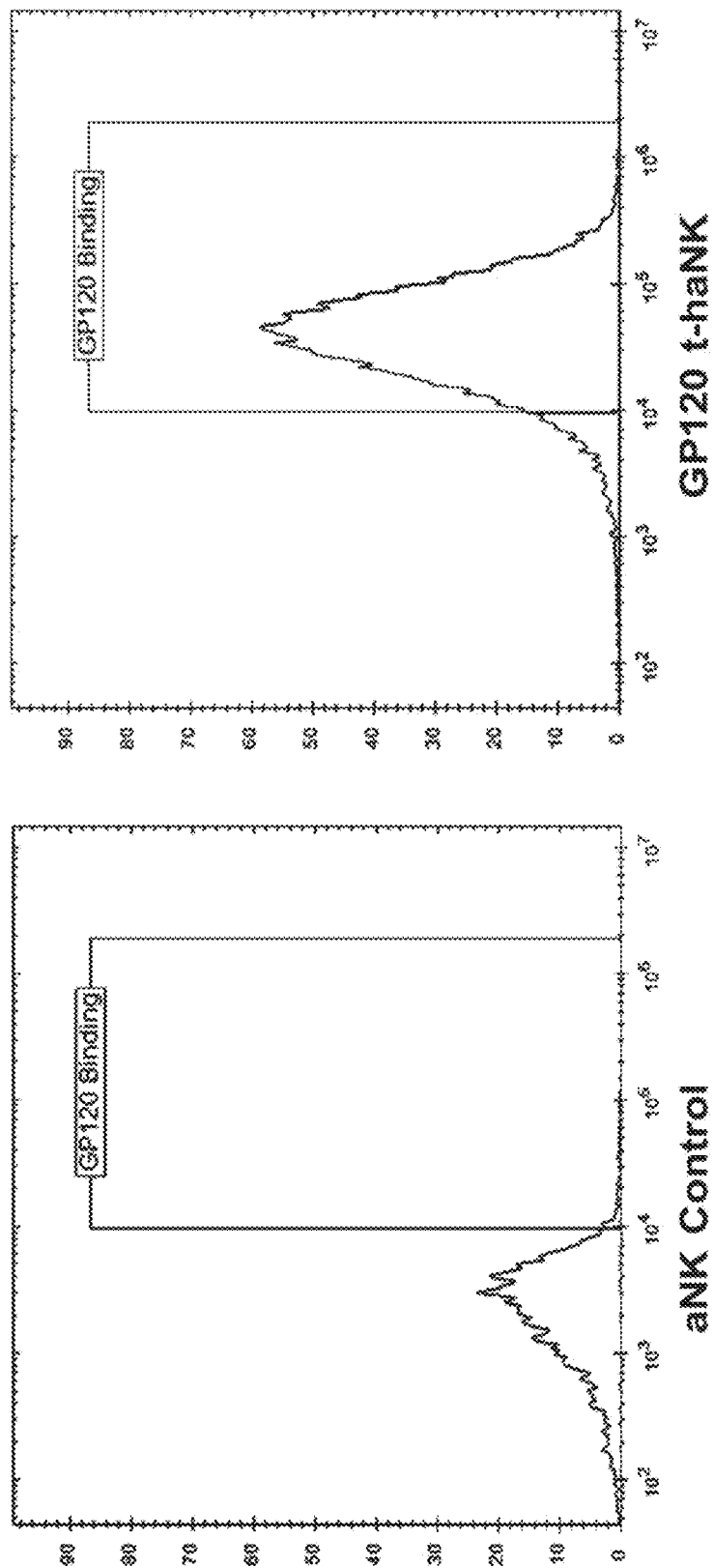
FIG. 58 shows exemplary results for GP120 binding of gp120.CAR-t-haNK cells.
Figure 59:
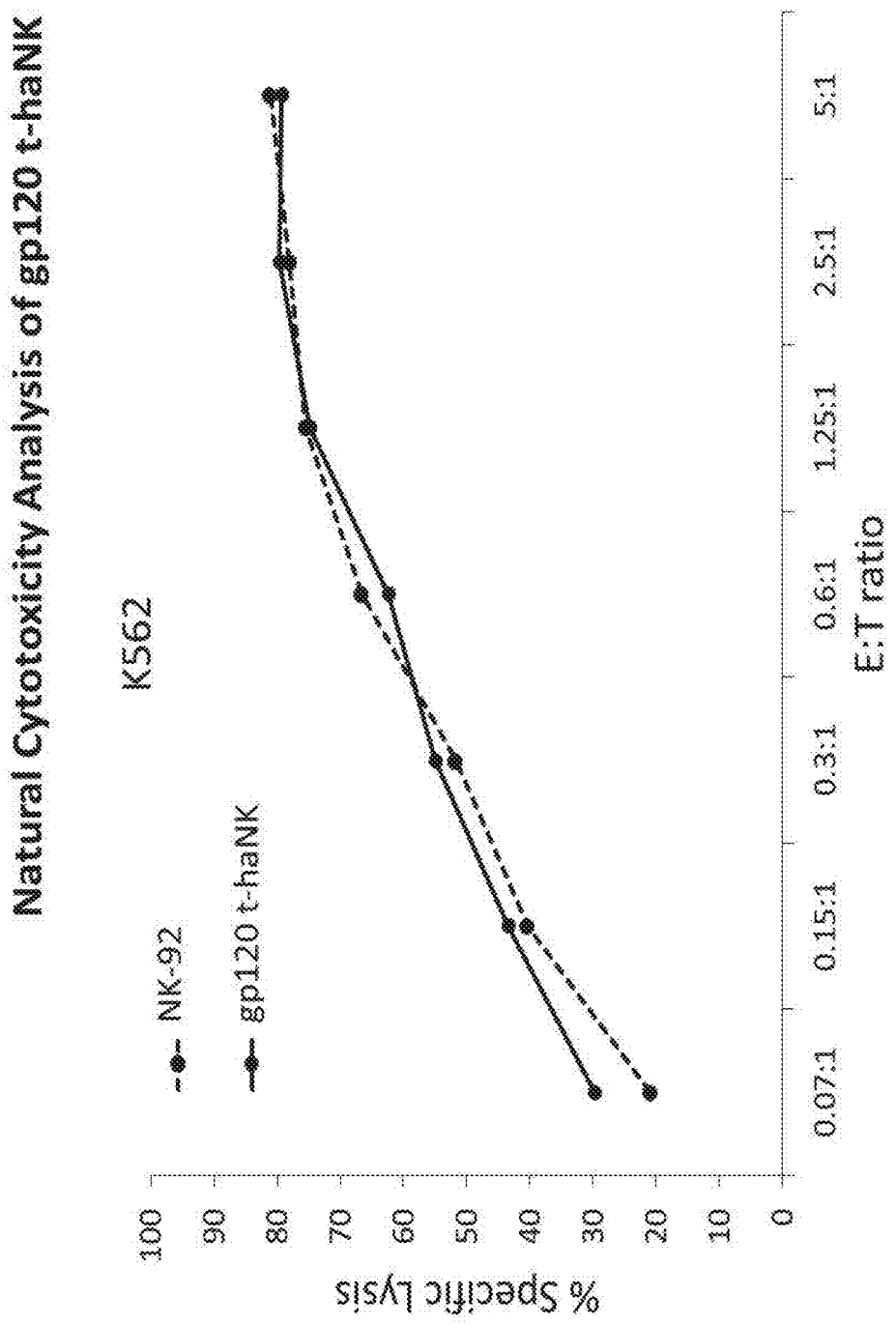
FIG. 59 shows exemplary results for natural cytotoxicity of gp120.CAR-t-haNK cells.
Figure 60:
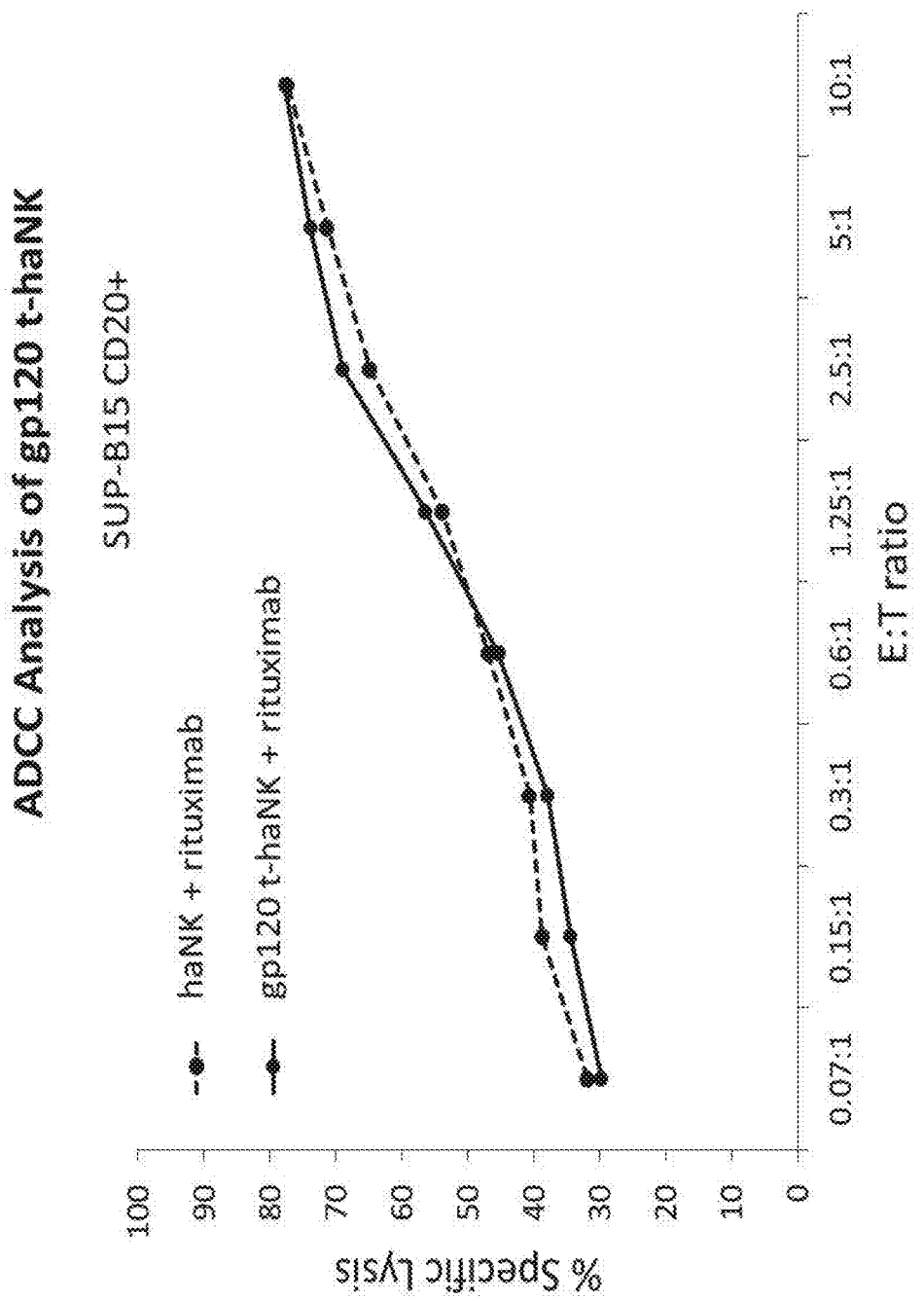
FIG. 60 shows exemplary results for ADCC of gp120.CAR-t-haNK cells.

The inventors further demonstrated that so generated cells expressed significant quantities of CD16 and gp120CAR as can be seen from FIG. 57. Binding of GP120 to the gp120CAR was shown as demonstrated in FIG. 58 versus non-recombinant aNK cells as negative control. Natural cytotoxicity of the so generated cells is shown in FIG. 59, while corresponding ADCC data are shown in FIG. 60.

Example 15: B7-H4-CAR with FcεRIγ Signaling Domain

In this example, the inventors constructed a $1^{st}$ generation CARs with a FcεRIγ signaling domain that included an anti-B7-H4 scFv coupled to a CD8 hinge, that in turn was coupled to a CD28 transmembrane domain, which was coupled to a FcεRIγ signaling domain. The so constructed B7-H4-CAR had a nucleic acid sequence of SEQ ID NO:68.

Example 16: BCMA-CAR with FcεRIγ Signaling Domain

In this example, the inventors constructed a $1^{st}$ generation CARs with a FcεRIγ signaling domain that included an anti-BCMA scFv coupled to a CD8 hinge, that in turn was coupled to a CD28 transmembrane domain, which was coupled to a FcεRIγ signaling domain. The so constructed BCMA-CAR had a nucleic acid sequence of SEQ ID NO:69.

Figure 54:
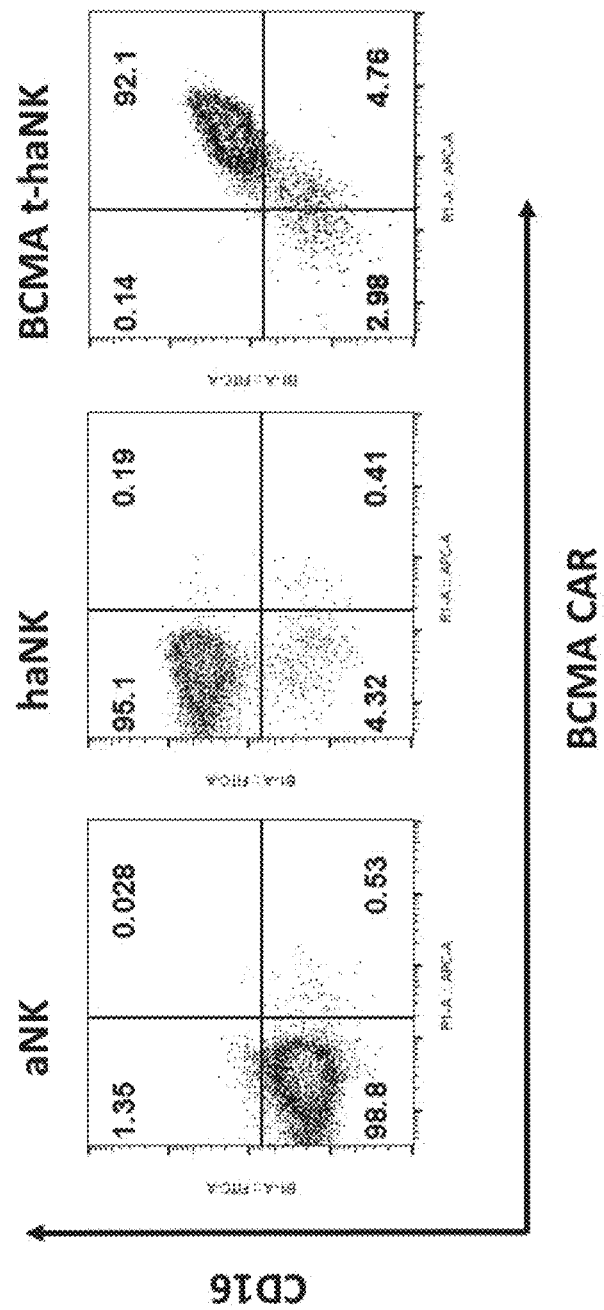
FIG. 54 shows exemplary results for CD16 and BCMA.CAR expression.
Figure 55:
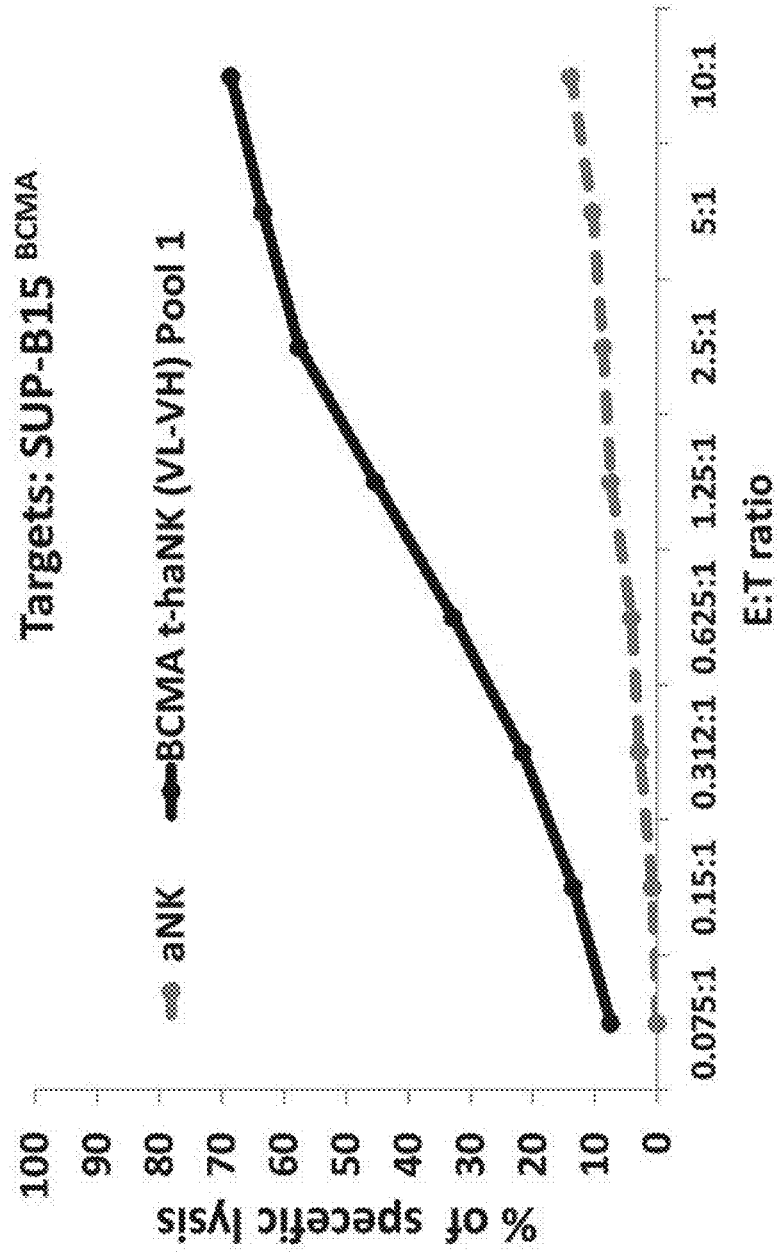
FIG. 55 shows exemplary results for CAR mediated cytotoxicity of BCMA.CAR-t-haNK cells.
Figure 56:
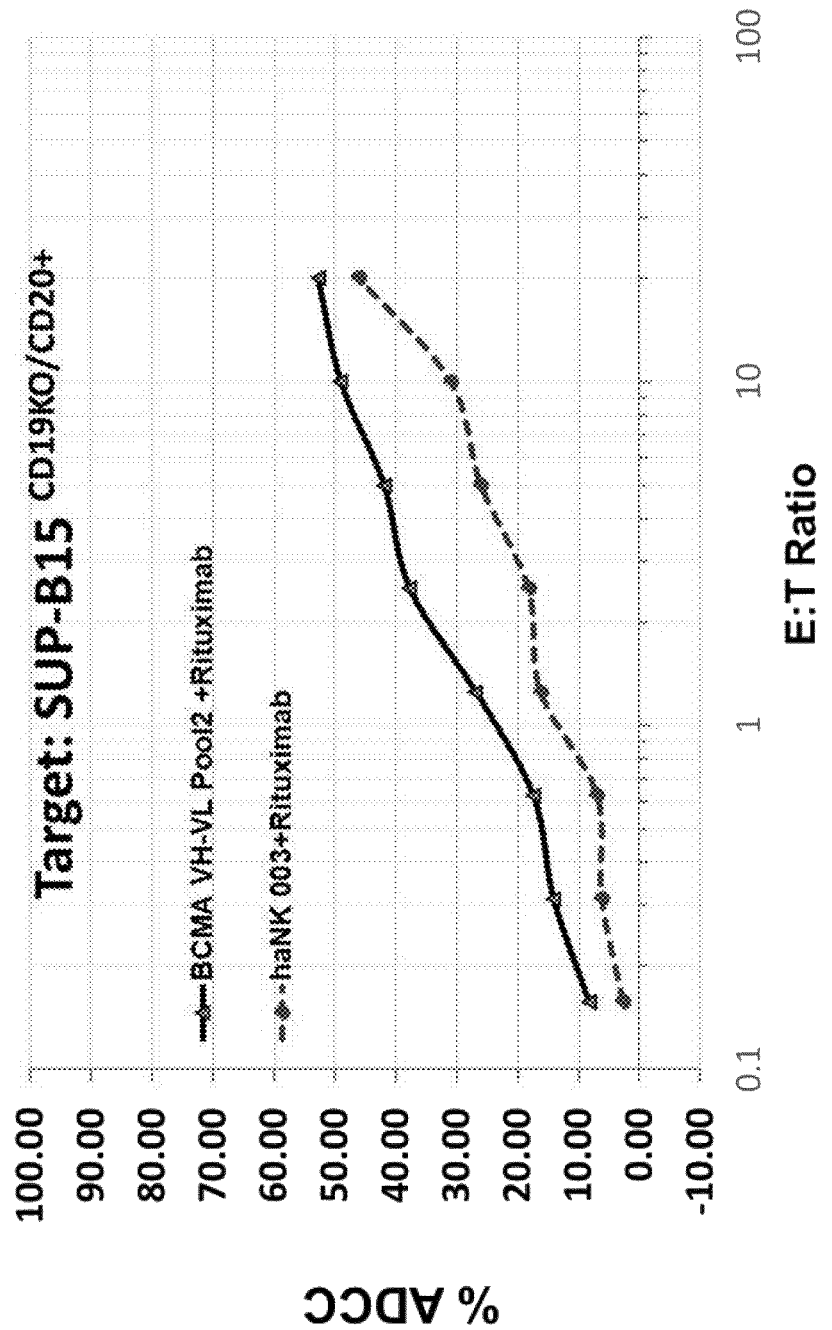
FIG. 56 shows exemplary results for ADCC of BCMA.CAR-t-haNK cells.

BCMA expression was confirmed as is shown in the exemplary results of FIG. 54, and CAR mediated cytotoxicity was demonstrated against target cells as is shown in FIG. 55. Similarly, as can be seen from the results in FIG. 56, recombinant cells had significant ADCC using rituximab as antibody against the target cells.

Example 17: GD2-CAR with FcεRIγ Signaling Domain

In this example, the inventors constructed a $1^{st}$ generation CARs with a FcεRIγ signaling domain that included an anti-GD2 scFv coupled to a CD8 hinge, that in turn was coupled to a CD28 transmembrane domain, which was coupled to a FcεRIγ signaling domain. The so constructed GD2-CAR had a nucleic acid sequence of SEQ ID NO:70.

Example 18: FAP-CAR with FcεRIγ Signaling Domain

Figure 61:
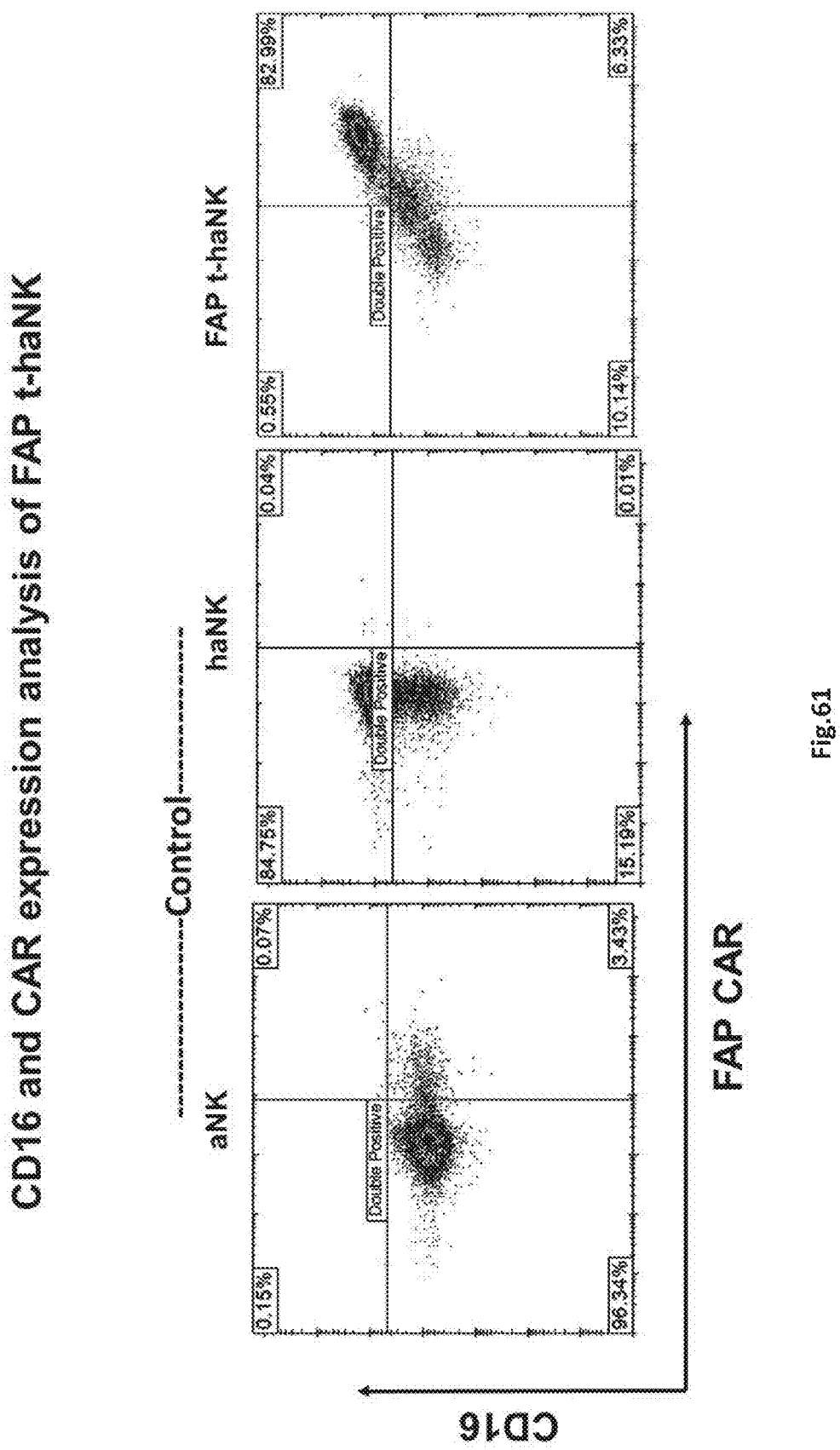
FIG. 61 shows exemplary results for CD16 and FAP.CAR expression.
Figure 62:
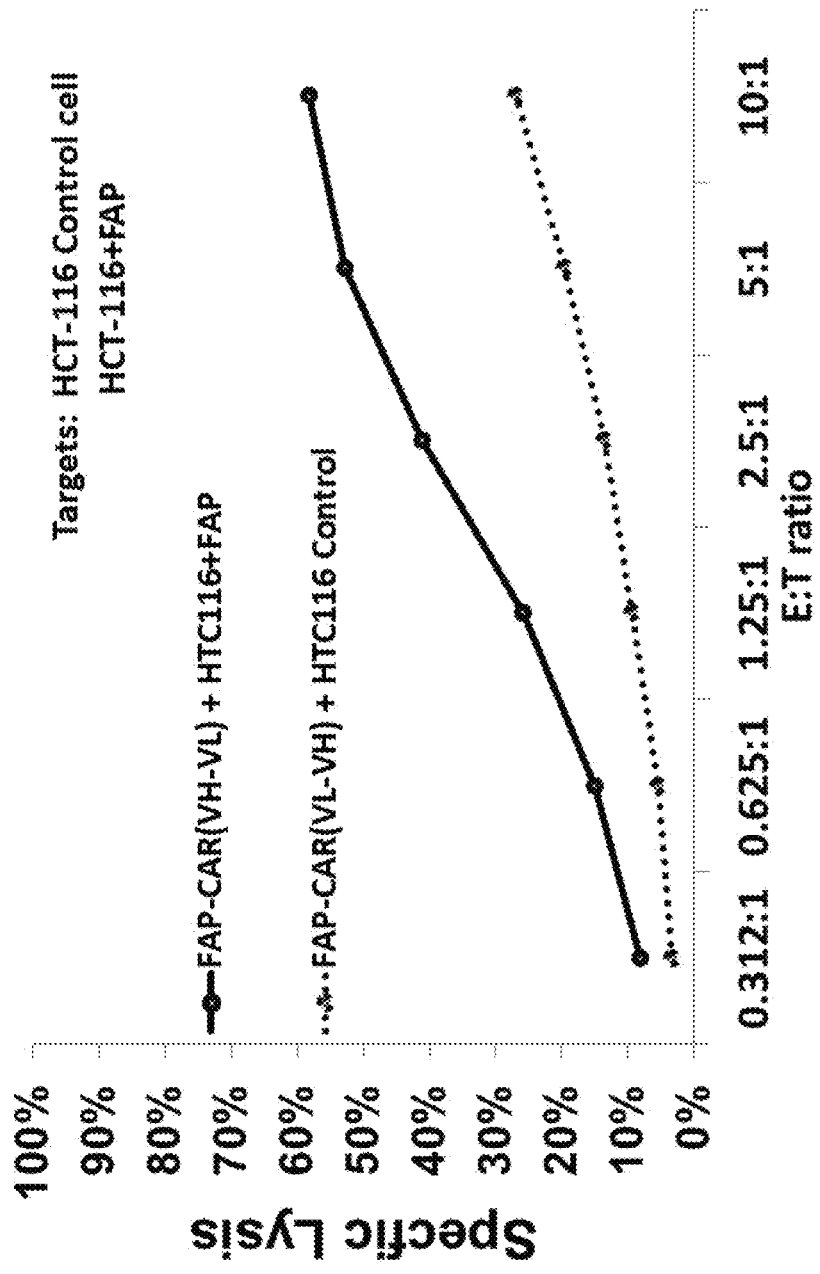
FIG. 62 shows exemplary results for CAR mediated cytotoxicity of FAP.CAR-t-haNK cells.

In this example, the inventors constructed a $1^{st}$ generation CARs with a FcεRIγ signaling domain that included an anti-FAP scFv coupled to a CD8 hinge, that in turn was coupled to a CD28 transmembrane domain, which was coupled to a FcεRIγ signaling domain. The so constructed FAP-CAR had a nucleic acid sequence of SEQ ID NO:71. Expression of the FAP-CAR is shown in the data of FIG. 61, and FAP.CAR cytotoxicity is demonstrated on target cells in the results of FIG. 62.

Example 19: CD20-CAR with FcεRIγ Signaling Domain

In this example, the inventors constructed a $1^{st}$ generation CARs with a FcεRIγ signaling domain that included an anti-CD20 scFv coupled to a CD8 hinge, that in turn was coupled to a CD28 transmembrane domain, which was coupled to a FcεRIγ signaling domain. The so constructed CD20-CAR had a nucleic acid sequence of SEQ ID NO:74.

Figure 29:
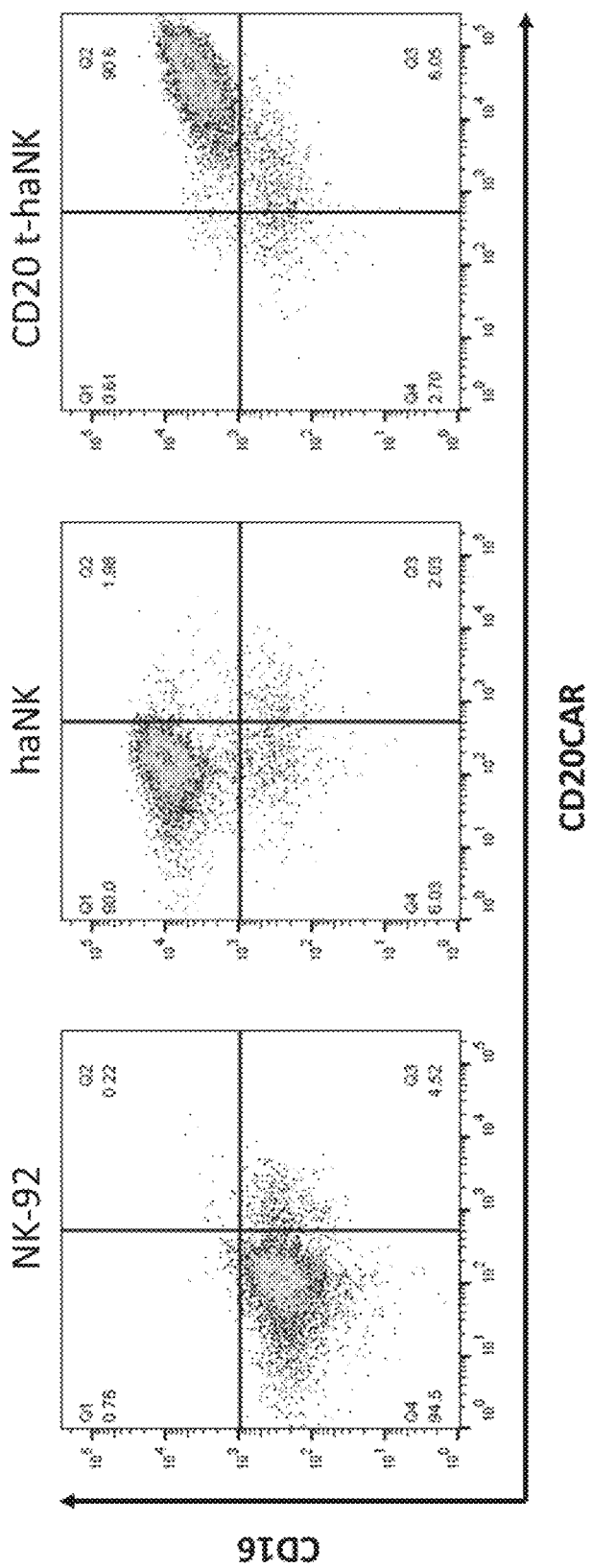
FIG. 29 shows exemplary comparative results for expression of CD16 and CD20.CAR.
Figure 30:
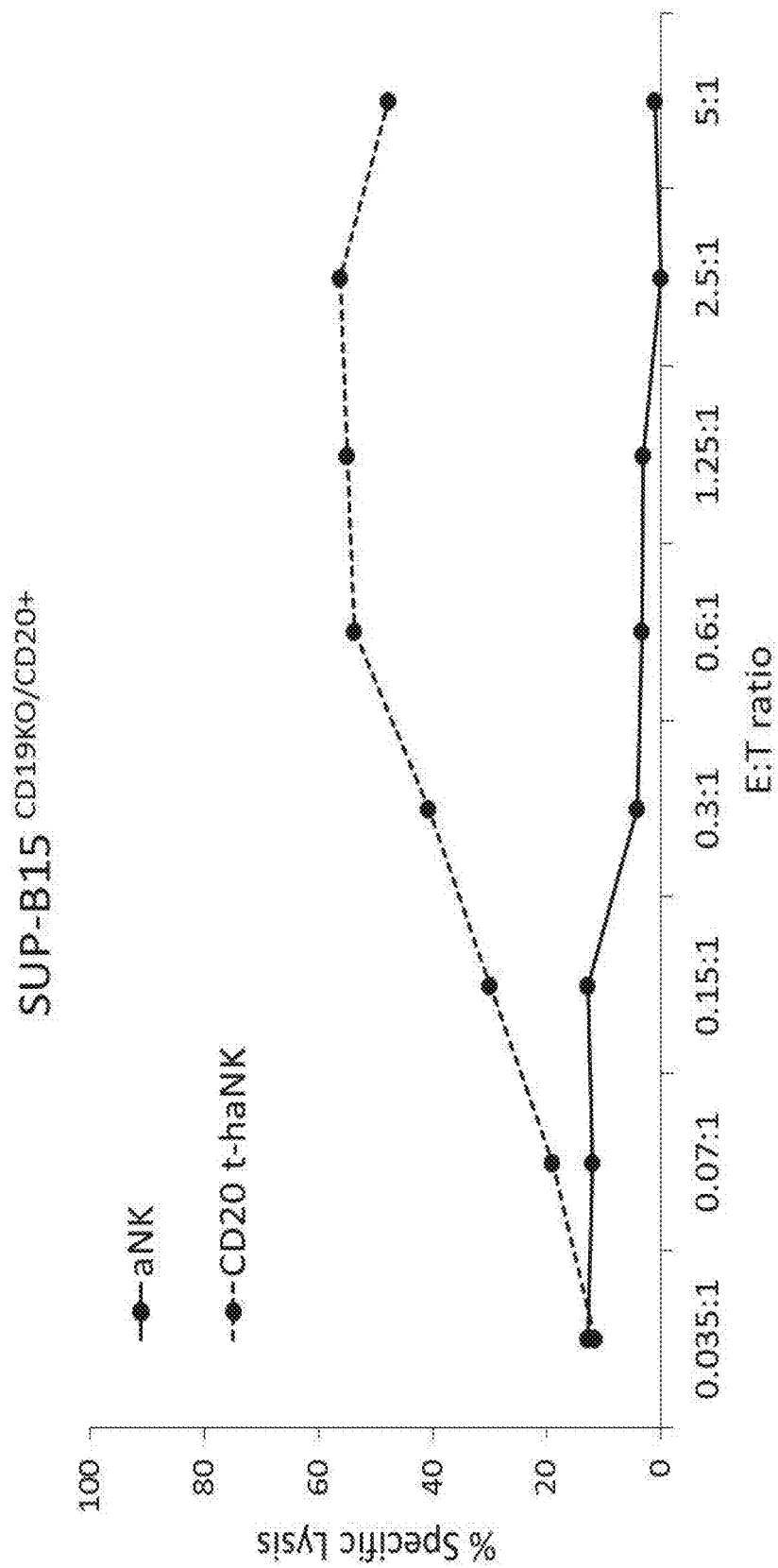
FIG. 30 shows exemplary results for natural cytotoxicity of CD20.CAR-t-haNK cells.

Expression of the CD20 CAR in NK-92 cells is shown in the results of FIG. 29. As can be readily seen, CD20.CAR is expressed strongly in the vast majority of recombinant cells (along with CD16 from the linearized DNA as noted above). FIG. 30 depicts exemplary results for cytotoxicity of the CD20.CAR NK cells against CD20$^+$ target cells.

Example 20: CSPG-4-CAR with FcεRIγ Signaling Domain

Figure 63:
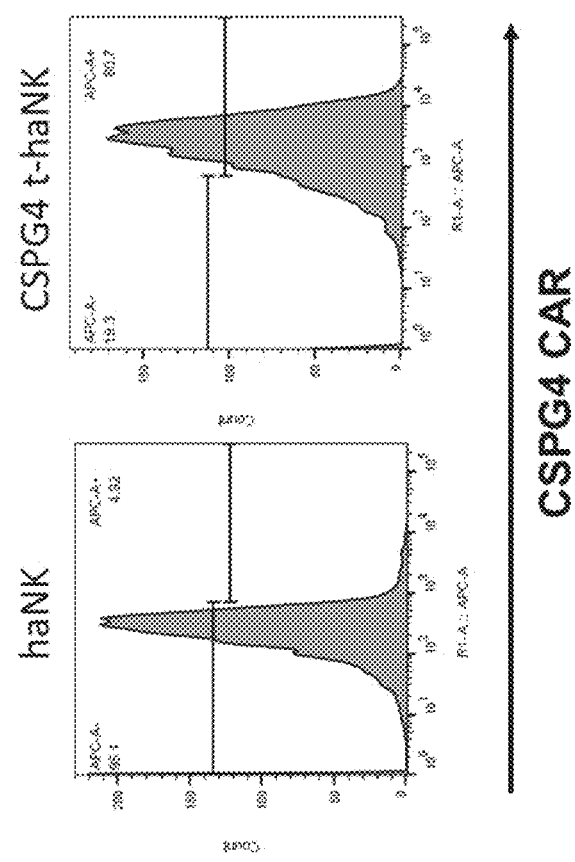
FIG. 63 shows exemplary results for CSPG4 expression in CSPG4.CAR-t-haNK cells.
Figure 64:
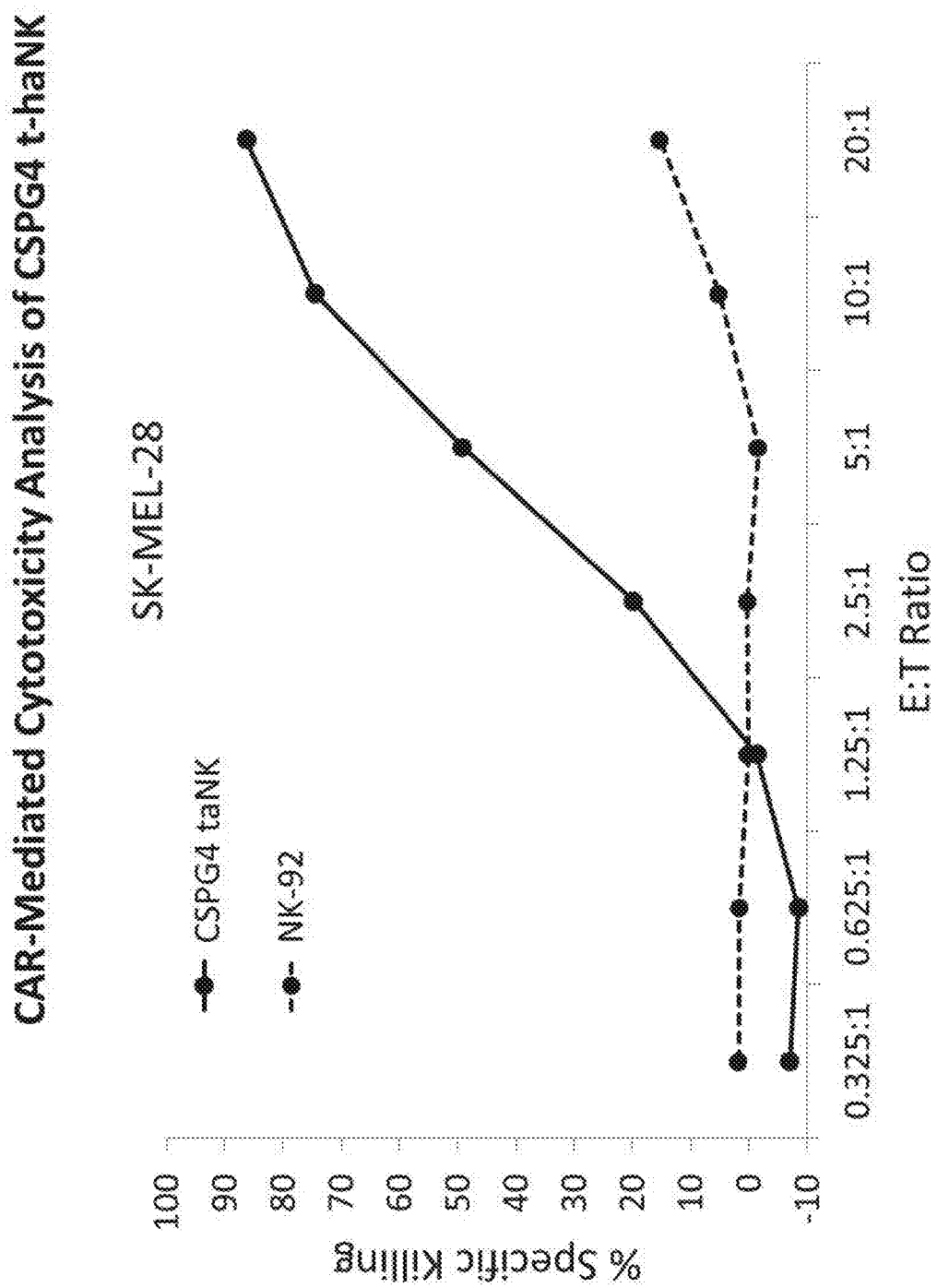
FIG. 64 shows exemplary results for CAR mediated cytotoxicity of CSPG4.CAR-t-haNK cells.

In this example, the inventors constructed a $1^{st}$ generation CARs with a FcεRIγ signaling domain that included an anti-CSPG-4 scFv coupled to a CD8 hinge, that in turn was coupled to a CD28 transmembrane domain, which was coupled to a FcεRIγ signaling domain. The so constructed CSPG-4-CAR had a nucleic acid sequence of SEQ ID NO:75. Expression of the CSPG-4-CAR was confirmed with FACS analysis and exemplary results are shown in FIG. 63. Thusly constructed cells also exhibited significant cytotoxicity as is shown in the exemplary data of FIG. 64.

Example 21: CD19-CAR with FcεcRIγ Signaling Domain

In this example, the inventors used the $1^{st}$ generation CARs as described above having a FcεRIγ signaling domain that included an anti-CD19 scFv coupled to a CD8 hinge, that in turn was coupled to a CD28 transmembrane domain, which was coupled to a FcεRIγ signaling domain and transfected NK-92cells with linearized DNA for functional testing.

Figure 19:
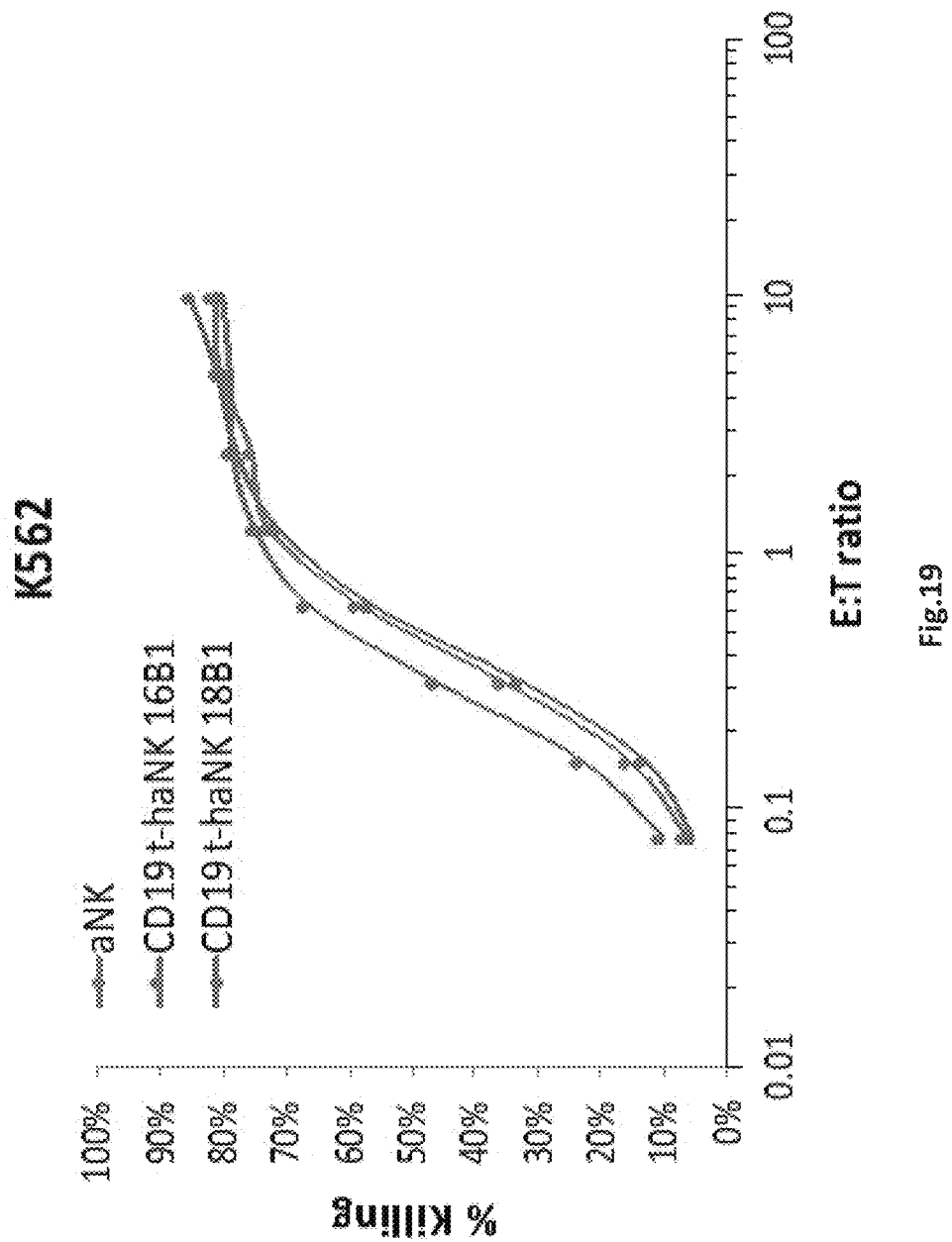
FIG. 19 shows exemplary results for cytotoxicity of CD19.CAR-t-haNK cells against K562 cells.
Figure 20:
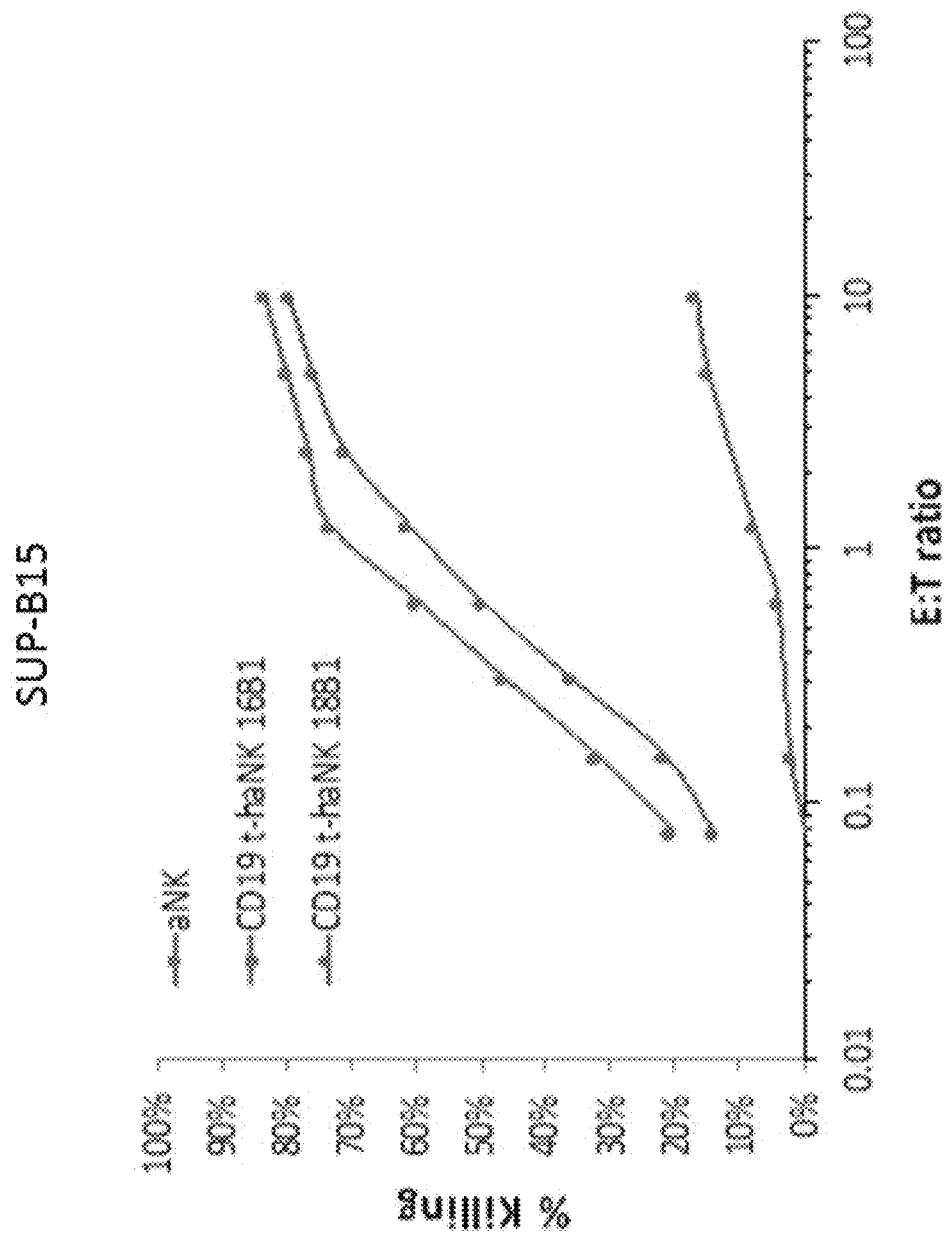
FIG. 20 shows exemplary results for cytotoxicity of CD19.CAR-t-haNK cells against SUP-B15 cells.
Figure 21:
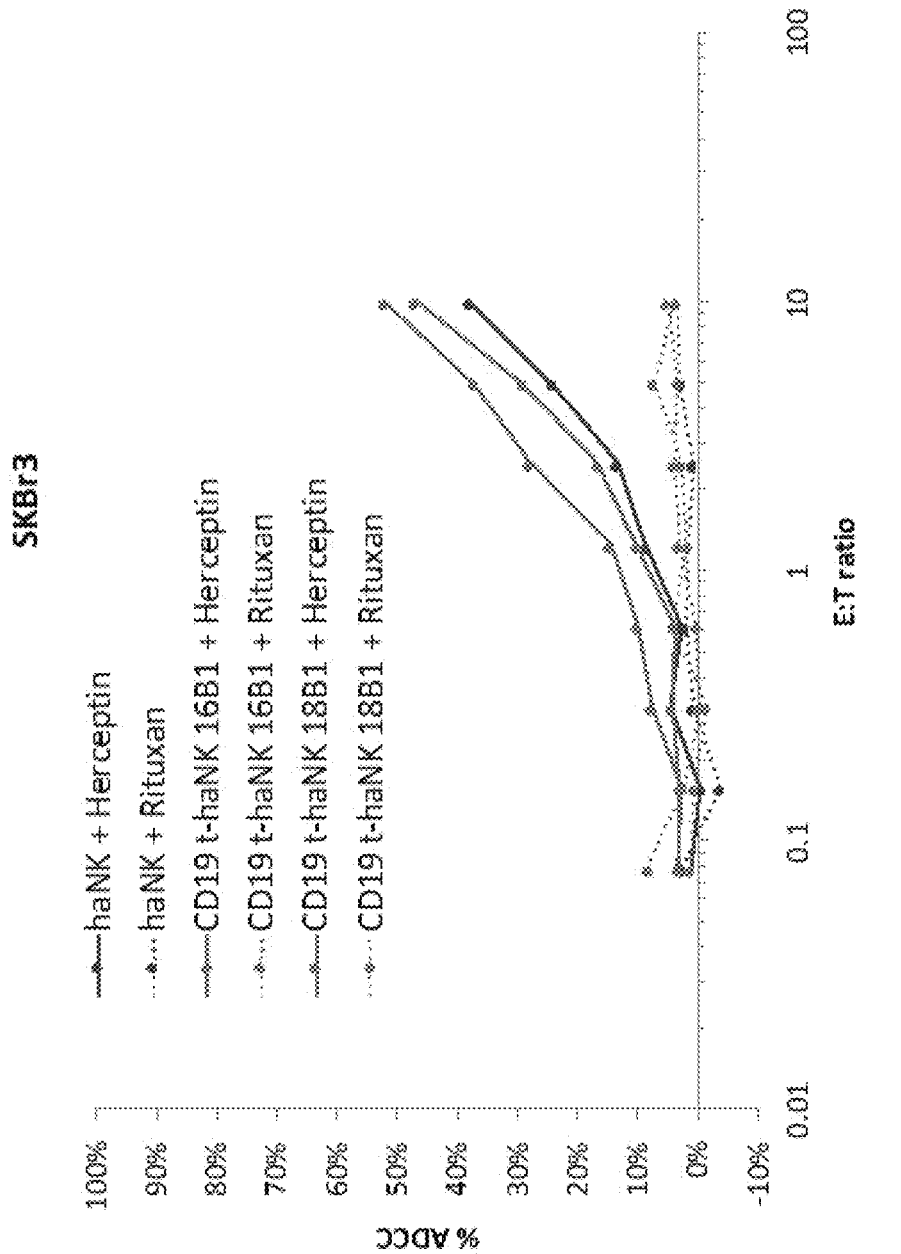
FIG. 21 shows exemplary results for ADCC of CD19.CAR-t-haNK cells against SKBr3 cells.

Functionality of the so constructed CD19.CAR-t-haNK cells was tested against K562 cells for determination of general cytotoxicity using a standard cytotoxicity assay and exemplary results are shown in FIG. 19. As can be readily seen, the CD19.CAR-t-haNK cells expressing the CAR with the FcεRIγ signaling domain exhibited significant cytotoxicity against the K562 target cells. In a further set of experiments, target specific cytotoxicity was determined using SUP-B15 cells in comparison with aNK cells as control, and exemplary results are shown in FIG. 20. Once more, CD19.CAR-t-haNK cells expressing the CAR with the FcεRIγ signaling domain exhibited significant and target specific cytotoxicity. In yet another set of experiments, target specific ADCC was determined using SKBr3 cells using Herceptin and Rituxan as antibodies, and exemplary results are shown in FIG. 21. Again, CD19.CAR-t-haNK cells expressing the CAR with the FcεRIγ signaling domain exhibited significant antibody and target specific ADCC. Notably, doubling times of the recombinant NK cells were substantially the same as aNK cells.

Figure 25:
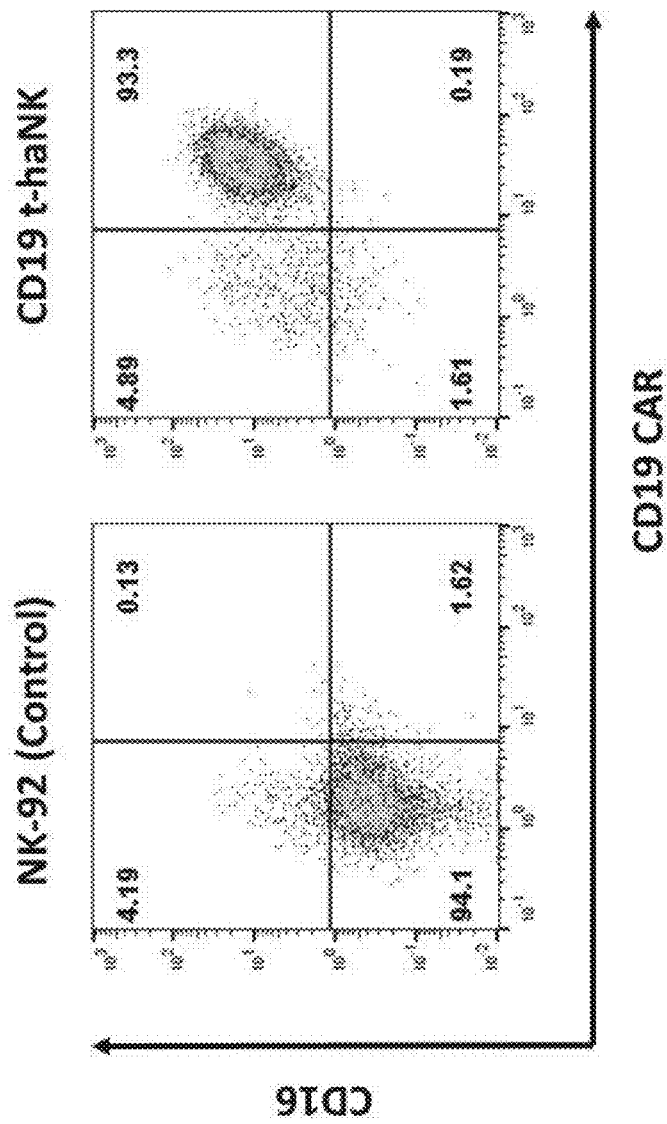
FIG. 25 shows exemplary results expression of CD16 and CD19.CAR.
Figure 26:
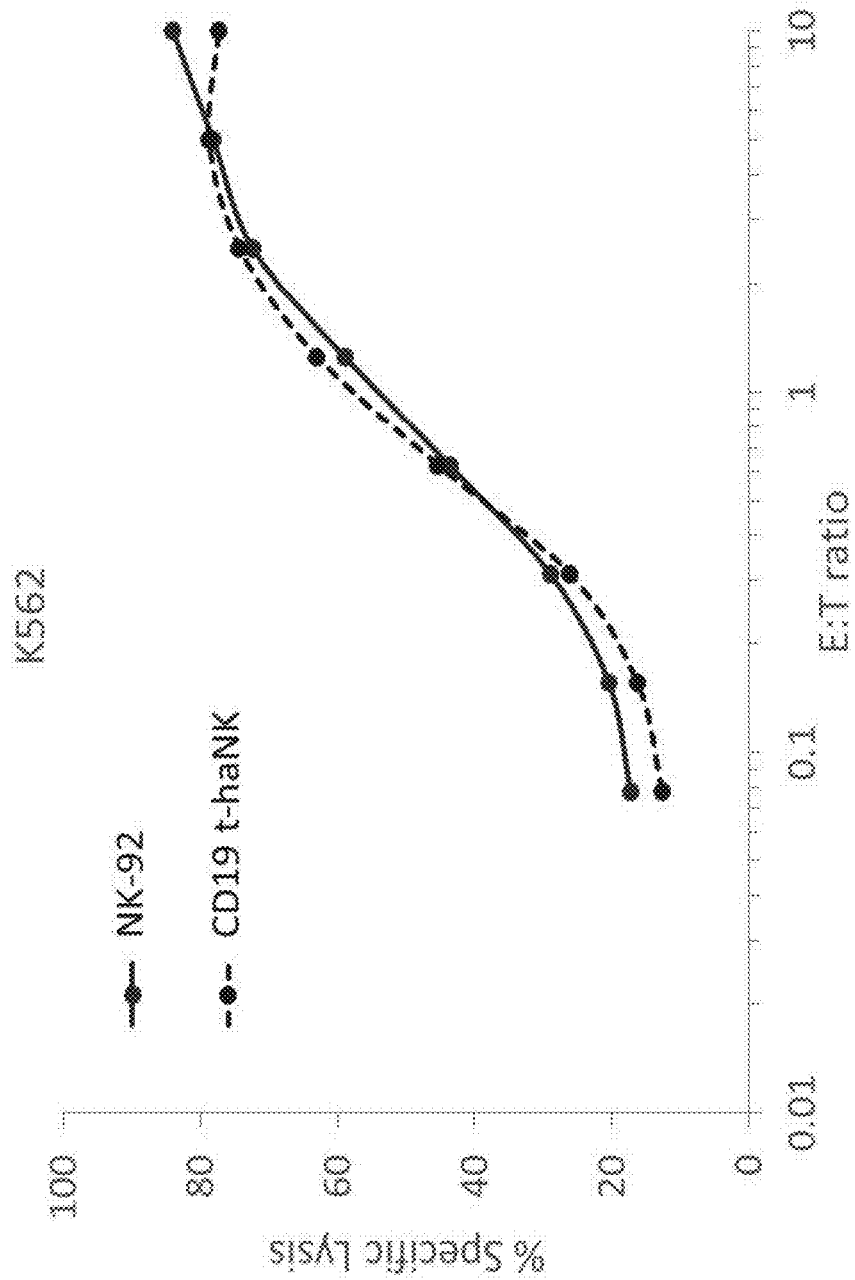
FIG. 26 shows exemplary results for natural cytotoxicity of CD19.CAR-t-haNK cells.
Figure 27:
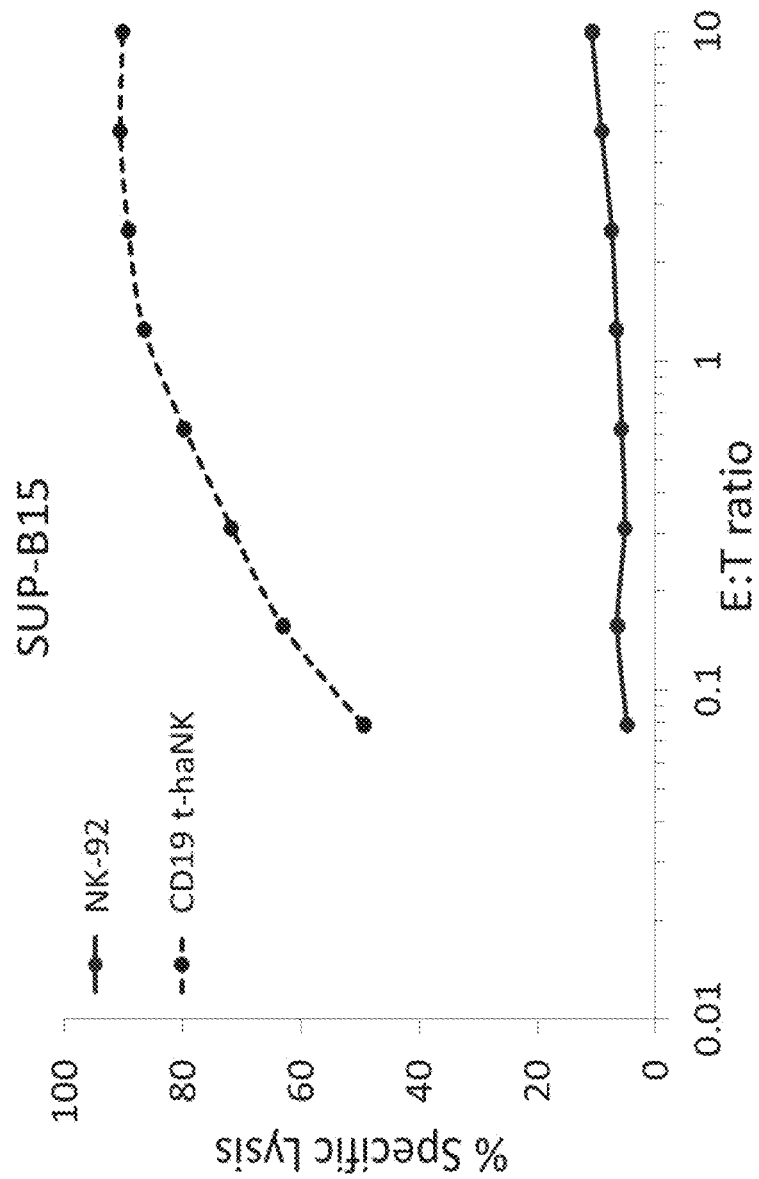
FIG. 27 shows exemplary results for CAR mediated cytotoxicity of CD19.CAR-t-haNK cells.
Figure 28:
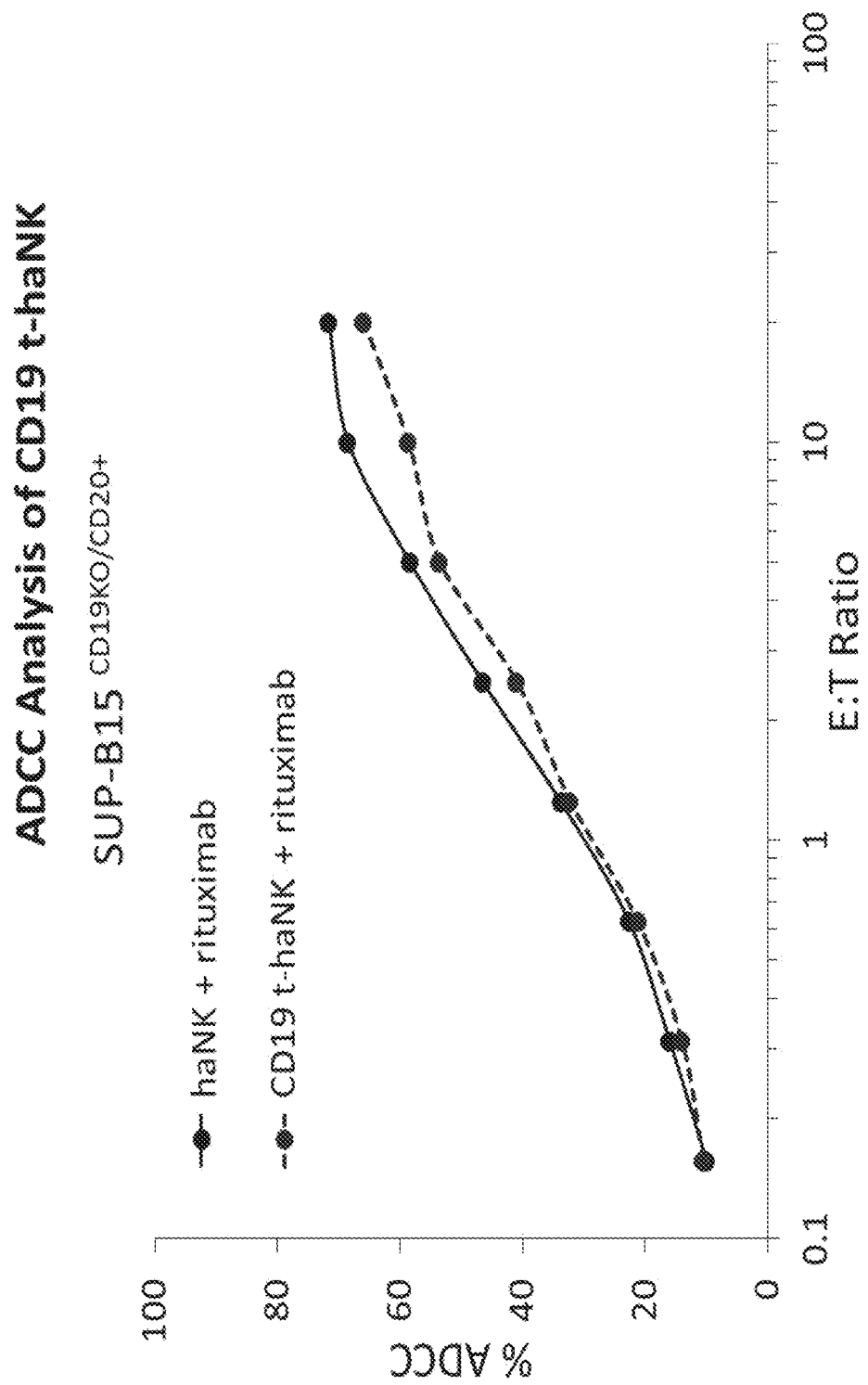
FIG. 28 shows exemplary results for ADCC of CD19.CAR-t-haNK cells.

FIG. 25 exemplarily illustrates CD19.CAR expression from linearized DNA that included a segment encodingCD16 and IL-$2^{ER}$ in NK-92 cells versus control. As can be seen form FIG. 25, the expression was very strong across the vast majority of cells. Additional results for natural cytotoxicity of CD19.CAR t-haNK cells against K562 cells and targeted cytotoxicity against SUP-B15 cells are depicted in FIG. 26 and FIG. 27. Exemplary further results for ADCC of CD19.CAR t-haNK cells against SUP-B15CD19$^{KO}$/CD20$^+$ cells are shown in FIG. 28.

Example 22: Anti-Tumor Activity of PD-L1-Targeting t-haNK Cells in Human Xenograft Models in NSG Mice MDA-MB-231 and HCC827 were used as validated xenograft models that are PD-L1 positive, and efficacy of PD-L1 t-haNK cells in varied formulations, dosing levels, and dosing routes (IV and IT) was evaluated.

Animals: Animal type: NSG mice (JAX), females, 9-10 weeks old; Number of animals for MDA-MB-231 model: 24 (fresh cells), and for HCC827 model: 24 (fresh cells)+6 (cryopreserved cells). Tumor model used the following cell line: MDA-MB-231 (human breast adenocarcinoma) and HCC827 (human lung adenocarcinoma), Route of inoculation was subcutaneous on both flanks, and average tumor burden upon treatment initiation was for MDA-MB-231 about 100 mm$^3$ and for HCC827 about 75-80 mm$^3$.

Treatment articles: Anti-PD-L1 t-haNK, freshly prepared, irradiated, at a concentration: 5E7 cells/mL or 2E7 cells/mL; Vehicle control was X-VIVO™ 10 medium; Method of administration was IV and IT as noted. Dosage for IV NK dosing was 1E7 cells/dose in 200 µL (Freshly prepared cells), 4E6 cells/dose in 200 µL (Cryopreserved cells); for IT NK dosing (fresh cells only) dose was 2.5E6 cells/tumor/dose in 50 µL. Dosing frequency was Twice a week (M/Th or T/F) for 4 consecutive weeks, and first day of dosing was defined as Day 1.

Study design for MDA-MB-231 is in Table 4 below (This study was ended on Day 27, when some animals in Groups A, C and D had reached combined tumor volume of >2000 mm$^3$)

TABLE 4

| Group | N | Tumor model | Treatment | Fresh or Frozen | NK Cell Dose | NK dosing route | Treatment Regimen | Dosing Volume |
|---|---|---|---|---|---|---|---|---|
| A | 6 | MDA-MB-231 SC, bilateral 1 × 10$^6$ | Vehicle | / | / | IV | BIW × 4 weeks | 200 µL |
| B | 6 | | PD-L1 t-haNK | Fresh | 1E7 | IV | BIW × 4 weeks | 200 µL |
| C | 6 | | Vehicle | / | / | IT | BIW × 4 weeks | 50 µL |
| D | 6 | | PD-L1 t-haNK | Fresh | 2.5E6 | IT | BIW × 4 weeks | 50 µL |

Study design for HCC827 is in Table 5 below (This study was ended on Day 29, when surviving animals were repurposed and transferred to another study).

TABLE 5

| Group | N | Tumor model | Treatment | Fresh or Frozen | NK Cell Dose | NK dosing route | Treatment Regimen | Dosing Volume |
|---|---|---|---|---|---|---|---|---|
| A | 6 | HCC827 SC, bilateral 1 × 10$^6$ | Vehicle | / | / | IV | BIW × 4 weeks | 200 µL |
| B | 6 | | PD-L1 t-haNK | Fresh | 1E7 | IV | BIW × 4 weeks | 200 µL |
| C | 6 | | Vehicle | / | / | IT | BIW × 4 weeks | 50 µL |
| D | 6 | | PD-L1 t-haNK | Fresh | 2.5E6 | IT | BIW × 4 weeks | 50 µL |
| Pilot | 6 | | PD-L1 t-haNK | Frozen | 4E6 | IV | BIW × 4 weeks | 200 µL |

Results: Freshly prepared PD-L1 t-haNK cells (1E7 cells/dose) led to marked and long-lasting tumor growth inhibition in both MDA-MB-231 and HCC827 models MDA-MB-231: tumor stasis: TGI on Day 16: 84% (peak); TGI on Day 26: 79% (last measurement).

HCC827: tumor regression: TGI on Day 16: 120% (peak); TGI on Day 29: 84% (study end).

Cryopreserved PD-L1 t-haNK cells (4E6 cells/dose) also showed statistically significant efficacy in suppressing tumor growth compared to X-VIVO™ 10 media: TGI on Day 26: 60% (peak), and TGI on Day 29: 40% (study end).

Freshly prepared PD-L1 t-haNK cells (1E7 cells/dose) also led to significant reduction of metastatic disease burden in the MDA-MB-231 model as shown in Table 6 below.

TABLE 6

| Group | Mouse | Macroscopic lesions found in: | Overall Summary |
|---|---|---|---|
| A (vehicle) | 1 | Liver, lungs | 100% animals developed metastases in multiple organs |
| | 2 | Ax LNs, liver, lungs | |
| | 3 | Ax LN (left), liver, lungs | |
| | 4 | Liver, lungs | |
| | 5 | Ax LNs, spleen, liver, lungs | |
| | 6 | Ax LNs, liver, lungs | |
| B (PD-L1 t-haNK) | 1 | None | 50% developed metastasis; all single-organ findings |
| | 2 | Lungs | |
| | 3 | Ax LNs | |
| | 4 | None | |
| | 5 | Ax LN (left) | |
| | 6 | None | |

The number of visible nodules in liver was in vehicle: 29±9, in the PD-L1 t-haNK group: 0 (P=0.0116 by unpaired 2-tailed t test).

Based on the experiments performed, IV dosing of freshly prepared PD-L1 t-haNK cells at the dosing level of 1E7 cells/dose, twice a week for 4 weeks, showed marked anti-tumor efficacy in both of the subcutaneous xenograft models tested: The treatment resulted in tumor stasis in MDA-MB-231 tumor-bearing mice, with a peak TGI of 84% on Day 16 and an end-of-study TGI of 79% (P<0.0001 for both time points by 2-way ANOVA followed by multiple comparison by Tukey test), and tumor regression in the HCC827 model, with a peak TGI of 120% on Day 16 and an end-of-study TGI of 84% (P<0.0001). IV dosing of cryopreserved PD-L1 t-haNK cells at the dosing level of 4E6 cells/dose, twice a week for 4 weeks, also showed significant therapeutic efficacy in the HCC827 tumor model, reaching a peak TGI of 60% (P<0.0001), and an end-of-study TGI of 40% (P<0.01). IT dosing of freshly prepared PD-L1 t-haNK cells at the dosing level of 2.5E6 cells/dose/tumor, twice a week for 4 weeks, effectively suppressed the growth of HCC827 tumors, resulting in a peak TGI of 70% on Day 20 and an end-of-study TGI of 49% (P<0.001).

Significant adverse reactions were observed for animals that received IV administrations of freshly prepared PD-L1 t-haNK cells (1E7 cells/dose). In contrast to freshly prepared PD-L1 t-haNK cells, cryopreserved cells (dosed at a lower level of 4E6 cells/dose) proved to be safe to the animals after IV administrations. PD-L1 t-haNK cells demonstrated remarkable efficacy in the two subcutaneous tumor models. Cryopreserved cells dosed at the lower 4E6 cells/dose level, also showed significant efficacy in suppressing tumor growth, and proved to be safe for the animals.

Of course, it should be recognized that for all nucleic acid sequences provided herein the corresponding encoded proteins are also expressly contemplated herein. Likewise, for all amino acid sequences, corresponding nucleic acids sequences are also contemplated herein (with any codon usage).

All patent applications, publications, references, and sequence accession numbers cited in the present specification are hereby incorporated by reference in their entirety.

Unless defined otherwise, all technical and scientific terms used herein have the same meaning as commonly understood by one of ordinary skill in the art to which this invention belongs.

In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

It is understood that all numerical values described herein (e.g., pH, temperature, time, concentration, amounts, and molecular weight, including ranges) include normal variation in measurements encountered by one of ordinary skill in the art. Thus, numerical values described herein include variation of +/−0.1 to 10%, for example, +/−0.1%, 0.5%, 1%, 2%, 3%, 4%, 5%, 6%, 7%, 8%, 9%, or 10%. It is to be understood, although not always explicitly stated, that all numerical designations may be preceded by the term "about." Thus, the term about includes variation of +/−0.1 to 10%, for example, +/−0.1%, 0.5%, 1%, 2%, 3%, 4%, 5%, 6%, 7%, 8%, 9%, or 10% of the numerical value. It is also to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein include the end points of the range, and include all values between the end points of the range. All ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

It is also to be understood, although not always explicitly stated, that the reagents described herein are merely exemplary and that equivalents of such are known in the art.

"Optional" or "optionally" means that the subsequently described event or circumstance can or cannot occur, and that the description includes instances where the event or circumstance occurs and instances where it does not.

The term "comprising" is intended to mean that the compositions and methods include the recited elements, but not excluding others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this disclosure.

As used herein, "immunotherapy" refers to the use of NK-92 cells, modified or unmodified, naturally occurring or modified NK cell or T-cell, whether alone or in combination, and which are capable of inducing cytotoxicity when contacting a target cell.

As used herein, "natural killer (NK) cells" are cells of the immune system that kill target cells in the absence of a specific antigenic stimulus, and without restriction according to major histocompatibility complex (MHC) class. Target cells may be tumor cells or cells harboring a virus. NK cells are characterized by the presence of CD56 and the absence of CD3 surface markers.

The term "endogenous NK cells" is used to refer to NK cells derived from a donor (or the patient), as distinguished from the NK-92 cell line. Endogenous NK cells are generally heterogeneous populations of cells within which NK cells have been enriched. Endogenous NK cells may be intended for autologous or allogeneic treatment of a patient.

The term "NK-92" refers to natural killer cells derived from the highly potent unique cell line described in Gong et al. (1994), rights to which are owned by NantKwest (hereafter, "NK-92™ cells"). The immortal NK cell line was originally obtained from a patient having non-Hodgkin's lymphoma. Unless indicated otherwise, the term "NK-92™" is intended to refer to the original NK-92 cell lines as well as NK-92 cell lines that have been modified (e.g., by introduction of exogenous genes). NK-92™ cells and exemplary and non-limiting modifications thereof are described in U.S. Pat. Nos. 7,618,817; 8,034,332; 8,313,943; 9,181,322; 9,150,636; and published U.S. application Ser. No. 10/008,955, all of which are incorporated herein by reference in their entireties, and include wild type NK-92™, NK-92™-CD16, NK-92™-CD16-γ, NK-92™-CD16-ζ, NK-92™-CD16(F176V), NK-92™MI, and NK-92™CI. NK-92 cells are known to persons of ordinary skill in the art, to whom such cells are readily available from NantKwest, Inc.

The term "aNK" refers to an unmodified natural killer cells derived from the highly potent unique cell line described in Gong et al. (1994), rights to which are owned by NantKwest (hereafter, "aNK™ cells"). The term "haNK" refers to natural killer cells derived from the highly potent unique cell line described in Gong et al. (1994), rights to which are owned by NantKwest, modified to express CD16 on the cell surface (hereafter, "CD16+ NK-92™ cells" or "haNK® cells"). In some embodiments, the CD16+ NK-92™ cells comprise a high affinity CD16 receptor on the cell surface. The term "taNK" refers to natural killer cells derived from the highly potent unique cell line described in Gong et al. (1994), rights to which are owned by NantKwest, modified to express a chimeric antigen receptor (hereafter, "CAR-modified NK-92™ cells" or "taNK® cells"). The term "t-haNK" refers to natural killer cells derived from the highly potent unique cell line described in Gong et al. (1994), rights to which are owned by NantkWest, modified to express CD 16 on the cell surface and to express a chimeric antigen receptor (hereafter, "CAR-modified CD16+NK-92™ cells" or "t-haNK™ cells"). In some embodiments, the t-haNK™ cells express a high affinity CD16 receptor on the cell surface.

A "modified NK-92 cell" refers to an NK-92 cell that expresses an exogenous gene or protein, such as an Fc receptor, a CAR, a cytokine (such as IL-2 or IL-12), and/or a suicide gene. In some embodiments, the modified NK-92 cell comprises a vector that encodes for a transgene, such as an Fc receptor, a CAR, a cytokine (such as IL-2 or IL-12), and/or a suicide gene. In one embodiment, the modified NK-92 cell expresses at least one transgenic protein.

As used herein, "non-irradiated NK-92 cells" are NK-92 cells that have not been irradiated. Irradiation renders the cells incapable of growth and proliferation. It is envisioned that the NK-92 cells will be irradiated at the treatment facility or some other point prior to treatment of a patient, since the time between irradiation and infusion should be no longer than four hours in order to preserve optimal activity. Alternatively, NK-92 cells may be prevented from proliferating by another mechanism.

As used herein, "inactivation" of the NK-92 cells renders them incapable of growth. Inactivation may also relate to the death of the NK-92 cells. It is envisioned that the NK-92 cells may be inactivated after they have effectively purged an ex vivo sample of cells related to a pathology in a therapeutic application, or after they have resided within the body of a mammal a sufficient period of time to effectively kill many or all target cells residing within the body. Inactivation may be induced, by way of non-limiting example, by administering an inactivating agent to which the NK-92 cells are sensitive.

As used herein, the terms "cytotoxic" and "cytolytic," when used to describe the activity of effector cells such as NK-92 cells, are intended to be synonymous. In general, cytotoxic activity relates to killing of target cells by any of a variety of biological, biochemical, or biophysical mechanisms. Cytolysis refers more specifically to activity in which the effector lyses the plasma membrane of the target cell, thereby destroying its physical integrity. This results in the killing of the target cell. Without wishing to be bound by theory, it is believed that the cytotoxic effect of NK-92 cells is due to cytolysis.

The term "kill" with respect to a cell/cell population is directed to include any type of manipulation that will lead to the death of that cell/cell population.

The term "Fc receptor" refers to a protein found on the surface of certain cells (e.g., natural killer cells) that contribute to the protective functions of the immune cells by binding to part of an antibody known as the Fc region. Binding of the Fc region of an antibody to the Fc receptor (FcR) of a cell stimulates phagocytic or cytotoxic activity of a cell via antibody-mediated phagocytosis or antibody-dependent cell-mediated cytotoxicity (ADCC). FcRs are classified based on the type of antibody they recognize. For example, Fc-gamma receptors (FCγR) bind to the IgG class of antibodies. FCγRIII-A (also called CD16; SEQ ID NO:20) is a low affinity Fc receptor bind to IgG antibodies and activate ADCC. FCγRIII-A are typically found on NK cells. NK-92 cells do not express FCγRIII-A. Fc-epsilon receptors (FcεR) bind to the Fc region of IgE antibodies.

The term "chimeric antigen receptor" (CAR), as used herein, refers to an extracellular antigen-binding domain that is fused to an intracellular signaling domain. CARs can be expressed in T cells or NK cells to increase cytotoxicity. In general, the extracellular antigen-binding domain is a scFv that is specific for an antigen found on a cell of interest. A CAR-expressing NK-92 cell is targeted to cells expressing certain antigens on the cell surface, based on the specificity of the scFv domain. The scFv domain can be engineered to recognize any antigen, including tumor-specific antigens and virus-specific antigens. For example, CD19CAR recognizes CD19, a cell surface marker expressed by some cancers.

The term "tumor-specific antigen" as used herein refers to antigens that are present on a cancer or neoplastic cell but not detectable on a normal cell derived from the same tissue or lineage as the cancer cell. Tumor-specific antigens, as used herein, also refers to tumor-associated antigens, that is, antigens that are expressed at a higher level on a cancer cell as compared to a normal cell derived from the same tissue or lineage as the cancer cell.

The term "virus-specific antigen" as used herein refers to antigens that are present on a virus-infected cell but not detectable on a normal cell derived from the same tissue or lineage as the virus-infected cell. In one embodiment, a virus-specific antigen is a viral protein expressed on the surface of an infected cell.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

As used herein, "percent identity" refers to sequence identity between two peptides or between two nucleic acid molecules. Percent identity can be determined by comparing a position in each sequence which may be aligned for purposes of comparison. When a position in the compared sequence is occupied by the same base or amino acid, then the molecules are identical at that position. Homologous nucleotide sequences include those sequences coding for naturally occurring allelic variants and mutations of the nucleotide sequences set forth herein. Homologous nucleotide sequences include nucleotide sequences encoding for a protein of a mammalian species other than humans. Homologous amino acid sequences include those amino acid sequences which contain conservative amino acid substitutions and which polypeptides have the same binding and/or activity. In some embodiments, a homologous amino acid sequence has no more than 15, nor more than 10, nor more than 5 or no more than 3 conservative amino acid substitutions. In some embodiments, a nucleotide or amino acid sequence has at least 60%, at least 65%, at least 70%, at least 80%, or at least 85% or greater percent identity to a sequence described herein. In some embodiments, a nucleotide or amino acid sequence has at least 90%, 91%, 92%, 93%, 94%, 95%, 96%, 97%, 98% or 99% identity to a sequence described herein. Percent identity can be determined by, for example, the Gap program (Wisconsin Sequence Analysis Package, Version 8 for UNIX, Genetics Computer Group, University Research Park, Madison Wis.), using default settings, which uses the algorithm of Smith and Waterman (Adv. Appl. Math., 1981, 2, 482-489). Algorithms suitable for determining percent sequence identity include the BLAST and BLAST 2.0 algorithms, which are described in Altschul et al. (Nuc. Acids Res. 25:3389-402, 1977), and Altschul et al. (J. Mol. Biol. 215:403-10, 1990), respectively. Software for performing BLAST analyses is publicly available through the National Center for Biotechnology Information (see the internet at ncbi.nlm.nih.gov). The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4.

In some embodiments, a nucleic acid sequence is codon optimized for expression in a particular species, for example, a mouse sequence can be codon optimized for expression in humans (expression of the protein encoded by the codon-optimized nucleic acid sequence). Thus, in some embodiments, a codon-optimized nucleic acid sequence has at least 60%, at least 65%, at least 70%, at least 80%, or at least 85% or greater percent identity to a nucleic acid sequence described herein. In some embodiments, a codon-optimized nucleic acid sequence acid sequence has at least 90%, 91%, 92%, 93%, 94%, 95%, 96%, 97%, 98% or 99% identity to a sequence described herein.

The term "express" refers to the production of a gene product (e.g., a protein). The term "transient" when referring to expression means a polynucleotide is not incorporated into the genome of the cell. The term "stable" when referring to expression means a polynucleotide is incorporated into the genome of the cell, or a positive selection marker (i.e., an exogenous gene expressed by the cell that confers a benefit under certain growth conditions) is utilized to maintain expression of the transgene.

The term "cytokine" or "cytokines" refers to the general class of biological molecules which affect cells of the immune system. Exemplary cytokines include but are not limited to interferons and interleukins (IL)—in particular IL-2, IL-12, IL-15, IL-18 and IL-21. In preferred embodiments, the cytokine is IL-2.

As used herein, the term "vector" refers to a non-chromosomal nucleic acid comprising an intact replicon such that the vector may be replicated when placed within a permissive cell, for example by a process of transformation. A vector may replicate in one cell type, such as bacteria, but have limited or no ability to replicate in another cell, such as mammalian cells. Vectors may be viral or non-viral. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA. In one embodiment, the vector is a viral vector, e.g. adenovirus. Viral vectors are well known in the art.

As used herein, the term "targeted," when referring to protein expression, is intended to include, but is not limited to, directing proteins or polypeptides to appropriate destinations in the cell or outside of it. The targeting is typically achieved through signal peptides or targeting peptides, which are a stretch of amino acid residues in a polypeptide chain. These signal peptides can be located anywhere within a polypeptide sequence, but are often located on the N-terminus. Polypeptides can also be engineered to have a signal peptide on the C-terminus. Signal peptides can direct a polypeptide for extracellular section, location to plasma membrane, golgi, endosomes, endoplasmic reticulum, and other cellular compartments. For example, polypeptides with a particular amino acid sequence on their C-terminus (e.g., KDEL) are retained in the ER lumen or transported back the ER lumen.

As used herein, the term "target," when referring to targeting of a tumor, refers to the ability of NK-92 cells to recognize and kill a tumor cell (i.e., target cell). The term "targeted" in this context refers, for example, to the ability of a CAR expressed by the NK-92 cell to recognize and bind to a cell surface antigen expressed by the tumor.

As used herein, the term "transfect" refers to the insertion of nucleic acid into a cell. Transfection may be performed using any means that allows the nucleic acid to enter the cell. DNA and/or mRNA may be transfected into a cell. Preferably, a transfected cell expresses the gene product (i.e., protein) encoded by the nucleic acid.

The term "suicide gene" refers to a transgene that allows for the negative selection of cells expressing that transgene. A suicide gene is used as a safety system, allowing the cells expressing the gene to be killed by introduction of a selective agent. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene (see also, for example, Yazawa K, Fisher W E, Brunicardi F C: Current progress in suicide gene therapy for cancer. World J. Surg. 2002 July; 26(7):783-9). In one embodiment, the suicide gene is the thymidine kinase (TK) gene. The TK gene may be a wild-type or mutant TK gene (e.g., tk30, tk75, sr39tk). Cells expressing the TK protein can be killed using ganciclovir.

What is claimed is:

1. A genetically modified NK cell carrying a non-viral vector encoding a membrane bound recombinant chimeric antigen receptor (CAR), wherein the CAR comprises in a single polypeptide chain: an extracellular scFv domain according to SEQ ID NO:38, a hinge domain, a transmembrane domain, and a FcεRIγ signaling domain according to SEQ ID NO:1; and wherein the NK cell is an NK-92 cell.

2. The genetically modified NK cell of claim 1, wherein the hinge domain and/or the transmembrane domain comprise a CD8 hinge domain according to SEQ ID NO:6 or SEQ ID NO:45, and/or a CD28 transmembrane domain according to SEQ ID NO:7.

3. The genetically modified NK cell of claim 1, further carrying a membrane bound recombinant CD16.

4. The genetically modified NK cell of claim 1, further comprising a recombinant cytokine with an endoplasmic retention sequence.

5. A genetically modified NK cell, comprising:
a recombinant nucleic acid encoding a chimeric antigen receptor (CAR), wherein the recombinant nucleic acid is a transfected plasmid;
wherein the NK cell is an NK-92 cell;
wherein the CAR comprises in a single polypeptide chain an extracellular binding domain according to SEQ ID NO:38, a hinge domain, a transmembrane domain, and a FcεRIγ signaling domain according to SEQ ID NO:1.

6. The genetically modified NK cell of claim 5, wherein the recombinant nucleic acid is an RNA.

7. The genetically modified NK cell of claim 6, wherein the RNA is a polycistronic RNA that further encodes a CD16 and/or a cytokine with an endoplasmic retention sequence.

8. The genetically modified NK cell of claim 5, wherein the extracellular binding domain comprises a scFv.

9. The genetically modified NK cell of claim 5, wherein the extracellular binding domain specifically binds to a tumor-specific antigen, a tumor associated antigen, or a patient- and tumor-specific antigen.

10. The genetically modified NK cell of claim 9, wherein the tumor-specific antigen is HER-2.

11. The genetically modified NK cell of claim 5, wherein the hinge domain and/or the transmembrane domain comprise a CD8 hinge domain and/or a CD28 transmembrane domain.

12. The genetically modified NK cell of claim 1, wherein the CAR is encoded by the nucleic acid sequence of SEQ ID NO:60.

13. The genetically modified NK cell of claim 1, wherein the CAR comprises in a single polypeptide chain: an extracellular scFv domain according to SEQ ID NO:38, a hinge domain according to SEQ ID NO:6 or SEQ ID NO:45, a transmembrane domain according to SEQ ID NO:7, and a FcεRIγ signaling domain according to SEQ ID NO:1.

* * * * *